United States Patent
Gu et al.

(10) Patent No.: US 8,933,233 B2
(45) Date of Patent: *Jan. 13, 2015

(54) 1,3,4-OXADIAZOLE AND 1,3,4-THIADIAZOLE β-LACTAMASE INHIBITORS

(71) Applicant: Cubist Pharmaceuticals, Inc., Lexington, MA (US)

(72) Inventors: Yu Gui Gu, Acton, MA (US); Yong He, Bedford, MA (US); Ning Yin, Lexington, MA (US); Dylan C. Alexander, Watertown, MA (US); Jason B. Cross, Acton, MA (US); Chester A. Metcalf, III, Needham, MA (US)

(73) Assignee: Cubist Pharmaceuticals, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/853,443

(22) Filed: Mar. 29, 2013

(65) Prior Publication Data

US 2013/0303504 A1 Nov. 14, 2013

Related U.S. Application Data

(60) Provisional application No. 61/618,131, filed on Mar. 30, 2012, provisional application No. 61/790,579, filed on Mar. 15, 2013.

(51) Int. Cl.
| | | |
|---|---|---|
| C07D 471/08 | (2006.01) |
| A61K 31/546 | (2006.01) |
| A61K 31/439 | (2006.01) |
| A61K 31/545 | (2006.01) |
| A61K 31/407 | (2006.01) |
| A61K 45/06 | (2006.01) |
| A61K 31/436 | (2006.01) |
| A61K 31/427 | (2006.01) |

(52) U.S. Cl.
CPC ............. *A61K 31/546* (2013.01); *A61K 31/545* (2013.01); *A61K 31/407* (2013.01); *A61K 45/06* (2013.01); *C07D 471/08* (2013.01); *A61K 31/436* (2013.01); *A61K 31/439* (2013.01); *A61K 31/427* (2013.01)
USPC ........... 546/183; 546/121; 514/359; 514/203; 514/202; 514/300

(58) Field of Classification Search
USPC .......................................... 546/183; 514/359
See application file for complete search history.

(56) References Cited

U.S. PATENT DOCUMENTS 7,112,592 B2  9/2006  Lampilas et al.
7,612,087 B2  11/2009  Aszodi et al.
(Continued)

FOREIGN PATENT DOCUMENTS

EP  2135959 A1  12/2012
FR  2 835 186 A  8/2003
(Continued)

OTHER PUBLICATIONS

Crompton, et al: Beta-Lactamase inhibitors, the inhibition of serine beta-lactamases by specific boronic acids; Biochem J., 1988, vol. 251, pp. 453-459.

(Continued)

*Primary Examiner* — John Mabry
*Assistant Examiner* — Daniel Carcanague
(74) *Attorney, Agent, or Firm* — Lathrop & Gage LLP; Brian C. Trinque

(57) ABSTRACT

β-Lactamase inhibitor compounds (BLIs) are disclosed, including compounds that have activity against class A, class C or class D β-lactamases. Methods of manufacturing the BLIs, and uses of the compounds in the preparation of pharmaceutical compositions and antibacterial applications are also disclosed.

5 Claims, 31 Drawing Sheets

(56) References Cited

U.S. PATENT DOCUMENTS

| | | | |
|---|---|---|---|
| 7,732,610 | B2 | 6/2010 | Lampilas et al. |
| 8,178,554 | B2 | 5/2012 | Lampilas et al. |
| 8,288,553 | B2 | 10/2012 | Priour et al. |
| 8,471,025 | B2 | 6/2013 | Dedhiya et al. |
| 8,487,093 | B2 | 7/2013 | Blizzard et al. |
| 2010/0197928 | A1 | 8/2010 | Priour et al. |
| 2011/0046102 | A1 | 2/2011 | Ledoussal et al. |
| 2012/0016553 | A1 | 2/2012 | Abe et al. |
| 2012/0053350 | A1 | 3/2012 | Mangion et al. |
| 2012/0323010 | A1 | 12/2012 | Ronsheim et al. |
| 2013/0012712 | A1 | 1/2013 | Priour et al. |
| 2013/0059774 | A1 | 3/2013 | Patel et al. |
| 2013/0225554 | A1 | 8/2013 | Maiti et al. |
| 2013/0267480 | A1 | 10/2013 | Dedhiya et al. |
| 2013/0289012 | A1* | 10/2013 | Gu et al. .................. 514/203 |
| 2013/0296290 | A1* | 11/2013 | Gu et al. .................. 514/202 |
| 2013/0296291 | A1* | 11/2013 | Gu et al. .................. 514/202 |
| 2013/0296292 | A1* | 11/2013 | Gu et al. .................. 514/202 |
| 2013/0296293 | A1* | 11/2013 | Gu et al. .................. 514/202 |
| 2013/0296555 | A1* | 11/2013 | Gu et al. .................. 544/127 |
| 2013/0345190 | A1* | 12/2013 | Gu et al. .................. 514/207 |

FOREIGN PATENT DOCUMENTS

| | | |
|---|---|---|
| FR | 2 812 635 A | 2/2008 |
| FR | 2 930 553 A1 | 10/2009 |
| FR | 2 951 171 A | 4/2011 |
| KR | 2010130176 A | 12/2010 |
| WO | WO 02/010172 A1 | 7/2002 |
| WO | WO 03/063864 A2 | 7/2003 |
| WO | WO2005/108391 A1 | 11/2005 |
| WO | WO2006/125974 A1 | 11/2006 |
| WO | WO2007/129176 A2 | 11/2007 |
| WO | WO 2009/091856 A2 | 7/2009 |
| WO | WO2009/133442 A1 | 11/2009 |
| WO | WO 2010-118361 A1 | 1/2010 |
| WO | WO 2010-056827 A1 | 5/2010 |
| WO | WO2010/126820 A1 | 11/2010 |
| WO | WO 2011/042560 A1 | 4/2011 |
| WO | WO2011/101710 A1 | 8/2011 |
| WO | WO2012/086241 A1 | 6/2012 |
| WO | WO2012/172368 A1 | 12/2012 |
| WO | WO 2013/014496 A1 | 1/2013 |
| WO | WO 2013/014497 A1 | 1/2013 |
| WO | WO 2013/030735 A1 | 3/2013 |
| WO | WO 2013/038330 A1 | 3/2013 |
| WO | WO2013/180197 A1 | 12/2013 |

OTHER PUBLICATIONS

International Search Report, PCT/US2013/034562, dated Jul. 30, 2013, 6 pages.
Written Opinion, PCT/US2013/034562, dated Jul. 30, 2013, 5 pages.
Patani, et al: Bioisosterism: A Rational Approach in Drug Design; Chem Rev, 1996, vol. 96, pp. 3147-3176.
International Search Report, PCT/US2013/034589, dated Jul. 29, 2013, 4 pages.
Written Opinion, PCT/US2013/034589, dated Jul. 29, 2013, 5 pages.
Mangion, et al: A Concise of a beta-Lactamase Inhibitor; Organic Letters, Oct. 21, 2011, 13(2), pp. 5480-5483.
Blizzard et al: Side chain SAR of bicyclic beta-lactamase inhibitors (BLIs). 1. discovery of a class C BLI for combination with imipinem; Bioorganic & Medicinal Chemistry Letters; 2010, vol. 20, pp. 918-921.
Coleman: Diazabicyclooctanes (DSOs): a potent new class of non-beta-lactam beta-lactamase inhibitors; Current Opinion in Microbiology; 2011, vol. 14, pp. 1-6.
Miller et al: Practical and Cost-Effective Manufacturing Route for the Synthesis of a beta-Lactamase Inhibitor; Organic Letters, 2014, vol. 16, No. 1, pp. 174-177.
Yoshizawa, H. et al.; "New broad-spectrum parenteral cephalosporins exhibiting potent activity against both methicillin-resistant *Staphylococcus aureus* (MRSA) and *Pseudomonas aeruginosa*. Part 2: Synthesis and stucture—activity relationships in the S-3578 series"; Bioorganic and Medicinal Chemistry 2004, vol. 12, pp. 4211-4219.
Yoshizawa, H. et al.; "New broad-spectrum parenteral cephalosporins exhibiting potent activity against both methicillin-resistant *Staphylococcus aureus* (MRSA) and *Pseudomonas aeruginosa*. Part 3: 7b-[2-(5-Amino-1,2,4-thiadiazol-3-yl)-2-ethoxyiminoacetamido] cephalosporins bearing 4-[3-(aminoalkyl)-ureido]-1-pyridinium at C-3'"; Bioorganic and Medicinal Chemistry 2004, vol. 12, pp. 4221-4231.
Yoshizawa, H. et al.; "S-3578, A New Broad Spectrum Parenteral Cephalosporin Exhibiting Potent Activity Against both Methicillin-resistant *Staphylococcus aureus* (MRSA) and *Pseudomonas aeruginosa* Synthesis and Structure-activity Relationships"; The Journal of Antibiotics 2002, vol. 55, No. 11, pp. 975-992.
Ida, T. et al. "CP6679, a new injectable cephalosporin with broad spectrum and potent activities against methicillin-resistant *Staphylococcus aureus* and *Pseudomonas aeruginosa*"; Journal of Infection and Chemotherapy 2002, vol. 8, pp. 138-144.

* cited by examiner

FIGURE 1A

Table I

Compounds of Formula A-II

| Cmpd. No. | X | R¹ | R |
|---|---|---|---|
| 701 | O | H | —OSO₃H |
| 702 | O | H₂N–CH₂– | —OSO₃H |
| 703 | O | H₂N–CH₂CH₂– | —OSO₃H |
| 704 | O | H₂N–C(=NH)–NH–CH₂– | —OSO₃H |
| 705 | O | H₂N–C(=NH)–NH–CH₂CH₂– | —OSO₃H |
| 706 | O | H₂N–C(=O)–CH< | —OSO₃H |
| 707 | O | –NH₂ | —OSO₃H |
| 708 | O | azetidin-3-yl (HN-azetidine) | —OSO₃H |
| 709 | O | N-carbamimidoyl-azetidin-3-yl | —OSO₃H |
| 710 | O | pyrrolidin-3-yl (HN-pyrrolidine) | —OSO₃H |

FIGURE 1B

Table I

Compounds of Formula A-II

| Cmpd. No. | X | R¹ | R |
|---|---|---|---|
| 711 | O | piperidin-4-yl (HN in ring) | —OSO₃H |
| 712 | O | 1-(aminoiminomethyl)piperidin-4-yl | —OSO₃H |
| 713 | O | piperazin-1-yl (HN in ring) | —OSO₃H |
| 714 | O | H₂N-C(=NH)-NH-(CH₂)₃- (guanidinopropyl) | —OSO₃H |
| 715 | O | H₂N-CH₂-CH(OH)- | —OSO₃H |
| 716 | O | H₂N-CH₂CH₂-NH-CH₂CH₂- | —OSO₃H |
| 717 | O | H₂N-CH₂-CH(NH₂)- | —OSO₃H |
| 718 | S | H₂N-CH₂CH₂- | —OSO₃H |
| 719 | S | piperidin-4-yl (HN in ring) | —OSO₃H |
| 720 | O | H₂N-(CH₂)₃- | —OSO₃H |
| 721 | S | H₂N-C(=NH)-NH-CH₂- | —OSO₃H |
| 722 | O | CH₃-NH-CH₂CH₂- | —OSO₃H |

FIGURE 1C
Table I
Compounds of Formula A-II
| Cmpd. No. | X | R¹ | R |
|---|---|---|---|
| 723 | O | 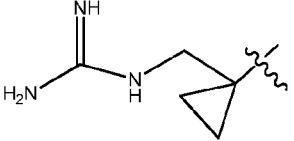 | 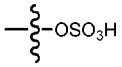—OSO₃H |
| 724 | O |  | —OSO₃H |
| 725 | O | 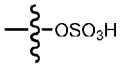 | —OSO₃H |
| 726 | O | 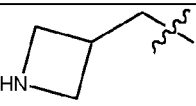 | —OSO₃H |
| 727 | O | 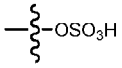 | —OSO₃H |
| 728 | O | 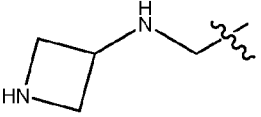 | —OSO₃H |
| 729 | O | 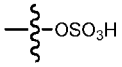 | —OSO₃H |
| 730 | O | 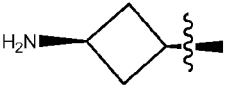 | —OSO₃H |
| 731 | O |  | —OSO₃H |
| 732 | O | 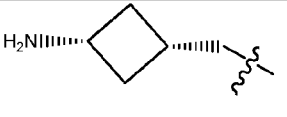 | —OSO₃H |

FIGURE 1D

Table I
Compounds of Formula A-II

| Cmpd. No. | X | R¹ | R |
|---|---|---|---|
| 733 | O | H₂N–CH₂–CH(OH)–CH₂–⁓ (1-amino-2-hydroxypropyl) | –OSO₃H |
| 734 | O | CH₃–NH–CH₂CH₂CH₂–⁓ | –OSO₃H |
| 735 | O | H₂N–(CH₂)₄–⁓ | –OSO₃H |
| 736 | O | HO–CH₂CH₂–NH–CH₂CH₂–⁓ | –OSO₃H |
| 737 | O | H₂N–C(CH₃)₂–CH₂–⁓ | –OSO₃H |
| 738 | O | H₂N–C(=NH)–NH–CH₂–⁓ (guanidinomethyl) | –OSO₃H |
| 739 | O | H₂N–C(=NH)–NH–(1-cyclopropyl)–CH₂–⁓ | –OSO₃H |
| 740 | O | 3-azabicyclo[3.1.0]hexyl | –OSO₃H |
| 741 | O | 1-(aminoiminomethyl)azetidin-3-yl–CH₂–⁓ | –OSO₃H |
| 742 | O | azetidin-3-yl–CH₂CH₂–⁓ | –OSO₃H |
| 743 | O | azetidin-3-yl–CH₂CH₂CH₂–⁓ | –OSO₃H |
| 744 | O | azetidin-3-yl–O–CH₂–⁓ | –OSO₃H |
| 745 | O | azetidin-3-yl–NH–CH₂CH₂–⁓ | –OSO₃H |

FIGURE 1E

Table 1
Compounds of Formula A-II

| Cmpd. No. | X | R¹ | R |
|---|---|---|---|
| 746 | O | 3-(guanidinyl-azetidin-1-yl)ethylamino (HN=C(NH₂)–N-azetidine-3-NH-CH₂CH₂–) | –OSO₃H |
| 747 | O | cis-3-aminocyclobutyl | –OSO₃H |
| 748 | O | trans-3-guanidinylcyclobutyl | –OSO₃H |
| 749 | O | cis-3-guanidinylcyclobutyl | –OSO₃H |
| 750 | O | 2-azaspiro[3.3]heptan-6-yl methyl | –OSO₃H |
| 751 | O | trans-3-aminocyclobutylmethyl | –OSO₃H |
| 752 | O | 3-guanidinylcyclobutylmethyl | –OSO₃H |
| 753 | O | trans-3-aminocyclobutyl-ethyl | –OSO₃H |
| 754 | O | cis-3-aminocyclobutyl-ethyl | –OSO₃H |
| 755 | O | (3-aminocyclobutyl)aminomethyl | –OSO₃H |
| 756 | O | trans-(3-aminocyclobutyl)aminomethyl | –OSO₃H |

FIGURE 1F
Table I
Compounds of Formula A-II
| Cmpd. No. | X | R¹ | R |
|---|---|---|---|
| 757 | O | 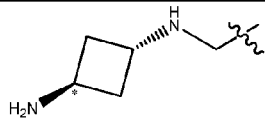 |  −OSO₃H |
| 758 | O |  | −OSO₃H |
| 759 | O |  | −OSO₃H |
| 760 | O |  | −OSO₃H |
| 761 | O |  | −OSO₃H |
| 762 | O | 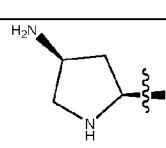 | −OSO₃H |
| 763 | O |  | −OSO₃H |
| 764 | O | 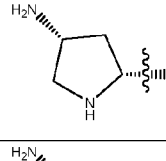 | −OSO₃H |
| 765 | O |  | −OSO₃H |
| 766 | O | 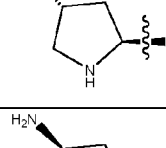 | −OSO₃H |
| 767 | O |  | −OSO₃H |

FIGURE 1G

Table I
Compounds of Formula A-II

| Cmpd. No. | X | R¹ | R |
|---|---|---|---|
| 768 | O | (aminocyclopentyl) | —OSO₃H |
| 769 | O | (piperidinyl-NH-CH₂-) | —OSO₃H |
| 770 | O | (piperidinyl-NH-CH₂CH₂-) | —OSO₃H |
| 771 | O | (piperidinyl-NH-(CH₂)₃-) | —OSO₃H |
| 772 | O | (piperidinyl-NH-(CH₂)₄-) | —OSO₃H |
| 773 | O | (4-amino-piperidin-1-yl) | —OSO₃H |
| 774 | O | (4-amino-piperidin-1-yl-CH₂-) | —OSO₃H |
| 775 | O | (4-amino-piperidin-1-yl-CH₂CH₂-) | —OSO₃H |
| 776 | O | (piperazin-1-yl-CH₂CH₂-) | —OSO₃H |
| 777 | O | (piperazin-1-yl-CH₂-) | —OSO₃H |
| 778 | O | (piperazin-2-yl) | —OSO₃H |
| 779 | O | (piperazin-2-yl, stereo) | —OSO₃H |
| 780 | O | (4-aminocyclohexyl) | —OSO₃H |

FIGURE 1H

Table I

Compounds of Formula A-II

| Cmpd. No. | X | R¹ | R |
|---|---|---|---|
| 781 | O | H₂N-cyclohexyl (trans) | −OSO₃H |
| 782 | O | N-methylpyridinium | −OSO₃H |
| 783 | S | H₂N-cyclobutyl (trans) | −OSO₃H |
| 784 | S | guanidinyl-cyclobutyl | −OSO₃H |
| 785 | S | guanidinyl-cyclobutyl (trans) | −OSO₃H |
| 786 | S | N-methylpyridinium | −OSO₃H |
| 787 | O | H₂N-spiro[3.3]heptyl | −OSO₃H |
| 788 | O | 2-azaspiro[3.5]nonyl | −OSO₃H |
| 789 | O | 3-aminocyclobutyloxyethyl | −OSO₃H |
| 790 | O | pyrrolidin-3-yl | −OSO₃H |
| 791 | O | pyrrolidin-3-yl | −OSO₃H |
| 792 | O | piperazinyl-propyl | −OSO₃H |

FIGURE 1I

Table I

Compounds of Formula A-II

| Cmpd. No. | X | R¹ | R |
|---|---|---|---|
| 793 | O | azetidin-3-ylamino-propyl | —OSO₃H |
| 794 | S | guanidinoethyl | —OSO₃H |
| 795 | S | 3-aminocyclobutyl | —OSO₃H |
| 796 | S | 1,1-dimethylpiperidin-4-yl | —OSO₃H |
| 797 | S | piperazin-1-yl | —OSO₃H |
| 798 | S | pyridin-4-yl | —OSO₃H |

FIGURE 2A

Table II Standard BLI Potentiation MIC Assay in Combination with Ceftolozane Against a Panel of Isogenic and Clinical Strains Expressing β-Lactamases

| Strain # | β-Lactamase | Bkgd | No BLI | CCC | 701 | 702 | 703 | 704 | 705 | 707 | 708 | 709 | 710 | 711 | 712 | 713 | 719 | 721 |
|---|---|---|---|---|---|---|---|---|---|---|---|---|---|---|---|---|---|---|
| Eco.2806 | KPC-2 | isogenic | E | B | A | B | B | C | A | B | B | A | B | B | B | B | B | A |
| Pae.2808 | KPC-2 | clinical | E | C | C | C | B | D | B | C | B | C | C | B | B | C | C | B |
| Kpn.2478 | KPC-3, TEM+ | clinical | E | C | C | C | B | D | B | C | B | C | B | C | C | C | C | B |
| Kpn.2490 | KPC-3, SHV1, TEM+ | clinical | E | B | A | B | A | C | A | B | A | A | B | A | A | B | A | B |
| Kpn.2783 | CTX-M-15, SHV−, TEM+ | clinical | E | A | B | B | A | C | A | B | B | B | B | B | B | B | B | B |
| Kpn.571 | TEM-26 | clinical | D | AA | A | A | A | A | A | A | A | A | A | A | A | B | A | A |
| Pae.2885 | AmpC | clinical | B | A | A | B | A | B | AA | B | A | A | A | A | B | B | A | A |
| Cfr.568 | AmpC | clinical | E | C | B | C | C | D | B | C | C | C | C | C | C | C | C | B |
| Ecl.569 | AmpC | clinical | E | B | A | A | B | B | B | A | B | A | B | B | B | B | A | A |
| Kpn.2914 | KPC-2, SHV+ | clinical | D | B | B | B | B | C | B | B | B | B | B | B | B | B | B | B |
| Kpn.2913 | KPC-2, SHV1 | clinical | D | A | A | B | A | A | A | B | A | B | A | B | A | A | A | A |
| Kpn.2917 | KPC-2, SHV+ | clinical | D | A | A | B | A | A | A | A | A | A | A | B | A | B | A | A |
| Kpn.2918 | KPC-3, SHV+, TEM1 | clinical | E | C | B | C | B | D | B | C | B | B | B | C | C | C | C | B |
| Kpn.2909 | KPC-3, SHV+, TEM+ | clinical | E | B | B | B | B | C | B | B | B | B | C | B | B | B | B | B |
| Eco.2711 | KPC | clinical | D | A | A | A | A | B | A | A | A | A | A | A | A | B | A | A |
| Eco.2781 | KPC-2, TEM+ | clinical | C | AA | A | A | A | A | A | A | A | A | A | A | A | A | A | AA |
| Kpn.2926 | CTX-M-15, OXA-48 | clinical | E | B | B | B | B | C | B | B | B | B | B | B | C | B | C | B |
| Pae.2757 | AmpC over-expn | clinical | C | B | B | B | B | B | A | B | B | B | B | B | B | B | B | B |
| Pae.2863 | AmpC de-repress | clinical | C | B | B | B | B | C | B | B | B | B | B | B | B | B | B | A |
| Eco.2843 | DHA-1 | isogenic | E | A | A | B | A | A | A | B | A | A | A | A | A | A | A | AA |
| Eco.2491 | CMY-2 | clinical | D | A | A | B | A | A | A | B | A | A | A | B | A | A | B | A |
| Eco.2902 | Aba-ADC-33 | isogenic | F | B | B | B | B | C | B | C | B | B | B | B | B | B | A | A |
| Eco.2840 | KPC-4 | isogenic | E | D | C | D | B | D | B | C | D | C | C | C | D | D | D | D |
| Eco.2845 | OXA-15 | isogenic | E | D | B | D | B | D | B | B | B | C | C | C | C | B | C | B |
| MIC90 | | | E | C | B | C | B | D | B | C | B | B | B | B | C | C | B | B |
| MIC50 | | | E | B | B | B | B | C | A | B | B | B | B | B | B | B | B | A |

Table II Standard BLI Potentiation MIC Assay in Combination with Ceftolozane Against a Panel of Isogenic and Clinical Strains Expressing β-Lactamases

| Strain # | β-Lactamase | Bkgd | No BLI | CCC | 730 | 731 | 732 | 733 | 734 | 735 | 736 | 737 | 738 | 739 | 740 | 741 | 742 | 743 |
|---|---|---|---|---|---|---|---|---|---|---|---|---|---|---|---|---|---|---|
| Eco.2806 | KPC-2 | isogenic | E | B | A | B | A | B | A | B | B | B | B | B | B | A | B | A |
| Pae.2808 | KPC-2 | clinical | E | C | C | B | A | D | C | B | C | C | C | C | C | B | B | C |
| Kpn.2478 | KPC-3, TEM+ | clinical | E | C | C | B | B | C | C | B | B | C | C | C | B | C | C | C |
| Kpn.2490 | KPC-3, SHV−, TEM I | clinical | E | B | B | A | A | B | AA | B | B | B | A | B | A | A | B | A |
| Kpn.2783 | CTX-M-15, SHV+, TEM+ | clinical | E | A | B | A | A | B | B | B | B | B | B | B | B | B | B | B |
| Kpn.571 | TEM-26 | clinical | D | AA | A | A | AA | B | A | A | B | A | AA | A | A | A | A | A |
| Pae.2885 | AmpC | clinical | B | A | A | B | A | B | B | A | B | B | B | B | C | A | A | A |
| Cfr.568 | AmpC | clinical | E | C | B | B | B | C | C | B | C | C | B | B | C | B | B | B |
| Ecl.569 | AmpC | clinical | E | B | B | A | A | C | A | B | B | B | A | A | A | B | A | A |
| Kpn.2914 | KPC-2, SHV− | clinical | D | B | C | A | B | C | B | B | B | A | B | B | A | B | B | B |
| Kpn.2913 | KPC-2, SHV− | clinical | D | A | B | A | B | A | A | A | A | A | A | A | A | A | A | A |
| Kpn.2917 | KPC-2, SHV− | clinical | D | A | A | A | A | B | AA | A | B | A | AA | A | A | A | A | A |
| Kpn.2918 | KPC-3, SHV−, TEM+ | clinical | E | C | C | B | B | C | C | B | C | C | B | C | B | C | C | C |
| Kpn.2909 | KPC-3, SHV−, TEM I | clinical | E | B | B | B | B | C | B | A | C | B | B | C | B | B | B | C |
| Eco.2711 | KPC | clinical | D | A | A | A | B | B | AA | B | A | A | A | B | A | B | A | A |
| Eco.2781 | KPC-2, TEM+ | clinical | C | AA | AA | A | A | B | AA | A | A | AA | B | A | A | A | A | A |
| Kpn.2926 | CTX-M-15, OXA-48 | clinical | E | B | B | B | B | C | B | B | E | B | B | B | A | B | B | B |
| Pae.2757 | AmpC over-expn | clinical | C | B | B | B | B | B | D | B | B | B | B | B | B | B | B | B |
| Pae.2863 | AmpC de-repress | clinical | C | B | C | B | A | C | B | C | C | B | B | B | B | B | B | B |
| Eco.2843 | DHA-1 | isogenic | E | A | A | A | A | A | B | A | A | B | A | A | A | A | A | A |
| Eco.2491 | CMY-2 | clinical | D | A | A | A | A | B | A | B | A | A | A | A | A | A | A | A |
| Eco.2902 | Aba-ADC-33 | isogenic | E | B | C | B | B | D | B | B | B | A | C | B | B | B | B | B |
| Eco.2840 | KPC-4 | isogenic | F | D | D | D | D | E | C | F | D | C | D | D | D | D | D | C |
| Eco.2845 | OXA-15 | isogenic | E | D | C | C | B | C | B | C | C | C | C | C | C | C | C | C |
| MIC90 | | | E | C | C | B | B | D | B | B | C | B | B | B | B | B | B | B |
| MIC50 | | | E | B | B | A | B | B | B | B | B | A | B | A | A | A | B | B |

Table II Standard BLI Potentiation MIC Assay in Combination with Ceftolozane Against a Panel of Isogenic and Clinical Strains Expressing β-Lactamases

| Strain # | β-Lactamase | Bkgd | No BLI | CCC | 744 | 745 | 746 | 747 | 748 | 749 | 750 | 751 | 752 | 753 | 754 | 755 | 756 | 757 |
|---|---|---|---|---|---|---|---|---|---|---|---|---|---|---|---|---|---|---|---|
| Eco.2806 | KPC-2 | isogenic | E | B | B | A | B | B | B | B | B | B | A | B | B | B | B | B |
| Pae.2808 | KPC-2 | clinical | E | C | C | C | C | C | C | B | C | C | C | C | C | B | C | C |
| Kpn.2478 | KPC-3, TEM- | clinical | E | C | C | C | D | C | C | C | C | C | C | C | C | C | C | C |
| Kpn.2490 | KPC-3, SHV+, TEM- | clinical | E | B | B | B | A | B | A | A | B | B | B | A | B | B | B | B |
| Kpn.2783 | CTX-M-15, SHV+, TEM- | clinical | E | A | B | B | B | A | B | A | B | B | A | B | B | B | B | B |
| Kpn.571 | TEM-26 | clinical | D | AA | A | A | A | A | A | A | A | A | A | A | A | A | A | B |
| Pae.2885 | AmpC | clinical | B | A | C | B | A | A | C | C | B | B | C | C | C | B | A | B |
| Cfr.568 | AmpC | clinical | E | C | C | C | C | B | A | C | C | D | B | C | C | B | B | C |
| Ecl.569 | AmpC | clinical | E | B | A | A | B | A | A | A | B | B | A | B | B | A | B | B |
| Kpn.2914 | KPC-2, SHV+ | clinical | D | B | B | C | C | C | B | B | C | B | B | B | B | B | C | C |
| Kpn.2913 | KPC-2, SHV+ | clinical | D | A | A | B | A | A | A | A | C | A | A | A | A | A | A | A |
| Kpn.2917 | KPC-2, SHV+ | clinical | D | A | A | B | A | A | A | A | A | A | A | A | A | B | A | A |
| Kpn.2918 | KPC-3, SHV+, TEM- | clinical | E | C | C | C | A | C | C | C | C | C | C | C | C | C | C | C |
| Kpn.2909 | KPC-3, SHV+, TEM- | clinical | E | B | B | C | B | C | B | B | C | B | C | B | C | C | B | B |
| Eco.2711 | KPC | clinical | D | A | A | B | A | A | B | A | A | A | A | A | A | A | A | A |
| Eco.2781 | KPC-2, TEM- | clinical | C | AA | AA | A | A | A | AA | A | A | A | A | AA | A | AA | A | A |
| Kpn.2926 | CTX-M-15, OXA-48 | clinical | E | B | B | C | A | C | B | B | E | C | B | B | B | B | C | D |
| Pae.2757 | AmpC over-expn | clinical | C | B | B | B | B | B | B | B | B | B | B | B | B | B | B | B |
| Pae.2863 | AmpC de-repress | clinical | C | B | B | C | C | B | B | B | C | B | B | B | B | B | C | C |
| Eco.2843 | DHA-1 | isogenic | E | A | A | B | A | B | A | A | B | A | A | A | A | A | A | B |
| Eco.2491 | CMY-2 | clinical | D | A | A | A | B | A | A | A | B | A | A | A | A | A | A | A |
| Eco.2902 | Aha-ADC-33 | isogenic | F | B | C | C | B | D | B | C | C | C | B | C | C | C | C | C |
| Eco.2840 | KPC-4 | isogenic | E | D | D | E | D | D | C | C | D | D | D | C | D | D | D | E |
| Eco.2845 | OXA-15 | isogenic | E | D | C | D | C | C | C | C | C | C | C | C | C | C | D | D |
| MIC90 | | | E | C | C | C | C | C | C | C | C | C | C | C | C | C | C | C |
| MIC50 | | | E | B | B | B | B | B | B | B | B | B | B | B | B | B | B | B |

Table II Standard BLI Potentiation MIC Assay in Combination with Ceftolozane Against a Panel of Isogenic and Clinical Strains Expressing β-Lactamases

| Strain # | β-Lactamase | Bkgd | No BLI | CCC | 758 | 759 | 760 | 761 | 762 | 763 | 764 | 765 | 766 | 767 | 768 | 769 | 770 | 771 |
|---|---|---|---|---|---|---|---|---|---|---|---|---|---|---|---|---|---|---|
| Eco.2806 | KPC-2 | isogenic | E | B | B | B | B | B | A | B | B | B | B | A | A | B | B | B |
| Pae.2808 | KPC-2 | clinical | E | C | C | B | B | B | C | D | B | C | B | B | B | C | C | C |
| Kpn.2478 | KPC-3, TEM+ | clinical | E | C | B | C | C | C | C | D | C | C | C | C | B | C | C | C |
| Kpn.2490 | KPC-3, SHV+, TEM+ | clinical | E | B | B | B | B | B | B | B | B | B | B | B | A | B | B | B |
| Kpn.2783 | CTX-M-15, SHV+, TEM+ | clinical | E | A | A | B | A | A | B | B | C | B | A | B | B | B | B | B |
| Kpn.571 | TEM-26 | clinical | D | AA | A | A | A | A | A | A | A | A | A | A | A | A | A | A |
| Pae.2885 | AmpC | clinical | B | A | C | C | A | B | C | A | A | A | A | A | A | A | A | A |
| Cfr.568 | AmpC | clinical | E | C | C | C | C | B | C | C | C | B | B | C | B | C | C | C |
| Ecl.569 | AmpC | clinical | E | B | A | A | B | B | B | B | A | A | B | C | B | B | B | B |
| Kpn.2914 | KPC-2, SHV+ | clinical | D | B | B | B | B | C | C | C | B | B | B | B | B | C | C | C |
| Kpn.2913 | KPC-2, SHV+ | clinical | D | A | A | A | A | A | A | A | A | A | A | A | A | A | A | B |
| Kpn.2917 | KPC-2, SHV+ | clinical | D | A | C | A | A | A | A | A | A | A | A | A | A | A | A | A |
| Kpn.2918 | KPC-3, SHV+, TEM+ | clinical | E | C | C | C | C | C | C | D | C | C | C | C | C | C | C | C |
| Kpn.2909 | KPC-3, SHV, TEM | clinical | E | B | C | B | B | B | C | C | B | B | C | B | B | C | B | C |
| Eco.2711 | KPC | clinical | D | A | A | A | A | A | A | A | A | A | A | A | A | A | B | B |
| Eco.2781 | KPC-2, TEM+ | clinical | C | AA | A | A | A | A | A | A | A | A | A | A | A | A | A | A |
| Kpn.2926 | CTX-M-15, OXA-48 | clinical | E | B | B | B | B | B | C | E | B | B | B | C | B | D | D | C |
| Pae.2757 | AmpC over-expn | clinical | C | B | B | B | B | B | B | B | C | B | B | B | B | B | B | B |
| Pae.2863 | AmpC de-repress | clinical | C | B | B | B | B | B | B | C | B | B | B | B | B | C | B | B |
| Eco.2843 | DHA-1 | isogenic | E | A | A | A | A | A | A | B | A | A | A | A | A | A | A | A |
| Eco.2491 | CMY-2 | clinical | D | A | B | B | A | A | B | C | C | A | A | A | A | C | A | A |
| Eco.2902 | Aba-ADC-33 | isogenic | E | B | B | B | B | C | B | E | B | B | B | C | B | C | B | B |
| Eco.2840 | KPC-4 | isogenic | E | D | E | D | D | D | D | E | D | D | D | D | B | D | D | D |
| Eco.2845 | OXA-15 | isogenic | E | D | C | C | B | C | C | C | C | C | C | D | B | C | C | C |
| MIC90 | | | E | C | C | C | B | B | C | C | B | B | B | D | B | C | C | C |
| MIC50 | | | E | B | B | B | B | B | B | B | B | B | B | B | B | B | B | B |

Table II Standard BLI Potentiation MIC Assay in Combination with Ceftolozane Against a Panel of Isogenic and Clinical Strains Expressing β-Lactamases

| Strain # | β-Lactamase | Bkgd | No BLI | CCC | 772 | 773 | 774 | 775 | 776 | 777 | 778 | 779 | 780 | 781 | 782 | 783 | 784 | 785 | 786 |
|---|---|---|---|---|---|---|---|---|---|---|---|---|---|---|---|---|---|---|---|
| Eco.2806 | KPC-2 | isogenic | E | B | B | B | B | A | A | B | B | A | B | B | B | B | B | B | B |
| Pae.2808 | KPC-2 | clinical | E | C | C | C | C | D | C | C | C | C | C | C | B | C | C | C | C |
| Kpn.2478 | KPC-3, TEM+ | clinical | F | C | C | C | C | C | C | C | C | C | D | C | C | C | C | C | C |
| Kpn.2490 | KPC-3, SHV+, TEM+ | clinical | E | B | B | B | A | B | A | B | B | B | B | A | B | B | B | B | B |
| Kpn.2783 | CTX-M-15, SHV+, TEM+ | clinical | E | A | A | B | B | D | A | A | B | B | B | B | B | B | B | C | B |
| Kpn.571 | TEM-26 | clinical | D | AA | A | B | A | B | A | A | A | A | A | A | B | A | A | B | A |
| Pae.2885 | AmpC | clinical | B | A | A | B | A | B | A | A | A | B | A | A | A | A | A | A | B |
| Cfr.568 | AmpC | clinical | E | C | C | C | B | C | B | B | B | C | C | C | B | C | C | C | C |
| Ecl.569 | AmpC | clinical | E | B | B | B | A | D | B | B | A | A | A | A | A | A | B | B | B |
| Kpn.2914 | KPC-2, SHV+ | clinical | D | B | B | B | B | D | B | B | B | B | C | C | A | B | B | B | B |
| Kpn.2913 | KPC-2, SHV+ | clinical | D | A | A | A | C | C | A | A | A | A | B | B | A | A | A | A | A |
| Kpn.2917 | KPC-2, SHV+ | clinical | D | A | B | B | C | B | A | A | B | A | B | A | A | A | A | A | A |
| Kpn.2918 | KPC-3, SHV+, TEM1 | clinical | E | C | C | C | C | D | C | C | C | C | B | C | B | C | C | C | C |
| Kpn.2909 | KPC-3, SHV+, TEM+ | clinical | E | B | C | C | C | D | B | B | B | B | C | B | B | B | B | C | B |
| Eco.2711 | KPC | clinical | D | A | A | B | C | B | A | A | B | A | A | A | B | A | A | A | A |
| Eco.2781 | KPC-2, TEM+ | clinical | C | AA | AA | A | C | B | A | A | A | B | A | A | AA | A | A | A | A |
| Kpn.2926 | CTX-M-15, OXA-48 | clinical | E | B | C | D | C | E | B | C | D | B | E | D | B | C | B | D | C |
| Pae.2757 | AmpC over-expn | clinical | C | B | B | B | B | C | B | B | C | B | B | B | B | B | B | B | B |
| Pae.2863 | AmpC de-repress | clinical | C | B | B | C | C | D | B | B | C | C | B | B | B | B | B | B | B |
| Eco.2843 | DHA-1 | isogenic | F | A | A | B | C | B | A | A | B | A | B | A | A | A | A | A | A |
| Eco.2491 | CMY-2 | clinical | D | B | A | A | A | B | C | A | B | C | B | A | A | B | A | A | B |
| Eco.2902 | Aba-ADC-33 | isogenic | E | D | C | C | C | D | C | B | C | B | E | D | C | D | D | D | D |
| Eco.2840 | KPC-4 | isogenic | E | D | D | D | D | D | D | D | E | D | D | C | D | C | C | D | D |
| Eco.2845 | OXA-15 | isogenic | E | C | C | C | C | D | C | C | C | B | D | C | C | C | C | C | C |
| MIC90 | | | E | B | B | B | B | D | B | B | C | B | B | B | B | B | B | D | C |
| MIC50 | | | E | B | B | B | B | C | B | B | B | B | B | B | B | B | B | B | B |

Table II Standard BLI Potentiation MIC Assay in Combination with Ceftolozane Against a Panel of Isogenic and Clinical Strains Expressing β-Lactamases

| Strain # | β-Lactamase | Bkgd | No BLI | CCC | 792 | 793 | 794 | 795 | 796 | 797 | 798 | 722 | 723 | 724 | 725 | 726 | 727 | 728 | 729 |
|---|---|---|---|---|---|---|---|---|---|---|---|---|---|---|---|---|---|---|---|
| Eco.2806 | KPC-2 | isogenic | E | B | B | B | B | B | B | B | B | B | B | A | B | B | A | A | A |
| Pae.2808 | KPC-2 | clinical | E | C | D | D | B | C | C | D | B | C | C | C | B | B | B | C | C |
| Kpn.2478 | KPC-3, TEM- | clinical | E | C | C | D | B | C | D | D | C | B | B | C | C | C | B | B | B |
| Kpn.2490 | KPC-3, SHV+, TEM+ | clinical | E | B | A | B | A | B | B | B | B | A | B | A | B | B | A | A | A |
| Kpn.2783 | CTX-M-15, SHV1, TEM+ | clinical | F | A | B | C | A | B | C | B | B | A | B | B | B | B | A | A | B |
| Kpn.571 | TEM-26 | clinical | D | AA | A | B | AA | A | B | A | B | A | A | A | A | A | A | AA | A |
| Pae.2885 | AmpC' | clinical | B | A | B | B | A | A | A | A | A | A | A | A | A | A | A | A | B |
| Cfr.568 | AmpC | clinical | E | C | B | C | B | C | C | C | C | B | C | B | C | C | B | B | B |
| Ecl.569 | AmpC | clinical | E | B | B | C | A | A | B | A | C | B | A | A | B | B | A | A | A |
| Kpn.2914 | KPC-2, SHV1 | clinical | D | B | C | C | A | B | C | C | B | B | B | B | B | B | B | B | A |
| Kpn.2913 | KPC-2, SHV+ | clinical | D | A | A | B | AA | B | B | B | B | A | A | B | A | A | A | A | A |
| Kpn.2917 | KPC-2, SHV+ | clinical | D | A | A | B | A | B | B | B | A | A | A | A | A | A | A | A | A |
| Kpn.2918 | KPC-3, SHV+, TEM+ | clinical | F | C | C | D | B | C | C | D | C | B | B | B | C | C | B | C | C |
| Kpn.2909 | KPC-3, SHV+, TEM+ | clinical | E | B | B | C | A | B | C | C | C | B | B | B | B | C | B | B | B |
| Eco.2711 | KPC | clinical | D | A | A | B | AA | A | A | A | B | A | A | A | A | A | A | A | A |
| Eco.2781 | KPC-2, TEM- | clinical | C | AA | A | A | AA | A | A | B | A | A | A | A | AA | A | A | AA | A |
| Kpn.2926 | CTX-M-15, OXA-48 | clinical | E | B | C | D | B | C | D | C | D | B | B | B | C | C | B | B | B |
| Pae.2757 | AmpC over-expn | clinical | C | B | B | C | B | B | B | B | C | B | A | B | B | B | B | B | B |
| Pae.2863 | AmpC de-repress | clinical | C | B | C | D | A | B | D | C | B | C | A | B | B | B | B | B | B |
| Eco.2843 | DHA-1 | isogenic | E | A | A | A | A | A | B | A | A | A | AA | A | A | A | A | A | A |
| Eco.2491 | CMY-2 | clinical | D | A | A | A | A | A | A | A | A | A | A | A | B | B | A | B | A |
| Eco.2902 | Aba-ADC-33 | isogenic | E | B | C | C | B | C | B | B | C | C | A | B | C | C | B | C | B |
| Eco.2845 | KPC-4 | isogenic | E | D | D | E | D | E | E | D | D | D | D | D | D | D | D | C | D |
| Eco.2845 | OXA-15 | isogenic | E | D | C | D | C | D | D | C | D | C | B | B | C | C | C | C | B |
| MIC90 | | | F | C | C | D | B | C | D | D | C | B | B | B | C | C | B | C | B |
| MIC50 | | | E | B | B | B | A | B | B | B | B | B | A | A | B | B | A | A | B |

Table II Standard BLI Potentiation MIC Assay in Combination with Ceftolozane Against a Panel of Isogenic and Clinical Strains Expressing β-Lactamases

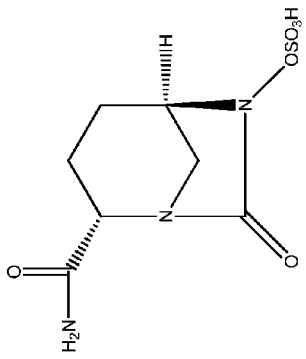

Eco is *Escherichia coli*,
Kpn is *Klebsiella pneumoniae*,
Pae is *Pseudomonas aeruginosa*;

CCC is comparator compound:

| Strain # | β-Lactamase | Bkgd | No BLI | CCC | 706 | 714 | 715 | 716 | 717 | 718 | 720 |
|---|---|---|---|---|---|---|---|---|---|---|---|
| Eco.2806 | KPC-2 | isogenic | E | B | B | B | B | B | B | B | A |
| Pae.2808 | KPC-2 | clinical | E | C | C | B | B | C | C | C | B |
| Kpn.2478 | KPC-3, TEM+ | clinical | E | C | C | B | C | C | C | C | AA |
| Kpn.2490 | KPC-3, SHV+, TEM+ | clinical | E | B | A | A | B | B | B | B | AA |
| Kpn.2783 | CTX-M-15, SHV+, TEM+ | clinical | E | A | B | A | B | B | B | B | B |
| Kpn.571 | TEM-26 | clinical | D | AA | AA | A | A | A | A | A | AA |
| Pae.2885 | AmpC | clinical | B | AA | A | A | A | A | A | A | A |
| Cfr.568 | AmpC | clinical | E | C | B | B | B | B | C | B | A |
| Ecl.569 | AmpC | clinical | E | B | A | A | A | A | A | A | A |
| Kpn.2914 | KPC-2, SHV+ | clinical | D | B | A | A | B | B | B | B | AA |
| Kpn.2913 | KPC-2, SHV+ | clinical | D | A | AA | A | A | A | A | A | AA |
| Kpn.2917 | KPC-2, SHV+ | clinical | D | A | AA | AA | A | A | A | A | AA |
| Kpn.2918 | KPC-3, SHV+, TEM+ | clinical | E | C | B | B | C | C | C | C | B |
| Kpn.2909 | KPC-3, SHV+, TEM+ | clinical | E | B | B | B | B | C | C | C | AA |
| Eco.2711 | KPC | clinical | D | A | A | A | A | A | A | A | AA |
| Eco.2781 | KPC-2, TEM+ | clinical | C | AA | AA | AA | AA | A | AA | AA | AA |
| Kpn.2926 | CTX-M-15, OXA-48 | clinical | E | B | B | C | B | B | C | B | A |
| Pae.2757 | AmpC over-expn | clinical | C | B | B | B | B | B | B | B | B |
| Pae.2863 | AmpC de-repress | clinical | C | B | B | C | B | B | C | B | B |
| Eco.2843 | DHA-1 | isogenic | E | A | A | A | B | B | A | A | AA |
| Eco.2491 | CMY-2 | clinical | D | A | A | A | A | A | A | A | AA |
| Eco.2902 | Aba-ADC-33 | isogenic | E | B | A | B | C | C | C | B | A |
| Eco.2840 | KPC-4 | isogenic | E | D | C | D | D | D | D | E | C |
| Eco.2845 | OXA-15 | isogenic | E | C | C | C | C | C | D | D | B |
| MIC90 | | | E | D | B | B | C | C | C | D | B |
| MIC50 | | | E | B | A | A | B | B | B | C | A |

Table III: Synergy MIC (sMIC) Against a Panel of Isogenic and Clinical Strains Expressing β-lactamases

| β-Lactamase | Bkgd | Sp | β-Lactam (4 µg/mL) | CCC | 701 | 702 | 703 | 704 | 705 | 706 | 707 | 708 | 709 | 710 | 711 | 712 | 713 | 719 | 720 | 721 |
|---|---|---|---|---|---|---|---|---|---|---|---|---|---|---|---|---|---|---|---|---|
| none | isogenic | Eco | none | D | F | E | F | F | F | F | F | F | F | F | F | F | F | F | D | F |
| KPC-2 | isogenic | Eco | CXA-101 | B | A | A | A | C | A | A | B | A | A | A | A | A | B | B | B | A |
| OXA-15 | isogenic | Eco | CXA-101 | D | B | C | C | D | C | B | C | C | C | C | C | C | C | B | B | C |
| CTX-M-15 | isogenic | Eco | CXA-101 | A | A | A | A | B | A | A | A | B | B | B | B | B | A | C | A | B |
| SHV-12 | isogenic | Eco | CXA-101 | B | B | B | C | C | C | C | B | C | C | C | C | C | C | C | B | B |
| P99 | isogenic | Eco | CXA-101 | A | A | A | A | B | AA | B | B | AA | A | A | A | B | A | A | B | A |
| KPC-3 | clinical | Kpn | CXA-101 | C | C | C | C | D | B | C | C | C | B | B | C | C | C | C | B | B |
| KPC-2 | clinical | Pae | CXA-101 | B | C | C | B | D | C | C | C | B | B | B | C | C | C | C | B | B |

AA = < 0.25 µg/mL; A = 0.25-0.5 µg/mL; B = 1-2 µg/mL; C = 4-8 µg/mL; D = 16-32 µg/mL; E = 64 µg/mL; F = ≥128 µg/mL
CXA-101 is Ceftolozane   Eco is *Escherichia coli*, Kpn is *Klebsiella pneumoniae*, Pae is *Pseudomonas aeruginosa*

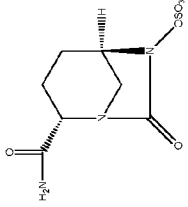

CCC is comparator compound

FIGURE 3B

Table III: Synergy MIC (sMIC) Against a Panel of Isogenic and Clinical Strains Expressing β-lactamases

| β-Lactamase | Bkgd | Sp | β-Lactam (4 μg/mL) | CCC | 730 | 731 | 732 | 733 | 734 | 735 | 736 | 737 | 738 | 739 | 740 | 741 | 742 | 743 | 744 | 745 |
|---|---|---|---|---|---|---|---|---|---|---|---|---|---|---|---|---|---|---|---|---|
| none | isogenic | Eco | none | D | E | D | F | D | C | D | F | F | F | F | F | F | F | F | F | F |
| KPC-2 | isogenic | Eco | CXA-101 | B | A | A | A | B | A | A | A | A | B | A | A | A | A | A | A | A |
| OXA-15 | isogenic | Eco | CXA-101 | D | D | C | C | C | C | C | D | C | C | C | B | C | C | C | C | C |
| CTX-M-15 | isogenic | Eco | CXA-101 | A | B | A | A | B | B | A | B | B | C | A | B | A | B | A | A | B |
| SHV-12 | isogenic | Eco | CXA-101 | B | D | B | B | C | B | C | C | B | C | C | C | A | C | C | C | C |
| P99 | isogenic | Eco | CXA-101 | A | A | A | A | B | A | B | B | A | B | A | A | A | B | C | A | B |
| KPC-3 | clinical | Kpn | CXA-101 | C | D | C | B | C | C | C | C | C | D | C | C | C | C | C | C | C |
| KPC-2 | clinical | Pae | CXA-101 | B | C | B | B | C | C | B | C | C | D | C | C | C | C | C | C | C |

AA=< 0.25 μg/mL; A = 0.25-0.5 μg/mL; B = 1-2 μg/mL; C = 4-8 μg/mL; D = 16-32 μg/mL; E = 64 μg/mL; F = ≥128 μg/mL

CXA-101 is Ceftolozane

Eco is *Escherichia coli*, Kpn is *Klebsiella pneumoniae*, Pae is *Pseudomonas aeruginosa*

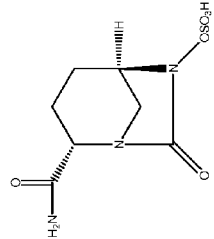

CCC is comparator compound

FIGURE 3C

Table III: Synergy MIC (sMIC) Against a Panel of Isogenic and Clinical Strains Expressing β-lactamases

| β-Lactamase | Bkgd | Sp | β-Lactam (4 µg/mL) | CCC | 746 | 747 | 748 | 749 | 750 | 751 | 752 | 753 | 754 | 755 | 756 | 757 | 758 | 759 | 760 | 761 | 762 |
|---|---|---|---|---|---|---|---|---|---|---|---|---|---|---|---|---|---|---|---|---|---|
| none | isogenic | Eco | none | D | F | F | F | F | F | F | F | F | F | F | F | F | F | F | F | F | F |
| KPC-2 | isogenic | Eco | CXA-101 | B | A | A | B | A | A | A | A | A | A | A | A | B | A | A | A | A | B |
| OXA-15 | isogenic | Eco | CXA-101 | D | C | C | C | C | C | C | C | C | C | C | C | C | C | C | C | C | D |
| CTX-M-15 | isogenic | Eco | CXA-101 | A | A | B | A | A | B | B | A | A | A | A | A | B | B | B | A | A | B |
| SHV-12 | isogenic | Eco | CXA-101 | B | C | C | C | B | C | B | C | C | C | C | C | C | C | C | C | C | C |
| P99 | isogenic | Eco | CXA-101 | A | A | B | A | B | B | B | B | A | B | A | A | B | A | A | A | A | B |
| KPC-3 | clinical | Kpn | CXA-101 | C | C | C | C | C | C | C | C | C | C | C | C | C | C | B | C | C | C |
| KPC-2 | clinical | Pae | CXA-101 | B | C | B | C | B | B | B | C | C | C | C | C | C | B | B | C | C | C |

AA=< 0.25 µg/mL; A = 0.25-0.5 µg/mL; B = 1-2 µg/mL; C = 4-8 µg/mL; D = 16-32 µg/mL; E = 64 µg/mL; F = ≥128 µg/mL

CXA-101 is Ceftolozane

Eco is *Escherichia coli*, Kpn is *Klebsiella pneumoniae*, Pae is *Pseudomonas aeruginosa*

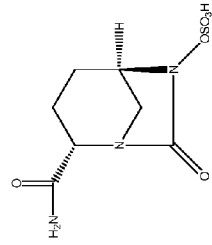

CCC is comparator compound

FIGURE 3D

Table III: Synergy MIC (sMIC) Against a Panel of Isogenic and Clinical Strains Expressing β-lactamases

| β-Lactamase | Bkgd | Sp | β-Lactam (4 µg/mL) | CCC | 763 | 764 | 765 | 766 | 767 | 768 | 769 | 770 | 771 | 772 | 773 | 774 | 775 | 776 | 777 | 778 | 779 |
|---|---|---|---|---|---|---|---|---|---|---|---|---|---|---|---|---|---|---|---|---|---|
| none | isogenic | Eco | none | D | F | F | F | F | F | F | F | F | F | F | F | F | F | F | F | F | F |
| KPC-2 | isogenic | Eco | CXA-101 | B | A | A | A | A | A | A | B | A | A | A | B | A | B | A | A | B | A |
| OXA-15 | isogenic | Eco | CXA-101 | D | D | C | C | D | C | C | C | C | C | C | C | C | D | D | C | C | C |
| CTX-M-15 | isogenic | Eco | CXA-101 | A | B | B | A | B | A | B | B | A | A | B | A | B | B | B | B | B | B |
| SHV-12 | isogenic | Eco | CXA-101 | B | C | B | C | C | B | C | C | C | B | C | C | C | C | C | C | C | C |
| P99 | isogenic | Eco | CXA-101 | A | B | A | A | B | A | A | A | B | B | B | B | B | B | B | B | B | B |
| KPC-3 | clinical | Kpn | CXA-101 | C | C | B | C | C | B | C | C | C | C | C | C | C | C | C | C | C | C |
| KPC-2 | clinical | Pae | CXA-101 | B | C | B | C | C | B | B | C | C | C | C | C | C | C | C | C | C | C |

AA=< 0.25 µg/mL; A = 0.25-0.5 µg/mL; B = 1-2 µg/mL; C = 4-8 µg/mL; D = 16-32 µg/mL; E = 64 µg/mL; F =≥128 µg/mL

CXA-101 is Ceftolozane

Eco is *Escherichia coli*; Kpn is *Klebsiella pneumoniae*, Pae is *Pseudomonas aeruginosa*

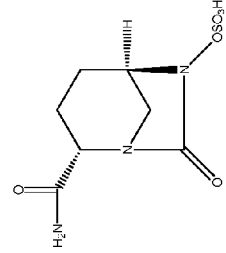

CCC is comparator compound

FIGURE 3E

Table III: Synergy MIC (sMIC) Against a Panel of Isogenic and Clinical Strains Expressing β-lactamases

| β-Lactamase | Bkgd | Sp | β-Lactam (4 µg/mL) | CCC | 780 | 781 | 782 | 783 | 784 | 785 | 786 | 792 | 793 | 794 | 795 | 796 | 797 | 798 | 722 | 723 | 724 |
|---|---|---|---|---|---|---|---|---|---|---|---|---|---|---|---|---|---|---|---|---|---|
| none | isogenic | Eco | none | D | F | F | F | F | F | F | F | F | F | E | E | F | F | F | F | F | F |
| KPC-2 | isogenic | Eco | CXA-101 | B | B | B | AA | A | A | B | A | B | B | A | A | B | B | C | A | A | A |
| OXA-15 | isogenic | Eco | CXA-101 | D | C | C | C | C | D | D | D | C | D | C | C | E | C | F | C | C | C |
| CTX-M-15 | isogenic | Eco | CXA-101 | A | B | B | B | B | B | B | F | B | C | B | C | D | B | D | A | A | A |
| SHV-12 | isogenic | Eco | CXA-101 | B | C | C | C | B | B | B | B | C | C | B | B | C | C | E | F | B | C |
| P99 | isogenic | Eco | CXA-101 | A | B | B | A | A | A | B | A | B | A | A | A | B | B | B | A | A | A |
| KPC-3 | clinical | Kpn | CXA-101 | C | C | C | B | C | C | C | C | D | D | B | D | D | D | F | B | C | C |
| KPC-2 | clinical | Pae | CXA-101 | B | C | C | B | C | C | C | B | D | D | B | C | C | D | F | B | C | D |

AA = < 0.25 µg/mL; A = 0.25–0.5 µg/mL; B = 1–2 µg/mL; C = 4–8 µg/mL; D = 16–32 µg/mL; E = 64 µg/mL; F = ≥128 µg/mL

CXA-101 is Ceftolozane

Eco is *Escherichia coli*, Kpn is *Klebsiella pneumoniae*, Pae is *Pseudomonas aeruginosa*

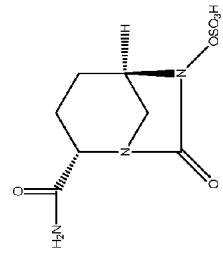

CCC is comparator compound

FIGURE 3F

Table III: Synergy MIC (sMIC) Against a Panel of Isogenic and Clinical Strains Expressing β-lactamases

| β-Lactamase | Bkgd | Sp | β-Lactam (4 µg/mL) | CCC | 725 | 726 | 727 | 728 | 729 | 714 | 715 | 716 | 717 | 718 |
|---|---|---|---|---|---|---|---|---|---|---|---|---|---|---|
| none | isogenic | Eco | none | D | F | F | F | F | F | F | F | F | F | F |
| KPC-2 | isogenic | Eco | CXA-101 | B | B | A | A | A | A | A | B | B | B | B |
| OXA-15 | isogenic | Eco | CXA-101 | D | D | C | C | C | C | C | C | C | C | D |
| CTX-M-15 | isogenic | Eco | CXA-101 | A | B | A | B | B | B | A | B | B | B | C |
| SHV-12 | isogenic | Eco | CXA-101 | B | C | C | C | C | C | B | C | C | D | B |
| P99 | isogenic | Eco | CXA-101 | A | B | B | A | A | A | A | A | A | A | A |
| KPC-3 | clinical | Kpn | CXA-101 | C | C | C | C | C | C | B | C | C | C | D |
| KPC-2 | clinical | Pae | CXA-101 | B | C | B | C | B | B | B | C | C | C | C |

COMPOUNDS

AA=< 0.25 µg/mL; A = 0.25-0.5 µg/mL; B = 1-2 µg/mL; C = 4-8 µg/mL; D = 16-32 µg/mL; E = 64 µg/mL; F = ≥128µg/mL

CXA-101 is Ceftolozane

Eco is *Escherichia coli*, Kpn is *Klebsiella pneumoniae*, Pae is *Pseudomonas aeruginosa*

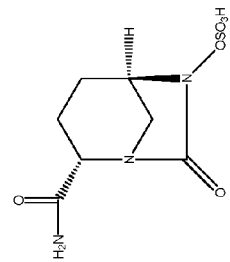

CCC is comparator compound

Table IV: Inhibition Kinetics for the KPC-2 β-lactamase

| Compound | CCC | 701 | 702 | 703 | 704 | 705 | 706 | 707 | 708 | 709 | 710 | 711 | 712 | 713 | 719 | 720 | 721 |
|---|---|---|---|---|---|---|---|---|---|---|---|---|---|---|---|---|---|
| Kinact/K mM$^{-1}$s$^{-1}$ | C | B | B | B | C | B | B | B | C | B | C | B | B | B | C | C | C |

| Compound | CCC | 714 | 715 | 716 | 717 | 718 |
|---|---|---|---|---|---|---|
| Kinact/K mM$^{-1}$s$^{-1}$ | C | B | C | C | C | C |

A = 1000-5000 mM$^{-1}$s$^{-1}$; B = 100-999 mM$^{-1}$s$^{-1}$; C = 1-99 mM$^{-1}$s$^{-1}$

CCC is comparator compound

Table IV: Inhibition Kinetics for the KPC-2 β-lactamase

| | CCC | 730 | 731 | 732 | 733 | 734 | 735 | 736 | 737 | 738 | 739 | 740 | 741 | 742 | 743 | 744 | 745 | 746 | 747 |
|---|---|---|---|---|---|---|---|---|---|---|---|---|---|---|---|---|---|---|---|
| Kinact/K mM⁻¹s⁻¹ | C | B | C | C | C | C | C | C | C | C | C | B | B | B | B | C | B | B | C |

| | CCC | 748 | 749 | 750 | 751 | 752 | 753 | 754 | 755 | 756 | 757 | 758 | 759 | 760 | 761 | 762 | 763 | 764 | 765 |
|---|---|---|---|---|---|---|---|---|---|---|---|---|---|---|---|---|---|---|---|
| Kinact/K mM⁻¹s⁻¹ | C | B | C | C | C | B | B | C | C | C | C | C | C | C | C | C | C | C | C |

A = 1000-5000 mM⁻¹s⁻¹; B = 100-999 mM⁻¹s⁻¹; C = 1-99 mM⁻¹s⁻¹

CCC is comparator compound

Table IV: Inhibition Kinetics for the KPC-2 β-lactamase

| | CCC | 766 | 767 | 768 | 769 | 770 | 771 | 772 | 773 | 774 | 775 | 776 | 777 | 778 | 779 | 780 | 781 | 782 | 783 |
|---|---|---|---|---|---|---|---|---|---|---|---|---|---|---|---|---|---|---|---|
| Kinact/K mM⁻¹s⁻¹ | C | C | B | C | C | B | C | C | C | C | B | C | C | C | B | C | B | B | C |

$A = 1000\text{-}5000 \text{ mM}^{-1}\text{s}^{-1}; B = 100\text{-}999 \text{ mM}^{-1}\text{s}^{-1}; C = 1\text{-}99 \text{ mM}^{-1}\text{s}^{-1}$

| | CCC | 784 | 785 | 786 | 792 | 793 | 794 | 795 | 796 | 797 | 798 | 722 | 723 | 724 | 725 | 726 | 727 | 728 | 729 |
|---|---|---|---|---|---|---|---|---|---|---|---|---|---|---|---|---|---|---|---|
| Kinact/K mM⁻¹s⁻¹ | C | C | B | C | C | C | B | C | C | C | B | C | C | C | C | C | C | C | C |

$A = 1000\text{-}5000 \text{ mM}^{-1}\text{s}^{-1}; B = 100\text{-}999 \text{ mM}^{-1}\text{s}^{-1}; C = 1\text{-}99 \text{ mM}^{-1}\text{s}^{-1}$ CCC is comparator compound

FIGURE 5A

Table V: Synergy MIC (sMIC) of Comparator Compounds Against a Panel of Isogenic and Clinical Strains Expressing β-lactamases

| β-Lactamase | Bkgd | Sp | β-Lactam (4 μg/mL) | Structure 1 | Structure 2 | Structure 3 | Structure 4 | Structure 5 |
|---|---|---|---|---|---|---|---|---|
| none | isogenic | Eco | none | D | F | F | F | F |
| KPC-2 | isogenic | Eco | CXA-101 | C | F | C | C | C |
| OXA-15 | isogenic | Eco | CXA-101 | ND | ND | ND | ND | F |
| CTX-M-15 | isogenic | Eco | CXA-101 | C | F | D | B | D |
| SHV-12 | isogenic | Eco | CXA-101 | C | F | D | C | D |
| P99 | isogenic | Eco | CXA-101 | C | F | B | B | C |
| KPC-3 | clinical | Kpn | CXA-101 | D | F | C | D | E |
| KPC-2 | clinical | Pae | CXA-101 | F | F | D | F | D |

AA = < 0.25 μg/mL; A = 0.25-0.5 μg/mL; B = 1-2 μg/mL; C = 4-8 μg/mL; D = 16-32 μg/mL; E = 64 μg/mL; F = ≥128 μg/mL

CXA-101 is Ceftolozane

Eco is *Escherichia coli*, Kpn is *Klebsiella pneumoniae*, Pae is *Pseudomonas aeruginosa*

FIGURE 5B

Table V: Synergy MIC (sMIC) of Comparator Compounds Against a Panel of Isogenic and Clinical Strains Expressing β-lactamases

| β-Lactamase | Bkgd | Sp | β-Lactam (4 µg/mL) | [pyrazole-OSO₃H] | [methylpyrazole-OSO₃H] | [pyrazole-NH-OSO₃H] | [oxazole-OSO₃H] |
|---|---|---|---|---|---|---|---|
| none | isogenic | Eco | none | E | F | F | F |
| KPC-2 | isogenic | Eco | CXA-101 | A | D | C | B |
| OXA-15 | isogenic | Eco | CXA-101 | ND | F | F | D |
| CTX-M-15 | isogenic | Eco | CXA-101 | D | F | D | B |
| SHV-12 | isogenic | Eco | CXA-101 | B | C | C | B |
| P99 | isogenic | Eco | CXA-101 | A | C | B | A |
| KPC-3 | clinical | Kpn | CXA-101 | E | F | F | D |
| KPC-2 | clinical | Pae | CXA-101 | E | F | F | D |

AA=< 0.25 µg/mL; A = 0.25-0.5 µg/mL; B = 1-2 µg/mL; C = 4-8 µg/mL; D = 16-32 µg/mL; E = 64 µg/mL; F =≥128 µg/Ml

CXA-101 is Ceftolozane

Eco is *Escherichia coli*, Kpn is *Klebsiella pneumoniae*, Pae is *Pseudomonas aeruginosa*

FIGURE 6

Table VI: Standard BLI Potentiation MIC Assay of Compounds Partnered with CXA-101 Against a Panel of Isogenic and Clinical Strains Expressing β-Lactamases

| Strain # | β-Lactamase | Bkgd | No BLI | CCC | 701 | 720 | 727 | 722 | 726 |
|---|---|---|---|---|---|---|---|---|---|
| Eco.2781 | KPC-2, TEM+ | clinical | C | A | A | AA | A | A | A |
| Kpn.2914 | KPC-2, SHV+ | clinical | D | B | B | A | B | B | B |
| Kpn.2913 | KPC-2, SHV+ | clinical | D | A | A | AA | A | A | A |
| Kpn.2917 | KPC-2, SHV+ | clinical | D | A | A | AA | A | A | A |
| Kpn.2478 | KPC-3, TEM-1 | clinical | E | C | C | A | C | B | C |
| Kpn.2918 | KPC-3, SHV+, TEM+ | clinical | E | C | B | B | B | B | C |
| Kpn.2909 | KPC-3, SHV+, TEM+ | clinical | E | B | B | AA | B | B | B |
| Kpn.571 | TEM-26 | clinical | E | A | AA | AA | A | A | A |
| Kpn.2783 | CTX-M-15, SHV+, TEM+ | clinical | E | B | B | AA | B | B | B |
| Pae.2885 | AmpC | clinical | B | A | A | A | A | A | A |
| Cfr.568 | AmpC | clinical | E | B | B | AA | B | B | C |
| Eco.2491 | CMY-2 | clinical | D | A | A | AA | A | A | B |
| Pae.2757 | AmpC over-expn | clinical | C | B | B | B | B | B | B |
| Pae.2863 | AmpC de-repress | clinical | C | B | B | B | B | B | B |
| Kpn.2926 | CTX-M-15, OXA-48 | clinical | E | B | B | A | B | B | C |
| Kpn.3095 | NDM-1, CTX-M-15 | clinical | E | E | E | E | E | E | E |
| | MIC90 | | E | C | B | B | B | B | C |
| | MIC50 | | D | B | B | A | B | B | B |

AA=<0.25 µg/mL; A=0.25-0.5 µg/mL; B=1-2 µg/mL; C=4-8 µg/mL; D=16-32 µg/mL; E≥64 µg/mL

CXA-101 is Ceftolozane. Eco is *Escherichia coli*, Kpn is *Klebsiella pneumoniae*, Pae is *Pseudomonas aeruginosa*

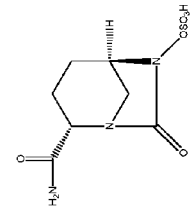

CCC is comparator compound

FIGURE 7

Table VII: Standard BLI Potentiation MIC Assay of Compounds Partnered with Ceftazidime Against a Panel of Isogenic and Clinical Strains Expressing β-Lactamases

| Strain # | β-Lactamase | Bkgd | No BLI | CCC | 701 | 720 | 727 | 722 | 726 |
|---|---|---|---|---|---|---|---|---|---|
| Eco.2781 | KPC-2, TEM+ | clinical | D | A | A | AA | A | A | A |
| Kpn.2914 | KPC-2, SHV+ | clinical | E | B | B | A | B | B | B |
| Kpn.2913 | KPC-2, SHV+ | clinical | D | A | A | AA | A | A | B |
| Kpn.2917 | KPC-2, SHV+ | clinical | D | A | A | AA | A | B | B |
| Kpn.2478 | KPC-3, TEM-1 | clinical | E | C | C | B | C | C | C |
| Kpn.2918 | KPC-3, SHV+, TEM+ | clinical | E | C | C | B | C | C | C |
| Kpn.2909 | KPC-3, SHV+, TEM+ | clinical | E | B | B | AA | C | C | C |
| Kpn.571 | TEM-26 | clinical | E | A | A | AA | A | B | B |
| Kpn.2783 | CTX-M-15, SHV+, TEM+ | clinical | E | A | B | AA | B | B | B |
| Pae.2885 | AmpC | clinical | E | C | B | B | C | C | C |
| Cfr.568 | AmpC | clinical | E | B | B | B | B | B | B |
| Eco.2491 | CMY-2 | clinical | E | A | A | A | A | A | B |
| Pae.2757 | AmpC over-expn | clinical | D | C | C | B | C | D | D |
| Pae.2863 | AmpC de-repress | clinical | E | D | D | C | D | D | D |
| Kpn.2926 | CTX-M-15, OXA-48 | clinical | E | B | B | A | B | B | B |
| Kpn.3095 | NDM-1, CTX-M-15 | clinical | E | E | E | E | E | E | E |
| | MIC90 | | E | C | C | B | C | D | D |
| | MIC50 | | E | B | B | A | B | B | B |

AA=<0.25 µg/mL; A=0.25-0.5 µg/mL; B=1-2 µg/mL; C=4-8 µg/mL; D=16-32 µg/mL; E≥64 µg/mL

Eco is *Escherichia coli*, Kpn is *Klebsiella pneumoniae*, Pae is *Pseudomonas aeruginosa*

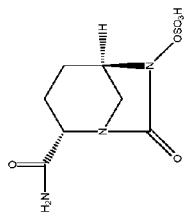

CCC is comparator compound

FIGURE 8

Table VIII: Standard BLI Potentiation MIC Assay of Compounds Partnered with Aztreonam Against a Panel of Isogenic and Clinical Strains Expressing β-Lactamases

| Strain # | β-Lactamase | Bkgd | No BLI | CCC | 701 | 720 | 727 | 722 | 726 |
|---|---|---|---|---|---|---|---|---|---|
| Eco.2781 | KPC-2, TEM+ | clinical | E | AA | AA | AA | AA | AA | AA |
| Kpn.2914 | KPC-2, SHV+ | clinical | E | A | A | A | B | B | B |
| Kpn.2913 | KPC-2, SHV+ | clinical | E | AA | AA | AA | AA | AA | A |
| Kpn.2917 | KPC-2, SHV+ | clinical | E | AA | A | AA | AA | AA | A |
| Kpn.2478 | KPC-3, TEM-1 | clinical | E | B | B | A | B | B | C |
| Kpn.2918 | KPC-3, SHV+, TEM+ | clinical | E | B | B | A | B | B | B |
| Kpn.2909 | KPC-3, SHV+, TEM+ | clinical | E | A | A | AA | AA | B | B |
| Kpn.571 | TEM-26 | clinical | D | AA | AA | AA | AA | AA | AA |
| Kpn.2783 | CTX-M-15, SHV+, TEM+ | clinical | E | A | C | A | A | A | A |
| Pae.2885 | AmpC | clinical | D | C | C | B | C | C | C |
| Cfr.568 | AmpC | clinical | E | B | B | A | B | B | C |
| Eco.2491 | CMY-2 | clinical | D | AA | AA | AA | AA | A | A |
| Pae.2757 | AmpC over-expn | clinical | D | B | B | B | C | B | C |
| Pae.2863 | AmpC de-repress | clinical | E | C | C | C | D | C | D |
| Kpn.2926 | CTX-M-15, OXA-48 | clinical | E | AA | A | AA | A | D | A |
| Kpn.3095 | NDM-1, CTX-M-15 | clinical | E | AA | AA | AA | AA | AA | C |
| | MIC90 | | E | C | C | B | C | C | C |
| | MIC50 | | E | A | A | A | B | B | B |

AA=<0.25 µg/mL; A=0.25-0.5 µg/mL; B=1-2 µg/mL; C=4-8 µg/mL; D=16-32 µg/mL; E≥64 µg/mL

Eco is *Escherichia coli*, Kpn is *Klebsiella pneumoniae*, Pae is *Pseudomonas aeruginosa*

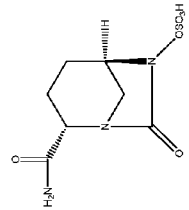

CCC is comparator compound

FIGURE 9

Table IX: Standard BLI Potentiation MIC Assay of Compounds Partnered with Meropenem Against a Panel of Isogenic and Clinical Strains Expressing β-Lactamases

| Strain # | β-Lactamase | Bkgd | No BLI | CCC | 701 | 720 | 727 | 722 | 726 |
|---|---|---|---|---|---|---|---|---|---|
| Eco.2781 | KPC-2, TEM+ | clinical | D | AA | AA | AA | AA | AA | AA |
| Kpn.2914 | KPC-2, SHV+ | clinical | E | C | C | C | C | C | D |
| Kpn.2913 | KPC-2, SHV+ | clinical | E | B | B | A | B | B | B |
| Kpn.2917 | KPC-2, SHV+ | clinical | C | AA | AA | AA | AA | AA | A |
| Kpn.2478 | KPC-3, TEM-1 | clinical | E | B | B | A | B | B | C |
| Kpn.2918 | KPC-3, SHV+, TEM+ | clinical | E | B | B | A | B | B | B |
| Kpn.2909 | KPC-3, SHV+, TEM+ | clinical | E | AA | A | AA | B | A | A |
| Kpn.571 | TEM-26 | clinical | AA | AA | AA | AA | AA | AA | AA |
| Kpn.2783 | CTX-M-15, SHV+, TEM+ | clinical | E | A | A | A | A | A | A |
| Pae.2885 | AmpC | clinical | C | B | B | B | B | B | B |
| Cfr.568 | AmpC | clinical | B | A | A | A | A | A | A |
| Eco.2491 | CMY-2 | clinical | B | A | A | AA | A | A | A |
| Pae.2757 | AmpC over-expn | clinical | D | D | D | C | D | D | D |
| Pae.2863 | AmpC de-repress | clinical | C | B | B | B | B | B | B |
| Kpn.2926 | CTX-M-15, OXA-48 | clinical | D | B | B | A | C | C | C |
| Kpn.3095 | NDM-1, CTX-M-15 | clinical | E | E | E | C | E | E | E |
| | MIC90 | | E | C | C | C | C | C | D |
| | MIC50 | | D | B | B | A | B | B | C |

AA=<0.02 μg/mL; A=0.03125-0.0625 μg/mL; B=0.125-0.5 μg/mL; C=1-2 μg/mL; D=4-8 μg/mL; E≥16 μg/mL

Eco is *Escherichia coli*, Kpn is *Klebsiella pneumoniae*, Pae is *Pseudomonas aeruginosa*

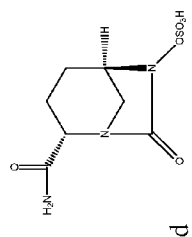

CCC is comparator compound

SEQUENCE LISTING

<160> NUMBER OF SEQ ID NOS: 13

<210> SEQ ID NO 1
<211> LENGTH: 32
<212> TYPE: DNA
<213> ORGANISM: Artificial Sequence
<220> FEATURE:
<223> OTHER INFORMATION: Sythetic primer: pBR-Pbla

<400> SEQUENCE: 1
cgcatatgac tcttcctttt tcaatattat tg                                    32

<210> SEQ ID NO 2
<211> LENGTH: 28
<212> TYPE: DNA
<213> ORGANISM: Artificial Sequence
<220> FEATURE:
<223> OTHER INFORMATION: Sythetic primer: pBR-vec-1

<400> SEQUENCE: 2
gcggatccct gtcagaccaa gtttactc                                         28

<210> SEQ ID NO 3
<211> LENGTH: 28
<212> TYPE: DNA
<213> ORGANISM: Artificial Sequence
<220> FEATURE:
<223> OTHER INFORMATION: Sythetic primer: Pbla-cat

<400> SEQUENCE: 3
gccatatgat ggagaaaaaa atcactgg                                         28

<210> SEQ ID NO 4
<211> LENGTH: 28
<212> TYPE: DNA
<213> ORGANISM: Artificial Sequence
<220> FEATURE:
<223> OTHER INFORMATION: Sythetic primer: Vec-1-cat

<400> SEQUENCE: 4
cgggatccct agagaatagg aacttcgg                                         28

<210> SEQ ID NO 5
<211> LENGTH: 4236
<212> TYPE: DNA
<213> ORGANISM: Artificial Sequence
<220> FEATURE:
<223> OTHER INFORMATION: Synthetic construct: pBR-CBST-cat

<400> SEQUENCE: 5
ttcttgaaga cgaaagggcc tcgtgatacg cctattttta taggttaatg tcatgataat     60

```
aatggtttct tagacgtcag gtggcacttt tcggggaaat gtgcgcggaa cccctatttg    120
tttatttttc taaatacatt caaatatgta tccgctcatg agacaataac cctgataaat    180
gcttcaataa tattgaaaaa ggaagagtca tatggagaaa aaaatcactg gatataccac    240
cgttgatata tcccaatggc atcgtaaaga acattttgag gcatttcagt cagttgctca    300
atgtacctat aaccagaccg ttcagctgga tattacggcc ttttttaaaga ccgtaaagaa    360 aaataagcac aagttttatc cggcctttat tcacattctt gcccgcctga tgaatgctca    420
tacggaattt cgtatggcaa tgaaagacgg tgagctggtg atatgggata gtgttcaccc    480
ttgttacacc gttttccatg agcaaactga aacgttttca tcgctctgga gtgaatacca    540
cgacgatttc cggcagtttc tacacatata ttcgcaagat gtggcgtgtt acggtgaaaa    600
cctggcctat ttccctaaag ggtttattga gaatatgttt ttcgtctcag ccaatccctg    660
ggtgagtttc accagttttg atttaaacgt ggccaatatg gacaacttct tcgcccccgt    720
tttcactatg ggcaaatatt atacgcaagg cgacaaggtg ctgatgccgc tggcgattca    780
ggttcatcat gccgtctgtg atggcttcca tgtcggcaga atgcttaatg aattacaaca    840
gtactgcgat gagtggcagg gcggggcgta agtggcaggg cggggcgtaa ggcgcgccat    900
ttaaatgaag ttcctattcc gaagttccta ttctctaggg atccctgtca gaccaagttt    960
actcatatat actttagatt gatttaaaac ttcattttta atttaaaagg atctaggtga   1020
agatcctttt tgataatctc atgaccaaaa tcccttaacg tgagttttcg ttccactgag   1080
cgtcagaccc cgtagaaaag atcaaaggat cttcttgaga tcctttttttt ctgcgcgtaa   1140 tctgctgctt gcaaacaaaa aaaccaccgc taccagcggt ggtttgtttg ccggatcaag   1200
agctaccaac tcttttccg aaggtaactg gcttcagcag agcgcagata ccaaatactg   1260
tccttctagt gtagccgtag ttaggccacc acttcaagaa ctctgtagca ccgcctacat   1320
acctcgctct gctaatcctg ttaccagtgg ctgctgccag tggcgataag tcgtgtctta   1380
ccgggttgga ctcaagacga tagttaccgg ataaggcgca gcggtcgggc tgaacggggg   1440
gttcgtgcac acagcccagc ttggagcgaa cgacctacac cgaactgaga tacctacagc   1500
gtgagctatg agaaagcgcc acgcttcccg aaggagaaa ggcggacagg tatccggtaa   1560
gcggcagggt cggaacagga gagcgcacga gggagcttcc agggggaaac gcctggtatc   1620
tttatagtcc tgtcgggttt cgccacctct gacttgagcg tcgatttttg tgatgctcgt   1680
caggggggcg gagcctatgg aaaaacgcca gcaacgcggc cttttttacgg ttcctggcct   1740 tttgctggcc ttttgctcac atgttctttc ctgcgttatc ccctgattct gtggataacc   1800
gtattaccgc ctttgagtga gctgataccg ctcgccgcag ccgaacgacc gagcgcagcg   1860
agtcagtgag cgaggaagcg gaagagcgcc tgatgcggta ttttctcctt acgcatctgt   1920
gcggtatttc acaccgcatt tggtgcactc tcagtacaat ctgctctgat gccgcatagt   1980
taagccagta tacactccgc tatcgctacg tgactgggtc atggctgcgc cccgacaccc   2040
gccaacaccc gctgacgcgc cctgacgggc ttgtctgctc ccggcatccg cttacagaca   2100
agctgtgacc gtctccggga gctgcatgtg tcagaggttt tcaccgtcat caccgaaacg   2160
cgcgaggcag ctgcggtaaa gctcatcagc gtggtcgtga agcgattcac agatgtctgc   2220
ctgttcatcc gcgtccagct cgttgagttt ctccagaagc gttaatgtct ggcttctgat   2280
aaagcgggcc atgttaaggg cggttttttc ctgtttggtc actgatgcct ccgtgtaagg   2340
gggatttctg ttcatggggg taatgatacc gatgaaacga gagaggatgc tcacgatacg   2400
ggttactgat gatgaacatg cccggttact ggaacgttgt gagggtaaac aactggcggt   2460
```

```
atggatgcgg cgggaccaga gaaaaatcac tcagggtcaa tgccagcgct tcgttaatac    2520
agatgtaggt gttccacagg gtagccagca gcatcctgcg atgcagatcc ggaacataat    2580
ggtgcagggc gctgacttcc gcgtttccag actttacgaa acacggaaac cgaagaccat    2640
tcatgttgtt gctcaggtcg cagacgtttt gcagcagcga tcgcttcacg ttcgctcgcg    2700
tatcggtgat tcattctgct aaccagtaag gcaaccccgc cagcctagcc gggtcctcaa    2760
cgacaggagc acgatcatgc gcacccgtgg ccaggaccca acgctgcccg agatgcgccg    2820
cgtgcggctg ctggagatgg cggacgcgat ggatatgttc tgccaagggt tggtttgcgc    2880
attcacagtt ctccgcaaga attgattggc tccaattctt ggagtggtga atccgttagc    2940
gaggtgccgc cggcttccat tcaggtcgag gtggcccggc tccatgcacc gcgacgcaac    3000
gcggggaggc agacaaggta tagggcggcg cctacaatcc atgccaaccc gttccatgtg    3060
ctcgccgagg cggcataaat cgccgtgacg atcagcggtc cagtgatcga agttaggctg    3120
gtaagagccg cgagcgatcc ttgaagctgt ccctgatggt cgtcatctac ctgcctggac    3180
agcatggcct gcaacgcggg catcccgatg ccgccggaag cgagaagaat cataatgggg    3240
aaggccatcc agcctcgcgt cgcgaacgcc agcaagacgt agcccagcgc gtcggccgcc    3300
atgccggcga taatggcctg cttctcgccg aaacgtttgg tggcgggacc agtgacgaag    3360
gcttgagcga gggcgtgcaa gattccgaat accgcaagcg acaggccgat catcgtcgcg    3420
ctccagcgaa agcggtcctc gccgaaaatg acccagagcg ctgccggcac ctgtcctacg    3480
agttgcatga taaagaagac agtcataagt gcggcgacga tagtcatgcc ccgcgcccac    3540
cggaaggagc tgactgggtt gaaggctctc aagggcatcg gtcgacgctc tcccttatgc    3600
gactcctgca ttaggaagca gcccagtagt aggttgaggc cgttgagcac cgccgccgca    3660
aggaatggtg catgcaagga gatggcgccc aacagtcccc cggccacggg gcctgccacc    3720
atacccacgc cgaaacaagc gctcatgagc ccgaagtggc gagcccgatc ttccccatcg    3780
gtgatgtcgg cgatataggc gccagcaacc gcacctgtgg cgccggtgat gccggccacg    3840
atgcgtccgg cgtagaggat tcacaggacg ggtgtggtcg ccatgatcgc gtagtcgata    3900
gtggctccaa gtagcgaagc gagcaggact gggcggcggc caaagcggtc ggacagtgct    3960
ccgagaacgg gtgcgcatag aaattgcatc aacgcatata gcgctagcag cacgccatag    4020
tgactggcga tgctgtcgga atggacgata tcccgcaaga ggcccggcag taccggcata    4080
accaagccta tgcctacagc atccagggtg acggtgccga ggatgacgat gagcgcattg    4140
ttagatttca tacacggtgc ctgactgcgt tagcaattta actgtgataa actaccgcat    4200
taaagcttat cgatgataag ctgtcaaaca tgagaa                              4236
```

<210> SEQ ID NO 6  
<211> LENGTH: 4391  
<212> TYPE: DNA  
<213> ORGANISM: Artificial Sequence  
<220> FEATURE:  
<223> OTHER INFORMATION: Synthetic construct: pBR-CBST-KPC-2

<400> SEQUENCE: 6

```
ttcttgaaga cgaaagggcc tcgtgatacg cctattttta taggttaatg tcatgataat     60
aatggtttct tagacgtcag gtggcacttt tcggggaaat gtgcgcggaa cccctatttg    120
tttatttttc taaatacatt caaatatgta tccgctcatg agacaataac cctgataaat    180
gcttcaataa tattgaaaaa ggaagagtca tatgtcactg tatcgccgtc tagttctgct    240
```

-continued

```
gtcttgtctc tcatggccgc tggctggctt ttctgccacc gcgctgacca acctcgtcgc    300
ggaaccattc gctaaactcg aacaggactt tggcggctcc atcggtgtgt acgcgatgga    360
taccggctca ggcgcaactg taagttaccg cgctgaggag cgcttcccac tgtgcagctc    420
attcaagggc tttcttgctg ccgctgtgct ggctcgcagc cagcagcagg ccggcttgct    480
ggacacaccc atccgttacg gcaaaaatgc gctggttccg tggtcaccca tctcggaaaa    540
atatctgaca caggcatga cggtggcgga gctgtccgcg gccgccgtgc aatacagtga    600
taacgccgcc gccaatttgt tgctgaagga gttgggcggc ccggccgggc tgacggcctt    660
catgcgctct atcggcgata ccacgttccg tctggaccgc tgggagctgg agctgaactc    720
cgccatccca ggcgatgcgc gcgataccta atcgccgcgc gccgtgacgg aaagcttaca    780
aaaactgaca ctgggctctg cactggctgc gccgcagcgg cagcagtttg ttgattggct    840
aaagggaaac acgaccggca accaccgcat ccgcgcggcg gtgccggcag actgggcagt    900
cggagacaaa accggaacct gcggagtgta tggcacggca aatgactatg ccgtcgtctg    960
gcccactggg cgcgcaccta ttgtgttggc cgtctacacc cgggcgccta acaaggatga   1020
caagcacagc gaggccgtca tcgccgctgc ggctagactc gcgctcgagg gattgggcgt   1080
caacgggcag taaggatccc tgtcagacca agtttactca tatatacttt agattgattt   1140
aaaacttcat ttttaattta aaaggatcta ggtgaagatc ctttttgata atctcatgac   1200
caaaatccct aacgtgagt tttcgttcca ctgagcgtca gaccccgtag aaaagatcaa   1260
aggatcttct tgagatcctt ttttctgcg cgtaatctgc tgcttgcaaa caaaaaaacc   1320
accgctacca gcggtggttt gtttgccgga tcaagagcta ccaactcttt ttccgaaggt   1380
aactggcttc agcagagcgc agataccaaa tactgtcctt ctagtgtagc cgtagttagg   1440
ccaccacttc aagaactctg tagcaccgcc tacatacctc gctctgctaa tcctgttacc   1500
agtggctgct gccagtggcg ataagtcgtg tcttaccggg ttggactcaa gacgatagtt   1560
accggataag cgcagcggt cgggctgaac ggggggttcg tgcacacagc ccagcttgga   1620
gcgaacgacc tacaccgaac tgagatacct acagcgtgag ctatgagaaa gcgccacgct   1680
tcccgaaggg agaaaggcgg acaggtatcc ggtaagcggc agggtcggaa caggagagcg   1740
cacgagggag cttccagggg gaaacgcctg gtatctttat agtcctgtcg ggtttcgcca   1800
cctctgactt gagcgtcgat ttttgtgatg ctcgtcaggg gggcggagcc tatgaaaaaa   1860
cgccagcaac gcggccttttt acggttcct ggccttttgc tggccttttg ctcacatgtt   1920
ctttcctgcg ttatccctg attctgtgga taaccgtatt accgcctttg agtgagctga   1980
taccgctcgc cgcagccgaa cgaccgagcg cagcgagtca gtgagcgagg aagcggaaga   2040
gcgcctgatg cggtattttc tccttacgca tctgtgcggt atttcacacc gcatttggtg   2100
cactctcagt acaatctgct ctgatgccgc atagttaagc cagtatacac tccgctatcg   2160
ctacgtgact gggtcatggc tgcgccccga cacccgccaa cacccgctga cgcgccctga   2220
cgggcttgtc tgctcccggc atccgcttac agacaagctg tgaccgtctc cgggagctgc   2280
atgtgtcaga ggttttcacc gtcatcaccg aaacgcgcga ggcagctgcg gtaaagctca   2340
tcagcgtggt cgtgaagcga ttcacagatg tctgcctgtt catccgcgtc cagctcgttg   2400
agtttctcca gaagcgttaa tgtctggctt ctgataaagc gggccatgtt aagggcggtt   2460
ttttcctgtt tggtcactga tgcctccgtg taagggggat ttctgttcat ggggtaatg   2520
ataccgatga aacgagagag gatgctcacg atacgggtta ctgatgatga acatgcccgg   2580
ttactggaac gttgtgaggg taaacaactg gcggtatgga tgcggcggga ccagagaaaa   2640
```

```
atcactcagg gtcaatgcca gcgcttcgtt aatacagatg taggtgttcc acagggtagc    2700
cagcagcatc ctgcgatgca gatccggaac ataatggtgc agggcgctga cttccgcgtt    2760
tccagacttt acgaaacacg gaaaccgaag accattcatg ttgttgctca ggtcgcagac    2820
gttttgcagc agcagtcgct tcacgttcgc tcgcgtatcg gtgattcatt ctgctaacca    2880
gtaaggcaac cccgccagcc tagccgggtc ctcaacgaca ggagcacgat catgcgcacc    2940
cgtggccagg acccaacgct gcccgagatg cgccgcgtgc ggctgctgga gatggcggac    3000
gcgatggata tgttctgcca agggttggtt tgcgcattca cagttctccg caagaattga    3060
ttggctccaa ttcttggagt ggtgaatccg ttagcgaggt gccgccggct tccattcagg    3120
tcgaggtggc ccggctccat gcaccgcgac gcaacgcggg gaggcagaca aggtataggg    3180
cggcgcctac aatccatgcc aacccgttcc atgtgctcgc cgaggcggca taaatcgccg    3240
tgacgatcag cggtccagtg atcgaagtta ggctggtaag agccgcgagc gatccttgaa    3300
gctgtccctg atggtcgtca tctacctgcc tggacagcat ggcctgcaac gcgggcatcc    3360
cgatgccgcc ggaagcgaga agaatcataa tggggaaggc catccagcct cgcgtcgcga    3420
acgccagcaa gacgtagccc agcgcgtcgg ccgccatgcc ggcgataatg gcctgcttct    3480
cgccgaaacg tttggtggcg ggaccagtga cgaaggcttg agcgagggcg tgcaagattc    3540
cgaataccgc aagcgacagg ccgatcatcg tcgcgctcca gcgaaagcgg tcctcgccga    3600
aaatgaccca gagcgctgcc ggcacctgtc ctacgagttg catgataaag aagacagtca    3660
taagtgcggc gacgatagtc atgccccgcg cccaccggaa ggagctgact gggttgaagg    3720
ctctcaaggg catcggtcga cgctctccct tatgcgactc ctgcattagg aagcagccca    3780
gtagtaggtt gaggccgttg agcaccgccg ccgcaaggaa tggtgcatgc aaggagatgg    3840
cgcccaacag tcccccggcc acgggcctg ccaccatacc cacgccgaaa caagcgctca    3900
tgagcccgaa gtggcgagcc cgatcttccc catcggtgat gtcggcgata taggcgccag    3960
caaccgcacc tgtggcgccg gtgatgccgg ccacgatgcg tccggcgtag aggattcaca    4020
ggacgggtgt ggtcgccatg atcgcgtagt cgatagtggc tccaagtagc gaagcgagca    4080
ggactgggcg gcggccaaag cggtcggaca gtgctccgag aacgggtgcg catagaaatt    4140
gcatcaacgc atatagcgct agcagcacgc catagtgact ggcgatgctg tcggaatgga    4200
cgatatcccg caagagggcc ggcagtaccg gcataaccaa gcctatgcct acagcatcca    4260
gggtgacggt gccgaggatg acgatgagcg cattgttaga tttcatacac ggtgcctgac    4320
tgcgttagca atttaactgt gataaactac cgcattaaag cttatcgatg ataagctgtc    4380
aaacatgaga a                                                        4391
```

<210> SEQ ID NO 7
<211> LENGTH: 4116
<212> TYPE: DNA
<213> ORGANISM: Artificial Sequence
<220> FEATURE:
<223> OTHER INFORMATION: Synthetic construct: pBR-CBST-CTX-M-15

<400> SEQUENCE: 7

```
ttcttgaaga cgaaagggcc tcgtgatacg cctatttta taggttaatg tcatgataat      60
aatggtttct tagacgtcag gtggcacttt tcggggaaat gtgcgcggaa cccctatttg     120
tttatttttc taaatacatt caaatatgta tccgctcatg agacaataac cctgataaat     180
gcttcaataa tattgaaaaa ggaagagtca tatggaatct gttaaatcag cgagttgaga     240
```

-continued

```
tcaaaaaatc tgaccttgtt aactataatc cgattgcgga aaagcacgtc aatgggacga      300
tgtcactggc tgagcttagc gcggccgcgc tacagtacag cgataacgtg gcgatgaata      360
agctgattgc tcacgttggc ggcccggcta gcgtcaccgc gttcgcccga cagctgggag      420
acgaaacgtt ccgtctcgac cgtaccgagc cgacgttaaa caccgccatt ccgggcgatc      480
cgcgtgatac cacttcacct cgggcaatgg cgcaaactct gcggaatctg acgctgggta      540
aagcattggg cgacagccaa cgggcgcagc tggtgacatg gatgaaaggc aataccaccg      600
gtgcagcgag cattcaggct ggactgcctg cttcctgggt tgtggggat aaaaccggca       660 gcggtggcta tggcaccacc aacgatatcg cggtgatctg gccaaaagat cgtgcgccgc      720
tgattctggt cacttacttc acccagcctc aacctaaggc agaaagccgt cgcgatgtat      780
tagcgtcggc ggctaaaatc gtcaccgacg gtttgtaagg atccctgtca gaccaagttt      840
actcatatat actttagatt gatttaaaac ttcattttta atttaaaagg atctaggtga      900
agatcctttt tgataatctc atgaccaaaa tcccttaacg tgagttttcg ttccactgag      960
cgtcagaccc cgtagaaaag atcaaaggat cttcttgaga tcctttttt ctgcgcgtaa     1020 tctgctgctt gcaaacaaaa aaaccaccgc taccagcggt ggtttgtttg ccggatcaag     1080
agctaccaac tctttttccg aaggtaactg gcttcagcag agcgcagata ccaaatactg     1140
tccttctagt gtagccgtag ttaggccacc acttcaagaa ctctgtagca ccgcctacat     1200
acctcgctct gctaatcctg ttaccagtgg ctgctgccag tggcgataag tcgtgtctta     1260
ccgggttgga ctcaagacga tagttaccgg ataaggcgca gcggtcgggc tgaacggggg     1320
gttcgtgcac acagcccagc ttggagcgaa cgacctacac cgaactgaga tacctacagc     1380
gtgagctatg agaaagcgcc acgcttcccg aagggagaaa ggcggacagg tatccggtaa     1440
gcggcagggt cggaacagga gagcgcacga gggagcttcc agggggaaac gcctggtatc     1500
tttatagtcc tgtcgggttt cgccacctct gacttgagcg tcgatttttg tgatgctcgt     1560 cagggggggcg agcctatgg aaaaacgcca gcaacgcggc cttttttacgg ttcctggcct      1620 tttgctggcc ttttgctcac atgttctttc ctgcgttatc ccctgattct gtggataacc     1680
gtattaccgc ctttgagtga gctgataccg ctcgccgcag ccgaacgacc gagcgcagcg     1740
agtcagtgag cgaggaagcg gaagagcgcc tgatgcggta ttttctcctt acgcatctgt     1800
gcggtatttc acaccgcatt tggtgcactc tcagtacaat ctgctctgat gccgcatagt     1860
taagccagta tacactccgc tatcgctacg tgactgggtc atggctgcgc cccgacaccc     1920
gccaacaccc gctgacgcgc cctgacgggc ttgtctgctc ccggcatccg cttacagaca     1980
agctgtgacc gtctccggga gctgcatgtg tcagaggttt tcaccgtcat caccgaaacg     2040
cgcgaggcag ctgcggtaaa gctcatcagc gtggtcgtga agcgattcac agatgtctgc     2100
ctgttcatcc gcgtccagct cgttgagttt ctccagaagc gttaatgtct ggcttctgat     2160
aaagcgggcc atgttaaggg cggttttttc ctgtttggtc actgatgcct ccgtgtaagg     2220
gggatttctg ttcatggggg taatgatacc gatgaaacga gagaggatgc tcacgatacg     2280
ggttactgat gatgaacatg cccggttact ggaacgttgt gagggtaaac aactggcggt     2340
atggatgcgg cgggaccaga gaaaaatcac tcagggtcaa tgccagcgct tcgttaatac     2400
agatgtaggt gttccacagg gtagccagca gcatcctgcg atgcagatcc ggaacataat     2460
ggtgcagggc gctgacttcc gcgtttccag actttacgaa acacggaaac cgaagaccat     2520
tcatgttgtt gctcaggtcg cagacgtttt gcagcagcag tcgcttcacg ttcgctcgcg     2580
tatcggtgat tcattctgct aaccagtaag gcaacccccgc cagcctagcc gggtcctcaa     2640
```

```
cgacaggagc acgatcatgc gcacccgtgg ccaggaccca acgctgcccg agatgcgccg   2700
cgtgcggctg ctggagatgg cggacgcgat ggatatgttc tgccaagggt tggtttgcgc   2760
attcacagtt ctccgcaaga attgattggc tccaattctt ggagtggtga atccgttagc   2820
gaggtgccgc cggcttccat tcaggtcgag gtggcccggc tccatgcacc gcgacgcaac   2880
gcggggaggc agacaaggta tagggcggcg cctacaatcc atgccaaccc gttccatgtg   2940
ctcgccgagg cggcataaat cgccgtgacg atcagcggtc cagtgatcga agttaggctg   3000
gtaagagccg cgagcgatcc ttgaagctgt ccctgatggt cgtcatctac ctgcctggac   3060
agcatggcct gcaacgcggg catcccgatg ccgccggaag cgagaagaat cataatgggg   3120
aaggccatcc agcctcgcgt cgcgaacgcc agcaagacgt agcccagcgc gtcggccgcc   3180
atgccggcga taatggcctg cttctcgccg aaacgtttgg tggcgggacc agtgacgaag   3240
gcttgagcga gggcgtgcaa gattccgaat accgcaagcg acaggccgat catcgtcgcg   3300
ctccagcgaa agcggtcctc gccgaaaatg acccagagcg ctgccggcac ctgtcctacg   3360
agttgcatga taaagaagac agtcataagt gcggcgacga tagtcatgcc ccgcgcccac   3420
cggaaggagc tgactgggtt gaaggctctc aagggcatcg gtcgacgctc tcccttatgc   3480
gactcctgca ttaggaagca gcccagtagt aggttgaggc cgttgagcac cgccgccgca   3540
aggaatggtg catgcaagga gatggcgccc aacagtcccc cggccacggg gcctgccacc   3600
atacccacgc cgaaacaagc gctcatgagc ccgaagtggc gagcccgatc ttccccatcg   3660
gtgatgtcgg cgatataggc gccagcaacc gcacctgtgg cgccggtgat gccggccacg   3720
atgcgtccgg cgtagaggat tcacaggacg ggtgtggtcg ccatgatcgc gtagtcgata   3780
gtggctccaa gtagcgaagc gagcaggact gggcggcggc caaagcggtc ggacagtgct   3840
ccgagaacgg gtgcgcatag aaattgcatc aacgcatata gcgctagcag cacgccatag   3900
tgactggcga tgctgtcgga atggacgata tcccgcaaga ggcccggcag taccggcata   3960
accaagccta tgcctacagc atccagggtg acggtgccga ggatgacgat gagcgcattg   4020
ttagatttca tacacggtgc ctgactgcgt tagcaattta actgtgataa actaccgcat   4080
taaagcttat cgatgataag ctgtcaaaca tgagaa                            4116
```

<210> SEQ ID NO 8
<211> LENGTH: 4370
<212> TYPE: DNA
<213> ORGANISM: Artificial Sequence
<220> FEATURE:
<223> OTHER INFORMATION: Synthetic construct: pBR-CBST-SHV-12

<400> SEQUENCE: 8

```
ttcttgaaga cgaaagggcc tcgtgatacg cctatttttta taggttaatg tcatgataat    60 aatggttttct tagacgtcag gtggcacttt tcggggaaat gtgcgcggaa cccctatttg   120
tttatttttc taaatacatt caaatatgta tccgctcatg agacaataac cctgataaat   180
gcttcaataa tattgaaaaa ggaagagtca tatgcgttat attcgcctgt gtattatctc   240
cctgttagcc accctgccgc tggcggtaca cgccagcccg cagccgcttg agcaaattaa   300
acaaagcgaa agccagctgt cgggccgcgt aggcatgata gaaatggatc tggccagcgg   360
ccgcacgctg accgcctggc gcgccgatga acgctttccc atgatgagca cctttaaagt   420
agtgctctgc ggcgcagtgc tggcgcgggt ggatgccggt gacgaacagc tggagcgaaa   480
gatccactat cgccagcagg atctggtgga ctactcgccg gtcagcgaaa aacaccttgc   540
```

```
cgacggcatg acggtcggcg aactctgcgc cgccgccatt accatgagcg ataacagcgc    600
cgccaatctg ctgctggcca ccgtcggcgg ccccgcagga ttgactgcct ttttgcgcca    660
gatcggcgac aacgtcaccc gccttgaccg ctgggaaacg gaactgaatg aggcgcttcc    720
cggcgacgcc cgccgacacca ctaccccggc cagcatggcc gcgaccctgc gcaagctgct   780
gaccagccag cgtctgagcg cccgttcgca acggcagctg ctgcagtgga tggtggacga    840
tcgggtcgcc ggaccgttga tccgctccgt gctgccggcg ggctggttta cgccgataa    900
gaccggagct agcaagcggg gtgcgcgcgg gattgtcgcc ctgcttggcc cgaataacaa    960
agcagagcgc attgtggtga tttatctgcg ggatacccg cgagcatgg ccgagcgaaa     1020
tcagcaaatc gccgggatcg gcgcggcgct gatcgagcac tggcaacgct aaggatccct    1080
gtcagaccaa gtttactcat atatacttta gattgattta aaacttcatt tttaatttaa    1140
aaggatctag gtgaagatcc ttttttgataa tctcatgacc aaaatcccctt aacgtgagtt   1200
ttcgttccac tgagcgtcag accccgtaga aagatcaaa ggatcttctt gagatccttt    1260
ttttctgcgc gtaatctgct gcttgcaaac aaaaaaacca ccgctaccag cggtggtttg    1320
tttgccggat caagagctac caactctttt tccgaaggta actggcttca gcagagcgca    1380
gataccaaat actgtccttc tagtgtagcc gtagttaggc caccacttca agaactctgt    1440
agcaccgcct acatacctcg ctctgctaat cctgttacca gtggctgctg ccagtggcga    1500
taagtcgtgt cttaccgggt tggactcaag acgatagtta ccggataagg cgcagcggtc    1560
gggctgaacg gggggttcgt gcacacagcc cagcttggag cgaacgacct acaccgaact    1620
gagataccta cagcgtgagc tatgagaaag cgccacgctt cccgaaggga aaaggcgga    1680
caggtatccg gtaagcggca gggtcggaac aggagagcgc acgagggagc ttccaggggg    1740
aaacgcctgg tatctttata gtcctgtcgg gtttcgccac ctctgacttg agcgtcgatt    1800
tttgtgatgc tcgtcagggg ggcggagcct atggaaaaac gccagcaacg cggccttttt    1860
acggttcctg gccttttgct ggccttttgc tcacatgttc tttcctgcgt tatcccctga    1920
ttctgtggat aaccgtatta ccgcctttga gtgagctgat accgctcgcc gcagccgaac    1980
gaccgagcgc agcgagtcag tgagcgagga agcggaagag cgcctgatgc ggtattttct    2040
ccttacgcat ctgtgcggta tttcacaccg catttggtgc actctcagta caatctgctc    2100
tgatgccgca tagttaagcc agtatacact ccgctatcgc tacgtgactg ggtcatggct    2160
gcgccccgac acccgccaac acccgctgac gcgccctgac gggcttgtct gctcccggca    2220
tccgcttaca gacaagctgt gaccgtctcc gggagctgca tgtgtcagag gttttcaccg    2280
tcatcaccga aacgcgcgag gcagctgcgg taaagctcat cagcgtggtc gtgaagcgat    2340
tcacagatgt ctgcctgttc atccgcgtcc agctcgttga gtttctccag aagcgttaat    2400
gtctggcttc tgataaagcg ggccatgtta agggcggttt ttcctgtttt ggtcactgat    2460
gcctccgtgt aagggggatt tctgttcatg ggggtaatga taccgatgaa acgagagagg    2520
atgctcacga tacgggttac tgatgatgaa catgcccggt tactggaacg ttgtgagggt    2580
aaacaactgg cggtatggat gcggcgggac cagagaaaaa tcactcaggg tcaatgccag    2640
cgcttcgtta atacagatgt aggtgttcca cagggtagcc agcagcatcc tgcgatgcag    2700
atccggaaca taatggtgca gggcgctgac ttccgcgttt ccagacttta cgaaacacgg    2760
aaaccgaaga ccattcatgt tgttgctcag gtcgcagacg ttttgcagca gcagtcgctt    2820
cacgttcgct cgcgtatcgg tgattcattc tgctaaccag taaggcaacc ccgccagcct    2880
agccgggtcc tcaacgacag gagcacgatc atgcgcaccc gtggccagga cccaacgctg    2940
```

```
cccgagatgc gccgcgtgcg gctgctggag atggcggacg cgatggatat gttctgccaa    3000 ggggttggttt gcgcattcac agttctccgc aagaattgat tggctccaat tcttggagtg    3060
gtgaatccgt tagcgaggtg ccgccggctt ccattcaggt cgaggtggcc cggctccatg    3120
caccgcgacg caacgcgggg aggcagacaa ggtatagggc ggcgcctaca atccatgcca    3180
acccgttcca tgtgctcgcc gaggcggcat aaatcgccgt gacgatcagc ggtccagtga    3240
tcgaagttag gctggtaaga gccgcgacg atccttgaag ctgtccctga tggtcgtcat    3300
ctacctgcct ggacagcatg gcctgcaacg cgggcatccc gatgccgccg aagcgagaa    3360 gaatcataat ggggaaggcc atccagcctc gcgtcgcgaa cgccagcaag acgtagccca    3420
gcgcgtcggc cgccatgccg gcgataatgg cctgcttctc gccgaaacgt tggtggcgg    3480 gaccagtgac gaaggcttga gcgagggcgt gcaagattcc gaataccgca agcgacaggc    3540
cgatcatcgt cgcgctccag cgaaagcggt cctcgccgaa aatgacccag agcgctgccg    3600
gcacctgtcc tacgagttgc atgataaaga agacagtcat aagtgcgcg acgatagtca    3660 tgccccgcgc ccaccggaag gagctgactg ggttgaaggc tctcaagggc atcggtcgac    3720
gctctccctt atgcgactcc tgcattagga agcagcccag tagtaggttg aggccgttga    3780
gcaccgccgc cgcaaggaat ggtgcatgca aggagatggc gcccaacagt cccccggcca    3840
cggggcctgc caccataccc acgccgaaac aagcgctcat gagcccgaag tggcgagccc    3900
gatcttcccc atcggtgatg tcggcgatat aggcgccagc aaccgcacct gtggcgccgg    3960
tgatgccggc cacgatgcgt ccggcgtaga ggattcacag gacgggtgtg gtcgccatga    4020
tcgcgtagtc gatagtggct ccaagtagcg aagcgagcag gactgggcgg cggccaaagc    4080
ggtcggacag tgctccgaga acgggtgcgc atagaaattg catcaacgca tatagcgcta    4140
gcagcacgcc atagtgactg gcgatgctgt cggaatggac gatatcccgc aagaggcccg    4200
gcagtaccgg cataaccaag cctatgccta cagcatccag ggtgacggtg ccgaggatga    4260
cgatgagcgc attgttagat tcatacacg gtgcctgact gcgttagcaa tttaactgtg    4320
ataaactacc gcattaaagc ttatcgatga taagctgtca acatgagaa    4370
```

<210> SEQ ID NO 9
<211> LENGTH: 4655
<212> TYPE: DNA
<213> ORGANISM: Artificial Sequence
<220> FEATURE:
<223> OTHER INFORMATION: Synthetic construct: pBR-CBST-P99

<400> SEQUENCE: 9

```
ttcttgaaga cgaaagggcc tcgtgatacg cctattttta taggttaatg tcatgataat      60
aatggtttct tagacgtcag gtggcacttt tcggggaaat gtgcgcggaa cccctatttg     120
tttatttttc taaatacatt caaatatgta tccgctcatg agacaataac cctgataaat     180
gcttcaataa tattgaaaaa ggaagagtca tatgatgaga aaatcccttt gctgcgccct    240
gctgctcggc atctcttgct ctgctctcgc cacgccagtg tcagaaaaac agctggcgga    300
ggtggtcgcg aatacgatta ccccgctgat gaaagcccag tctgttccag gcatggcggt    360
ggccgttatt tatcagggaa aaccgcacta ttacacattt gcaaggccg atatcgcggc    420 gaataaaccc gttacgcctc agaccctgtt cgagctgggt tctataagta aaaccttcac    480
cggcgtttta ggtggggatg ccattgctcg cggtgaaatt tcgctggacg atgcggtgac    540
cagatactgg ccacagctga cgggcaagca gtggcagggt attcgtatgc tggatctcgc    600
```

```
cacctacacc gctggcggcc tgccgctaca ggtaccggat gaggtcacgg ataacgcctc    660
cctgctgcgc ttttatcaaa actggcagcc gcagtggaag cctggcacaa cgcgtcttta    720
cgccaacgcc agcatcggtc tttttggtgc gctggcggtc aaaccttctg gcatgcccta    780
tgagcaggca atgacgacgc gggtccttaa gccgctcaag ctggaccata cctggattaa    840
cgtgccgaaa gcggaagagg cgcattacgc ctggggctat cgtgacggta aagcggtgcg    900
cgtttcgccg gtatgctgg atgcacaagc ctatggcgtg aaaaccaacg tgcaggatat    960
ggcgaactgg gtcatggcaa acatggcgcc ggagaacgtt gctgatgcct cacttaagca   1020
gggcatcgcg ctggcgcagt cgcgctactg gcgtatcggg tcaatgtatc agggtctggg   1080
ctgggagatg ctcaactggc ccgtggaggc caacacggtg gtcgagggca gcgacagtaa   1140
ggtagcactg gcgccgttgc ccgtggcaga agtgaatcca ccggctcccc cggtcaaagc   1200
gtcctgggtc cataaaacgg gctctactgg cgggtttggc agctacgtgg cctttattcc   1260
tgaaaagcag atcggtattg tgatgctcgc gaatacaagc tatccgaacc cggcacgcgt   1320
tgaggcggca taccatatcc tcgaggcgct acagtaagga tccctgtcag accaagttta   1380
ctcatatata ctttagattg atttaaaact tcattttaa tttaaaagga tctaggtgaa    1440
gatccttttt gataatctca tgaccaaaat cccttaacgt gagttttcgt tccactgagc    1500
gtcagacccc gtagaaaaga tcaaaggatc ttcttgagat ccttttttc tgcgcgtaat    1560
ctgctgcttg caaacaaaaa aaccaccgct accagcggtg gtttgtttgc cggatcaaga   1620
gctaccaact cttttccga aggtaactgg cttcagcaga gcgcagatac caaatactgt    1680
ccttctagtg tagccgtagt taggccacca cttcaagaac tctgtagcac cgcctacata   1740
cctcgctctg ctaatcctgt taccagtggc tgctgccagt ggcgataagt cgtgtcttac   1800
cgggttggac tcaagacgat agttaccgga taaggcgcag cggtcgggct gaacggggg    1860
ttcgtgcaca cagcccagct tggagcgaac gacctacacc gaactgagat acctacagcg   1920
tgagctatga gaaagcgcca cgcttcccga agggagaaag gcggacaggt atccggtaag   1980
cggcagggtc ggaacaggag agcgcacgag ggagcttcca gggggaaacg cctggtatct   2040
ttatagtcct gtcgggtttc gccacctctg acttgagcgt cgatttttgt gatgctcgtc   2100
agggggcggg agcctatgga aaaacgccag caacgcggcc ttttacggt tcctggcctt    2160
ttgctggcct tttgctcaca tgttctttcc tgcgttatcc cctgattctg tggataaccg   2220
tattaccgcc tttgagtgag ctgataccgc tcgccgcagc cgaacgaccg agcgcagcga   2280
gtcagtgagc gaggaagcgg aagagcgcct gatgcggtat tttctcctta cgcatctgtg   2340
cggtatttca caccgcattt ggtgcactct cagtacaatc tgctctgatg ccgcatagtt   2400
aagccagtat acactccgct atcgctacgt gactgggtca tggctgcgcc ccgacacccg   2460
ccaacacccg ctgacgcgcc ctgacgggct tgtctgctcc cggcatccgc ttacagacaa   2520
gctgtgaccg tctccgggag ctgcatgtgt cagaggtttt caccgtcatc accgaaacgc   2580
gcgaggcagc tgcggtaaag ctcatcagcg tggtcgtgaa gcgattcaca gatgtctgcc   2640
tgttcatccg cgtccagctc gttgagtttc tccagaagcg ttaatgtctg gcttctgata   2700
aagcgggcca tgttaagggc ggttttttcc tgtttggtca ctgatgcctc cgtgtaaggg   2760
ggatttctgt tcatgggggt aatgataccg atgaaacgag agaggatgct cacgatacgg   2820
gttactgatg atgaacatgc ccggttactg gaacgttgtg agggtaaaca actggcggta   2880
tggatgcggc gggaccagag aaaaatcact cagggtcaat gccagcgctt cgttaataca   2940
gatgtaggtg ttccacaggg tagccagcag catcctgcga tgcagatccg gaacataatg   3000
```

-continued

```
gtgcagggcg ctgacttccg cgtttccaga ctttacgaaa cacgaaaacc gaagaccatt    3060
catgttgttg ctcaggtcgc agacgttttg cagcagcagt cgcttcacgt tcgctcgcgt    3120
atcggtgatt cattctgcta accagtaagg caaccccgcc agcctagccg ggtcctcaac    3180
gacaggagca cgatcatgcg cacccgtggc caggacccaa cgctgcccga gatgcgccgc    3240
gtgcggctgc tggagatggc ggacgcgatg gatatgttct gccaagggtt ggtttgcgca    3300
ttcacagttc tccgcaagaa ttgattggct ccaattcttg gagtggtgaa tccgttagcg    3360
aggtgccgcc ggcttccatt caggtcgagg tggcccggct ccatgcaccg cgacgcaacg    3420
cggggaggca gacaaggtat agggcggcgc ctacaatcca tgccaacccg ttccatgtgc    3480
tcgccgaggc ggcataaatc gccgtgacga tcagcggtcc agtgatcgaa gttaggctgg    3540
taagagccgc gagcgatcct tgaagctgtc cctgatggtc gtcatctacc tgcctggaca    3600
gcatggcctg caacgcgggc atcccgatgc cgccggaagc gagaagaatc ataatgggga    3660
aggccatcca gcctcgcgtc gcgaacgcca gcaagacgta gcccagcgcg tcggccgcca    3720
tgccggcgat aatggcctgc ttctcgccga aacgtttggt ggcgggacca gtgacgaagg    3780
cttgagcgag ggcgtgcaag attccgaata ccgcaagcga caggccgatc atcgtcgcgc    3840
tccagcgaaa gcggtcctcg ccgaaaatga cccagagcgc tgccggcacc tgtcctacga    3900
gttgcatgat aaagaagaca gtcataagtg cggcgacgat agtcatgccc cgcgcccacc    3960
ggaaggagct gactgggttg aaggctctca agggcatcgg tcgacgctct cccttatgcg    4020
actcctgcat taggaagcag cccagtagta ggttgaggcc gttgagcacc gccgccgcaa    4080
ggaatggtgc atgcaaggag atggcgccca acagtccccc ggccacgggg cctgccacca    4140
tacccacgcc gaaacaagcg ctcatgagcc cgaagtggcg agcccgatct tccccatcgg    4200
tgatgtcggc gatataggcg ccagcaaccg cacctgtggc gccggtgatg ccggccacga    4260
tgcgtccggc gtagaggatt cacaggacgg gtgtggtcgc catgatcgcg tagtcgatag    4320
tggctccaag tagcgaagcg agcaggactg ggcggcggcc aaagcggtcg acagtgctc    4380
cgagaacggg tgcgcataga aattgcatca acgcatatag cgctagcagc acgccatagt    4440
gactggcgat gctgtcggaa tggacgatat cccgcaagag gcccggcagt accggcataa    4500
ccaagcctat gcctacagca tccagggtga cggtgccgag gatgacgatg agcgcattgt    4560
tagatttcat acacggtgcc tgactgcgtt agcaatttaa ctgtgataaa ctaccgcatt    4620
aaagcttatc gatgataagc tgtcaaacat gagaa    4655
```

<210> SEQ ID NO 10
<211> LENGTH: 4337
<212> TYPE: DNA
<213> ORGANISM: Artificial Sequence
<220> FEATURE:
<223> OTHER INFORMATION: Synthetic construct: pBR-CBST-OXA-15

<400> SEQUENCE: 10

```
ttcttgaaga cgaaagggcc tcgtgatacg cctattttta taggttaatg tcatgataat     60
aatggtttct tagacgtcag gtggcacttt tcggggaaat gtgcgcggaa cccctatttg    120
tttatttttc taaatacatt caaatatgta tccgctcatg agacaataac cctgataaat    180
gcttcaataa tattgaaaaa ggaagagtca tatggcaatc gaatcttcg cgatactttt    240
ctccattttt tctcttgcca ctttcgcgca tgcgcaagaa ggcacgctag aacgttctga    300
ctggaggaag ttttcagcg aatttcaagc caaaggcacg atagttgtgg cagacgaacg    360
```

```
ccaagcggat cgtgccatgt tggttttttga tcctgtgcga tcgaagaaac gctactcgcc    420
tgcatcgaca ttcaagatac ctcatacact ttttgcactt gatgcaggcg ctgttcgtga    480
tgagttccag attttttcgat gggacggcgt taacaggggc tttgcaggcc acaatcaaga   540
ccaagatttg cgatcagcaa tgcggaattc tactgtttgg gtgtatgagc tatttgcaaa    600
ggaaattggt gatgacaaag ctcggcgcta tttgaagaaa atcgactatg caacgccgg     660
tccttcgaca gtaatggcg attactggat agaaggcagc cttgcaatct cggcgcagga    720
gcaaattgca tttctcagga agctctatcg taacgagctg ccctttcggg tagaacatca   780
gcgcttggtc aaggatctca tgattgtgga agccggtcgc aactggatac tgcgtgcaaa   840
gacgggctgg gaaggccgta tgggttggtg ggtaggatgg gttgagtggc cgactggctc   900
cgtattcttc gcactgaata ttgatacgcc aaacagaatg gatgatcttt tcaagaggga   960
ggcaatcgtg cgggcaatcc ttcgctctat tgaagcgtta ccgcccaacc cggcagtcaa   1020
ctcggacgct gcgcgataag gatccctgtc agaccaagtt tactcatata tactttagat   1080
tgatttaaaa cttcattttt aatttaaaag gatctaggtg aagatccttt ttgataatct   1140
catgaccaaa atcccttaac gtgagttttc gttccactga gcgtcagacc ccgtagaaaa   1200
gatcaaagga tcttcttgag atccttttttt tctgcgcgta atctgctgct tgcaaacaaa   1260
aaaaccaccg ctaccagcgg tggtttgttt gccggatcaa gagctaccaa ctctttttcc   1320
gaaggtaact ggcttcagca gagcgcagat accaaatact gtccttctag tgtagccgta   1380
gttaggccac cacttcaaga actctgtagc accgcctaca tacctcgctc tgctaatcct   1440
gttaccagtg gctgctgcca gtggcgataa gtcgtgtctt accgggttgg actcaagacg   1500
atagttaccg gataaggcgc agcggtcggg ctgaacgggg ggttcgtgca cacagcccag   1560
cttggagcga acgacctaca ccgaactgag atacctacag cgtgagctat gagaaagcgc   1620
cacgcttccc gaagggagaa aggcggacag gtatccggta agcggcaggg tcggaacagg   1680
agagcgcacg agggagcttc caggggggaaa cgcctggtat ctttatagtc ctgtcgggtt   1740
tcgccacctc tgacttgagc gtcgattttt gtgatgctcg tcagggggggc ggagcctatg   1800
gaaaaacgcc agcaacgcgg ccttttttacg gttcctggcc ttttgctggc cttttgctca   1860
catgttcttt cctgcgttat cccctgattc tgtggataac cgtattaccg cctttgagtg   1920
agctgatacc gctcgccgca gccgaacgac cgagcgcagc gagtcagtga gcgaggaagc   1980
ggaagagcgc ctgatgcggt attttctcct tacgcatctg tgcggtattt cacaccgcat   2040
ttggtgcact ctcagtacaa tctgctctga tgccgcatag ttaagccagt atacactccg   2100
ctatcgctac gtgactgggt catggctgcg ccccgacacc cgccaacacc cgctgacgcg   2160
ccctgacggg cttgtctgct cccggcatcc gcttacagac aagctgtgac cgtctccggg   2220
agctgcatgt gtcagaggtt ttcaccgtca tcaccgaaac gcgcgaggca gctgcggtaa   2280
agctcatcag cgtggtcgtg aagcgattca cagatgtctg cctgttcatc cgcgtccagc   2340
tcgttgagtt tctccagaag cgttaatgtc tggcttctga taaagcgggc catgttaagg   2400
gcggtttttt cctgtttggt cactgatgcc tccgtgtaag ggggatttct gttcatgggg   2460
gtaatgatac cgatgaaacg agagaggatg ctcacgatac gggttactga tgatgaacat   2520
gcccggttac tggaacgttg tgagggtaaa caactggcgg tatggatgcg gcgggaccag   2580
agaaaaatca ctcagggtca atgccagcgc ttcgttaata cagatgtagg tgttccacag   2640
ggtagccagc agcatcctgc gatgcagatc cggaacataa tggtgcaggg cgctgacttc   2700
cgcgtttcca gactttacga aacacggaaa ccgaagacca ttcatgttgt tgctcaggtc   2760
```

```
gcagacgttt tgcagcagca gtcgcttcac gttcgctcgc gtatcggtga ttcattctgc    2820
taaccagtaa ggcaaccccg ccagcctagc cgggtcctca acgacaggag cacgatcatg    2880
cgcacccgtg gccaggaccc aacgctgccc gagatgcgcc gcgtgcggct gctggagatg    2940
gcggacgcga tggatatgtt ctgccaaggg ttggtttgcg cattcacagt tctccgcaag    3000
aattgattgg ctccaattct tggagtggtg aatccgttag cgaggtgccg ccggcttcca    3060
ttcaggtcga ggtggcccgg ctccatgcac cgcgacgcaa cgcggggagg cagacaaggt    3120
atagggcggc gcctacaatc catgccaacc cgttccatgt gctcgccgag gcggcataaa    3180
tcgccgtgac gatcagcggt ccagtgatcg aagttaggct ggtaagagcc gcgagcgatc    3240
cttgaagctg tccctgatgg tcgtcatcta cctgcctgga cagcatggcc tgcaacgcgg    3300
gcatcccgat gccgcggaa gcgagaagaa tcataatggg gaaggccatc cagcctcgcg    3360
tcgcgaacgc cagcaagacg tagcccagcg cgtcggccgc catgccggcg ataatggcct    3420
gcttctcgcc gaaacgtttg gtggcgggac cagtgacgaa ggcttgagcg agggcgtgca    3480
agattccgaa taccgcaagc gacaggccga tcatcgtcgc gctccagcga aagcggtcct    3540
cgccgaaaat gacccagagc gctgccggca cctgtcctac gagttgcatg ataaagaaga    3600
cagtcataag tgcggcgacg atagtcatgc cccgcgccca ccggaaggag ctgactgggt    3660
tgaaggctct caagggcatc ggtcgacgct ctcccttatg cgactcctgc attaggaagc    3720
agcccagtag taggttgagg ccgttgagca ccgccgccgc aaggaatggt gcatgcaagg    3780
agatggcgcc caacagtccc ccggccacgg ggcctgccac catacccacg ccgaaacaag    3840
cgctcatgag cccgaagtgg cgagcccgat cttccccatc ggtgatgtcg gcgatatagg    3900
cgccagcaac cgcacctgtg gcgccggtga tgccggccac gatgcgtccg gcgtagagga    3960
ttcacaggac gggtgtggtc gccatgatcg cgtagtcgat agtggctcca agtagcgaag    4020
cgagcaggac tgggcggcgg ccaaagcggt cggacagtgc tccgagaacg ggtgcgcata    4080
gaaattgcat caacgcatat agcgctagca gcacgccata gtgactggcg atgctgtcgg    4140
aatggacgat atcccgcaag aggcccggca gtaccggcat aaccaagcct atgcctacag    4200
catccagggt gacggtgccg aggatgacga tgagcgcatt gttagatttc atacacggtg    4260
cctgactgcg ttagcaattt aactgtgata aactaccgca ttaaagctta tcgatgataa    4320
gctgtcaaac atgagaa                                                  4337

<210> SEQ ID NO 11
<211> LENGTH: 4391
<212> TYPE: DNA
<213> ORGANISM: Artificial Sequence
<220> FEATURE:
<223> OTHER INFORMATION: Synthetic construct: pBR-CBST-KPC-4

<400> SEQUENCE: 11
ttcttgaaga cgaaagggcc tcgtgatacg cctatttta taggttaatg tcatgataat      60
aatggtttct tagacgtcag gtggcacttt tcggggaaat gtgcgcggaa ccctatttg     120 tttatttttc taaatacatt caaatatgta tccgctcatg agacaataac cctgataaat    180
gcttcaataa tattgaaaaa ggaagagtca tatgtcactg tatcgccgtc tagttctgct    240
gtcttgtctc tcatggccgc tggctggctt ttctgccacc gcgctgacca acctcgtcgc    300
ggaaccattc gctaaactcg aacaggactt tggcggctcc atcggtgtgt acgcgatgga    360
taccggctca ggcgcaactg taagttaccg cgctgaggag cgcttcccac tgtgcagctc    420
```

-continued

| | |
|---|---|
| attcaagggc tttcttgctg ccgctgtgct ggctcgcagc cagcagcagg ccggcttgct | 480 |
| ggacacaccc atccgttacg gcaaaaatgc gctggttcgg tggtcaccca tctcggaaaa | 540 |
| atatctgaca acaggcatga cggtggcgga gctgtccgcg gccgccgtgc aatacagtga | 600 |
| taacgccgcc gccaatttgt tgctgaagga gttgggcggc ccggccgggc tgacggcctt | 660 |
| catgcgctct atcggcgata ccacgttccg tctggaccgc tgggagctgg agctgaactc | 720 |
| cgccatccca ggcgatgcgc gcgataccctc atcgccgcgc gccgtgacgg aaagcttaca | 780 |
| aaaactgaca ctgggctctg cactggctgc gccgcagcgg cagcagtttg ttgattggct | 840 |
| aaagggaaac acgaccggca accaccgcat ccgcgcggcg gtgccggcag actgggcagt | 900 |
| cggagacaaa accggaacct gcggagggta tggcacggca aatgactatg ccgtcgtctg | 960 |
| gcccactggg cgcgcaccta ttgtgttggc cgtctacacc cgggcgccta caaggatga | 1020 |
| caagcacagc gaggccgtca tcgccgctgc ggctagactc gcgctcgagg gattgggcgt | 1080 |
| caacgggcag taaggatccc tgtcagacca agtttactca tatatacttt agattgattt | 1140 |
| aaaacttcat ttttaattta aaaggatcta ggtgaagatc cttttttgata atctcatgac | 1200 |
| caaaatccct taacgtgagt tttcgttcca ctgagcgtca ccccgtag aaaagatcaa | 1260 |
| aggatcttct tgagatcctt ttttttctgcg cgtaatctgc tgcttgcaaa caaaaaaacc | 1320 |
| accgctacca gcggtggttt gtttgccgga tcaagagcta ccaactcttt ttccgaaggt | 1380 |
| aactggcttc agcagagcgc agataccaaa tactgtcctt ctagtgtagc cgtagttagg | 1440 |
| ccaccacttc aagaactctg tagcaccgcc tacatacctc gctctgctaa tcctgttacc | 1500 |
| agtggctgct gccagtggcg ataagtcgtg tcttaccggg ttggactcaa gacgatagtt | 1560 |
| accggataag gcgcagcggt cgggctgaac ggggggttcg tgcacacagc ccagcttgga | 1620 |
| gcgaacgacc tacaccgaac tgagatacct acagcgtgag ctatgagaaa gcgccacgct | 1680 |
| tcccgaaggg agaaaggcgg acaggtatcc ggtaagcggc agggtcggaa caggagagcg | 1740 |
| cacgagggag cttccagggg gaaacgcctg gtatctttat agtcctgtcg ggtttcgcca | 1800 |
| cctctgactt gagcgtcgat ttttgtgatg ctcgtcaggg gggcggagcc tatggaaaaa | 1860 |
| cgccagcaac gcggcctttt tacggttcct ggccttttgc tggccttttg ctcacatgtt | 1920 |
| ctttcctgcg ttatcccctg attctgtgga taaccgtatt accgcctttg agtgagctga | 1980 |
| taccgctcgc cgcagccgaa cgaccgagcg cagcgagtca gtgagcgagg aagcggaaga | 2040 |
| gcgcctgatg cggtattttc tccttacgca tctgtgcggt atttcacacc gcatttggtg | 2100 |
| cactctcagt acaatctgct ctgatgccgc atagttaagc cagtatacac tccgctatcg | 2160 |
| ctacgtgact gggtcatggc tgcgccccga cacccgccaa cacccgctga cgcgccctga | 2220 |
| cgggcttgtc tgctcccggc atccgcttac agacaagctg tgaccgtctc cgggagctgc | 2280 |
| atgtgtcaga ggttttcacc gtcatcaccg aaacgcgcga ggcagctgcg gtaaagctca | 2340 |
| tcagcgtggt cgtgaagcga ttcacagatg tctgcctgtt catccgcgtc cagctcgttg | 2400 |
| agtttctcca gaagcgttaa tgtctggctt ctgataaagc gggccatgtt aagggcggtt | 2460 |
| ttttcctgtt tggtcactga tgcctccgtg taagggggat ttctgttcat gggggtaatg | 2520 |
| ataccgatga aacgagagag gatgctcacg atacgggtta ctgatgatga acatgcccgg | 2580 |
| ttactggaac gttgtgaggg taaacaactg gcggtatgga tgcggcggga ccagagaaaa | 2640 |
| atcactcagg gtcaatgcca gcgcttcgtt aatacagatg taggtgttcc acagggtagc | 2700 |
| cagcagcatc ctgcgatgca gatccggaac ataatggtgc agggcgctga cttccgcgtt | 2760 |
| tccagacttt acgaaacacg gaaaccgaag accattcatg ttgttgctca ggtcgcagac | 2820 |

```
gttttgcagc agcagtcgct tcacgttcgc tcgcgtatcg gtgattcatt ctgctaacca    2880
gtaaggcaac cccgccagcc tagccgggtc ctcaacgaca ggagcacgat catgcgcacc    2940
cgtggccagg acccaacgct gcccgagatg cgccgcgtgc ggctgctgga gatggcggac    3000
gcgatggata tgttctgcca agggttggtt tgcgcattca cagttctccg caagaattga    3060
ttggctccaa ttcttggagt ggtgaatccg ttagcgaggt gccgccggct tccattcagg    3120
tcgaggtggc ccggctccat gcaccgcgac gcaacgcggg gaggcagaca aggtataggg    3180
cggcgcctac aatccatgcc aacccgttcc atgtgctcgc cgaggcggca taaatcgccg    3240
tgacgatcag cggtccagtg atcgaagtta ggctggtaag agccgcgagc gatccttgaa    3300
gctgtccctg atggtcgtca tctacctgcc tggacagcat ggcctgcaac gcgggcatcc    3360
cgatgccgcc ggaagcgaga agaatcataa tggggaaggc catccagcct cgcgtcgcga    3420
acgccagcaa gacgtagccc agcgcgtcgg ccgccatgcc ggcgataatg gcctgcttct    3480
cgccgaaacg tttggtggcg ggaccagtga cgaaggcttg agcgagggcg tgcaagattc    3540
cgaataccgc aagcgacagg ccgatcatcg tcgcgctcca gcgaaagcgg tcctcgccga    3600
aaatgaccca gagcgctgcc ggcacctgtc ctacgagttg catgataaag aagacagtca    3660
taagtgcggc gacgatagtc atgccccgcg cccaccggaa ggagctgact gggttgaagg    3720
ctctcaaggg catcggtcga cgctctccct tatgcgactc ctgcattagg aagcagccca    3780
gtagtaggtt gaggccgttg agcaccgccg ccgcaaggaa tggtgcatgc aaggagatgg    3840
cgcccaacag tcccccggcc acggggcctg ccaccatacc cacgccgaaa caagcgctca    3900
tgagcccgaa gtggcgagcc cgatcttccc catcggtgat gtcggcgata taggcgccag    3960
caaccgcacc tgtggcgccg gtgatgccgg ccacgatgcg tccggcgtag aggattcaca    4020
ggacgggtgt ggtcgccatg atcgcgtagt cgatagtggc tccaagtagc gaagcgagca    4080
ggactgggcg gcggccaaag cggtcggaca gtgctccgag aacgggtgcg catagaaatt    4140
gcatcaacgc atatagcgct agcagcacgc atagtgact  ggcgatgctg tcggaatgga    4200
cgatatcccg caagaggccc ggcagtaccg gcataaccaa gcctatgcct acagcatcca    4260
gggtgacggt gccgaggatg acgatgagcg cattgttaga tttcatacac ggtgcctgac    4320
tgcgttagca atttaactgt gataaactac cgcattaaag cttatcgatg ataagctgtc    4380
aaacatgaga a                                                          4391

<210> SEQ ID NO 12
<211> LENGTH: 4649
<212> TYPE: DNA
<213> ORGANISM: Artificial Sequence
<220> FEATURE:
<223> OTHER INFORMATION: Synthetic construct: pBR-CBST-DHA-1

<400> SEQUENCE: 12
ttcttgaaga cgaaagggcc tcgtgatacg cctatttttta taggttaatg tcatgataat     60
aatggtttct tagacgtcag gtggcacttt tcggggaaat gtgcgcggaa cccctatttg    120
tttatttttc taaatacatt caaatatgta tccgctcatg agacaataac cctgataaat    180
gcttcaataa tattgaaaaa ggaagagtca tatgaaaaaa tcgttatctg caacactgat    240
ttccgctctg ctggcgtttt ccgccccggg gttttctgcc gctgataatg tcgcggcgt     300 ggtggacagc accattaaac cgctgatggc acagcaggat attcccggga tggcggttgc    360
cgtctccgta aagggtaagc cctattattt caattatggt tttgccgata ttcaggcaaa    420
```

```
acagccggtc actgaaaata cactatttga gctcggatct gtaagtaaaa ctttcacagg    480
tgtgctgggt gcggtttctg tggcgaaaaa agagatggcg ctgaatgatc cggcggcaaa    540
ataccagccg gagctggctc tgccgcagtg aaggggatc acattgctgg atctggctac     600
ctataccgca ggcggactgc cgttacaggt gccggatgcg gtaaaaagcc gtgcggatct    660
gctgaatttc tatcagcagt ggcagccgtc ccggaaaccg ggcgatatgc gtctgtatgc    720
aaacagcagt atcggcctgt ttggtgctct gaccgcaaac gcggcgggga tgccgtatga    780
gcagttgctg actgcacgca tcctggcacc gctggggtta tctcacacct ttattactgt    840
gccggaaagt gcgcaaagcc agtatgcgta cggttataaa aacaaaaaac cggtccgcgt    900
gtcgccggga cagcttgatg cggaatctta cggcgtgaaa tccgcctcaa aagatatgct    960
gcgctgggcg gaaatgaata tggagccgtc acgggccggt aatgcggatc tggaaatggc   1020
aatgtatctc gcccagaccc gctactataa aaccgccgcg attaaccagg ggctgggctg   1080
ggaaatgtat gactggccgc agcagaaaga tatgatcatt aacggtgtga ccaacgaggt   1140
cgcattgcag ccgcatccgg taacagacaa ccaggttcag ccgtataacc gtgcttcctg   1200
ggtgcataaa acgggcgcaa caactggttt cggcgcctat gtcgccttta ttccggaaaa   1260
acaggtggcg attgtgattc tggcgaataa aaactacccg aataccgaaa gagtcaaagc   1320
tgcacaggct attttgagtg cactggaata aggatccctg tcagaccaag tttactcata   1380
tatactttag attgatttaa aacttcattt ttaatttaaa aggatctagg tgaagatcct   1440
ttttgataat ctcatgacca aaatccctta acgtgagttt tcgttccact gagcgtcaga   1500
ccccgtagaa aagatcaaag gatcttcttg agatcctttt tttctgcgcg taatctgctg   1560
cttgcaaaca aaaaaaccac cgctaccagc ggtggtttgt ttgccggatc aagagctacc   1620
aactcttttt ccgaaggtaa ctggcttcag cagagcgcag ataccaaata ctgtccttct   1680
agtgtagccg tagttaggcc accacttcaa gaactctgta gcaccgccta catacctcgc   1740
tctgctaatc ctgttaccag tggctgctgc cagtggcgat aagtcgtgtc ttaccgggtt   1800
ggactcaaga cgatagttac cggataaggc gcagcggtcg ggctgaacgg ggggttcgtg   1860
cacacagccc agcttggagc gaacgaccta caccgaactg agatacctac agcgtgagct   1920
atgagaaagc gccacgcttc ccgaagggag aaaggcggac aggtatccgg taagcggcag   1980
ggtcggaaca ggagagcgca cgagggagct tccaggggga aacgcctggt atctttatag   2040
tcctgtcggg tttcgccacc tctgacttga gcgtcgattt tgtgatgct cgtcaggggg     2100
gcggagccta tggaaaaacg ccagcaacgc ggcctttta cggttcctgg ccttttgctg    2160
gccttttgct cacatgttct ttcctgcgtt atcccctgat tctgtggata accgtattac   2220
cgcctttgag tgagctgata ccgctcgccg cagccgaacg accgagcgca gcgagtcagt   2280
gagcgaggaa gcggaagagc gcctgatgcg gtattttctc cttacgcatc tgtgcggtat   2340
ttcacaccgc atttggtgca ctctcagtac aatctgctct gatgccgcat agttaagcca   2400
gtatacactc cgctatcgct acgtgactgg gtcatggctg cgccccgaca cccgccaaca   2460
cccgctgacg cgccctgacg ggcttgtctg ctcccggcat ccgcttacag acaagctgtg   2520
accgtctccg ggagctgcat gtgtcagagg ttttcaccgt catcaccgaa acgcgcgagg   2580
cagctgcggt aaagctcatc agcgtggtcg tgaagcgatt cacagatgtc tgcctgttca   2640
tccgcgtcca gctcgttgag tttctccaga agcgttaatg tctggcttct gataaagcgg   2700
gccatgttaa gggcggtttt ttcctgtttg gtcactgatg cctccgtgta agggggattt   2760
ctgttcatgg gggtaatgat accgatgaaa cgagagagga tgctcacgat acgggttact   2820
```

```
gatgatgaac atgcccggtt actggaacgt tgtgagggta acaaactggc ggtatggatg    2880
cggcgggacc agagaaaaat cactcagggt caatgccagc gcttcgttaa tacagatgta    2940
ggtgttccac agggtagcca gcagcatcct gcgatgcaga tccggaacat aatggtgcag    3000
ggcgctgact tccgcgtttc cagactttac gaaacacgga aaccgaagac cattcatgtt    3060
gttgctcagg tcgcagacgt tttgcagcag cagtcgcttc acgttcgctc gcgtatcggt    3120
gattcattct gctaaccagt aaggcaaccc cgccagccta gcgggtcct  caacgacagg    3180 agcacgatca tgcgcacccg tggccaggac ccaacgctgc ccgagatgcg ccgcgtgcgg    3240
ctgctggaga tggcggacgc gatggatatg ttctgccaag ggttggtttg cgcattcaca    3300
gttctccgca agaattgatt ggctccaatt cttggagtgg tgaatccgtt agcgaggtgc    3360
cgccggcttc cattcaggtc gaggtggccc ggctccatgc accgcgacgc aacgcgggga    3420
ggcagacaag gtatagggcg gcgcctacaa tccatgccaa cccgttccat gtgctcgccg    3480
aggcggcata atcgccgtg acgatcagcg gtccagtgat cgaagttagg ctggtaagag    3540
ccgcgagcga tccttgaagc tgtccctgat ggtcgtcatc tacctgcctg acagcatgg    3600 cctgcaacgc gggcatcccg atgccgccgg aagcgagaag aatcataatg gggaaggcca    3660
tccagcctcg cgtcgcgaac gccagcaaga cgtagcccag cgcgtcggcc gccatgccgg    3720
cgataatggc ctgcttctcg ccgaaacgtt tggtggcggg accagtgacg aaggcttgag    3780
cgagggcgtg caagattccg aataccgcaa gcgacaggcc gatcatcgtc gcgctccagc    3840
gaaagcggtc ctcgccgaaa atgacccaga gcgctgccgg cacctgtcct acgagttgca    3900
tgataaagaa gacagtcata agtgcggcga cgatagtcat gccccgcgcc caccggaagg    3960
agctgactgg gttgaaggct ctcaagggca tcggtcgacg ctctccctta tgcgactcct    4020
gcattaggaa gcagcccagt agtaggttga ggccgttgag caccgccgcc gcaaggaatg    4080
gtgcatgcaa ggagatggcg cccaacagtc ccccggccac ggggcctgcc accatacccca    4140 cgccgaaaca agcgctcatg agcccgaagt ggcgagcccg atcttcccca tcggtgatgt    4200
cggcgatata ggcgccagca accgcacctg tggcgccggt gatgccggcc acgatgcgtc    4260
cggcgtagag gattcacagg acgggtgtgg tcgccatgat cgcgtagtcg atagtggctc    4320
caagtagcga agcgagcagg actgggcggc ggccaaagcg gtcggacagt gctccgagaa    4380
cgggtgcgca tagaaattgc atcaacgcat atagcgctag cagcacgcca tagtgactgg    4440
cgatgctgtc ggaatggacg atatcccgca agaggcccgg cagtaccggc ataaccaagc    4500
ctatgcctac agcatccagg gtgacggtgc cgaggatgac gatgagcgca ttgttagatt    4560
tcatacacgg tgcctgactg cgttagcaat ttaactgtga taaactaccg cattaaagct    4620
tatcgatgat aagctgtcaa acatgagaa                                       4649
```

<210> SEQ ID NO 13
<211> LENGTH: 4664
<212> TYPE: DNA
<213> ORGANISM: Artificial Sequence
<220> FEATURE:
<223> OTHER INFORMATION: Synthetic construct: pBR-CBST-ADC-33

<400> SEQUENCE: 13

```
ttcttgaaga cgaaagggcc tcgtgatacg cctatttttta taggttaatg tcatgataat      60
aatggtttct tagacgtcag gtggcacttt tcggggaaat gtgcgcggaa ccccatttg     120 tttatttttc taaatacatt caaatatgta tccgctcatg agacaataac cctgataaat    180
```

```
gcttcaataa tattgaaaaa ggaagagtca tatgcgattt aaaaaaattt cttgtctact    240
tttatccccg cttttttattt ttagtacctc aatttatgcg ggcaatacac caaaagacca    300
agaaattaaa aaactggtag atcaaaactt taaaccgtta ttagaaaaat atgatgtgcc    360
aggtatggct gtgggtgtta ttcaaaataa taaaaagtat gaaatgtatt atggtcttca    420
atctgttcaa gataaaaaag ccgtaaatag cagtaccatt tttgagctag gttctgtcag    480
taaattattt accgcgacag caggtggata tgcaaaaaat aaaggaaaaa tctcttttga    540
cgatacgcct ggtaaatatt ggaaagaact aaaaaacaca ccgattgacc aagttaactt    600
acttcaactc gcgacgtata caagtggtaa ccttgccttg cagtttccag atgaagtaaa    660
aacagaccaa caagttttaa ctttttttcaa agactggaaa cctaaaaact caatcggtga    720
atacagacaa tattcaaatc caagtattgg cctatttgga aaggttgtgg ctttgtctat    780
gaataaacct ttcgaccaag tcttagaaaa aacaatttt ccggcccttg gcttaaaaca    840
tagctatgta aatgtaccta agacccagat gcaaaactat gcatttggtt ataaccaaga    900
aaatcagccg attcgagtta accgcggccc actcgatgcc gcccctgcgt atggcgtcaa    960
atcgacacta cccgacatgt tgagttttat tcatgccaac cttaacccac agaaatatcc   1020
ggctgatatt caacgggcaa ttaatgaaac acatcaaggg cgctatcaag taaataccat   1080
gtatcaggca ctcggttggg aagagttttc ttatccggca acgttacaaa ctttattaga   1140
cagtaattca gaacagattg tgatgaaacc taataaagtg actgctattt caaggaacc    1200 ttcagttaag atgtaccata aaactggctc aaccaacggt tcggaacgt atgtagtgtt    1260 tattcctaaa gaaaatattg gcttagtcat gttaaccaat aaacgtattc caaatgaaga    1320
gcgcattaag gcagcttatg ctgtgctgaa tgcaataaag aaataaggat ccctgtcaga    1380
ccaagtttac tcatatatac tttagattga tttaaaactt cattttttaat ttaaaaggat   1440 ctaggtgaag atcctttttg ataatctcat gaccaaaatc ccttaacgtg agttttcgtt    1500
ccactgagcg tcagaccccg tagaaaagat caaaggatct tcttgagatc ctttttttct    1560
gcgcgtaatc tgctgcttgc aaacaaaaaa accaccgcta ccagcggtgg tttgtttgcc    1620
ggatcaagag ctaccaactc tttttccgaa ggtaactggc ttcagcagag cgcagatacc    1680
aaatactgtc cttctagtgt agccgtagtt aggccaccac ttcaagaact ctgtagcacc    1740
gcctacatac ctcgctctgc taatcctgtt accagtggct gctgccagtg gcgataagtc    1800
gtgtcttacc gggttggact caagacgata gttaccggat aaggcgcagc ggtcgggctg    1860
aacggggggt tcgtgcacac agcccagctt ggagcgaacg acctacaccg aactgagata    1920
cctacagcgt gagctatgag aaagcgccac gcttcccgaa gggagaaagg cggacaggta    1980
tccggtaagc ggcagggtcg gaacaggaga gcgcacgagg gagcttccag ggggaaacgc    2040
ctggtatctt tatagtcctg tcgggtttcg ccacctctga cttgagcgtc gatttttgtg    2100
atgctcgtca gggggggcgga gcctatggaa aaacgccagc aacgcggcct ttttacggtt    2160
cctggccttt tgctggcctt ttgctcacat gttctttcct gcgttatccc ctgattctgt    2220
ggataaccgt attaccgcct ttgagtgagc tgataccgct cgccgcagcc gaacgaccga    2280
gcgcagcgag tcagtgagcg aggaagcgga agagcgcctg atgcggtatt ttctccttac    2340
gcatctgtgc ggtatttcac accgcatttg gtgcactctc agtacaatct gctctgatgc    2400
cgcatagtta agccagtata cactccgcta tcgctacgtg actgggtcat ggctgcgccc    2460
cgacacccgc caacacccgc tgacgcgccc tgacgggctt gtctgctccc ggcatccgct    2520
tacagacaag ctgtgaccgt ctccgggagc tgcatgtgtc agaggttttc accgtcatca    2580
```

```
ccgaaacgcg cgaggcagct gcggtaaagc tcatcagcgt ggtcgtgaag cgattcacag   2640
atgtctgcct gttcatccgc gtccagctcg ttgagtttct ccagaagcgt taatgtctgg   2700
cttctgataa agcgggccat gttaagggcg gttttttcct gtttggtcac tgatgcctcc   2760
gtgtaagggg gatttctgtt catgggggta atgataccga tgaaacgaga gaggatgctc   2820
acgatacggg ttactgatga tgaacatgcc cggttactgg aacgttgtga gggtaaacaa   2880
ctggcggtat ggatgcggcg ggaccagaga aaaatcactc agggtcaatg ccagcgcttc   2940
gttaatacag atgtaggtgt tccacagggt agccagcagc atcctgcgat gcagatccgg   3000
aacataatgg tgcagggcgc tgacttccgc gtttccagac tttacgaaac acggaaaccg   3060
aagaccattc atgttgttgc tcaggtcgca gacgttttgc agcagcagtc gcttcacgtt   3120
cgctcgcgta tcggtgattc attctgctaa ccagtaaggc aaccccgcca gcctagccgg   3180
gtcctcaacg acaggagcac gatcatgcgc acccgtggcc aggacccaac gctgcccgag   3240
atgcgccgcg tgcggctgct ggagatggcg gacgcgatgg atatgttctg ccaagggttg   3300
gtttgcgcat tcacagttct ccgcaagaat tgattggctc caattcttgg agtggtgaat   3360
ccgttagcga ggtgccgccg gcttccattc aggtcgaggt ggcccggctc catgcaccgc   3420
gacgcaacgc ggggaggcag acaaggtata gggcggcgcc tacaatccat gccaacccgt   3480
tccatgtgct cgccgaggcg gcataaatcg ccgtgacgat cagcggtcca gtgatcgaag   3540
ttaggctggt aagagccgcg agcgatcctt gaagctgtcc ctgatggtcg tcatctacct   3600
gcctggacag catggcctgc aacgcgggca tcccgatgcc gccggaagcg agaagaatca   3660
taatggggaa ggccatccag cctcgcgtcg cgaacgccag caagacgtag cccagcgcgt   3720
cggccgccat gccggcgata atggcctgct tctcgccgaa acgtttggtg cgggaccag   3780 tgacgaaggc ttgagcgagg gcgtgcaaga ttccgaatac cgcaagcgac aggccgatca   3840
tcgtcgcgct ccagcgaaag cggtcctcgc cgaaaatgac ccagagcgct gccggcacct   3900
gtcctacgag ttgcatgata aagaagacag tcataagtgc ggcgacgata gtcatgcccc   3960
gcgcccaccg gaaggagctg actgggttga aggctctcaa gggcatcggt cgacgctctc   4020
ccttatgcga ctcctgcatt aggaagcagc ccagtagtag gttgaggccg ttgagcaccg   4080
ccgccgcaag gaatggtgca tgcaaggaga tggcgcccaa cagtcccccg ccacggggc    4140 ctgccaccat acccacgccg aaacaagcgc tcatgagccc gaagtggcga gcccgatctt   4200
ccccatcggt gatgtcggcg atataggcgc cagcaaccgc acctgtggcg ccggtgatgc   4260
cggccacgat gcgtccggcg tagaggattc acaggacggg tgtggtcgcc atgatcgcgt   4320
agtcgatagt ggctccaagt agcgaagcga gcaggactgg gcggcggcca aagcggtcgg   4380
acagtgctcc gagaacgggt gcgcatagaa attgcatcaa cgcatatagc gctagcagca   4440
cgccatagtg actggcgatg ctgtcggaat ggacgatatc ccgcaagagg cccggcagta   4500
ccggcataac caagcctatg cctacagcat ccagggtgac ggtgccgagg atgacgatga   4560
gcgcattgtt agatttcata cacggtgcct gactgcgtta gcaatttaac tgtgataaac   4620
taccgcatta aagcttatcg atgataagct gtcaaacatg agaa                    4664
```

1,3,4-OXADIAZOLE AND 1,3,4-THIADIAZOLE β-LACTAMASE INHIBITORS

RELATED APPLICATIONS

This application claims priority to U.S. Provisional Application No. 61/618,131, filed Mar. 30, 2012, and U.S. Provisional Application No. 61/790,579, filed Mar. 15, 2013. The entire contents of these applications are incorporated herein by reference in their entireties.

TECHNICAL FIELD

This disclosure is directed to β-lactamase inhibitors (BLIs) which are effective as inhibitors of β-lactamases and, when used in combination with β-lactam antibiotics are useful in the treatment of bacterial infections. The compounds when combined with a β-lactam antibiotic are effective in treating infections caused by bacteria that are resistant to β-lactam antibiotics due to the presence of β-lactamases. Pharmaceutical compositions comprising such compounds, methods of using such compounds, and processes for preparing such compounds are also disclosed.

BACKGROUND

Bacterial resistance to β-lactam antibiotics, especially in Gram-negative bacteria, is most commonly mediated by β-lactamases. β-lactamases are enzymes that catalyze the hydrolysis of the β-lactam ring, which inactivates the antibacterial activity of the β-lactam antibiotic and allows the bacteria to become resistant Inhibition of the β-lactamase with a BLI slows or prevents degradation of the β-lactam antibiotic and restores β-lactam antibiotic susceptibility to β-lactamase producing bacteria. Many of these β-lactamases are not effectively inhibited by BLIs currently on the market rendering the β-lactam antibiotics ineffective in treating bacteria that produce these β-lactamases. There is an urgent need for novel BLIs that inhibit β-lactamases that are not effectively inhibited by the current clinical BLIs (e.g. KPC, class C and class D β-lactamases) and that could be used in combination with β-lactam antibiotics to treat infections caused by β-lactam resistant bacteria.

SUMMARY OF INVENTION

The present invention provides, in one aspect, compounds of chemical formula (I), or pharmaceutically-acceptable salts thereof, which are BLIs and are useful in combination with β-lactam antibiotics for the treatment of bacterial infections.

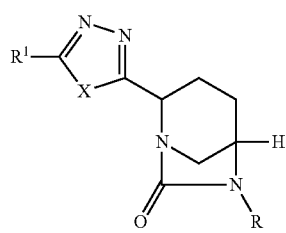

(I)

wherein X is selected from O and S;
R is selected from

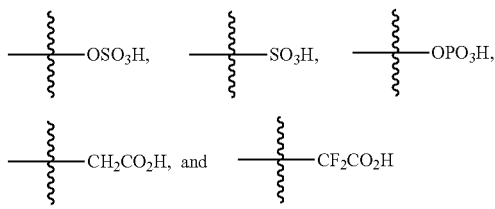

and,
$R^1$ is selected from:

a. hydrogen;

b. 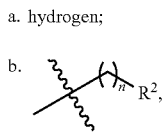

wherein $R^2$ is selected from

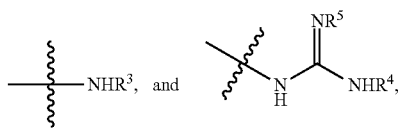

wherein each of $R^3$, $R^4$ and $R^5$ is independently selected from hydrogen, $(C_1$-$C_3)$-alkyl, aminoalkyl, aminocycloalkyl, and hydroxyalkyl, and n is selected from 1, 2 and 3;

c. 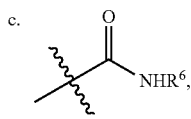

wherein $R^6$ is H, $(C_2$-$C_3)$alkylamino, and d. 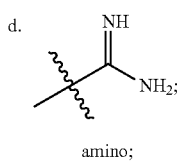

amino;

e. 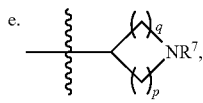

wherein $R^7$ is selected from H, $(C_1$-$C_3)$-unsubstituted alkyl, amino-$(C_2$-$C_3)$-alkyl, aminocycloalkyl, hydroxyalkyl, and

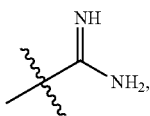

each of p and q is independently selected from 1 and 2; and

—CH(R$^8$)CH$_2$NH$_2$   f.

wherein R$^8$ is selected from amino and hydroxyl.

In another aspect, the invention provides compounds of chemical Formula (A-I) or a pharmaceutically acceptable salt thereof, which are BLIs and are useful in combination with β-lactam antibiotics for the treatment of bacterial infections.

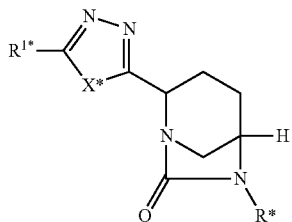

(A-I)

wherein X* is selected from O and S;
R* is selected from

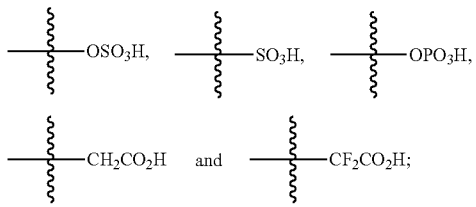

and
R$^{1*}$ is selected from:

a. hydrogen;

b. 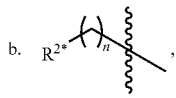, wherein R$^{2*}$ is selected from

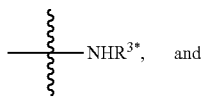 and 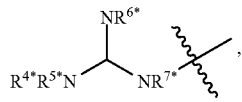,

R$^{3*}$ is selected from hydrogen, (C$_1$-C$_3$)-alkyl, aminoalkyl, aminocycloalkyl, hydroxyalkyl,

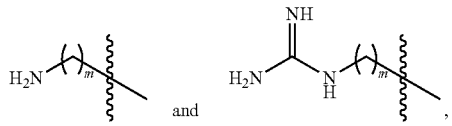

each of R$^{4*}$, R$^{5*}$, R$^{6*}$ and R$^{7*}$ is independently selected from hydrogen or (C$_1$-C$_6$)-alkyl, aminoalkyl, aminocycloalkyl, and hydroxyalkyl, provided that at least one of R$^{4*}$, R$^{5*}$, R$^{6*}$ and R$^{7*}$ is hydrogen,
n is selected from 1, 2, 3 and 4, and
m is selected from 1, 2 and 3;

c. 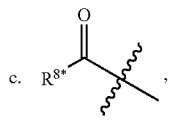, wherein R$^{8*}$ is selected from NH$_2$,

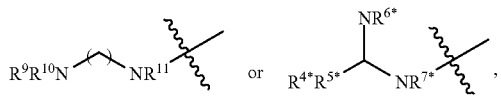

wherein each of R$^{4*}$, R$^{5*}$, R$^{6*}$ and R$^{7*}$ is as described previously and each of R$^9$, R$^{10}$, and R$^{11}$ is independently selected from hydrogen or (C$_1$-C$_6$)-alkyl, provided that at least one of R$^9$, R$^{10}$, and R$^{11}$ is hydrogen;

d. amino;

e. 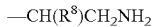

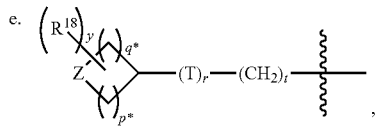

wherein Z is selected from CR$^{12}$R$^{13}$ or NR$^{14}$,
each of R$^{12}$ and R$^{13}$ is independently selected from H, NH$_2$ and

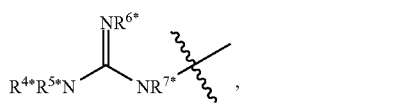, wherein each of R$^{4*}$, R$^{5*}$, R$^{6*}$ and R$^{7*}$ is as described previously,
alternatively, R$^{12}$ and R$^{13}$ together with the carbon to which they are attached, form a cycloalkyl or heterocyclyl ring containing 4-6 ring members,
R$^{14}$ is selected from H and

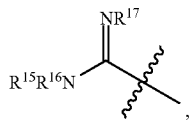, wherein each of $R^{15}$, $R^{16}$ and $R^{17}$ is independently selected from hydrogen, ($C_1$-$C_6$)-alkyl, aminoalkyl, aminocycloalkyl, and hydroxyalkyl, provided that at least one of $R^{15}$, $R^{16}$ and $R^{17}$ is hydrogen, $R^{18}$ is selected from $NH_2$ and

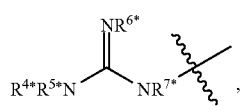

wherein each of $R^{4*}$, $R^{5*}$, $R^{6*}$ and $R^{7*}$ is as described previously, each of p* and q* is independently selected from 0, 1, 2 and 3, T is selected from NH and O t is selected from 0, 1, 2, 3, and 4, and each of r and y is independently selected from 0 and 1;

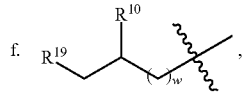

wherein $R^{19}$ is selected from $NH_2$ and

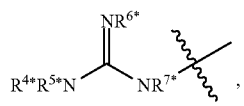

wherein each of $R^{4*}$, $R^{5*}$, $R^{6*}$ and $R^{7*}$ is as described previously, $R^{20}$ is selected from amino and hydroxyl, and w is selected from 0 and 1;

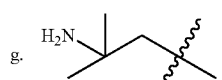

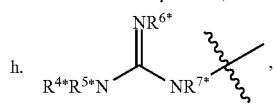

wherein each of $R^{4*}$, $R^{5*}$, $R^{6*}$ and $R^{7*}$ is as described previously;

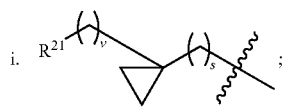

wherein $R^{21}$ is selected from $NH_2$, —NH($C_1$-$C_3$)-alkyl and

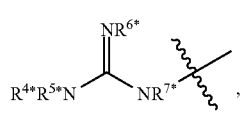

wherein each of $R^{4*}$, $R^{5*}$, $R^{6*}$ and $R^{7*}$ is as described previously, s is selected from 0 and 1, and v is selected from 0, 1, 2, and 3;

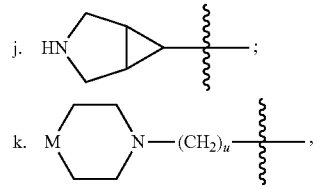

wherein M is selected from $NR^{22}$, $CR^{23}R^{24}$ and O, wherein $R^{22}$ is H or

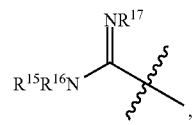

wherein each of $R^{15}$, $R^{16}$ and $R^{17}$ is as described previously, each of $R^{23}$ and $R^{24}$ is independently selected from H, $NH_2$ and

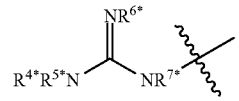

wherein each of $R^{4*}$, $R^{5*}$, $R^{6*}$ and $R^{7*}$ is as described previously, and u is selected from 0, 1 and 2;

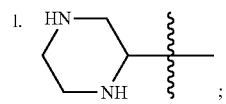

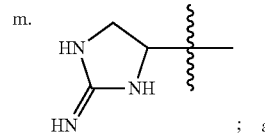

In one embodiment, the invention provides use of a compound of Formula I for inhibiting β-lactamases.

In one embodiment, the invention provides use of a compound of Formula A-I for inhibiting β-lactamases.

In one embodiment, the invention provides compounds of Formula I with high binding affinity for β-lactamase enzymes.

In one embodiment, the invention provides compounds of Formula A-I with high binding affinity for β-lactamase enzymes.

In one embodiment, the present invention also provides antibacterial compositions comprising compounds of Formula I and at least one β-lactam antibiotic.

In one embodiment, the present invention also provides antibacterial compositions comprising compounds of Formula A-I and at least one β-lactam antibiotic.

In one embodiment, the present invention provides pharmaceutical compositions comprising compounds of Formula I and at least one β-lactam antibiotic and methods of use thereof.

In one embodiment, the present invention provides pharmaceutical compositions comprising compounds of Formula A-I and at least one β-lactam antibiotic and methods of use thereof.

In one embodiment, the invention provides methods of use of the compounds of Formula I to treat bacterial infections in a subject.

In one embodiment, the invention provides methods of use of the compounds of Formula A-I to treat bacterial infections in a subject.

BRIEF DESCRIPTION OF THE DRAWINGS

FIGS. 1A-1I show Table I, Representative Compounds of Formula A-II

FIGS. 2A-2G show Table II, Standard BLI potentiation MIC assay against a panel of isogenic and clinical strains expressing β-lactamases.

FIGS. 3A-3F show Table III, the synergy MIC of representative compounds of Formula II-A against a panel of isogenic and clinical strains expressing β-lactamases.

FIGS. 5A-5B show Table V, Synergy MIC of Comparator Compounds Against a Panel of Isogenic and Clinical Strains Expressing β-lactamases FIG. 6 shows Table VI, Standard BLI Potentiation MIC Assay of Compounds Partnered with CXA-101 Against a Panel of Isogenic and Clinical Strains Expressing β-Lactamases FIG. 7 shows Table VII, Standard BLI Potentiation MIC Assay of Compounds Partnered with Ceftazidime Against a Panel of Isogenic and Clinical Strains Expressing β-Lactamases FIG. 8 shows Table VIII, Standard BLI Potentiation MIC Assay of Compounds Partnered with Aztreonam Against a Panel of Isogenic and Clinical Strains Expressing β-Lactamases FIG. 9 shows Table IX, Standard BLI Potentiation MIC Assay of Compounds Partnered with Meropenem Against a Panel of Isogenic and Clinical Strains Expressing β-Lactamases

DETAILED DESCRIPTION

Definitions

Figure 4A:
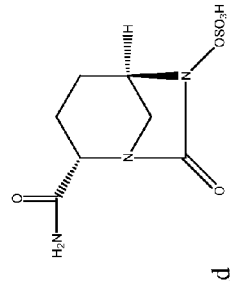
FIGS. 4A-4C show Table IV, an assay to determine inhibition kinetics of representative compounds of Formula II-A for the KPC-2 β-lactamase.

Molecular terms, when used in this application, have their common meaning unless otherwise specified.

The term "alkyl" is defined as a linear or branched, saturated radical having one to about twenty carbon atoms unless otherwise specified. Preferred alkyl radicals are "lower alkyl" radicals having one to about five carbon atoms. Examples of alkyl groups include, without limitation, methyl, ethyl, tert-butyl, isopropyl, and hexyl. A subset of the term alkyl is "$(C_1-C_3)$-unsubstituted alkyl" which is defined as an alkyl group that bears no substituent groups. Examples of $(C_1-C_3)$-unsubstituted alkyl groups include methyl, ethyl, propyl and isopropyl. It is understood that if a $(C_1-C_3)$-alkyl is "substituted" that one or more hydrogen atoms is replaced by a substitutent.

The term amino denotes a $NH_2$ radical.

The term "aminoalkyl" denotes an alkyl in which one or more of the alkyl hydrogen atoms has been replaced by an amino group.

The term "aminocycloalkyl" denotes a cycloalkyl in which one of the cycloalkyl hydrogen atoms has been replaced by an amino group.

The term "cycloalkyl" or "cycloalkyl ring" is defined as a saturated or partially unsaturated carbocyclic ring in a single or fused carbocyclic ring system having from three to twelve ring members. In a preferred embodiment, a cycloalkyl is a ring system having three to seven ring members. Examples of a cycloalkyl group include, without limitation, cyclopropyl, cyclobutyl, cyclohexyl, and cycloheptyl.

The term "hydroxyalkyl" denotes an alkyl radical in which one or more of the alkyl hydrogen atoms has been replaced by a hydroxyl group.

It will be understood by one of skill in the art that a

denote the point of attachment of a substituent group where indicated. For example

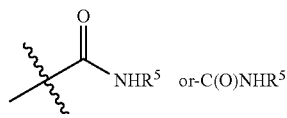

represent that the point of attachment of the amide moiety is at the carbonyl carbon.

The functional classification of β-lactamases and terms "Class A", "Class C", and "Class D" β-lactamases are understood by one of skill in the art and are described in "Updated Functional Classification of β-Lactamases", Bush, K.; Jacoby, G. A.; *Antimicrob. Agents Chemother.* 2010, 54, 969-976, herein incorporated by reference.

The salts of the compounds of the invention include acid addition salts and base addition salts. In a one embodiment, the salt is a pharmaceutically acceptable salt of the compound of Formula I. The term "pharmaceutically acceptable salts" embraces salts commonly used to form alkali metal salts and to form addition salts of free acids or free bases. The nature of the salt is not critical, provided that it is pharmaceutically-acceptable. Suitable pharmaceutically acceptable acid addition salts of the compounds of the invention may be prepared from an inorganic acid or an organic acid. Examples of such inorganic acids include, without limitation, hydrochloric, hydrobromic, hydroiodic, nitric, carbonic, sulfuric and phosphoric acid. Examples of appropriate organic acids may be selected from aliphatic, cycloaliphatic, aromatic, arylaliphatic, heterocyclic, carboxylic and sulfonic classes of organic acids, examples of which include, without limitation, formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, and galacturonic acid. Suitable pharmaceutically-acceptable base addition salts of compounds of the invention include, but are not limited to, metallic salts made from aluminum, calcium, lithium, magnesium, potassium, sodium and zinc or organic salts made from N,N'-dibenzylethylenediamine, chloroprocaine, choline, diethanolamine, ethylenediamine, N-methylglucamine, lysine and procaine. All of these salts may be prepared by conventional means from the corresponding compound of the invention by treating, for example, the compound of the invention with the appropriate acid or base.

The compounds of the invention can possess one or more asymmetric carbon atoms and are thus capable of existing in the form of optical isomers as well as in the form of racemic or non-racemic mixtures thereof. The compounds of the invention can be utilized in the present invention as a single isomer or as a mixture of stereochemical isomeric forms. Diastereoisomers, i.e., nonsuperimposable stereochemical isomers, can be separated by conventional means such as chromatography, distillation, crystallization or sublimation. The optical isomers can be obtained by resolution of the racemic mixtures according to conventional processes, for example by formation of diastereoisomeric salts by treatment with an optically active acid or base. Examples of appropriate acids include, without limitation, tartaric, diacetyltartaric, dibenzoyltartaric, ditoluoyltartaric and camphorsulfonic acid. The mixture of diastereomers can be separated by crystallization followed by liberation of the optically active bases from the optically active salts. An alternative process for separation of optical isomers includes the use of a chiral chromatography column optimally chosen to maximize the separation of the enantiomers. Still another available method involves synthesis of covalent diastereoisomeric molecules by treating compounds of the invention with an optically pure acid in an activated form or an optically pure isocyanate. The synthesized diastereoisomers can be separated by conventional means such as chromatography, distillation, crystallization or sublimation, and then hydrolyzed to obtain the enantiomerically pure compound. The optically active compounds of the invention can likewise be obtained by utilizing optically active starting materials. These isomers may be in the form of a free acid, a free base, an ester or a salt.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to 2H, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

The invention also embraces isolated compounds. An isolated compound refers to a compound which represents at least 10%, such as at least 20%, such as at least 50% and further such as at least 80% of the compound present in the mixture. In one embodiment, the compound, a pharmaceutically acceptable salt thereof, or a pharmaceutical composition comprising the compound exhibits detectable (i.e. statistically significant) activity when tested in conventional biological assays such as those described herein.

β-Lactamase Inhibitors (BLIs)

In one aspect, the invention provides compounds of Formula I or pharmaceutically-acceptable salts thereof:

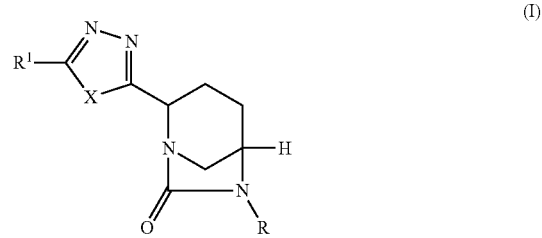

The substituent X of Formula I is selected from O and S. In one aspect of the invention X is S. In another aspect of the invention X is O.

Substituent R of Formula I is selected from

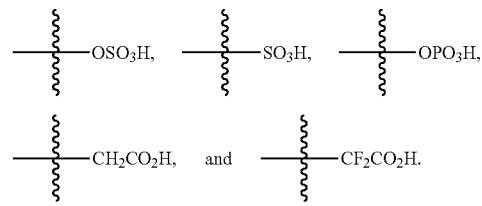

In a preferred embodiment, R is

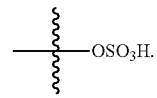

The group $R^1$ of Formula I is selected from:

a. hydrogen;

b. 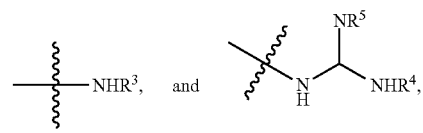

wherein $R^2$ is selected from

—NHR$^3$, and [structure with NR$^5$, NHR$^4$]

wherein each of $R^3$, $R^4$ and $R^5$ is independently selected from hydrogen, $(C_1-C_3)$-alkyl, aminoalkyl, aminocycloalkyl, and hydroxyalkyl, and n is selected from 1, 2 and 3;

c.

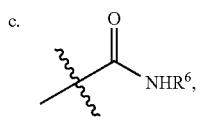

wherein R⁶ is H, (C₂-C₃) alkylamino, and

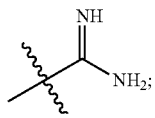

d. amino;

e.

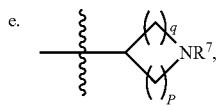

wherein R⁷ is selected from H, (C₁-C₃)-unsubstituted alkyl, amino-(C₂-C₃)-alkyl, aminocycloalkyl, hydroxyalkyl,
and

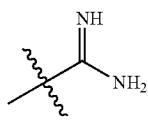

and each of p and q is independently selected from 1 and 2; and

—CH(R⁸)CH₂NH₂     f.

wherein R⁸ is selected from amino and hydroxyl.

In one aspect of the invention n is 1. In another aspect of the invention n is 2. In another aspect of the invention n is 3.

In one aspect of the invention R¹ is selected from H, —CH₂NH₂, —CH₂CH₂NH₂, —CONH₂, —NH₂, —CH(OH)CH₂NH₂, —CH(NH₂)CH₂NH₂, —CH₂CH₂NHCH₂CH₂NH₂,

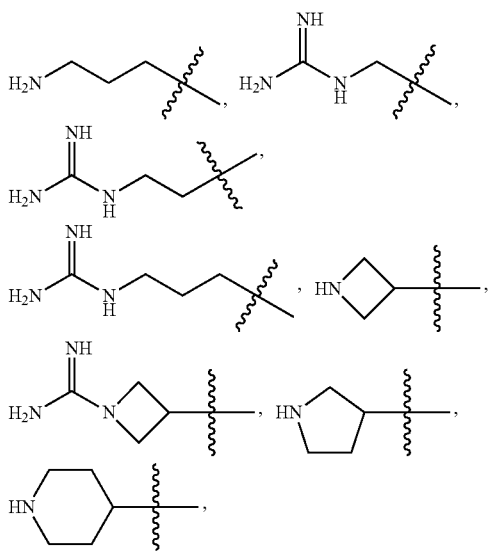

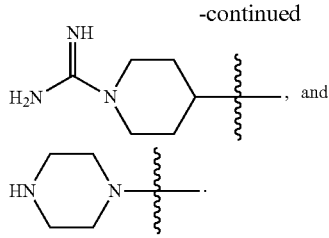

, and

In one embodiment of the invention R¹ is selected from H and

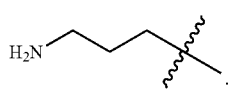

In one embodiment of the invention, the compounds of the invention are of the stereochemistry disclosed in Formula II.

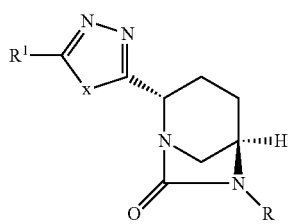

(II)

In another embodiment of the invention, the compound is of Formula II and X is O, R is —OSO₃H and R¹ is H.

In another embodiment of the invention, the compound is of Formula II and X is O, R is —OSO₃H and R¹ is —CH₂NH₂.

In another embodiment of the invention, the compound is of Formula II and X is O, R is —OSO₃H and R¹ is —CH₂CH₂NH₂.

In another embodiment of the invention, the compound is of Formula II and X is O, R is —OSO₃H and R¹ is

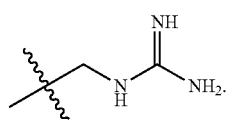 [SMILES: *CNC(=N)N]

In another embodiment of the invention, the compound is of Formula II and X is O, R is —OSO₃H and R¹ is

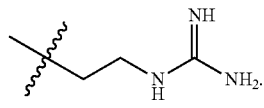 [SMILES: *CCNC(=N)N]

In another embodiment of the invention, the compound is of Formula II and X is O, R is —OSO₃H and R¹ is —CONH₂.

In another embodiment of the invention, the compound is of Formula II and X is O, R is —OSO₃H and R¹ is —NH₂.

In another embodiment of the invention, the compound is of Formula II and X is O, R is —OSO$_3$H and R$^1$ is

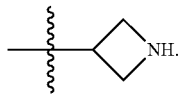

In another embodiment of the invention, the compound is of Formula II and X is O, R is —OSO$_3$H and R$^1$ is

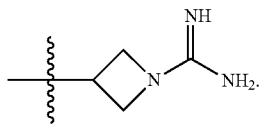 [SMILES: *C1CN(C(=N)N)C1]

In another embodiment of the invention, the compound is of Formula II and X is O, R is —OSO$_3$H and R$^1$ is

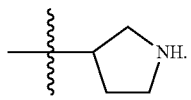 [SMILES: *C1CCNC1]

In another embodiment of the invention, the compound is of Formula II and X is O, R is —OSO$_3$H and R$^1$ is

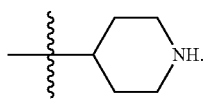 [SMILES: *C1CCNCC1]

In another embodiment of the invention, the compound is of Formula II and X is O, R is —OSO$_3$H and R$^1$ is

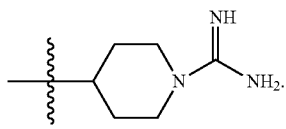 [SMILES: *C1CCN(C(=N)N)CC1]

In another embodiment of the invention, the compound is of Formula II and X is O, R is —OSO$_3$H and R$^1$ is

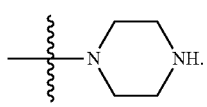

In another embodiment of the invention, the compound is of Formula II and X is O, R is —OSO$_3$H and R$^1$ is

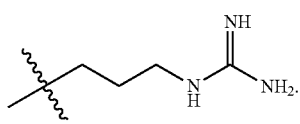 [SMILES: *CCCNC(=N)N]

In another embodiment of the invention, the compound is of Formula II and X is O, R is —OSO$_3$H and R$^1$ is —CH(OH)CH$_2$NH$_2$.

In another embodiment of the invention, the compound is of Formula II and X is O, R is —OSO$_3$H and R$^1$ is —CH$_2$CH$_2$NHCH$_2$CH$_2$NH$_2$.

In another embodiment of the invention, the compound is of Formula II and X is O, R is —OSO$_3$H and R$^1$ is —CH(NH$_2$)CH$_2$NH$_2$.

In another embodiment of the invention, the compound is of Formula II and X is S, R is —OSO$_3$H and R$^1$ is —CH$_2$CH$_2$NH$_2$.

In another embodiment of the invention, the compound is of Formula II and X is S, R is —OSO$_3$H and R$^1$ is

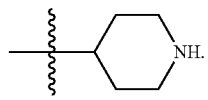

In another embodiment of the invention, the compound is of Formula II and X is O, R is —OSO$_3$H and R$^1$ is

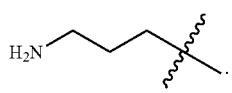

In another embodiment of the invention, the compound is of Formula and II X is S, R is —OSO$_3$H and R$^1$ is

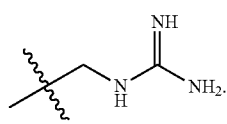 [SMILES: *CNC(=N)N]

Preferred compounds of Formula I are the compounds:

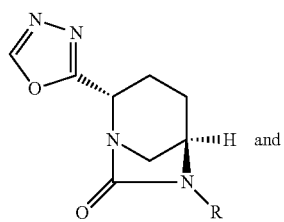

and

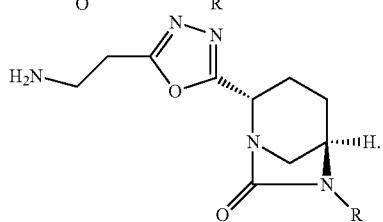

It will be understood by one of skill in the art that depending on the nature of R$^1$ and R, compounds of Formula I may exist in a salt or zwitterionic form.

In one aspect, the invention provides compounds of Formula A-I or pharmaceutically-acceptable salts thereof:

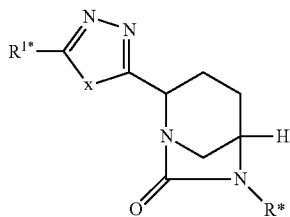

(A-I)

The substituent X* of Formula A-I is selected from O and S. In one aspect of the invention X* is S. In another aspect of the invention X* is O.

Substituent R* of Formula A-I is selected from

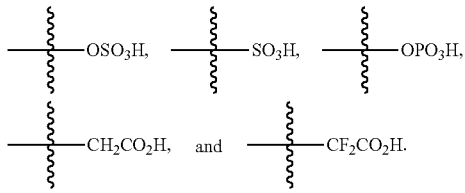

In a preferred embodiment, R* is

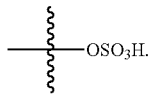

The group $R^{1*}$ of Formula I is selected from:

a. hydrogen;

b. 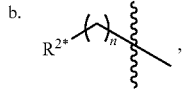

$R^{2*}$ is selected from

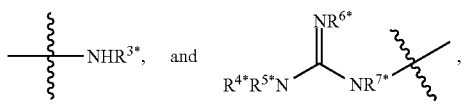

$R^{3*}$ is selected from hydrogen, $(C_1-C_3)$-alkyl, aminoalkyl, aminocycloalkyl, hydroxyalkyl,

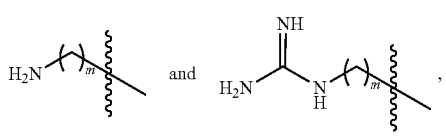

each of $R^{4*}$, $R^{5*}$, $R^{6*}$ and $R^{7*}$ is independently selected from hydrogen or $(C_1-C_6)$-alkyl, aminoalkyl, aminocycloalkyl, and hydroxyalkyl, provided that at least one of $R^{4*}$, $R^{5*}$, $R^{6*}$ and $R^{7*}$ is hydrogen, n is selected from 1, 2, 3 and 4, and
m is selected from 1, 2 and 3;

c. 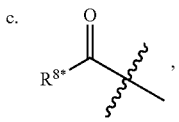

wherein $R^{8*}$ is selected from $NH_2$,

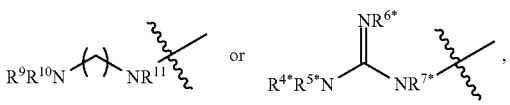

wherein each of $R^{4*}$, $R^{5*}$, $R^{6*}$ and $R^{7*}$ is as described previously and each of $R^9$, $R^{10}$, and $R^{11}$ is independently selected from hydrogen or $(C_1-C_6)$-alkyl, provided that at least one of $R^9$, $R^{10}$, and $R^{11}$ is hydrogen;

d. amino;

e. 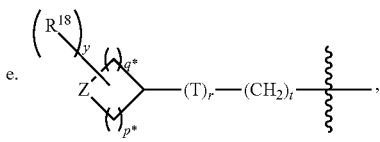

Z is selected from $CR^{12}R^{13}$ or $NR^{14}$,
each of $R^{12}$ and $R^{13}$ is independently selected from H, $NH_2$ and

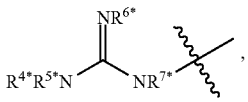

wherein each of $R^{4*}$, $R^{5*}$, $R^{6*}$ and $R^{7*}$ is as described previously,
alternatively, $R^{12}$ and $R^{13}$ together with the carbon to which they are attached, form a cycloalkyl or heterocyclyl ring containing 4-6 ring members,
$R^{14}$ is selected from H and

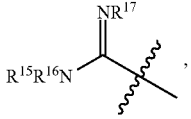

each of $R^{15}$, $R^{16}$ and $R^{17}$ is independently selected from hydrogen, $(C_1-C_6)$-alkyl, aminoalkyl, aminocycloalkyl, and hydroxyalkyl, provided that at least one of $R^{15}$, $R^{16}$ and $R^{17}$ is hydrogen,
$R^{18}$ is selected from $NH_2$ and

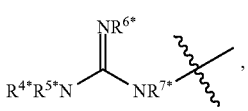

wherein each of $R^{4*}$, $R^{5*}$, $R^{6*}$ and $R^{7*}$ is as described previously, each of p* and q* is independently selected from 0, 1, 2 and 3,
T is selected from NH and O
t is selected from 0, 1, 2, 3, and 4, and
each of r and y is independently selected from 0 and 1;

f. 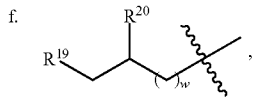, wherein $R^{19}$ is selected from $NH_2$ and

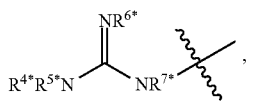, wherein each of $R^{4*}$, $R^{5*}$, $R^{6*}$ and $R^{7*}$ is as described previously,
$R^{20}$ is selected from amino and hydroxyl, and
w is selected from 0 and 1;

g. 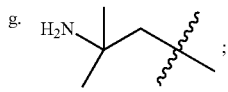;

h. 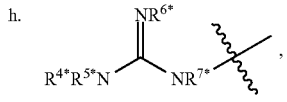, wherein each of $R^{4*}$, $R^{6*}$ and $R^{7*}$ is as described previously;

i. 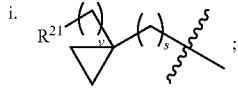;

wherein $R^{21}$ is selected from $NH_2$, —$NH(C_1$-$C_3)$-alkyl and

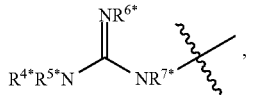, wherein each of $R^{4*}$, $R^{5*}$, $R^{6*}$ and $R^{7*}$ is as described previously,
s is selected from 0 and 1, and
v is selected from 0, 1, 2, and 3;

j. 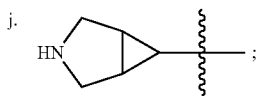;

k. 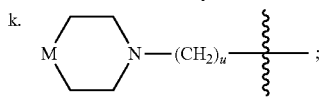;

wherein M is selected from $NR^{22}$, $CR^{23}R^{24}$ and O,
wherein $R^{22}$ is H and

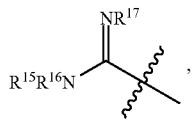, wherein each of $R^{15}$, $R^{16}$ and $R^{17}$ is as described previously,
each of $R^{23}$ and $R^{24}$ is independently selected from H, $NH_2$ and

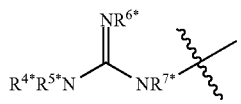

wherein each of $R^{4*}$, $R^{5*}$, $R^{6*}$ and $R^{7*}$ is as described previously, and
u is selected from 0, 1 and 2;

l. 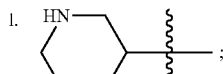;

m. 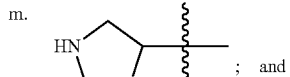; and n. 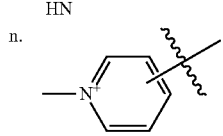.

In one aspect of the invention $R^{1*}$ is selected from

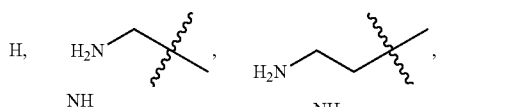

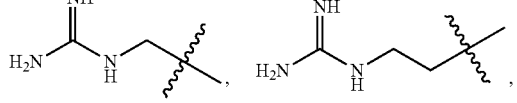

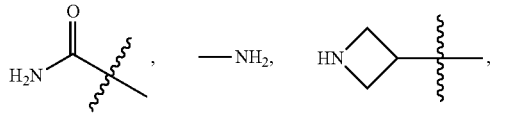

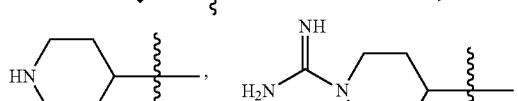

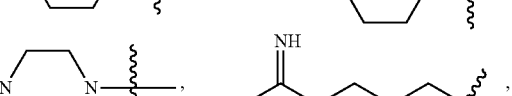

-continued
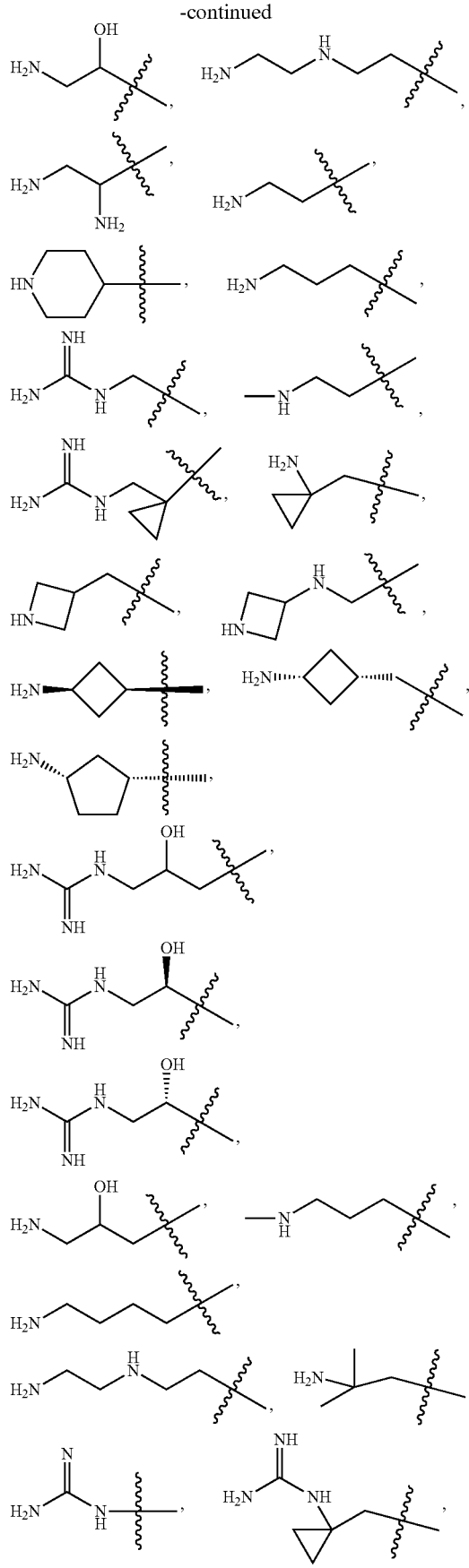
-continued
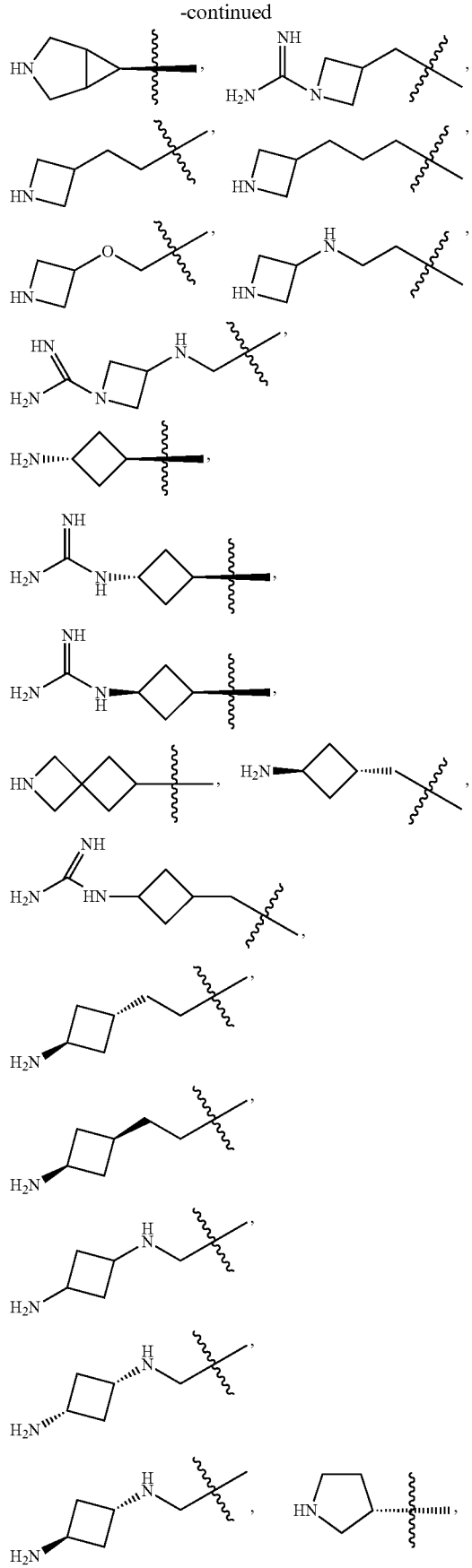

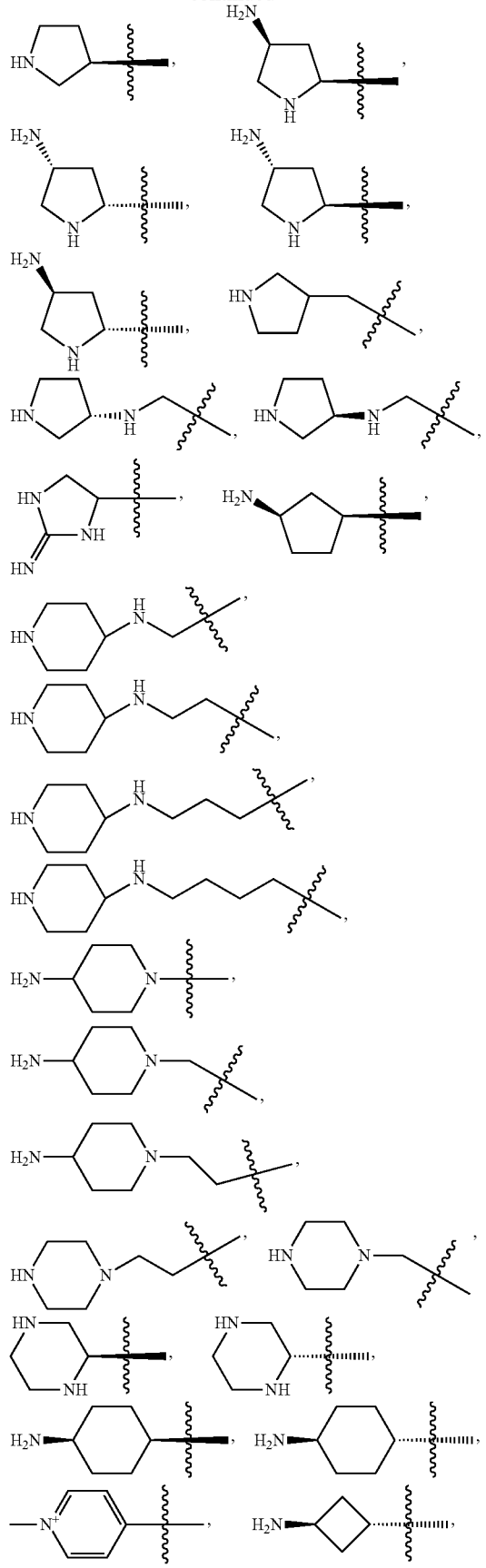
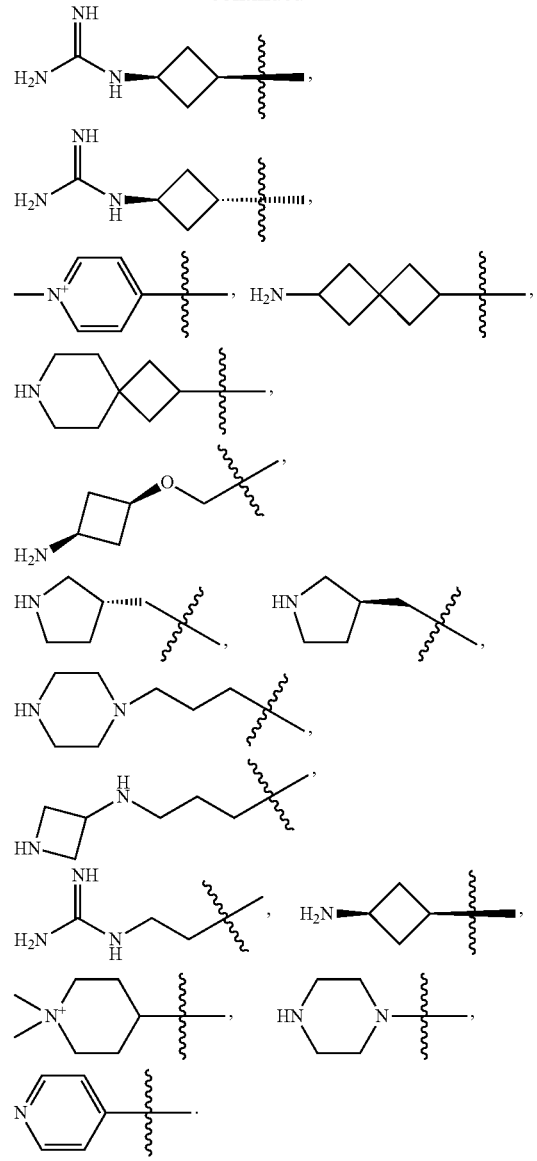
In one embodiment of the invention R$^{1*}$ is selected from
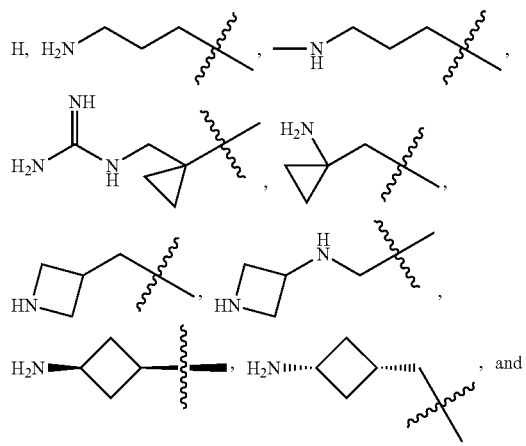

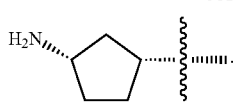

In one embodiment of the invention R[1*] is selected from

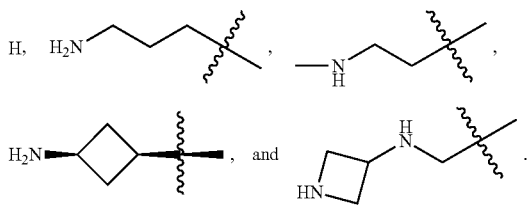

In one embodiment of the invention, the compounds of the invention are of the stereochemistry disclosed in Formula A-II.

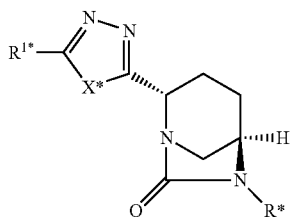
(A-II)

In another embodiment of the invention, X*, R* and R[1*] are chosen from the substituents listed in Table I (See FIG. 1).

Preferred compounds of Formula A-I are

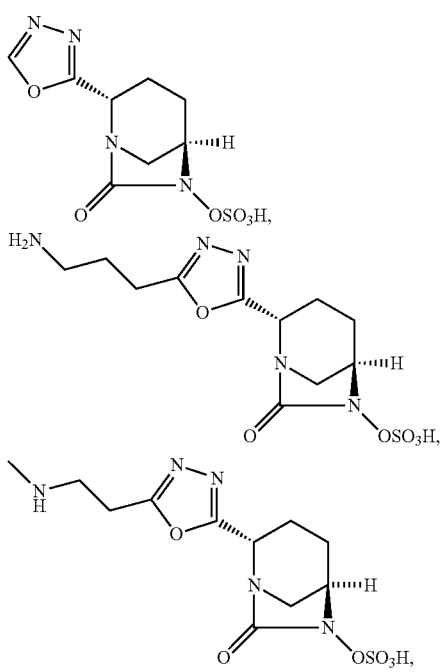

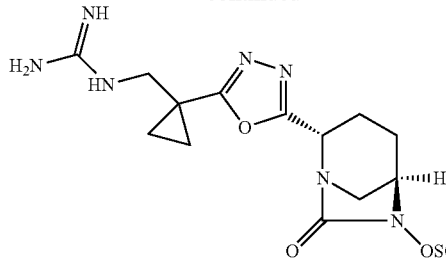

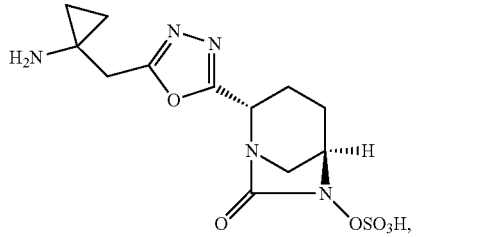

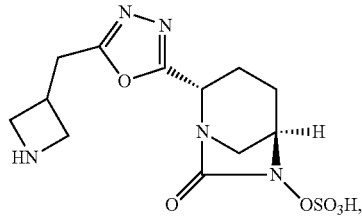

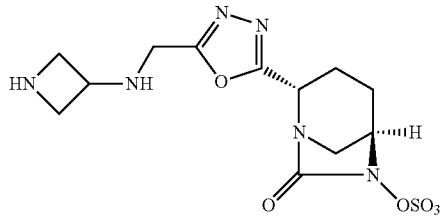

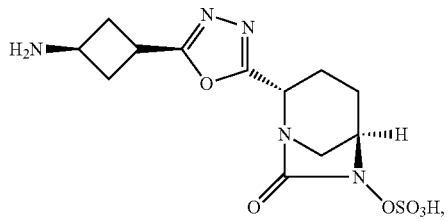

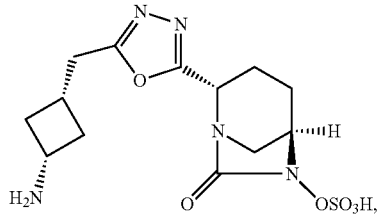

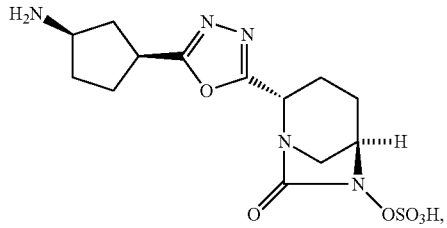

It will be understood by one of skill in the art that depending on the nature of R[1*] and R*, compounds of Formula I may exist in a salt or zwitterionic form.

Enzyme Inhibition and Binding Affinity

The compounds of the invention (e.g. compounds of Formula I, compounds of Formula A-I, compounds of Formula II, compounds of Formula A-II) are effective in inhibiting β-lactamase. In one aspect of the invention the compounds of Table I are effective β-lactamase inhibitors.

In one aspect the compound

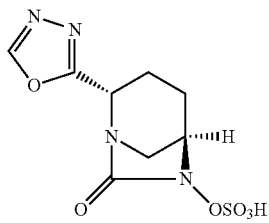

is effective in inhibiting β-lactamase.

In one aspect the compound

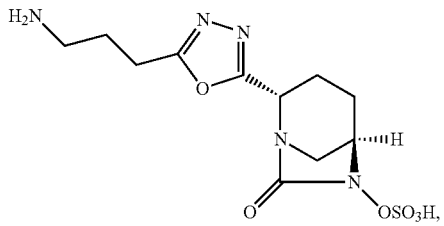

is effective in inhibiting β-lactamase.

In one aspect the compound

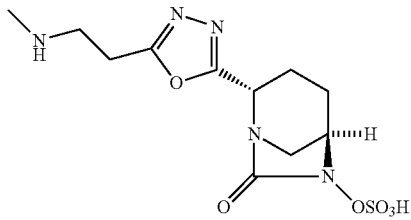

is effective in inhibiting β-lactamase.

In one aspect the compound

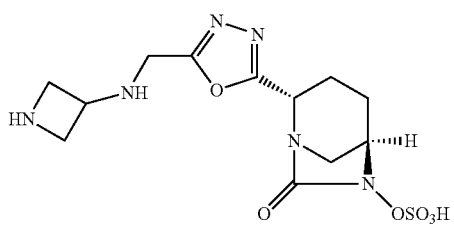

is effective in inhibiting β-lactamase.

In one aspect the compound

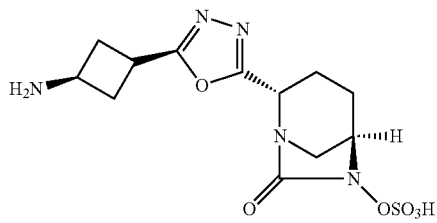

is effective in inhibiting β-lactamase.

When used in combination with β-lactam antibiotics, the compounds of the invention (e.g. compounds of Formula I, compounds of Formula A-I, compounds of Formula II, compounds of Formula A-II) potentiate the activity of the β-lactam antibiotic against microorganisms that are normally resistant to β-lactam antibiotics due to the presence of a β-lactamase or multiple β-lactamases.

In one aspect of the invention the compounds of the invention (e.g. compounds of Formula I, compounds of Formula A-I, compounds of Formula II, compounds of Formula A-II) inhibit β-lactamases selected from class A, class C or class D β-lactamases. In one aspect of the invention the compounds of Formula I, inhibit β-lactamases selected from class A, class C or class D β-lactamases. In one aspect of the invention the compounds of Formula A-I inhibit β-lactamases selected from class A, class C or class D β-lactamases. In one aspect of the invention the compounds of Formula II inhibit β-lactamases selected from class A, class C or class D β-lactamases. In one aspect of the invention the compounds of Formula A-II inhibit β-lactamases selected from class A, class C or class D β-lactamases. In one aspect of the invention the compounds of Table I inhibit β-lactamases selected from class A, class C or class D β-lactamases. In one aspect of the invention the compound of the Formula

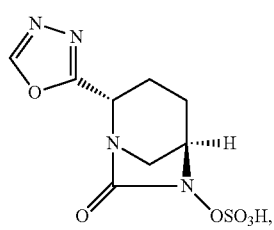

inhibits β-lactamases selected from class A, class C or class D β-lactamases. In one aspect of the invention the compound of the Formula

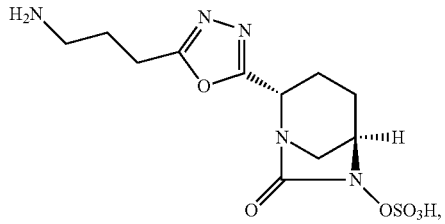

inhibits β-lactamases selected from class A, class C or class D β-lactamases. In one aspect of the invention the compound of the Formula

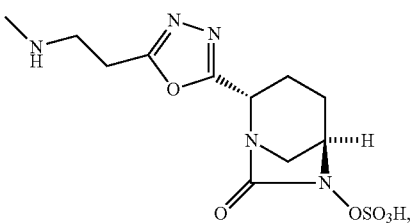

inhibits β-lactamases selected from class A, class C or class D β-lactamases. In one aspect of the invention the compound of the Formula

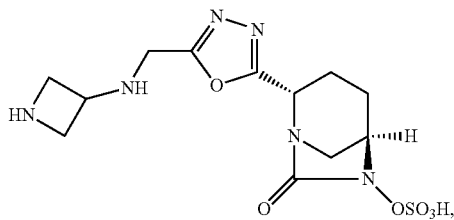

inhibits β-lactamases selected from class A, class C or class D β-lactamases. In one aspect of the invention the compound of the Formula

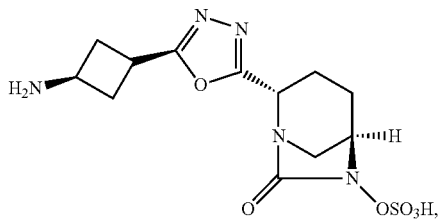

inhibits β-lactamases selected from class A, class C or class D β-lactamases. Class A β-lactamases for example, include, but are not limited to, TEM, SHV, CTX-M, KPC, GES, VEB, SME, and GEX. In a preferred aspect of the invention, the compounds of the invention (e.g. compounds of Formula I, compounds of Formula A-I, compounds of Formula II, compounds of Formula A-II) inhibit KPC β-lactamases. In a preferred aspect of the invention, the compounds of Formula I inhibit KPC β-lactamases. In a preferred aspect of the invention, the compounds of Formula A-I inhibit KPC β-lactamases. In a preferred aspect of the invention, the compounds of Formula II inhibit KPC β-lactamases. In a preferred aspect of the invention, the compounds of Formula A-II inhibit KPC β-lactamases. More preferably the compounds of the invention (e.g. compounds of Formula I, compounds of Formula A-I, compounds of Formula II, compounds of Formula A-II) inhibit KPC-2 or KPC-3 β-lactamases. More preferably the compounds of Formula I inhibit KPC-2 or KPC-3 β-lactamases. More preferably the compounds of Formula A-I inhibit KPC-2 or KPC-3 β-lactamases. More preferably the compounds of Formula II inhibit KPC-2 or KPC-3 β-lactamases. More preferably the compounds of Formula A-II inhibit KPC-2 or KPC-3 β-lactamases. In one aspect of the invention, the compounds of the invention (e.g. compounds of Formula I, compounds of Formula A-I, compounds of Formula II, compounds of Formula A-II) inhibit KPC-2 or KPC-3 β-lactamases in clinical strains (FIG. 2, Table II and FIGS. 6-9, Tables VI-IX). In one aspect of the invention, the compounds of Formula I inhibit KPC-2 or KPC-3 β-lactamases in clinical strains (FIG. 2, Table II and FIGS. 6-9, Tables VI-IX). In one aspect of the invention, the compounds of Formula A-I inhibit KPC-2 or KPC-3 β-lactamases in clinical strains (FIG. 2, Table II and FIGS. 6-9, Tables VI-IX). In one aspect of the invention, the compounds of Formula II inhibit KPC-2 or KPC-3 β-lactamases in clinical strains (FIG. 2, Table II and FIGS. 6-9, Tables VI-IX). In one aspect of the invention, the compounds of Formula A-II inhibit KPC-2 or KPC-3 β-lactamases in clinical strains (FIG. 2, Table II and FIGS. 6-9, Tables VI-IX). Class C β-lactamases for example, include, but are not limited to chromosomal AmpCs, and plasmid based ACC, DHA, CMY, FOX, ACT, MIR, LAT, MOX β-lactamases. Class D β-lactamase enzymes, for example, include, but are not limited to oxacillinases or OXA β-lactamases. In a preferred aspect of the invention, the compounds of the invention (e.g. compounds of Formula I, compounds of Formula A-I, compounds of Formula II, compounds of Formula A-II) inhibit OXA-15 β-lactamases. In a preferred aspect of the invention, the compounds of Formula I inhibit OXA-15 β-lactamases. In a preferred aspect of the invention, the compounds of Formula A-I inhibit OXA-15 β-lactamases. In a preferred aspect of the invention, the compounds of Formula II inhibit OXA-15 β-lactamases. In a preferred aspect of the invention, the compounds of Formula A-II inhibit OXA-15 β-lactamases.

Unless otherwise indicated, the activity of the BLI compounds can be described by the MIC value obtained from a Synergy MIC assay or a BLI potentiation assay (e.g as described herein), both of which are run in the presence of a β-lactam. The lower the sMIC or MIC value the more active the BLI, regardless of the mechanism of action of the BLI compound (e.g., including inhibition of β-lactamases by the BLI or any other mechanism of action or combination of mechanisms of action). The sMIC and BLI potentiation assay data supports that the compounds of the invention (e.g. compounds of Formula I, compounds of Formula A-I, compounds of Formula II, compounds of Formula A-II) potentiate (i.e. make more potent) the activity of the β-lactam antibiotic against β-lactamase producing strains by inhibiting the β-lactamase.

In one embodiment, the BLI activity is measured by growth inhibition of a β-lactamase producing bacterial strains in a Synergy MIC (sMIC) assay. Preferably, the sMIC value for the compounds of the invention (e.g. compounds of Formula I, compounds of Formula A-I, compounds of Formula II, compounds of Formula A-II) is 8 μg/mL or less. In a more preferred aspect of the invention, the sMIC value for the compounds of the invention (e.g. compounds of Formula I, compounds of Formula A-I, compounds of Formula II, compounds of Formula A-II) is 4 μg/mL to 8 μg/mL. In an even more preferred aspect of the invention, the sMIC value for the compounds of the invention (e.g. compounds of Formula I, compounds of Formula A-I, compounds of Formula II, compounds of Formula A-II) is 1 to 2 μg/mL. In a still more preferred aspect of the invention, the sMIC value for the compounds of the invention (e.g. compounds of Formula I, compounds of Formula A-I, compounds of Formula II, compounds of Formula A-II) is 0.2 to 0.5 μg/mL. Synergy MICs for representative compounds of the invention are described in Table III (See FIG. 3). It will be understood by one of skill in the art that the growth inhibition of β-lactamase producing strains can also be measured by a checkerboard synergy assay like that disclosed in International Patent Application Number WO 2008/039420 or a standard BLI potentiation assay using a fixed concentration of BLI.

In one embodiment, the BLI activity is measured by growth inhibition of a β-lactamase producing bacterial strains in a standard BLI potentiation assay using a fixed concentration of BLI. Preferably, the MIC value for the compounds of the invention (e.g. compounds of Formula I, compounds of Formula A-I, compounds of Formula II, compounds of Formula A-II) is 8 µg/mL or less. In a more preferred aspect of the invention, the MIC value for the compounds of the invention (e.g. compounds of Formula I, compounds of Formula A-I, compounds of Formula II, compounds of Formula A-II) is 4 to 8 µg/mL. In an even more preferred aspect of the invention, the MIC value for the compounds of the invention (e.g. compounds of Formula I, compounds of Formula A-I, compounds of Formula II, compounds of Formula A-II) is 1 to 2 µg/mL. In a still more preferred aspect of the invention, the MIC value for the compounds of the invention (e.g. compounds of Formula I, compounds of Formula A-I, compounds of Formula II, compounds of Formula A-II) is 0.2 µg/mL to 0.5 µg/mL.

The compounds of the present invention (e.g. compounds of Formula I, compounds of Formula A-I, compounds of Formula II, compounds of Formula A-II) have a broad spectrum of activity across a wide variety of β-lactamase producing bacteria. It was surprisingly found that the compounds of the present invention (e.g. compounds of Formula I, compounds of Formula A-I, compounds of Formula II, compounds of Formula A-II) are active in potentiating activity of β-lactam antibiotics, in particular, Ceftolozane, against strains expressing class D β-lactamase OXA-15 β-lactamase. Currently marketed BLIs inhibit most of the class A β-lactamases, but poorly inhibit class A KPC β-lactamases and class C β-lactamases and have variable success in inhibiting penicillinase and carbapenemase-type class D β-lactamases. The compounds of the present invention (e.g. compounds of Formula I, compounds of Formula A-I, compounds of Formula II, compounds of Formula A-II) are active against a wide variety of bacterial strains that express class A and C β-lactamases and also, surprisingly are active against bacterial strains that express the class D cephalosporinase OXA-15 (Tables II and III). This increased activity against the class D β-lactamase is critical because differential effectiveness against different types of β-lactamase producing bacteria is necessary in order to effectively use β-lactam antibiotics to treat resistant strains of bacteria (vide infra).

In one embodiment, the compounds the invention (e.g. compounds of Formula I, compounds of Formula A-I, compounds of Formula II, compounds of Formula A-II) are unexpectedly more active against bacterial strains that express OXA-15 β-lactamases than the most structurally similar compound, Avibactam (comparator compound CCC). Compounds that are more active than Avibactam against bacterial strains that express the class D cephalosporinase OXA-15 are, for example, compounds 701, 702, 703, 704, 705, 706, 707, 708, 709, 710, 711, 712, 713, 714, 715, 716, 717, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 776, 777, 778, 779, 780, 781, 782, 783, 784, 792, 794, 795 and 797.

In one embodiment, the compounds of the invention (e.g. compounds of Formula I, compounds of Formula A-I, compounds of Formula II, compounds of Formula A-II) are unexpectedly more active against and/or show broader spectrum of activity against bacterial strains that express KPC β-lactamases than the most structurally similar compound, Avibactam. Compounds that are more active than Avibactam for at least one, bacterial strain that expresses KPC β-lactamase and/or show a better spectrum of activity against bacterial strains that express KPC β-lactamases than Avibactam are, for example, compounds 701, 702, 703, 705, 706, 708, 709, 710, 711, 712714, 720, 721, 722, 723, 724, 726, 727, 728, 729, 730, 731, 732, 734, 735, 736, 737, 738, 739, 740, 741, 742, 743, 744, 745, 746, 747, 749, 750, 751, 752, 753, 754, 755, 756, 758, 759, 760, 761, 762, 763, 764, 765, 766, 767, 768, 770, 771, 772, 774, 775, 776, 777, 779, 782, 783, 784, 786, 794, and 795.

In another aspect of the invention, the compounds of the invention (e.g. compounds of Formula I, compounds of Formula A-I, compounds of Formula II, compounds of Formula A-II) have high binding affinity for the β-lactamase enzyme. Consequently these compounds are better inhibitors of the β-lactamase enzyme. The inhibition kinetics of the compounds of the invention (e.g. compounds of Formula I, compounds of Formula A-I, compounds of Formula II, compounds of Formula A-II) was measured according to the procedure outlined in Example 102. The compounds of the invention (e.g. compounds of Formula I, compounds of Formula A-I, compounds of Formula II, compounds of Formula A-II) have a high binding affinity for the β-lactamase enzyme.

In one embodiment the compounds of the invention (e.g. compounds of Formula I, compounds of Formula A-I, compounds of Formula II, compounds of Formula A-II) have a binding affinity of 1000-5000 $mM^{-1}s^{-1}$.

In one embodiment the compounds of the invention (e.g. compounds of Formula I, compounds of Formula A-I, compounds of Formula II, compounds of Formula A-II) have a binding affinity of 100-999 $mM^{-1}s^{-1}$. Compounds that have a binding affinity of 100-999 $mM^{-1}s^{-1}$ are, for example, compounds 701, 702, 703, 705, 706, 707, 709, 711, 712, 713, 714, 720, 730, 740, 741, 742, 743, 745, 746, 748, 749, 752, 753, 767, 770, 775, 779, 781, 782, 785, 794, 798 (Table IV).

In one embodiment the compounds of the invention (e.g. compounds of Formula I, compounds of Formula A-I, compounds of Formula II, compounds of Formula A-II) have a binding affinity of 1-99 $mM^{-1}s^{-1}$. Compounds that have a binding affinity of 1-99 $mM^{-1}s^{-1}$ are, for example, compounds 704, 706, 708, 710, 715, 716, 717, 718, 719, 721, 722, 723, 724, 725, 726, 727, 728, 729, 731, 732, 733, 734, 735, 736, 737, 738, 739, 744, 747, 750, 751, 754, 755, 756, 757, 758, 759, 760, 761, 762, 763, 764, 765, 766, 769, 771, 772, 773, 774, 776, 777, 778, 780, 783, 784, 786, 792, 796, and 797 (Table IV).

Figure 4B:
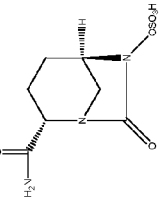
Figure 4C:
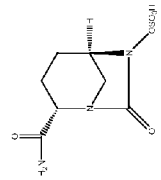

It was surprisingly found that the compounds of the present invention have a higher binding affinity for the β-lactamase enzyme than the closest structural comparator Avibactam (Table IV, See FIG. 4).

The compounds of the invention were also shown to be better BLIs than other comparator compounds as shown in FIG. 5.

Pharmaceutical Compositions Comprising the Compounds of the Invention and Use Thereof Another object of the invention is pharmaceutical compositions or formulations comprising compounds the invention (e.g. compounds of Formula I, compounds of Formula A-I, compounds of Formula II, compounds of Formula A-II), or salts thereof, preferably further comprising a β-lactam antibiotic. In one embodiment of the invention is pharmaceutical compositions or formulations comprising compounds of Formula I, or salts thereof, preferably further comprising a β-lactam antibiotic. In one embodiment of the invention is pharmaceutical compositions or formulations comprising compounds of Formula A-I, or salts thereof, preferably further comprising a β-lactam antibiotic. In one embodiment of the invention is pharmaceutical compositions or formulations comprising compounds of Formula II, or salts thereof, preferably further comprising a β-lactam antibiotic. In one embodiment of the invention is pharmaceutical compositions or formulations comprising compounds of Formula A-II, or salts thereof, preferably further comprising a β-lactam antibiotic. In one embodiment of the invention is pharmaceutical compositions or formulations comprising compounds of Table I. In one embodiment of the invention is pharmaceutical compositions or formulations comprising compounds of Formula

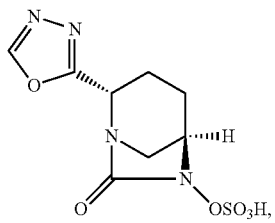

or salts thereof, preferably further comprising a β-lactam antibiotic. In one embodiment of the invention is pharmaceutical compositions or formulations comprising compounds of Formula

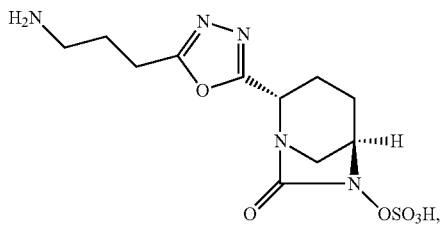

or salts thereof, preferably further comprising a β-lactam antibiotic. In one embodiment the invention is pharmaceutical compositions or formulations comprising compounds of Formula

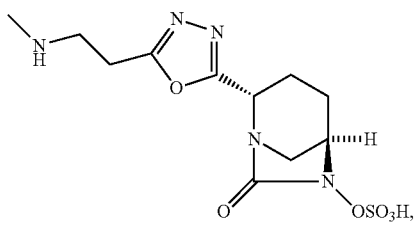

or salts thereof, preferably further comprising a β-lactam antibiotic. In one embodiment of the invention is pharmaceutical compositions or formulations comprising compounds of Formula

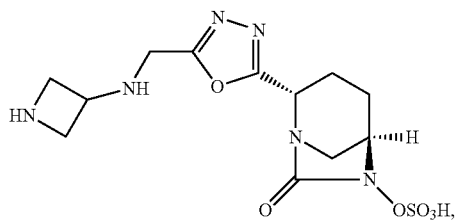

or salts thereof, preferably further comprising a β-lactam antibiotic. In one embodiment of the invention is pharmaceutical compositions or formulations comprising compounds of Formula

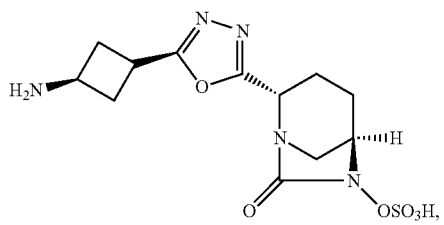

or salts thereof, preferably further comprising a β-lactam antibiotic.

The pharmaceutical compositions can be formulated for oral, intravenous, intramuscular, subcutaneous or parenteral administration for the therapeutic or prophylactic treatment of diseases, such as bacterial infections. Preferably, the pharmaceutical composition is formulated for intravenous administration.

The pharmaceutical preparations disclosed herein may be prepared in accordance with standard procedures and are administered at dosages that are selected to reduce, prevent or eliminate infection (see, e.g., Remington's Pharmaceutical Sciences, Mack Publishing Company, Easton, Pa. and Goodman and Gilman's "The Pharmaceutical Basis of Therapeutics," Pergamon Press, New York, N.Y., the contents of which are incorporated herein by reference, for a general description of the methods for administering various antimicrobial agents for human therapy).

The pharmaceutical compositions can comprise one or more of the compounds disclosed herein (e.g. one or more compounds of Formula I, compounds of Formula A-I, compounds of Formula II, compounds of Formula A-II), preferably a compound of Formula A-I or Formula A-II, in conjunction with a β-lactam antibiotic, in association with one or more nontoxic, pharmaceutically-acceptable carriers and/or diluents and/or adjuvants and/or excipients. As used herein, the phrase "pharmaceutically-acceptable carrier" refers to any and all solvents, dispersion media, coatings, antibacterial and antifungal agents, isotonic and absorption delaying agents, and the like, that are compatible with pharmaceutical administration. The use of such media and agents for pharmaceutically active substances is well known in the art. Non-limiting examples of carriers and excipients include corn starch or gelatin, lactose, sucrose, microcrystalline cellulose, kaolin, mannitol, dicalcium phosphate, sodium chloride and alginic acid. The compositions may contain croscarmellose sodium, microcrystalline cellulose, corn starch, sodium starch glycolate and alginic acid.

Tablet binders that can be included are acacia, methylcellulose, sodium carboxymethylcellulose, polyvinylpyrrolidone (Povidone), hydroxypropyl methylcellulose, sucrose, starch and ethylcellulose.

Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. It may also be desirable to add a coloring agent to make the dosage form more aesthetic in appearance or to help identify the product.

For oral or parenteral administration, compounds of the present invention (e.g. compounds of Formula I, compounds of Formula A-I, compounds of Formula II, compounds of Formula A-II) preferably a compound of Formula A-I or Formula A-II, in conjunction with a β-lactam antibiotic, can be mixed with conventional pharmaceutical carriers and excipients and used in the form of tablets, capsules, elixirs, suspensions, syrups, wafers and the like. The compositions comprising a compound of this invention may contain from about 0.1% to about 99% by weight of the active compound, such as from about 10% to about 30%.

For oral use, solid formulations such as tablets and capsules are useful. Sustained release or enterically coated preparations may also be devised. For pediatric and geriatric applications, one embodiment provides suspensions, syrups and chewable tablets. For oral administration, the pharmaceutical compositions are in the form of, for example, a tablet, capsule, suspension or liquid.

The pharmaceutical compositions may be made in the form of a dosage unit containing a therapeutically-effective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc; disintegrants, for example, potato starch, flavoring or coloring agents, or acceptable wetting agents. Oral liquid preparations generally are in the form of aqueous or oily solutions, suspensions, emulsions, syrups or elixirs, preparations of the invention may contain conventional additives such as suspending agents, emulsifying agents, non-aqueous agents, preservatives, coloring agents and flavoring agents. Non-limiting examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

For intravenous (IV) use, the pharmaceutical composition (e.g. compounds of Formula I, compounds of Formula A-I, compounds of Formula II, compounds of Formula A-II) preferably a compound of Formula A-I or Formula A-II, in conjunction with a β-lactam antibiotic, can be dissolved or suspended in any of the commonly used intravenous fluids and administered by infusion. Intravenous fluids include, without limitation, physiological saline or Ringer's solution. Intravenous administration may be accomplished by using, without limitation, syringe, mini-pump or intravenous line.

Pharmaceutical compositions of this invention (e.g. compounds of Formula I, compounds of Formula A-I, compounds of Formula II, compounds of Formula A-II) preferably a compound of Formula A-I or Formula A-II, for parenteral injection comprise pharmaceutically-acceptable aqueous or non-aqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, benzyl alcohol, polyols (such as glycerol, propylene glycol, and polyethylene glycol), and suitable mixtures thereof, vegetable oils (such as corn oil or olive oil), and injectable organic esters such as ethyl oleate. Proper fluidity can be maintained, for example, by the use of coating materials such as lecithin, by the maintenance of the required particle size in the case of dispersions, and by the use of surfactants. The compositions can include various buffers.

These compositions may also contain adjuvants such as preservatives, wetting agents, emulsifying agents, and dispersing agents. They may also contain taggants or other anti-counterfeiting agents, which are well known in the art. Prevention of the action of microorganisms may be ensured by the inclusion of various antibacterial and antifungal agents, for example, paraben, chlorobutanol, and phenol sorbic acid. It may also be desirable to include isotonic agents such as sugars and sodium chloride. Prolonged absorption of the injectable pharmaceutical form may be brought about by the inclusion of agents which delay absorption, such as aluminum monostearate and gelatin.

Injectable depot forms can be made by forming microencapsulating matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations can also be prepared by entrapping the drug in liposomes or microemulsions, which are compatible with body tissues.

The injectable formulations can be sterilized, for example, by filtration through a bacterial-retaining filter, or by incorporating sterilizing agents in the form of sterile solid compositions, which can be dissolved or dispersed in sterile water or other sterile injectable medium just prior to use.

Solid dosage forms for oral administration include capsules, tablets, pills, powders, and granules. Such forms may include forms that dissolve or disintegrate quickly in the oral environment. In such solid dosage forms, the active compound preferably a compound of Formula A-I or Formula A-II in conjunction with a β-lactam antibiotic, can be mixed with at least one inert, pharmaceutically-acceptable excipient or carrier. Suitable excipients include, for example, (a) fillers or extenders such as starches, lactose, sucrose, glucose, mannitol, and silicic acid; (b) binders such as cellulose and cellulose derivatives (such as hydroxypropylmethylcellulose, hydroxypropylcellulose, and carboxymethylcellulose), alginates, gelatin, polyvinylpyrrolidone, sucrose, and acacia; (c) humectants such as glycerol; (d) disintegrating agents such as sodium starch glycolate, croscarmellose, agar-agar, calcium carbonate, potato or tapioca starch, alginic acid, certain silicates, and sodium carbonate; (e) solution retarding agents such as paraffin; (f) absorption accelerators such as quaternary ammonium compounds; (g) wetting agents, such as cetyl alcohol and glycerol monostearate, fatty acid esters of sorbitan, poloxamers, and polyethylene glycols; (h) absorbents such as kaolin and bentonite clay; (i) lubricants such as talc, calcium stearate, magnesium stearate, solid polyethylene glycols, sodium lauryl sulfate, and mixtures thereof; and (j) glidants such as talc, and silicone dioxide. Other suitable excipients include, for example, sodium citrate or dicalcium phosphate. The dosage forms may also comprise buffering agents.

Solid dosage forms, including those of tablets, dragees, capsules, pills, and granules, can be prepared with coatings and shells such as functional and aesthetic enteric coatings and other coatings well known in the pharmaceutical formulating art. They may optionally contain opacifying agents and colorants. They may also be in a form capable of controlled or sustained release. Examples of embedding compositions that can be used for such purposes include polymeric substances and waxes.

The pharmaceutical compositions can be delivered using controlled (e.g., capsules) or sustained release (e.g., bioerodable matrices) delivery systems. Exemplary delayed release delivery systems for drug delivery that are suitable for administering the pharmaceutical compositions are described in U.S. Pat. No. 4,452,775 (issued to Kent), U.S. Pat. No. 5,039,660 (issued to Leonard), and U.S. Pat. No. 3,854,480 (issued to Zaffaroni).

In some cases, in order to prolong the effect of the drug, it may be desirable to slow the absorption of the drug following subcutaneous or intramuscular injection. This may be accomplished by the use of a liquid suspension of crystalline or amorphous material with poor water solubility. Amorphous material may be used alone or together with stabilizers as necessary. The rate of absorption of the drug then depends upon its rate of dissolution, which in turn, may depend upon crystal size and crystalline form. Alternatively, delayed absorption of a parenterally administered drug form can be accomplished by dissolving or suspending the drug in an oil vehicle.

For intramuscular preparations, a sterile formulation of compounds, preferably a compound of Formula A-I or Formula A-II in conjunction with a β-lactam antibiotic, or suitable soluble salt forms thereof, for example hydrochloride salts, can be dissolved and administered in a pharmaceutical diluent such as Water-for-Injection (WFI), physiological saline or 5% glucose. A suitable insoluble form of the compound may be prepared and administered as a suspension in an aqueous base or a pharmaceutically acceptable oil base, e.g., an ester of a long chain fatty acid such as ethyl oleate.

A dose of an intravenous, intramuscular, or parental formulation of compounds, preferably a compound of Formula A-I or Formula A-II in conjunction with a β-lactam antibiotic, may be administered as a bolus or by slow infusion. A bolus is a dose that is administered in less than 30 minutes. In one embodiment, a bolus is administered in less than 15 or less than 10 minutes. In another embodiment, a bolus is administered in less than 5 minutes. In yet another embodiment, a bolus is administered in one minute or less. An infusion is a dose that is administered at a rate of 30 minutes or greater. In one embodiment, the infusion is one hour or greater. In another embodiment, the infusion is substantially constant.

For topical use the pharmaceutical compositions, preferably a compound of Formula A-I or Formula A-II in conjunction with a β-lactam antibiotic, can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the pharmaceutical composition can be presented in liquid or semi-liquid form formulated in hydrophobic or hydrophilic bases as ointments, creams, lotions, paints or powders.

For rectal administration, the pharmaceutical compositions, preferably a compound of Formula A-I or Formula A-II in conjunction with a β-lactam antibiotic, can be administered in the form of suppositories admixed with conventional carriers such as cocoa butter, polyethylene glycol or a suppository wax or other glyceride that are solid at room temperature but liquid at body temperature and therefore melt in the rectum or vaginal cavity and release the active compound.

Alternatively, the pharmaceutical compositions can be in powder form for reconstitution in the appropriate pharmaceutically acceptable carrier at the time of delivery. In another embodiment, the unit dosage form of compounds, preferably a compound of Formula A-I or Formula A-II in conjunction with a β-lactam antibiotic, can be a solution of one or more compounds, or salts thereof, in a suitable diluent, in sterile hermetically sealed ampoules or sterile syringes. The concentration of the compounds, preferably a compound of Formula A-I or Formula A-II in conjunction with a β-lactam antibiotic, in the unit dosage may vary, e.g. from about 1 percent to about 50 percent, depending on the compound used and its solubility and the dose desired by the physician. If the compositions contain dosage units, each dosage unit can contain from 1-500 mg of the active material. For adult human treatment, the dosage employed can range from 5 mg to 10 g, per day, depending on the route and frequency of administration.

The pharmaceutical compositions disclosed herein can be placed in a pharmaceutically acceptable carrier and are delivered to a recipient subject (e.g., a human) in accordance with known methods of drug delivery. In general, the methods of delivering the pharmaceutical compositions in vivo utilize art-recognized protocols for delivering the agent with the only substantial procedural modification being the substitution of the compounds of the present invention for the drugs in the art-recognized protocols. Likewise, methods for using the claimed compositions for treating cells in culture, for example, to eliminate or reduce the level of bacterial contamination of a cell culture, utilize art-recognized protocols for treating cell cultures with antibacterial agent(s) with the only substantial procedural modification being the substitution of the compounds of the present invention, preferably in combination with a β-lactam antibiotic for the drugs in the art-recognized protocols.

Exemplary procedures for delivering an antibacterial agent are described in U.S. Pat. Nos. 6,468,967; 6,852,689; and 5,041,567, issued to Rogers and in PCT patent application number EP94/02552 (publication no. WO 95/05384), the disclosures of which are incorporated herein by reference in their entirety. In one embodiment, one or more compounds of the invention, preferably a compound of Formula A-I or Formula A-II in conjunction with a β-lactam antibiotic, or pharmaceutical compositions thereof are administered orally, rectally or via injection (intravenous, intramuscular or subcutaneous). In another embodiment, one or more compounds of the invention, preferably a compound of Formula A-I or Formula A-II in conjunction with a β-lactam antibiotic, or pharmaceutical compositions thereof are administered orally, rectally or via injection (intravenous, intramuscular or subcutaneous) to treat an infection caused by β-lactam resistant bacteria. In another embodiment, one or more compounds of the invention, preferably a compound of Formula A-I or Formula A-II in conjunction with a β-lactam antibiotic, or pharmaceutical compositions thereof are administered orally to treat an infection caused by β-lactamase producing bacteria.

As used herein, the phrases "therapeutically-effective dose" and "therapeutically-effective amount" refer to an amount of a compound that prevents the onset, alleviates the symptoms, stops the progression of a bacterial infection, or results in another desired biological outcome such as, e.g., improved clinical signs or reduced/elevated levels of lymphocytes and/or antibodies.

The term "treating" or "treatment" is defined as administering, to a subject, a therapeutically-effective amount of one or more compounds both to prevent the occurrence of an infection and to control or eliminate an infection. Those in need of treatment may include individuals already having a particular medical disease as well as those at risk for the disease (i.e., those who are likely to ultimately acquire the disorder).

The term "subject," as used herein, refers to a mammal, a plant, a lower animal, or a cell culture. In one embodiment, a subject is a human or other animal patient in need of antibacterial treatment.

The term "administering" or "administration" and the like, refers to providing the compound of the invention (e.g. compounds of Formula I, compounds of Formula A-I, compounds of Formula II, compounds of Formula A-II) to the subject in need of treatment. Preferably the subject is a mammal, more preferably a human. The present invention comprises administering the compound of the invention (e.g. compounds of Formula I, compounds of Formula A-I, compounds of Formula II, compounds of Formula A-II) in conjunction with a β-lactam antiobiotic. When a compound of the invention (e.g. compounds of Formula I, compounds of Formula A-I, compounds of Formula II, compounds of Formula A-II) is administered in conjunction with a β-lactam antiobiotic, the compound of the invention (e.g. compounds of Formula I, compounds of Formula A-I, compounds of Formula II, compounds of Formula A-II) and the β-lactam antiobiotic can be administered at the same time or different times. When the compounds of the invention (e.g. compounds of Formula I, compounds of Formula A-I, compounds of Formula II, compounds of Formula A-II) and the β-lactam antiobiotic are administered at the same time, they can be administered as a single composition or pharmaceutical composition or they can be administered separately. It is understood that when a compound of the invention (e.g. compounds of Formula I, compounds of Formula A-I, compounds of Formula II, compounds of Formula A-II) is administered in conjunction with a β-lactam antibiotic, that the active agents can be administered in a single combination or in multiple combinations. For example, when administered by IV, the compound of the invention (e.g. compounds of Formula I, compounds of Formula A-I, compounds of Formula II, compounds of Formula A-II) can be dissolved or suspended in any of the commonly used intravenous fluids and administered by infusion, then a β-lactam antibiotic can be dissolved or suspended in any of the commonly used intravenous fluids and administered by infusion. Conversely the β-lactam antibiotic can be dissolved or suspended in any of the commonly used intravenous fluids and administered by infusion, then a compound of Formula I can be dissolved or suspended in any of the commonly used intravenous fluids and administered by infusion. Alternatively, a pharmaceutical composition comprising a compound of the invention (e.g. compounds of Formula I, compounds of Formula A-I, compounds of Formula II, compounds of Formula A-II) and a β-lactam antibiotic can be dissolved or suspended in any of the commonly used intravenous fluids and administered by infusion.

In one embodiment of the invention, is provided a method of treating or preventing a bacterial infection comprising administering to a subject in need thereof a therapeutically-effective amount of the pharmaceutical composition comprising a compound of the invention (e.g. compounds of Formula I, compounds of Formula A-I, compounds of Formula II, compounds of Formula A-II) and a β-lactam antibiotic. In one embodiment of the invention, is provided a method of treating or preventing a bacterial infection comprising administering to a subject in need thereof a therapeutically-effective amount of the pharmaceutical composition comprising a compound of Formula I, and a β-lactam antibiotic. In one embodiment of the invention, is provided a method of treating or preventing a bacterial infection comprising administering to a subject in need thereof a therapeutically-effective amount of the pharmaceutical composition comprising a compound of Formula A-I, and a β-lactam antibiotic. In one embodiment of the invention, is provided a method of treating or preventing a bacterial infection comprising administering to a subject in need thereof a therapeutically-effective amount of the pharmaceutical composition comprising a compound of Formula II, and a β-lactam antibiotic. In one embodiment of the invention, is provided a method of treating or preventing a bacterial infection comprising administering to a subject in need thereof a therapeutically-effective amount of the pharmaceutical composition comprising a compound of Formula A-II, and a β-lactam antibiotic.

In one embodiment of the invention, is provided a method of treating or preventing a bacterial infection comprising administering to a subject in need thereof, a therapeutically-effective amount of a β-lactam antibiotic in conjunction with a compound of the invention (e.g. compounds of Formula I, compounds of Formula A-I, compounds of Formula II, compounds of Formula A-II). In one embodiment of the invention, is provided a method of treating or preventing a bacterial infection comprising administering to a subject in need thereof, a therapeutically-effective amount of a β-lactam antibiotic in conjunction with a compound of Formula I. In one embodiment of the invention, is provided a method of treating or preventing a bacterial infection comprising administering to a subject in need thereof, a therapeutically-effective amount of a β-lactam antibiotic in conjunction with a compound of Formula A-I. In one embodiment of the invention, is provided a method of treating or preventing a bacterial infection comprising administering to a subject in need thereof, a therapeutically-effective amount of a β-lactam antibiotic in conjunction with a compound of Formula II. In one embodiment of the invention, is provided a method of treating or preventing a bacterial infection comprising administering to a subject in need thereof, a therapeutically-effective amount of a β-lactam antibiotic in conjunction with a compound of Formula A-II. In one embodiment of the invention, is provided a method of treating or preventing a bacterial infection comprising administering to a subject in need thereof, a therapeutically-effective amount of a β-lactam antibiotic in conjunction with a compound of Table I. In one embodiment of the invention, is provided a method of treating or preventing a bacterial infection comprising administering to a subject in need thereof, a therapeutically-effective amount of a β-lactam antibiotic in conjunction with a compound of Formula

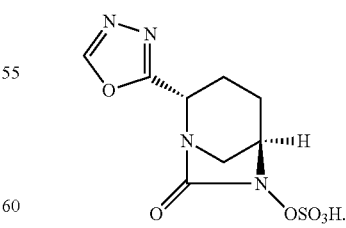

In one embodiment of the invention, is provided a method of treating or preventing a bacterial infection comprising administering to a subject in need thereof, a therapeutically-effective amount of a β-lactam antibiotic in conjunction with a compound of Formula

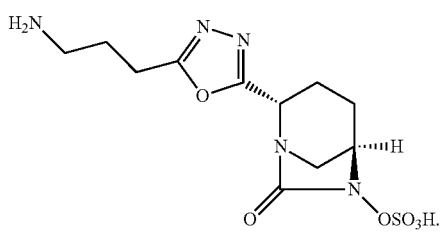

In one embodiment of the invention, is provided a method of treating or preventing a bacterial infection comprising administering to a subject in need thereof, a therapeutically-effective amount of a β-lactam antibiotic in conjunction with a compound of Formula

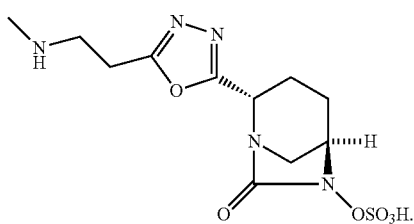

In one embodiment of the invention, is provided a method of treating or preventing a bacterial infection comprising administering to a subject in need thereof, a therapeutically-effective amount of a β-lactam antibiotic in conjunction with a compound of Formula

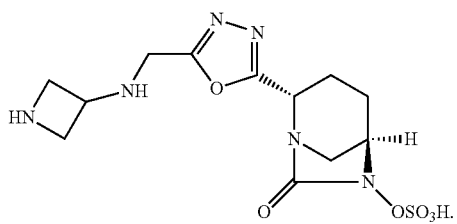

In one embodiment of the invention, is provided a method of treating or preventing a bacterial infection comprising administering to a subject in need thereof, a therapeutically-effective amount of a β-lactam antibiotic in conjunction with a compound of Formula

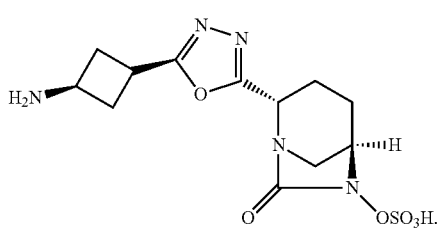

In one embodiment of the invention, is provided a method of treating or preventing a bacterial infection in a subject comprising the steps of
  a. administering to the subject a compound of the invention; and
  b. administering to the subject a therapeutically-effective amount of a β-lactam antibiotic.

In one embodiment the compound in step a is a compound of Formula I. In one embodiment the compound in step a is a compound of Formula A-I. In one embodiment the compound in step a is a compound of Formula II. In one embodiment the compound in step a is a compound of Formula A-II. In one embodiment the compound in step a is a compound of Table I. In one embodiment the compound in step a is a compound of Formula A-II. In one embodiment the compound in step a is a compound of Formula

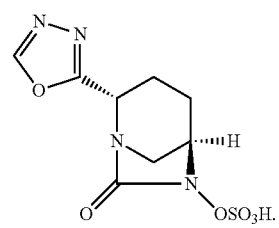

In one embodiment the compound in step a is a compound of Formula

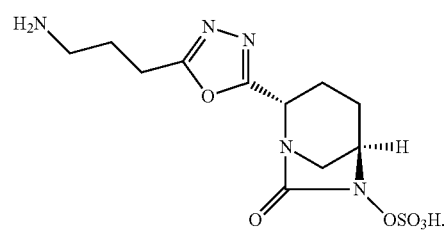

In one embodiment the compound in step a is a compound of Formula

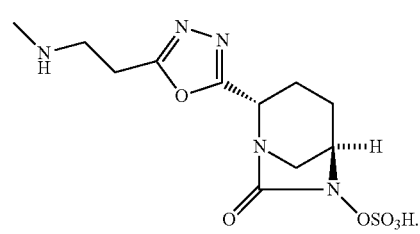

In one embodiment the compound in step a is a compound of Formula

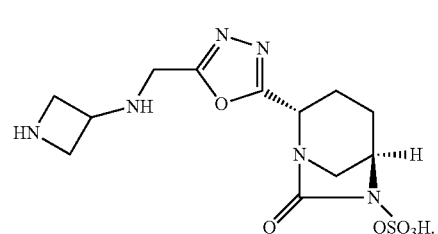

In one embodiment the compound in step a is a compound of Formula

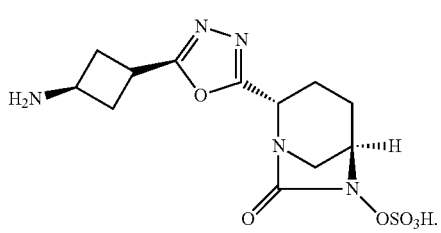

In one embodiment, the β-lactam antibiotic in step b is Ceftolozane, Ceftazidime, Aztreonam or Meropenem, or more preferably, Ceftolozane or Ceftazidime.

In one embodiment the compound in step a is a compound of Formula

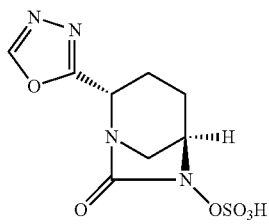

and the β-lactam antibiotic in step b is Ceftolozane. In one embodiment the compound in step a is a compound of Formula

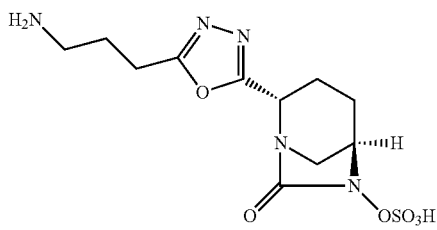

and the β-lactam antibiotic in step b is Ceftolozane.

In one embodiment the compound in step a is a compound of Formula

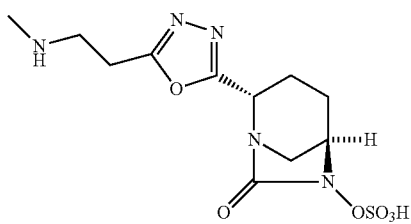

and the β-lactam antibiotic in step b is Ceftolozane.

In one embodiment the compound in step a is a compound of Formula

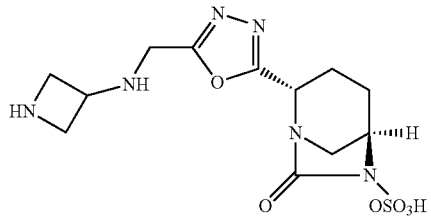

and the β-lactam antibiotic in step b is Ceftolozane.

In one embodiment the compound in step a is a compound of Formula

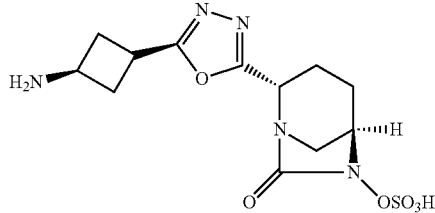

and the ft-lactam antibiotic in step b is Ceftolozane.

In one embodiment of the invention, is provided a method of treating or preventing a bacterial infection in a subject comprising the steps of
a. administering to the subject a therapeutically-effective amount of a β-lactam antibiotic; and
b. administering to the subject a compound of the invention.

In one embodiment the compound in step b is a compound of Formula I. In one embodiment the compound in step b is a compound of Formula A-I. In one embodiment the compound in step b is a compound of Formula II. In one embodiment the compound in step b is a compound of Formula A-II. In one embodiment the compound in step b is a compound of Formula II. In one embodiment the compound in step b is a compound of Table I. In one embodiment the compound in step b is a compound of Formula

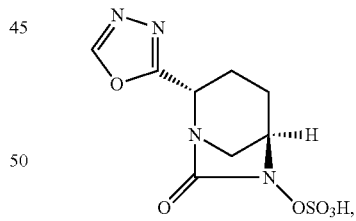

In one embodiment the compound in step b is a compound of Formula

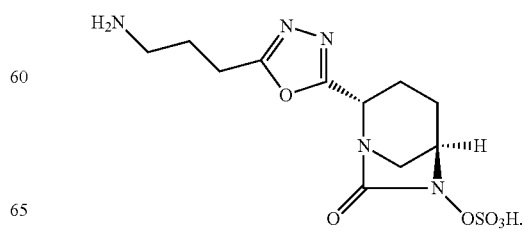

In one embodiment the compound in step b is a compound of Formula

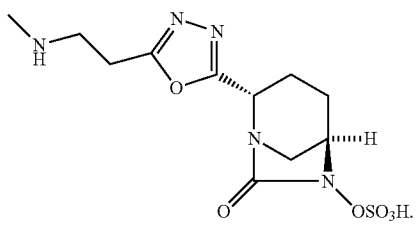

In one embodiment the compound in step b is a compound of Formula

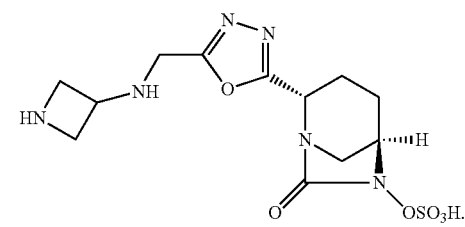

In one embodiment the compound in step b is a compound of Formula

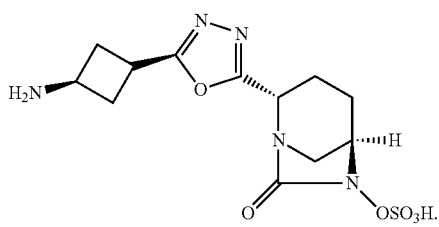

In one embodiment, the β-lactam antibiotic in step a is Ceftolozane, Ceftazidime, Aztreonam or Meropenem, or more preferably, Ceftolozane or Ceftazidime. In one embodiment the compound in step b is a compound of Formula

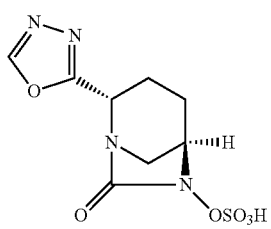

and the β-lactam antibiotic in step a is Ceftolozane. In one embodiment the compound in step b is a compound of Formula

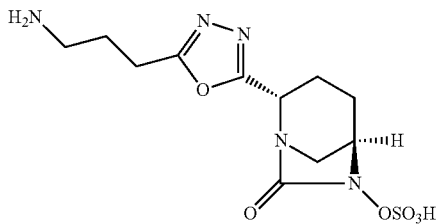

and the β-lactam antibiotic in step a is Ceftolozane.

In one embodiment the compound in step b is a compound of Formula

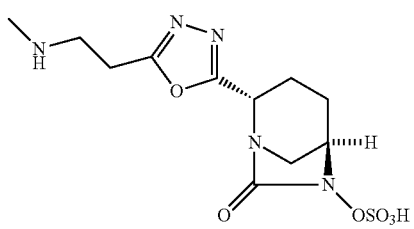

and the β-lactam antibiotic in step a is Ceftolozane.

In one embodiment the compound in step b is a compound of Formula

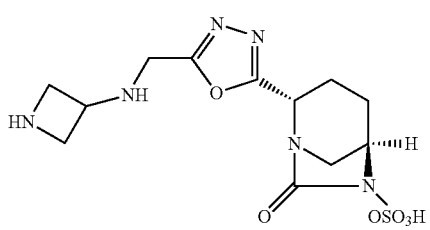

and the β-lactam antibiotic in step a is Ceftolozane.

In one embodiment the compound in step b is a compound of Formula

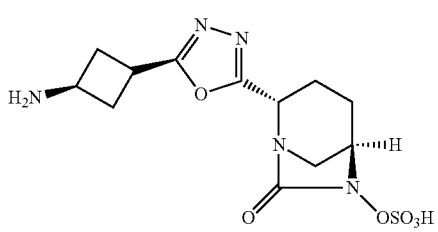

and the β-lactam antibiotic in step a is Ceftolozane.

In one embodiment, the invention provides a method for treating an infection in a subject by administering a therapeutically-effective amount of one or more compounds of the invention (e.g. compounds of Formula I, compounds of Formula A-I, compounds of Formula II, compounds of Formula A-II), preferably a compound of Formula A-I or Formula A-II in conjunction with a β-lactam antibiotic, or compositions thereof. In one embodiment, the method comprises administering to a subject in need thereof a pharmaceutical composition comprising at least one of the compounds described herein, preferably a compound of Formula A-I or Formula A-II in conjunction with a β-lactam antibiotic. In one embodiment the compound is of Formula

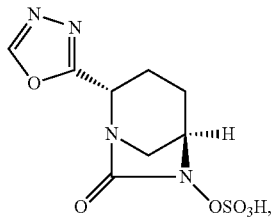

in conjunction with a β-lactam antibiotic, preferably Ceftolozane, Ceftazidime, Aztreonam or Meropenem, or more preferably, Ceftolozane or Ceftazidime, or compositions thereof. In one embodiment the compound is of Formula

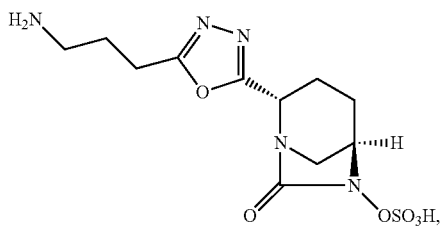

in conjunction with a β-lactam antibiotic, preferably Ceftolozane, Ceftazidime, Aztreonam or Meropenem, or more preferably, Ceftolozane or Ceftazidime, or compositions thereof. In one embodiment the compound is of Formula

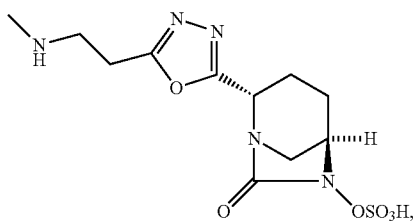

in conjunction with a β-lactam antibiotic, preferably Ceftolozane, Ceftazidime, Aztreonam or Meropenem, or more preferably, Ceftolozane or Ceftazidime, or compositions thereof. In one embodiment the compound is of Formula

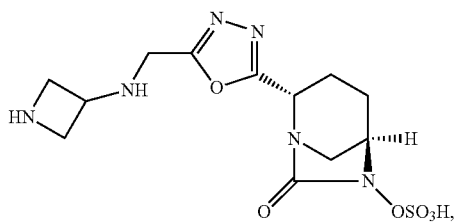

in conjunction with a β-lactam antibiotic, preferably Ceftolozane, Ceftazidime, Aztreonam or Meropenem, or more preferably, Ceftolozane or Ceftazidime, or compositions thereof. In one embodiment the compound is of Formula

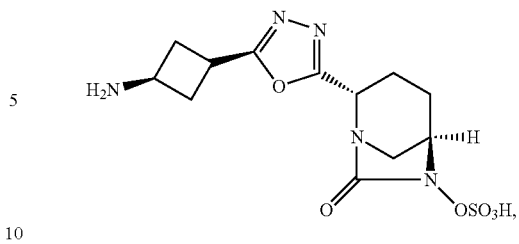

in conjunction with a β-lactam antibiotic, preferably Ceftolozane, Ceftazidime, Aztreonam or Meropenem, or more preferably, Ceftolozane or Ceftazidime, or compositions thereof. In one embodiment, the pharmaceutical composition can comprise any one of the compounds described herein as the sole active compound or in combination with another compound, composition, or biological material. The compound may be administered orally, parenterally, by inhalation, topically, rectally, nasally, buccally, vaginally, or by an implanted reservoir, external pump or catheter. The compound may be prepared for ophthalmic or aerosolized uses. The compounds of the present invention can be administered as an aerosol for the treatment of pneumonia or other lung-based infections. In one embodiment, the aerosol delivery vehicle is an anhydrous or dry powder inhaler. One or more compounds of the invention (e.g. compounds of Formula I, compounds of Formula A-I, compounds of Formula II, compounds of Formula A-II), preferably a compound of Formula A-I or Formula A-II in conjunction with a β-lactam antibiotic, or pharmaceutical compositions thereof also may be directly injected or administered into an abscess, ventricle or joint. Parenteral administration includes subcutaneous, intravenous, intramuscular, intra-articular, intra-synovial, cisternal, intrathecal, intrahepatic, intralesional and intracranial injection or infusion. In one embodiment, one or more compounds of the invention (e.g. compounds of Formula I, compounds of Formula A-I, compounds of Formula II, compounds of Formula A-II), preferably a compound of Formula A-I or Formula A-II in conjunction with a β-lactam antibiotic, are administered intravenously, subcutaneously or orally. In one embodiment for administering one or more compounds according to the invention (e.g. compounds of Formula I, compounds of Formula A-I, compounds of Formula II, compounds of Formula A-II), preferably a compound of Formula A-I or Formula A-II in conjunction with a β-lactam antibiotic to a cell culture, the one or more compounds may be administered in a nutrient medium.

In one embodiment, one or more compounds according to the invention (e.g. compounds of Formula I, compounds of Formula A-I, compounds of Formula II, compounds of Formula A-II), preferably a compound of Formula A-I or A-II in conjunction with a β-lactam antibiotic, may be used to treat a subject having a bacterial infection in which the infection is caused or exacerbated by any type of bacteria, such as Gram-negative bacteria. In one aspect of the invention, the bacterial infection is caused by β-lactam resistant bacteria. In one aspect the bacterial infection is caused by β-lactamase producing bacteria. In another aspect the bacterial infection is caused by class A, class C or class D β-lactamase producing bacteria. In another aspect the bacterial infection is caused by class A β-lactamase producing bacteria. In another aspect the infection is caused by class C β-lactamase producing bacteria. In still another aspect the infection is caused by class D β-lactamase producing bacteria. In still another aspect the infection is caused by KPC β-lactamase producing bacteria. In still another aspect the infection is caused by OXA β-lactamase producing bacteria. In still another aspect, the bacterial infection is caused by a bacteria that produces multiple β-lactamases. Bacteria that produce multiple β-lactamases may produce β-lactamases of the same class or of different classes (e.g class A and class A or class A and class C or class A and class D etc).

Representative Gram-negative pathogens known to express β-lactamases include, but are not limited to *Acinetobacter* spp. (including *Acinetobacter baumannii*), *Citrobacter* spp., *Escherichia* spp. (including *Escherichia coli*), *Haemophilus influenzae, Morganella morganii, Pseudomonas aeruginosa, Klebsiella* spp. (including *Klebsiella pneumoniae*), *Enterobacter* spp. (including *Enterobacter cloacae* and *Enterobacter aerogenes*), *Pasteurella* spp., *Proteus* spp. (including *Proteus mirabilis*), *Serratia* spp. (including *Serratia marcescens*), and *Providencia* spp. Bacterial infections can be caused or exacerbated by Gram-negative bacteria including strains which express β-lactamases that may confer resistance to penicillins, cephalosporins, monobactams and/ or carbapenems. The co-administration of a novel BLI that inhibits these β-lactamases with a β-lactam antibiotic could be used to treat infections caused by β-lactam resistant bacteria.

In one aspect of the invention the infection is caused by a β-lactamase producing bacteria selected from *Acinetobacter* spp, *Citrobacter* spp, *Escherichia coli, Enterobacter cloacae*), *Haemophilus influenzae, Pseudomonas aeruginosa, Proteus mirabilis, Serratia marcescens*, and *Klebsiella pneumoniae*, β-Lactam antibiotics that may be administered concurrently with compounds of the invention (e.g. compounds of Formula I, compounds of Formula A-I, compounds of Formula II, compounds of Formula A-II) include, but are not limited to cephalosporin, carbapenem, monobactam, penem and penicillin classes of antibiotics.

In one embodiment of the invention, the β-lactam antibiotic is a cephalosporin. Examples of cephalosporins include, but are not limited to, Cefacetrile (cephacetrile), Cefadroxil (cefadroxyl), Cefalexin (cephalexin), Cefaloglycin (cephaloglycin), Cefalonium (cephalonium), Cefaloridine (cephaloradine), Cefalotin (cephalothin), Cefapirin (cephapirin), Cefatrizine, Cefazaflur, Cefazedone, Cefazolin (cephazolin), Cefradine (cephradine), Cefroxadine, Ceftezole, Cefaclor, Cefamandole, Cefmetazole, Cefonicid, Cefotetan, Cefoxitin, Cefprozil (cefproxil), Cefuroxime, Cefuzonam, Cefcapene, Cefdaloxime, Cefdinir, Cefditoren, Cefetamet, Cefixime, Cefmenoxime, Cefodizime, Cefotaxime, Cefpimizole, Cefpodoxime, Cefteram, Ceftibuten, Ceftiofur, Ceftiolene, Ceftizoxime, Ceftriaxone, Cefoperazone, Ceftazidime, Cefclidine, Cefepime, Cefluprenam, Cefoselis, Cefozopran, Cefpirome, Cefquinome, Cefaclomezine, Cefaloram, Cefaparole, Cefcanel, Cefedrolor, Cefempidone, Cefetrizole, Cefivitril, Cefmatilen, Cefmepidium, Cefovecin, Cefoxazole, Cefrotil, Cefsumide, Ceftaroline, Ceftioxide, Cefuracetime, cefbuperazone, cefminox, ceforanide, cefotiam, cefpiramide, cefsulodin, ceftobiprole latamoxef, loracarbef and Ceftolozane. In one embodiment the cephalosporin is Ceftolozane or Ceftazidime.

In one embodiment of the invention, the β-lactam antibiotic is a carbapen. Examples of carbapenem antibiotics include, but are not limited to, Imipenem, Imipenem/Cilastatin, Biapenem, Doripenem, Meropenem, Ertapenem and Panipenem. In one embodiment the Carbapenem is Imipenem/Cilastatin or Meropenem.

In one embodiment of the invention, the β-lactam antibiotic is a monobactam. Examples of monobactam antibiotics include, but are not limited to Aztreonam, Tigemonam, Carumonam, BAL30072 and Nocardicin A.

In one embodiment of the invention, the β-lactam antibiotic is a penem. In one embodiment of the invention, the β-lactam antibiotic is a penicillin. Examples of penicillin antibiotics include, but are not limited to Amoxicillin, Ampicillin, Azlocillin, Mezlocillin, Apalcillin, Hetacillin, Becampicillin, Carbenicillin, Sulbenicillin, Ticarcillin, Piperacillin, Azlocillin, Mecillinam, Pivmecillinam, Methicillin, Ciclacillin, Talampicillin, Aspoxicillin, Oxacillin, Cloxacillin, Dicloxacillin, Flucloxacillin, Nafcillin and Pivampicillin.

In one embodiment the cephalosporin is Ceftolozane, Ceftazidime, Aztreonam or Meropenem, or more preferably, Ceftolozane or Ceftazidime.

The pharmaceutical compositions, preferably a compound of the invention (e.g. compounds of Formula I, compounds of Formula A-I, compounds of Formula II, compounds of Formula A-II) in conjunction with a β-lactam antibiotic, can be used to treat a bacterial infection of any organ or tissue in the body caused by β-lactam resistant bacteria, preferably, Gram-negative β-lactam resistant bacteria. These organs or tissue include, without limitation, skeletal muscle, skin, bloodstream, kidneys, heart, lung and bone. For example, a pharmaceutical composition comprising at least one compound of the invention (e.g. compounds of Formula I, compounds of Formula A-I, compounds of Formula II, compounds of Formula A-II), preferably a compound of Formula A-I or Formula A-II in conjunction with a β-lactam antibiotic, can be administered to a subject to treat, without limitation, skin and soft tissue infections (e.g., complex skin infections), bacteremia, intra-abdominal infections and urinary tract infections (e.g., cUTI). In addition, a compound of the invention (e.g. compounds of Formula I, compounds of Formula A-I, compounds of Formula II, compounds of Formula A-II) may be used to treat community acquired respiratory infections, including, without limitation, otitis media, sinusitis, chronic bronchitis and pneumonia (including community-acquired pneumonia, hospital-acquired pneumonia and ventilator associated pneumonia), including pneumonia caused by drug-resistant *Pseudomonas aeruginosa*. At least one compound of the invention (e.g. compounds of Formula I, compounds of Formula A-I, compounds of Formula II, compounds of Formula A-II), preferably a compound of Formula A-I or Formula A-II in conjunction with a β-lactam antibiotic, can be administered to a subject to treat mixed infections that comprise different types of Gram-negative bacteria, or which comprise both Gram-positive and Gram-negative bacteria. These types of infections include intra-abdominal infections and obstetrical/gynecological infections. At least one compound of the invention (e.g. compounds of Formula I, compounds of Formula A-I, compounds of Formula II, compounds of Formula A-II), preferably a compound of Formula A-I or Formula A-II in conjunction with a β-lactam antibiotic, may also be administered to a subject to treat an infection including, without limitation, endocarditis, nephritis, septic arthritis, intra-abdominal sepsis, bone and joint infections and osteomyelitis. At least one compound of the invention (e.g. compounds of Formula I, compounds of Formula A-I, compounds of Formula II, compounds of Formula A-II), preferably compound of Formula A-I or Formula A-II in conjunction with a β-lactam antibiotic, or pharmaceutical compositions thereof, may also be directly injected or administered into an abscess, ventricle or joint. Pharmaceutical compositions of the invention (e.g. compounds of Formula I, compounds of Formula A-I, compounds of Formula II, compounds of Formula A-II), preferably compound of Formula A-I or Formula A-II in conjunction with a β-lactam antibiotic, may be administered as an aerosol for the treatment of pneumonia or other lung-based infections. In one embodiment, the aerosol delivery vehicle is an anhydrous, liquid or dry powder inhaler.

Actual dosage levels of active ingredients in the pharmaceutical compositions of one or more compounds according to the invention (e.g. compounds of Formula I, compounds of Formula A-I, compounds of Formula II, compounds of Formula A-II), preferably a compound of Formula A-I or Formula A-II in conjunction with a β-lactam antibiotic, may be varied so as to obtain a therapeutically-effective amount of the active compound(s) to achieve the desired therapeutic response for a particular patient, compositions, and mode of administration. The effective amount can be determined as described herein. The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. In one embodiment, the data obtained from the assays can be used in formulating a range of dosage for use in humans. It will be understood by one of skill in the art that the when the composition comprises a compound of the invention (e.g. compounds of Formula I, compounds of Formula A-I, compounds of Formula II, compounds of Formula A-II) and a β-lactam antibiotic, both the compound of the invention (e.g. compounds of Formula I, compounds of Formula A-I, compounds of Formula II, compounds of Formula A-II) and the β-lactam antibiotic are active compounds.

The method comprises administering to the subject an effective dose of one or more compounds of the invention (e.g. compounds of Formula I, compounds of Formula A-I, compounds of Formula II, compounds of Formula A-II), preferably in conjunction with a β lactam antibiotic. An effective dose of a compound of the invention (e.g. compounds of Formula I, compounds of Formula A-I, compounds of Formula II, compounds of Formula A-II) is generally between 125 mg/day to 2000 mg/day. In one embodiment, an effective dose is from about 0.1 to about 100 mg/kg of one or more compounds of the invention (e.g. compounds of Formula I, compounds of Formula A-I, compounds of Formula II, compounds of Formula A-II) or pharmaceutically acceptable salts thereof. In one embodiment, the dose is from about 0.1 to about 50 mg/kg of one or more compounds of the invention (e.g. compounds of Formula I, compounds of Formula A-I, compounds of Formula II, compounds of Formula A-II) or pharmaceutically acceptable salts thereof. In another embodiment, the dose is from about 1 to about 25 mg/kg of one or more compounds of the invention (e.g. compounds of Formula I, compounds of Formula A-I, compounds of Formula II, compounds of Formula A-II) or pharmaceutically acceptable salts thereof. In another embodiment, the dose is from about 1 to about 12 mg/kg of one or more compounds of the invention (e.g. compounds of Formula I, compounds of Formula A-I, compounds of Formula II, compounds of Formula A-II). In another embodiment, the dose is about 1, 2, 3, 4, 5, 6, 7, 8, 9, 10, 11, or 12 mg/kg of one or more compounds of the invention (e.g. compounds of Formula I, compounds of Formula A-I, compounds of Formula II, compounds of Formula A-II). In another embodiment, the compounds of the invention (e.g. compounds of Formula I, compounds of Formula A-I, compounds of Formula II, compounds of Formula A-II) are administered to a human at a dose of 100 mg to 1000 mg per dose up to four times per day. In another embodiment, the compounds of the invention (e.g. compounds of Formula I, compounds of Formula A-I, compounds of Formula II, compounds of Formula A-II) are administered to a human at a dose of 125 mg to 750 mg per dose up to four times per day. In another embodiment, the compounds of the invention (e.g. compounds of Formula I, compounds of Formula A-I, compounds of Formula II, compounds of Formula A-II) are administered to a human at a dose of 250 mg to 500 mg per dose up to four times a day. An effective dose for cell culture is usually between about 0.1 and about 1000 μg/mL. In one embodiment, the effect dose for cell culture is between about 0.1 and about 200 μg/mL.

In one embodiment, a β-lactam antibiotic and a compound of the invention (e.g. compounds of Formula I, compounds of Formula A-I, compounds of Formula II, compounds of Formula A-II) are administered in ratio of 1:4 to 8:1 antibiotic: compound of the invention (e.g. compounds of Formula I, compounds of Formula A-I, compounds of Formula II, compounds of Formula A-II). In one embodiment the ratio is 1:4. In another embodiment the ratio is 3:4. In another embodiment the ratio is 5:4. In another embodiment the ratio is 7:4. In another embodiment the ratio is 1:2. In another embodiment the ratio is 3:2. In another embodiment the ratio is 5:2. In another embodiment the ratio is 7:2. In another embodiment the ratio is 1:3. In another embodiment the ratio is 2:3. In another embodiment the ratio is 4:3. In another embodiment the ratio is 5:3. In another embodiment the ratio is 7:3. In another embodiment the ratio is 1:2. In another embodiment the ratio is 3:2. In another embodiment the ratio is 5:2. In another embodiment the ratio is 7:2. In another embodiment the ratio is 1:1. In another embodiment the ratio is 2:1. In another embodiment the ratio is 3:1. In another embodiment the ratio is 4:1. In another embodiment the ratio is 5:1. In another embodiment the ratio is 6:1. In another embodiment the ratio is 7:1. In another embodiment the ratio is 8:1. It will be understood by one of skill in the art that the β-lactam antibiotic and compound of the invention (e.g. compounds of Formula I, compounds of Formula A-I, compounds of Formula II, compounds of Formula A-II) can be administered within the range of ratios provided regardless of the method of drug delivery. It will also be understood by one of skill in the art that the β-lactam antibiotic and compound of the invention (e.g. compounds of Formula I, compounds of Formula A-I, compounds of Formula II, compounds of Formula A-II) can be administered within the range of ratios provided together, for example, in a pharmaceutical composition, or sequentially, i.e. the β-lactam antibiotic is administered, followed by administration of a compound of the invention (e.g. compounds of Formula I, compounds of Formula A-I, compounds of Formula II, compounds of Formula A-II) or vice versa.

One or more compounds of the invention (e.g. compounds of Formula I, compounds of Formula A-I, compounds of Formula II, compounds of Formula A-II) may also be administered in the diet or feed of a patient or animal. If administered as part of a total dietary intake, the amount of compound employed can be less than 1% by weight of the diet, such as no more than 0.5% by weight. The diet for animals can be normal foodstuffs to which the compound can be added or it can be added to a premix.

One or more compounds of the invention (e.g. compounds of Formula I, compounds of Formula A-I, compounds of Formula II, compounds of Formula A-II), preferably a compound of Formula A-I or Formula A-II in conjunction with a β-lactam antibiotic, can be administered as a single daily dose or in multiple doses per day. In one embodiment, one or more compounds of the invention (e.g. compounds of Formula I, compounds of Formula A-I, compounds of Formula II, compounds of Formula A-II), preferably a compound of Formula A-I or Formula A-II in conjunction with a β-lactam antibiotic, is administered as a single dose per day. In another embodiment, one or more compounds of the invention (e.g. compounds of Formula I, compounds of Formula A-I, compounds of Formula II, compounds of Formula A-II), preferably a compound of Formula A-I of Formula A-II in conjunction with a β-lactam antibiotic is administered as two equal doses per day. In another embodiment, the compounds of the invention (e.g. compounds of Formula I, compounds of Formula A-I, compounds of Formula II, compounds of Formula A-II), preferably a compound of Formula A-I or Formula A-II in conjunction with a β-lactam antibiotic is administered in three equal doses per day. In another embodiment, the compounds of the invention (e.g. compounds of Formula I, compounds of Formula A-I, compounds of Formula II, compounds of Formula A-II), preferably a compound of Formula A-I or Formula A-II in conjunction with a β-lactam antibiotic is administered in four equal doses per day. The treatment regime may require administration over extended periods of time, e.g., for several days or for from two to four weeks. The amount per administered dose or the total amount administered will depend on such factors as the nature and severity of the infection, the age and general health of the patient, the tolerance of the patient to the compound of the invention and the β-lactam antibiotic and the microorganism or microorganisms involved in the infection. The treatment regimen for one type of infection may differ greatly from the treatment regimen of another infection. For example, one type of infection may require administration via intravenous administration once daily, while another infection may require a treatment regimen of multiple dosing orally.

One or more compounds of the invention (e.g. compounds of Formula I, compounds of Formula A-I, compounds of Formula II, compounds of Formula A-II), preferably a compound of Formula A-I or Formula A-II in conjunction with a β-lactam antibiotic, may be administered according to this method until the bacterial infection is eradicated or reduced. In one embodiment, one or more compounds of the invention (e.g. compounds of Formula I, compounds of Formula A-I, compounds of Formula II, compounds of Formula A-II), preferably a compound of Formula A-I or Formula A-II in conjunction with a β-lactam antibiotic, are administered for a period of time from 3 days to 6 months. In another embodiment, one or more compounds of the invention (e.g. compounds of Formula I, compounds of Formula A-I, compounds of Formula II, compounds of Formula A-II), preferably a compound of Formula A-I or Formula A-II in conjunction with a β-lactam antibiotic, are administered for 7 to 56 days. In another embodiment, one or more compounds of the invention (e.g. compounds of Formula I, compounds of Formula A-I, compounds of Formula II, compounds of Formula A-II), preferably a compound of Formula A-I or Formula A-II in conjunction with a β-lactam antibiotic, are administered for 7 to 28 days. In a further embodiment, one or more compounds of the invention (e.g. compounds of Formula I, compounds of Formula A-I, compounds of Formula II, compounds of Formula A-II), preferably a compound of Formula A-I or Formula A-II in conjunction with a β-lactam antibiotic, are administered for 7 to 14 days. Compounds of the present invention may be administered for a longer or shorter time period if it is so desired.

Other embodiments of the invention include:

A pharmaceutical composition comprising a compound of the invention (e.g. compounds of Formula I, compounds of Formula A-I, compounds of Formula II, compounds of Formula A-II), preferably a compound of Formula A-I or Formula A-II and at least 1 β-lactam antibiotic or a pharmaceutically acceptable salt thereof.

A pharmaceutical composition comprising a compound of the invention (e.g. compounds of Formula I, compounds of Formula A-I, compounds of Formula II, compounds of Formula A-II), preferably a compound of Formula A-I or Formula A-II and at least 1 cephalosporin antibiotic or a pharmaceutically acceptable salt thereof.

A pharmaceutical composition comprising a compound of the invention (e.g. compounds of Formula I, compounds of Formula A-I, compounds of Formula II, compounds of Formula A-II), preferably a compound of Formula A-I or Formula A-II and Ceftolozane or a pharmaceutically acceptable salt thereof.

A pharmaceutical composition comprising a compound of the invention (e.g. compounds of Formula I, compounds of Formula A-I, compounds of Formula II, compounds of Formula A-II), preferably a compound of Formula A-I or Formula A-II and at least 1 carbapenem antibiotic or a pharmaceutically acceptable salt thereof.

A pharmaceutical composition comprising a compound of the invention (e.g. compounds of Formula I, compounds of Formula A-I, compounds of Formula II, compounds of Formula A-II), preferably a compound of Formula A-I or Formula A-II and at least 1 monobactam antibiotic or a pharmaceutically acceptable salt thereof.

The embodiments described herein provide compounds of the invention (e.g. compounds of Formula I, compounds of Formula A-I, compounds of Formula II, compounds of Formula A-II), preferably a compound of Formula A-I or Formula A-II that are novel and active β-lactamase inhibitors. Other embodiments described herein provide novel compounds of the invention (e.g. compounds of Formula I, compounds of Formula A-I, compounds of Formula II, compounds of Formula A-II), preferably a compound of Formula A-I or Formula A-II in conjunction with β-lactam antibiotics for treatment of infections. Further embodiments described herein provide novel compounds of the invention (e.g. compounds of Formula I, compounds of Formula A-I, compounds of Formula II, compounds of Formula A-II), preferably a compound of Formula A-I or Formula A-II that show unexpected activity against β-lactamases that other compounds in the class do not have.

Preparation of Compounds of the Invention

A compound of the invention (e.g. compounds of Formula I, compounds of Formula A-I, compounds of Formula II, compounds of Formula A-II) can be prepared by a variety of synthetic routes, including synthetic schemes described herein. These synthetic routes can be applied to large scale synthesis with appropriate adjustment of reaction sequence, reaction conditions, isolation/purification methods and choice of solvents which are environmentally friendly and cost-effective.

The following abbreviations have the following meanings unless otherwise indicated. Abbreviations not defined below have their generally accepted meaning Bn=benzyl
Boc=tert-butoxycarbonyl
$Boc_2O$=di-tert-butyldicarbonate
Burgess reagent=methyl N-triethylammoniumsulfonyl) carbamate
CDI=carbonyldiimidazole
CFU=colony-forming units
CLSI=Clinical Laboratory Standards Institute
cSSSI=complicated skin and skin structure infections
DBU=1,8-diazabicyclo[5.4.0]undec-7-ene DCM=dichloromethane
DEAD=diethyl azodicarboxylate
DIAD=diisopropyl azodicarboxylate
DIPEA=diisopropylethylamine
DMF=N,N-dimethylformamide
DMAc=N,N-dimethylacetamide
DMSO=dimethyl sulfoxide
EDCI=1-ethyl-3-(3'-dimethylaminopropyl)carbodiimide
ELSD=evaporative light scattering detector
EtOAc=ethyl acetate
ESI-MS=electrospray ionization mass spectrometry
Fmoc=Fluorenylmethyloxycarbonyl
HAP=Hospital-Acquired Pneumonia
HATU=2-(7-aza-1H-benzotriazole-1-yl)-1,1,3,3-tetramethyluronium hexafluorophosphate
HCl=hydrochloride
HOBt=1-hydroxybenzotrizole
Hrs=hours
HPLC=high performance liquid chromatography
Hunig's base=N,N-Diisopropylethylamine
Lawesson's reagent=2,4-bis(4-methoxyphenyl)-1,3,2,4-dithiadiphosphetane-2,4-disulfide
MIC=minimum inhibitory concentration
mL=milliliter
MS=mass spectrometry
MRSA=methicillin-resistant *Staphylococcus aureus*
NMR=nuclear magnetic resonance
Ns=nitrobenzenesulfonyl
Pa=*Pseudomonas aeruginosa*
Prep=preparative
Ppm=parts per million
Py=pyridine
sat.=saturated
rt=room temperature
TBAF=tetrabutylammonium fluoride
TBS=t-butyldimethylsilyl
TES=triethylsilyl
TEA=triethylamine
TEMPO=2,2,6,6-tetramethyl-1-piperidinyloxy, free radical
THF=tetrahydrofuran
TFA=trifluoroacetic acid
TMS=trimethylsilyl
TLC=thin layer chromatography
VAP=Ventilator-Associated Pneumonia The compounds of the invention (e.g. compounds of Formula I, compounds of Formula A-I, compounds of Formula II, compounds of Formula A-II) can be prepared from intermediate 1, according to the following reaction schemes and examples, or modifications thereof, using readily available starting materials, reagents and conventional synthetic procedures including, for example, procedures described in U.S. Pat. No. 7,112,592 and WO2009/091856.

As depicted in Scheme 1, compound 3 can be synthesized following standard oxadiazole ring formation chemistry from the diacylhydrazide intermediate 2g (see, e.g., Jakopin, Z.; Dolenc, M. S. *Curr. Org. Chem.* 2008, 12, 850-898; Walker, D. G.; Brodfuehrer, P. R.; Brundidge, S. P. Shih, K. M.; Sapino, C. Jr. *J. Org. Chem.* 1988, 53, 983-991 and references cited therein). Diacylhydrazide intermediate 2g can be prepared via standard amide coupling reactions from acylhydrazide intermediate 2f. Alternatively, 2g can be made by an amide coupling reaction of acylhydrazine derivative 2h and acid intermediate 2a, which can be prepared from ester intermediate 1. It may be necessary to protect certain functionalities in the molecule depending on the nature of the $R^1$ group. Protecting these functionalities should be within the expertise of one skilled in the art. See, e.g P. G. M. Wuts and T. W. Greene, *Protective Groups in Organic Synthesis*, Fourth Edition, John Wiley and Sons, 2006, hereafter Greene.

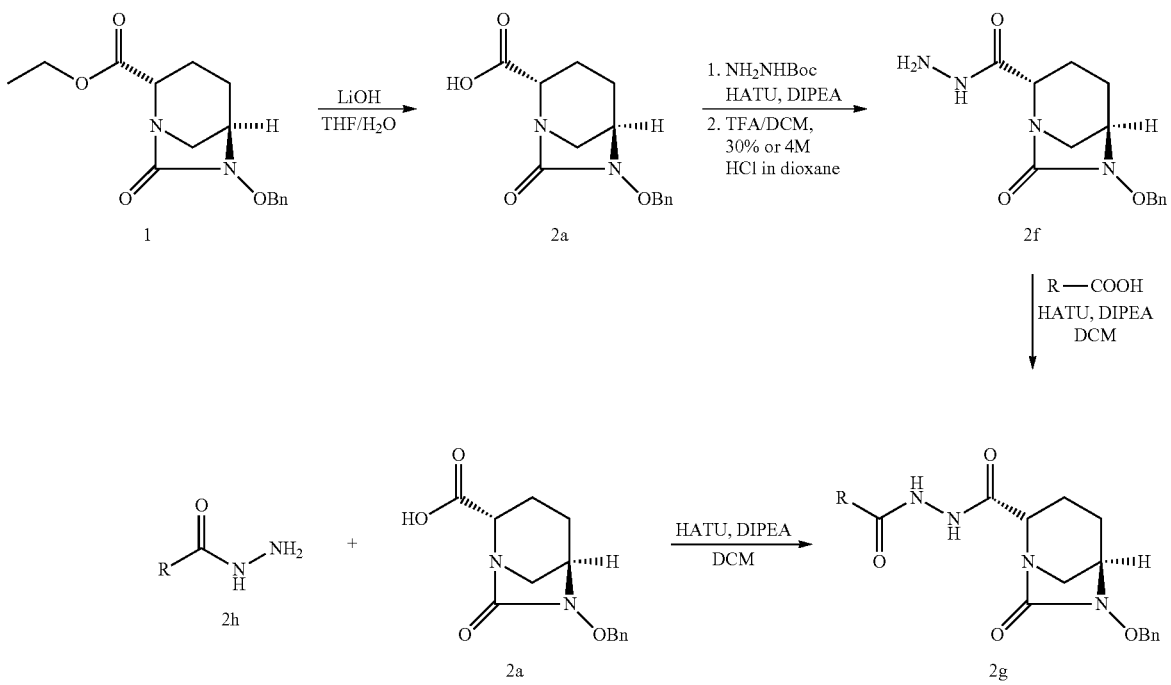

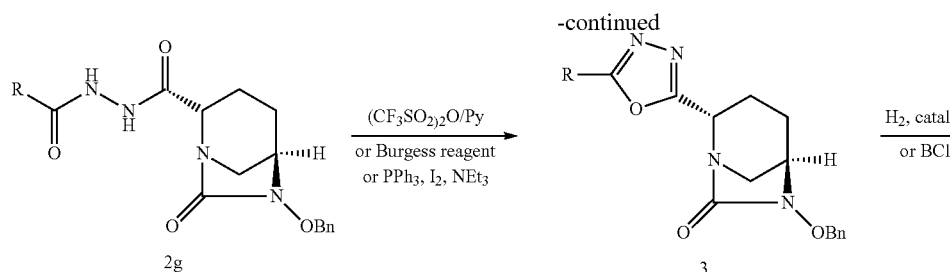

-continued

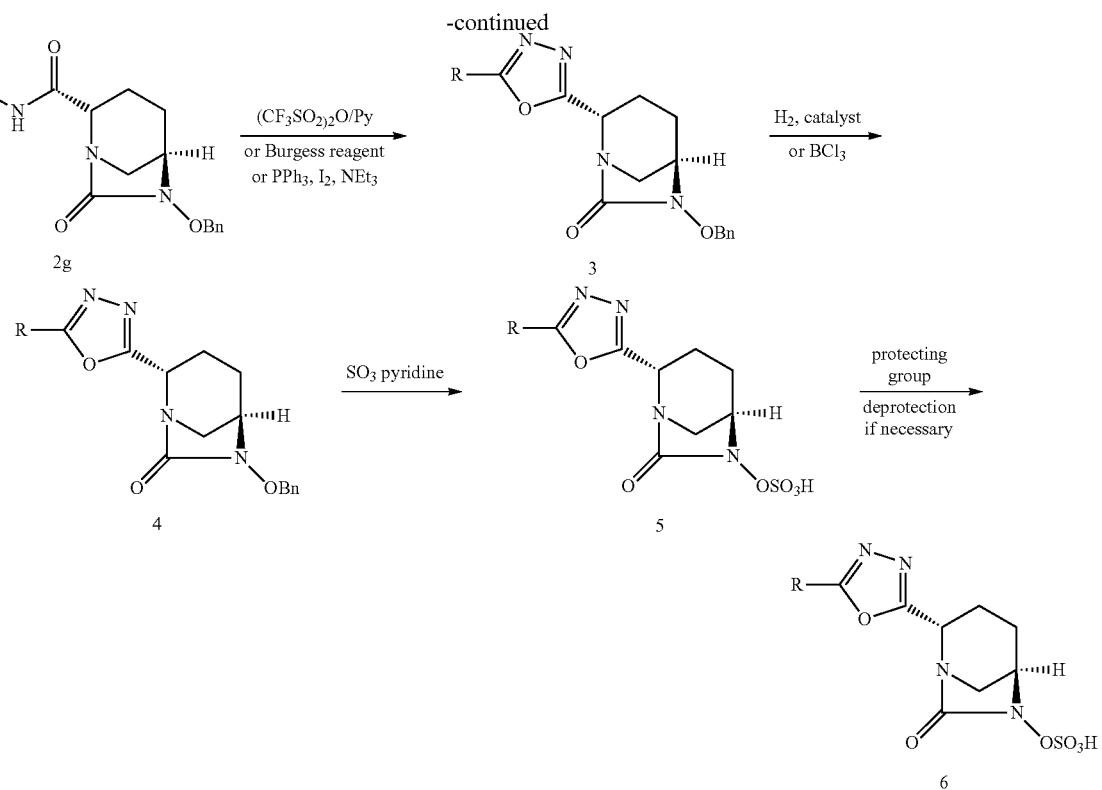

The benzylic ether protecting group in 3 can be removed via standard hydrogenolysis conditions, such as, but not limited to, Pd/H$_2$ in MeOH or THF or by acid-catalysed hydrolysis, such as, but not limited to, BCl$_3$ in DCM to provide the hydroxy-urea intermediate 4, which can be used directly in the next step without further purification. Sulfation of 4 can be achieved by treatment with a sulfating reagent, such a, but not limited to, SO$_3$.pyridine complex, in an appropriate solvent, such as pyridine, DMF or DMAc at a temperature of 0-80° C., preferable at room temperature. Compound 5 can then be isolated and purified via conventional methods. For example, 5 can be purified by standard reverse phase prep-HPLC using appropriate buffer system, i.e. ammonium formate buffer. In some cases, 5 can be purified by normal phase silica gel chromatography after converting to an appropriate salt form, such as sulfate tetrabutyl ammonium salt. The tetrabutyl ammonium salt can then be converted to a sodium salt by cation exchange. When a protecting group(s) is present in the sidechain (i.e. Boc or Fmoc for amine and guanidine protection, TBS or TES for alcohol protection, etc), a deprotection step is needed to convert 5 to its final product 6, which can be purified by prep-HPLC using the conditions mentioned above. For example, for N-Boc deprotection, 5 can be treated with an acid, such as TFA, in an appropriate solvent, such as DCM at a temperature of 0-30° C., preferable at 0° C. to rt to give 6. For an O-TBS, or O-TES deprotection, a fluoride reagent such as HF.pyridine, HF.NEt$_3$, or TBAF can be used. For Fmoc deprotection, amines can be used, such as diethylamine, DBU, piperidine, etc can be used.

Similarly, as shown in Scheme 2, thiadiazole derivative 3a can be synthesized from diacylhydrazide intermediate 2g by treatment with Lawesson's reagent under heating. 3a can then be converted to the final product 6a using similar chemistry as described previously.

Scheme 2

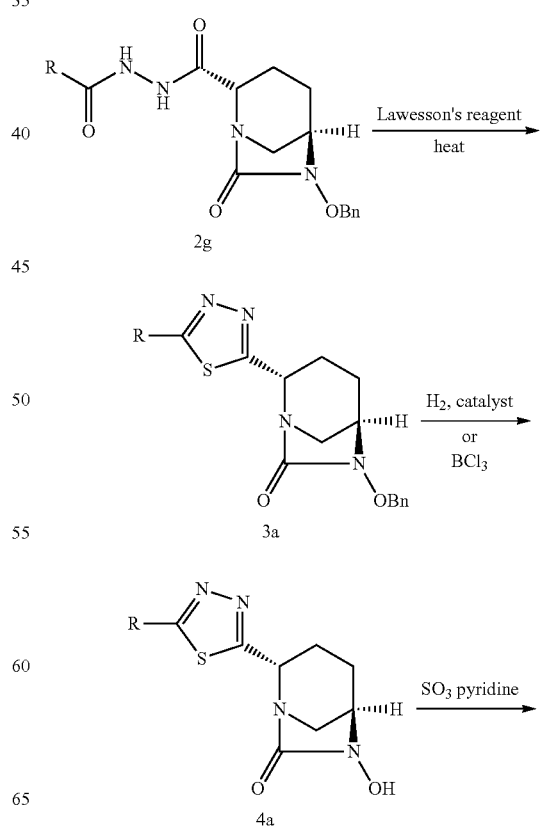

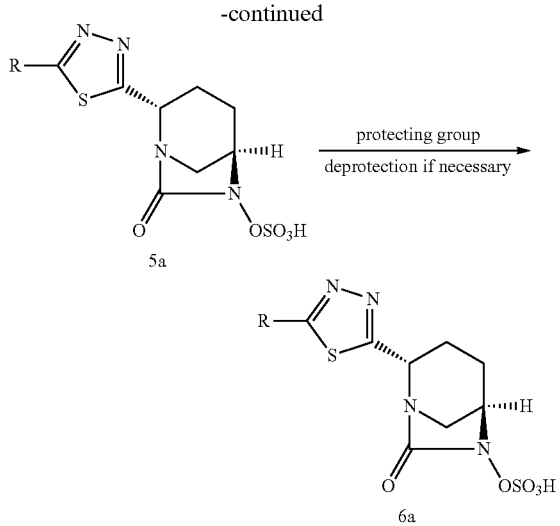

EXAMPLES

The specific examples which follow illustrate the synthesis of certain compounds. The methods disclosed may be adopted to variations in order to produce compounds of the invention (e.g. compounds of Formula I, compounds of Formula A-I, compounds of Formula II, compounds of Formula A-II) but not otherwise specifically disclosed. Further, the disclosure includes variations of the methods described herein to produce the compounds of the invention (e.g. compounds of Formula I, compounds of Formula A-I, compounds of Formula II, compounds of Formula A-II) that would be understood by one skilled in the art based on the instant disclosure.

All temperatures are understood to be in Centigrade (C) when not specified. The nuclear magnetic resonance (NMR) spectral characteristics refer to chemical shifts (γ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (br s), broad doublet (br d), singlet (s), multiplet (m), doublet (d), quartet (q), doublet of doublet (dd), doublet of triplet (dt), and doublet of quartet (dq). The solvents employed for taking NMR spectra are DMSO-d6 (perdeuterodimethysulfoxide), D$_2$O (deuterated water), CDCl$_3$ (deuterochloroform) and other conventional deuterated solvents. The prep-HPLC conditions are: Waters SunFire® C18 (30×100 mm, 5 μm OBD) column; flow rate: 30-80 mL/minute, ELSD or Mass-triggered fraction collection; sample loading: Each injection loading varied from –300 mg for different crude samples depending on their solubility and purity profiles; Solvent system using ammonium formate buffer: solvent A: water with 20 mM ammonium formate, solvent B: 85% of acetonitrile in water with 20 mM ammonium formate. Solvent system using NH$_4$HCO$_3$ buffer: solvent A: water with 10 mM NH$_4$HCO$_3$, solvent B: acetonitrile. Solvent system using NH$_4$OH buffer: solvent A: water with 0.1% NH$_4$OH, solvent B: acetonitrile with 0.1% NH$_4$OH.

Example 1

Synthesis of (2S,5R)-ethyl 6-(benzyloxy)-7-oxo-1,6-diazabicyclo[3.2.1]octane-2-carboxylate (Intermediate Compound 1)

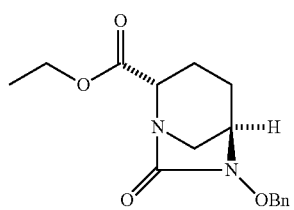

Step 1: Synthesis of (S)-1-tert-butyl 2-ethyl 5-oxopiperidine-1,2-dicarboxylate

Method A

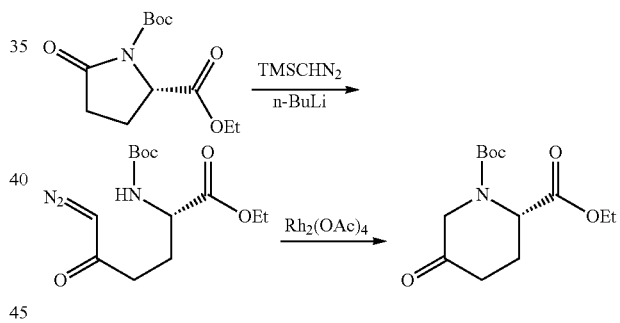

n-BuLi was added dropwise to a solution of TMSCHN$_2$ (690 mL, 1.38 mol) in dry THF (3 L) (600 mL, 1.5 mol) at –78° C., and the mixture was stirred at –78° C. for 30 minutes. The mixture was then transferred to a solution of (S)-1-tert-butyl 2-ethyl 5-oxopyrrolidine-1,2-dicarboxylate (300 g, 1.17 mol) in dry THF (3 L) via cannula, and the mixture was stirred at –78° C. for 30 minutes. The reaction mixture was then quenched with sat. NH$_4$Cl solution, and extracted with DCM three times. The combined organic layer was concentrated in vacuum and the crude product was purified by silica gel column chromatography (3:1 petroleum ether:EtOAc) to afford (S)-ethyl 2-((tert-butoxycarbonyl)amino)-6-diazo-5-oxohexanoate (262 g, 75%) as a yellow solid.

A solution of (S)-ethyl 2-((tert-butoxycarbonyl)amino)-6-diazo-5-oxohexanoate (350 g, 1.18 mol) in DCM (1500 mL) was added to a solution of Rh$_2$(OAc)$_4$ (3.5 g, 7.9 mmol) in DCM (750 mL) at 0° C. The reaction was then stirred at 20° C. overnight and then concentrated in vacuum. The crude sample was purified by silica gel column chromatography (5:1 petroleum ether/EtOAc) to afford (S)-1-tert-butyl 2-ethyl 5-oxopiperidine-1,2-dicarboxylate (175.9 g, 55%) as a yellow oil.

Method B

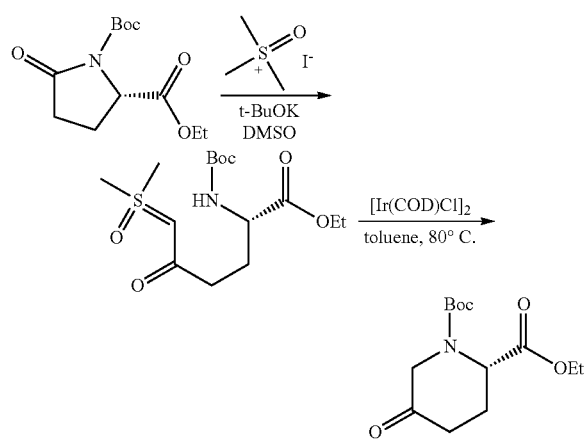

t-BuOK (330 g, 2.9 mol) was added to a solution of trimethylsulfoxonium iodide (750 g, 3.5 mol) in dry DMSO (3 L) and the mixture was stirred at rt for 1 h. (S)-1-tert-Butyl 2-ethyl 5-oxopyrrolidine-1,2-dicarboxylate (900 g, 3.5 mol) was added and the mixture was stirred at rt for 2-3 hrs. Water was added to quench the reaction and the mixture was extracted with EtOAc 5 times. The combined organic layer was concentrated in vacuum and the crude sample was purified by silica gel column chromatography (1:1 petroleum ether/EtOAc then 1:10 MeOH/DCM) to afford sulfoxonium ylide intermediate (977 g, 80%) as a white solid.

A solution of sulfoxonium ylide intermediate (156 g, 0.446 mol) and [Ir(COD)Cl]₂ (3 g, 4.46 mmol) in toluene (4 L) was degassed by bubbling nitrogen through the solution for 10 minutes. The reaction mixture was heated to 80-90° C. for 2-3 hrs and then cooled to 20° C. Then toluene was concentrated in vacuum, the residue was purified by silica gel column chromatography (10:1 to 3:1 gradient petroleum ether/EtOA) to afford (S)-1-tert-butyl 2-ethyl 5-oxopiperidine-1,2-dicarboxylate (140 g, 57.8%) as a yellow oil.

Step 2: Synthesis of (2S,5S)-1-tert-butyl 2-ethyl 5-hydroxypiperidine-1,2-dicarboxylate

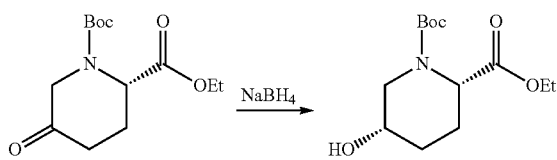

NaBH₄ (36 g, 1.0 mol) was added in portions to a solution of (S)-1-tert-butyl 2-ethyl 5-oxopiperidine-1,2-dicarboxylate (250 g, 0.92 mol) in EtOH (1500 mL) at −40° C. The reaction mixture was then stirred at −40° C. for 0.5 hr then quenched with 10% HOAc solution. After diluting with water, the mixture was extracted with DCM three times. The combined organic layer was concentrated in vacuum and purified by silica gel column chromatography (1:1 petroleum ether/EtOAc) to afford (2S,5S)-1-tert-butyl 2-ethyl 5-hydroxypiperidine-1,2-dicarboxylate (205 g, 80%) as a yellow oil.

Step 3: Synthesis of (2S,5R)-1-tert-butyl 2-ethyl 5-(N-(benzyloxy)-2-nitrophenylsulfonamido)piperidine-1,2-dicarboxylate

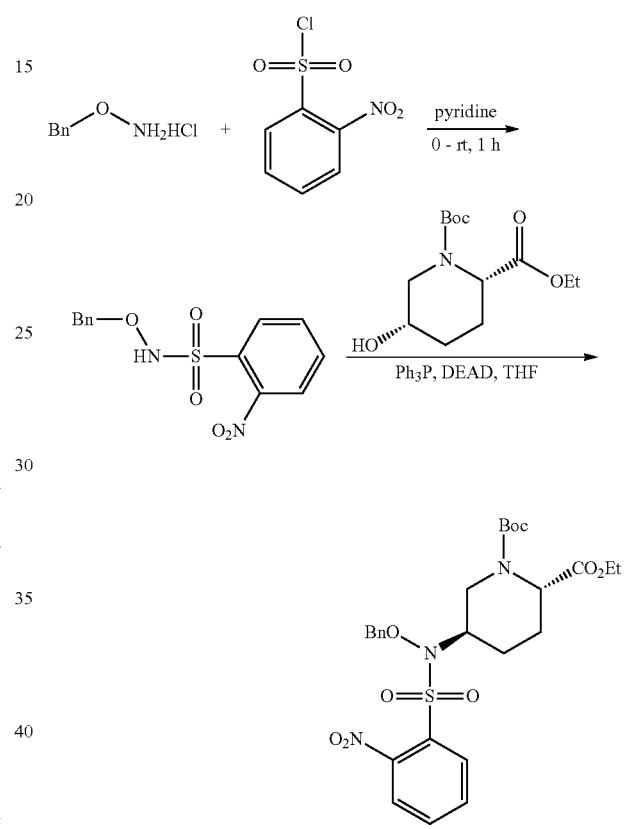

A solution of 2-nitrobenzene-1-sulfonyl chloride (500 g, 2.26 mol) in pyridine (1500 mL) was added dropwise to a solution of O-benzylhydroxylamine hydrochloride (400 g, 2.51 mol) in pyridine (1500 mL) at 0° C. The reaction mixture was then stirred at 20° C. overnight. The mixture was concentrated in vacuum, diluted with DCM and washed with HCl (10%) three times. The combined organic layer was concentrated in vacuum and re-crystallized with DCM to afford N-(benzyloxy)-2-nitrobenzenesulfonamide (485 g, 62.6%) as a yellow solid.

To a solution of N-(benzyloxy)-2-nitrobenzenesulfonamide (212 g, 0.69 mol) in THF (1000 mL) was added (2S,5S)-1-tert-butyl 2-ethyl 5-hydroxypiperidine-1,2-dicarboxylate (171 g, 0.63 mol) and PPh₃ (275 g, 1.05 mol), followed by dropwise addition of a solution of DEAD (195 g, 1.12 mol) in THF (500 mL). The mixture was then stirred at 20° C. overnight. The reaction mixture was then concentrated in vacuum and purified by silica gel column chromatography (3:1 petroleum ether/EtOAc) to afford (2S,5R)-1-tert-butyl 2-ethyl 5-(N-(benzyloxy)-2-nitrophenylsulfonamido)piperidine-1,2-dicarboxylate (283.8 g, 80%) as a yellow oil.

Step 4: Synthesis of (2S,5R)-1-tert-butyl 2-ethyl 5-((benzyloxy)amino)piperidine-1,2-dicarboxylate

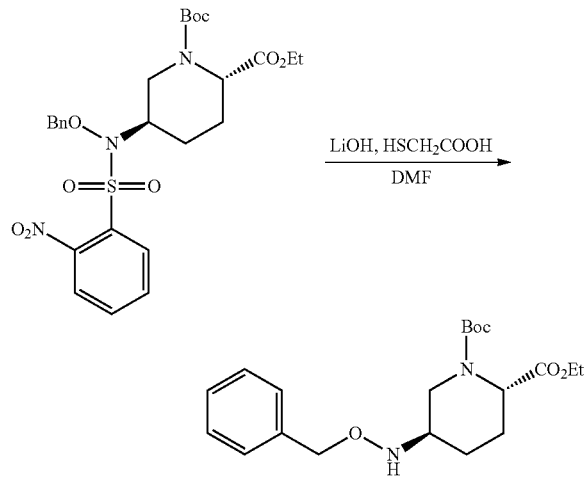

LiOH.H$_2$O (95 g, 2.3 mol) and 2-mercaptoacetic acid (124 g, 1.3 mol) were added to a solution of (2S,5R)-1-tert-butyl 2-ethyl 5-(N-(benzyloxy)-2-nitrophenylsulfonamido)piperidine-1,2-dicarboxylate (251 g, 0.45 mol) in DMF (1200 mL). The reaction mixture was then stirred at 20° C. overnight. The reaction mixture was diluted with water and extracted with EtOAc (3×). The combined organic layer was washed with brine (3×), concentrated in vacuum and purified by silica gel column chromatography (3:1 petroleum ether/EtOAc) to afford (2S,5R)-1-tert-butyl 2-ethyl 5-((benzyloxy)amino)piperidine-1,2-dicarboxylate (122.9 g, 85%) as a yellow solid.

Step 5: Synthesis of (2S,5R)-ethyl 5-((benzyloxy)amino)piperidine-2-carboxylate

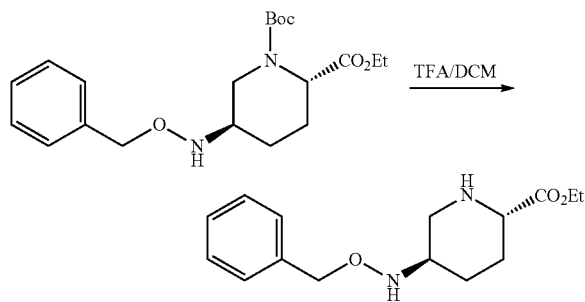

TFA (600 mL) was added to a solution of (2S,5R)-1-tert-butyl 2-ethyl 5-((benzyloxy)amino)piperidine-1,2-dicarboxylate (263 g, 0.7 mol) in DCM (600 mL) at 20° C. The mixture was stirred at rt overnight and then concentrated in vacuum. The crude product was adjusted to pH 10 with sat. NaHCO$_3$ solution, and then extracted with DCM three times. The combined organic layer was concentrated in vacuum and purified by silica gel column chromatography (20:1 DCM/ MeOH) to afford (2S,5R)-ethyl 5-((benzyloxy)amino)piperidine-2-carboxylate (184.9 g, 95%) as a yellow oil.

Step 6: Synthesis of (2S,5R)-ethyl 6-(benzyloxy)-7-oxo-1,6-diazabicyclo[3.2.1]octane-2-carboxylate

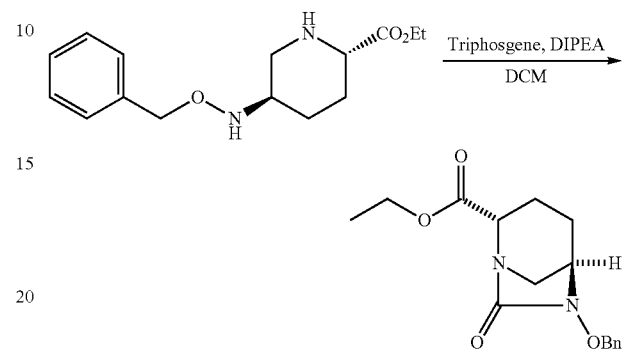

Triphosgene (21.3 g, 72 mmol) was added in portions to a solution of (2S,5R)-ethyl 5-((benzyloxy)amino)piperidine-2-carboxylate (50 g, 0.18 mol) and DIPEA (128 mL, 0.72 mol) in DCM (2000 mL) at 0° C. After stirring at 20° C. overnight, the reaction mixture was washed with H$_3$PO$_4$ (10%), sat. NaHCO$_3$ and saturated NaCl. The combined organic layer was concentrated in vacuum and purified by silica gel column chromatography (3:1 petroleum ether/ EtOAc) to afford (2S,5R)-ethyl 6-(benzyloxy)-7-oxo-1,6-diazabicyclo[3.2.1]octane-2-carboxylate (27.4 g, 50%) as a yellow solid. $^1$H NMR (400 Mz, CDCl$_3$): δ 7.43-7.36 (m, 5H), 5.06 (d, J=11.4 Hz, 1H), 4.90 (d, J=11.4 Hz, 1H), 4.24 (q, J=7.1 Hz, 2H), 4.11-4.08 (m, 1H), 3.32-3.31 (m, 1H), 3.08-3.05 (m, 1H), 2.93 (d, J=11.9 Hz, 1H), 2.14-2.05 (m, 2H), 2.05-2.00 (m, 1H), 1.71-1.63 (m, 1H), 1.29 (t, J=7.1 Hz, 3H).

Example 2

Synthesis of (2S,5R)-6-(benzyloxy)-7-oxo-1,6-diazabicyclo[3.2.1]octane-2-carboxylic acid (Intermediate Compound 2a)

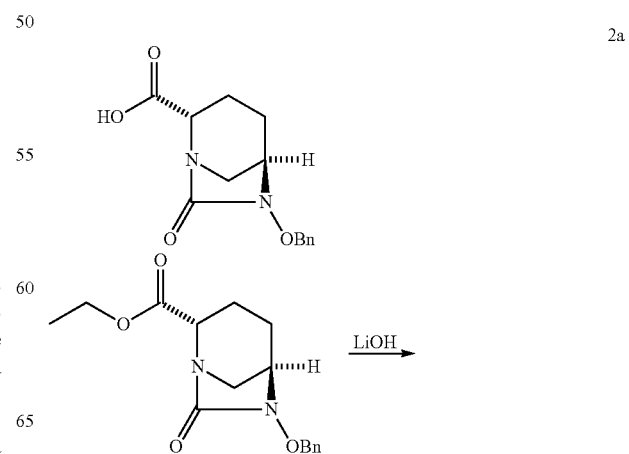

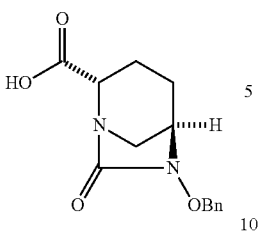

LiOH (1.2 g, 29.6 mmol) was added to a solution of (2S,5R)-ethyl 6-(benzyloxy)-7-oxo-1,6-diazabicyclo[3.2.1]octane-2-carboxylate (9 g, 29.6 mmol) in THF/H$_2$O (3:1, 240 mL). The mixture was then stirred at rt overnight. The reaction mixture was washed with EtOAc twice, then the aqueous solution was adjusted pH 2-3 with 1N HCl. The resulting mixture was extracted with DCM three times, and the combined organic layer was dried over saturated Na$_2$SO$_4$ and concentrated in vacuum to provide (2S,5R)-6-(benzyloxy)-7-oxo-1,6-diazabicyclo[3.2.1]octane-2-carboxylic acid (7.0 g, 77.7%), which was directly used in the next step without further purification. ESI-MS (EI$^+$, m/z): 277.31. $^1$H NMR (300 MHz, CDCl$_3$) δ 7.49-7.29 (m, 5H), 5.06 (d, J=11.4 Hz, 1H), 4.91 (d, J=11.4 Hz, 1H), 4.15-4.10 (m, 1H), 3.36-3.34 (m, 1H), 3.15-3.11 (m, 1H), 2.83 (d, J=11.8 Hz, 1H), 2.32-2.15 (m, 1H), 2.11-2.01 (m, 2H), 1.74-1.56 (m, 1H).

Example 3

Synthesis of (2S,5R)-2-(1,3,4-oxadiazol-2-yl)-7-oxo-1,6-diazabicyclo[3.2.1]octan-6-yl hydrogen sulfate (Compound 701)

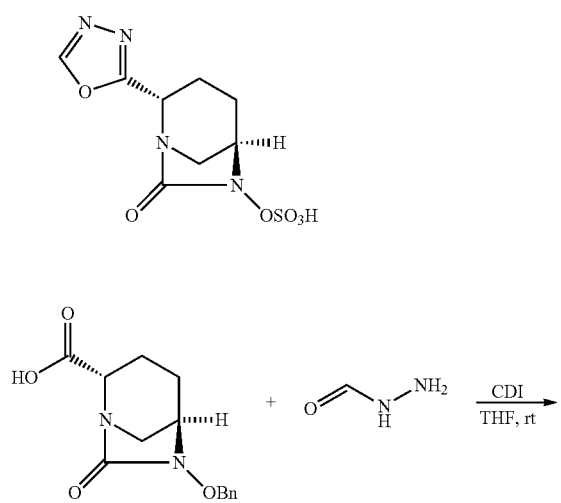

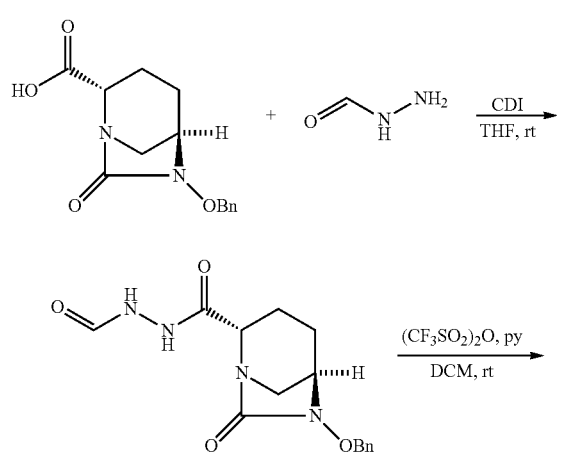

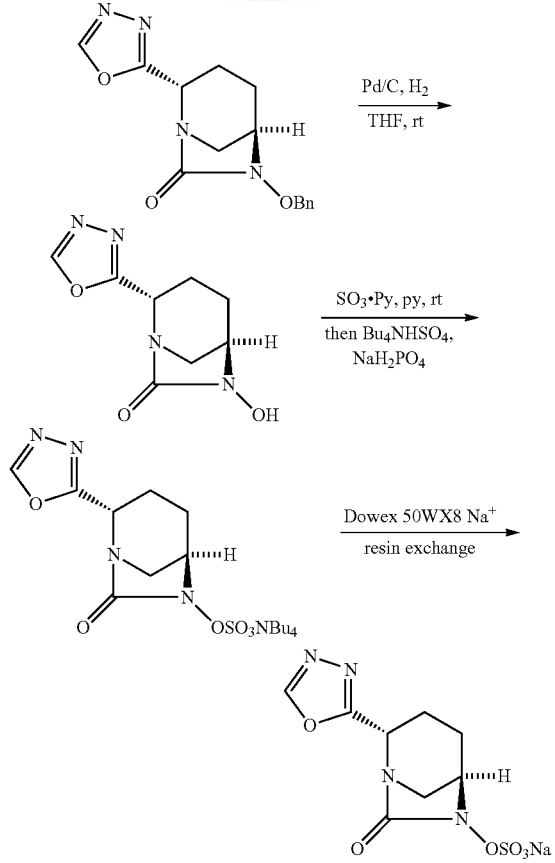

Step 1

1,1'-Carbonyldiimidazole (5.8 g, 36.2 mmol) was added to a 0° C. solution of (2S,5R)-6-(benzyloxy)-7-oxo-1,6-diazabicyclo[3.2.1]octane-2-carboxylic acid (5.0 g, 18.1 mmol) in dry THF (200 mL). The reaction mixture was allowed to warm to rt then was stirred at rt for 3 hrs. Formohydrazide (5.4 g, 90.5 mmol) was added in one portion, and the reaction mixture was stirred for additional 3 hrs. The mixture was then diluted with saturated sodium chloride and extracted with EtOAc (3×). The combined organic layer was washed with saturated sodium chloride (2×), dried over Na$_2$SO$_4$, and concentrated to afford crude (2S,5R)-6-(benzyloxy)-N'-formyl-7-oxo-1,6-diazabicyclo[3.2.1]octane-2-carbohydrazide (~11 g), which was directly used in the next step. ESI-MS (EI$^+$, m/z): 319.1 [M+H]$^+$.

Step 2

To a −10° C. solution of (2S,5R)-6-(benzyloxy)-N'-formyl-7-oxo-1,6-diazabicyclo[3.2.1]octane-2-carbohydrazide (11 g) in dry DCM (200 mL) was added pyridine (28 mL), followed by dropwise addition of (CF$_3$SO$_2$)$_2$O (28 mL). The reaction mixture was allowed to warm to rt and was stirred for 3 hrs. The reaction mixture was then cooled to −10° C. and quenched with sat. NaHCO$_3$. The organic layer was separated and the aqueous layer was extracted with EtOAc (3×). The combined organic layer was dried over Na$_2$SO$_4$, concentrated and purified by silica gel column chromatography (gradient elution 1:3 to 2:1 EtOAc/hexanes) to give (2S,5R)-6-(benzyloxy)-2-(1,3,4-oxadiazol-2-yl)-1,6-diazabicyclo[3.2.1]octan-7-one (4.6 g, 86% for two steps) as a slightly yellow solid. ESI-MS (EI+, m/z): 301.0 [M+H]+.

Step 3

To a solution of (2S,5R)-6-(benzyloxy)-2-(1,3,4-oxadiazol-2-yl)-1,6-diazabicyclo[3.2.1]octan-7-one (4.6 g, 15.3 mmol) in THF (150 mL) was added 10% Pd/C (1 g). The mixture was stirred under H₂ atmosphere at rt for 3 hrs. The reaction mixture was then filtered and concentrated to afford (2S,5R)-6-hydroxy-2-(1,3,4-oxadiazol-2-yl)-1,6-diazabicyclo[3.2.1]octan-7-one (2.9 g, 91%), which was used directly in the next step. ESI-MS (EI+, m/z): 211.1 [M+H]+.

Step 4

To a solution of (2S,5R)-6-hydroxy-2-(1,3,4-oxadiazol-2-yl)-1,6-diazabicyclo[3.2.1]octan-7-one (2.9 g, 13.8 mmol) in dry pyridine (60 mL) was added SO₃.Py (11.0 g, 69.0 mmol). The reaction mixture was stirred at rt for 8 hrs and then concentrated under vacuum. The residue was re-dissolved in aqueous NaH₂PO₄ (1.5 M, 100 mL) then tetrabutylammonium hydrogensulphate (5.88 g, 17.3 mmol) was added. The mixture was stirred at rt for 20 minutes, then was extracted with EtOAc (4×). The combined organic layer was dried and concentrated and the residue was purified by silica gel column chromatography (gradient elution 10:1 to 2:1 DCM/acetone) to afford tetrabutylammonium (2S,5R)-2-(1,3,4-oxadiazol-2-yl)-7-oxo-1,6-diazabicyclo[3.2.1]octan-6-yl sulfate (4.1 g, 97%) as a white solid. ESI-MS (E−, m/z): 289.0 [M−H]−. ¹H NMR (400 MHz, CDCl₃): δ 8.48 (s, 1H), 4.75 (d, J=6.5 Hz, 1H), 4.40 (br s, 1H), 3.34-3.26 (m, 9H), 2.82 (d, J=12.0 Hz, 1H), 2.37-2.25 (m, 3H), 2.06-1.98 (m, 1H), 1.71-1.65 (m, 8H), 1.49-1.42 (m, 8H), 1.01 (t, J=7.5 Hz, 12H).

Step 5: Resin Exchange

Tetrabutylammonium (2S,5R)-2-(1,3,4-oxadiazol-2-yl)-7-oxo-1,6-diaza-bicyclo[3.2.1]octan-6-yl sulfate (4.1 g, 7.72 mmol) was dissolved in a minimum amount of HPLC grade water (~40 mL) and passed through a column of 80 g of DOWEX 50WX 8 Na+ resin (the resin was prewashed with >4 L of HPLC grade water) and eluted with HPLC grade water to afford sodium (2S,5R)-2-(1,3,4-oxadiazol-2-yl)-7-oxo-1,6-diazabicyclo[3.2.1]octan-6-yl sulfate (2.2 g, 91%) as a white solid after lyophilization. ESI-MS (EI+, m/z): 291.2 [M+H]+. ¹H NMR (300 MHz, D₂O) δ 8.92 (s, 1H), 4.84 (d, J=6.7 Hz, 1H), 4.20 (br s, 1H), 3.25-3.16 (m, 1H), 2.92 (d, J=12.3 Hz, 1H), 2.41-2.26 (m, 1H), 2.26-2.11 (m, 2H), 2.04-1.89 (m, 1H).

Example 4

Synthesis of (2S,5R)-2-(5-(2-aminoethyl)-1,3,4-oxadiazol-2-yl)-7-oxo-1,6-diazabicyclo[3.2.1]octan-6-yl hydrogen sulfate (Compound 703)

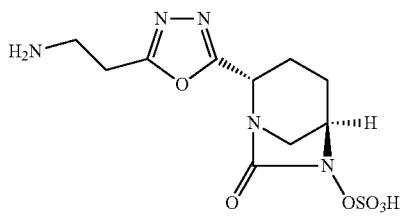

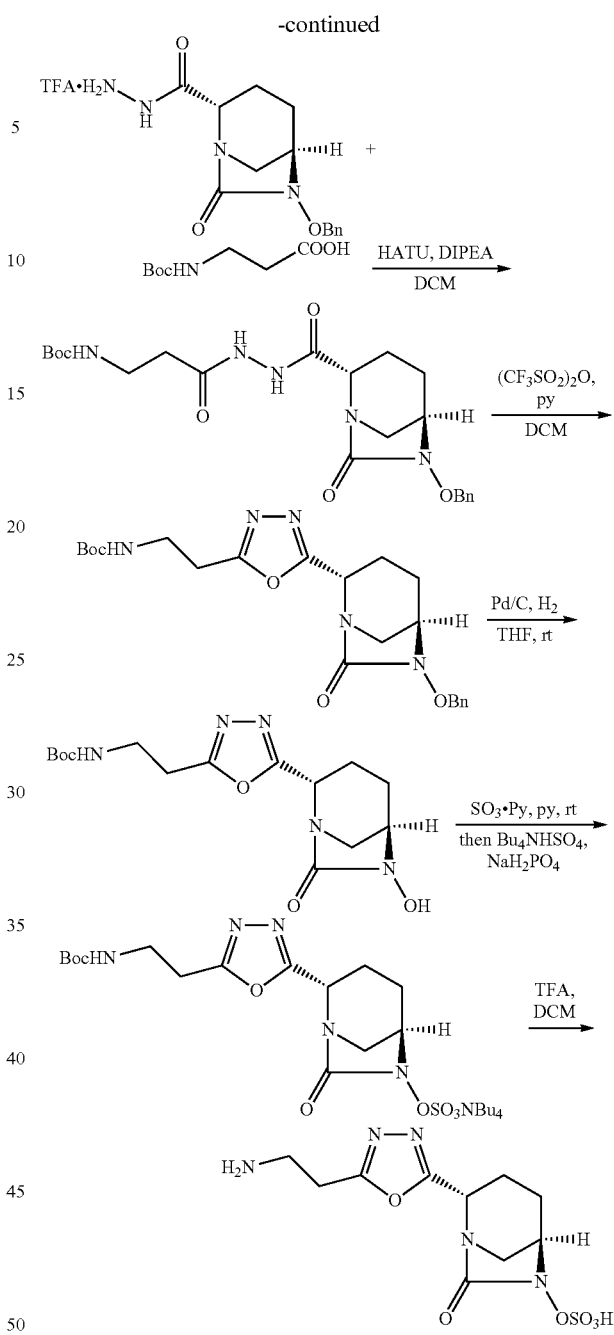

Step 1

DIPEA (1.1 g, 8.3 mmol) was added to a 0° C. solution of (2S,5R)-6-(benzyloxy)-7-oxo-1,6-diaza-bicyclo[3.2.1]ctane-2-carbohydrazide (1.0 g, 2.48 mmol) in DMF (10 mL). 3-((tert-Butoxycarbonyl)amino)propanoic acid (0.39 g, 2.07 mmol) and HATU (0.90 g, 2.48 mmol) were then added. The reaction mixture was stirred at 0° C. for 1 h and then quenched with saturated sodium chloride (50 mL). The organic layer was separated and the aqueous layer was exacted with EtOAc (3×). The combined organic layer was washed with saturated sodium chloride (2×), dried over Na₂SO₄, and concentrated. The residue was purified by silica gel column chromatography (gradient elution 10:1 to 2:1 hexanes/EtOAc) to afford tert-butyl (3-(2-((2S,5R)-6-(benzyloxy)-7-oxo-1,6-diazabicyclo[3.2.1]octane-2-carbonyl)hydrazinyl)-3-oxopropyl)carbamate (1.0 g, 87%). ESI-MS (EI+, m/z): 462 [M+H]+.

Step 2

(CF$_3$SO$_2$)$_2$O (1.0 mL) was slowly added to a −10° C. solution of tert-butyl (3-(2-((2S,5R)-6-(benzyloxy)-7-oxo-1,6-diazabicyclo[3.2.1]octane-2-carbonyl)hydrazinyl)-3-oxopropyl)carbamate (1.0 g, 2.17 mmol) and pyridine (1.0 mL) in dry DCM (10 mL). The reaction mixture was allowed to warm to rt and then was stirred at rt for 1 h. Then saturated NaHCO$_3$ was added at 0° C. very slowly. The organic layer was separated and the aqueous layer was exacted with EtOAc (3×). The combined organic layer was dried over Na$_2$SO$_4$ and concentrated. The residue was purified by silica gel column chromatography (gradient elution 10:1 to 4:1 petroleum ether/EtOAc) to give tert-butyl (2-(5-((2S,5R)-6-(benzyloxy)-7-oxo-1,6-diazabicyclo[3.2.1]octan-2-yl)-1,3,4-oxadiazol-2-yl)ethyl)carbamate (0.40 g, 42%) as a slight yellow solid. ESI-MS (EI+, m/z): 444 [M+H]+. $^1$H NMR (500 MHz, DMSO-d$_6$) δ 7.48-7.46 (m, 2H), 7.45-7.37 (m, 3H), 6.99 (t, J=5.5 Hz, 1H), 4.99-4.94 (m, 2H), 4.59 (d, J=7.0 Hz, 1H), 3.73 (br s, 1H), 3.32-3.26 (m, 2H), 2.96-2.92 (m, 2H), 2.85-2.81 (m, 2H), 2.19-2.15 (m, 1H), 2.05-1.99 (m, 2H), 1.86-1.83 (m, 1H), 1.34 (s, 9H).

Step 3

A mixture of tert-butyl (2-(5-((2S,5R)-6-(benzyloxy)-7-oxo-1,6-diazabicyclo[3.2.1]octan-2-yl)-1,3,4-oxadiazol-2-yl)ethyl)carbamate (400 mg, 0.90 mmol) and 10% Pd/C (50 mg) in THF (20 mL) was stirred under H$_2$ atmosphere at rt for 3 h. The reaction mixture was then filtered and concentrated to afford tert-butyl (2-(5-((2S,5R)-6-hydroxy-7-oxo-1,6-diazabicyclo[3.2.1]octan-2-yl)-1,3,4-oxadiazol-2-yl)ethyl)carbamate (300 mg, 94%) as a white solid, which was used directly in the next step. ESI-MS (EI+, m/z): 354.24 [M+H]+.

Step 4

To a solution of tert-butyl (2-(5-((2S,5R)-6-hydroxy-7-oxo-1,6-diazabicyclo[3.2.1]octan-2-yl)-1,3,4-oxadiazol-2-yl)ethyl)carbamate (300 mg, 0.85 mmol) in dry pyridine (4.0 mL) was added SO$_3$.Py (542 mg, 3.4 mmol). The mixture was stirred at rt overnight and then concentrated under vacuum. The residue was re-dissolved in aqueous NaH$_2$PO$_4$ (1.5 M, 20 mL) then tetrabutylammonium hydrogensulphate (345 mg, 1.02 mmol) was added. The mixture was stirred at rt for 20 minutes, then extracted with EtOAc (4×). The combined organic layer was dried and concentrated and the residue was purified by silica gel column chromatography (gradient elution 10:1 to 1:1 DCM/acetone) to afford tetrabutylammonium (2S,5R)-2-(5-(2-((tert-butoxycarbonyl)amino)ethyl)-1,3,4-oxadiazol-2-yl)-7-oxo-1,6-diazabicyclo[3.2.1]octan-6-yl sulfate (286 mg, 50%) as a white solid. ESI-MS (EI+, m/z): 434.22 [M+H]+.

Step 5

TFA (0.80 mL) was added to a 0° C. solution of tetrabutylammonium (2S,5R)-2-(5-(2-((tert-butoxycarbonyl)amino)ethyl)-1,3,4-oxadiazol-2-yl)-7-oxo-1,6-diazabicyclo[3.2.1]octan-6-yl sulfate (238 mg, 0.71 mmol) in dry DCM (2.0 mL). The reaction mixture was stirred at 0° C. for 30 minutes to 1 h and then diluted with ether. The precipitate was collected via centrifugation, washed with ether (3×) and further dried under high vacuum. The crude product TFA salt was purified by prep-HPLC using ammonium formate buffer to provide (2S,5R)-2-(5-(2-aminoethyl)-1,3,4-oxadiazol-2-yl)-7-oxo-1,6-diazabicyclo[3.2.1]octan-6-yl hydrogen sulfate (75 mg, 32%) as a white solid. ESI-MS (EI+, m/z): 334.1. $^1$H NMR (300 MHz, D$_2$O) δ 4.78 (d, J=6.2 Hz, 1H), 4.19 (br s, 1H), 3.44 (t, J=6.0 Hz, 2H), 3.31 (t, J=6.0 Hz, 2H), 3.20 (br d, J=12.8 Hz, 1H), 2.96 (d, J=12.3 Hz, 1H), 2.35-2.23 (m, 1H), 2.23-2.08 (m, 2H), 2.01-1.87 (m, 1H).

Example 5

Synthesis of (2S,5R)-2-(5-(2-guanidinoethyl)-1,3,4-oxadiazol-2-yl)-7-oxo-1,6-diazabicyclo[3.2.1]octan-6-yl hydrogen sulfate (Compound 705)

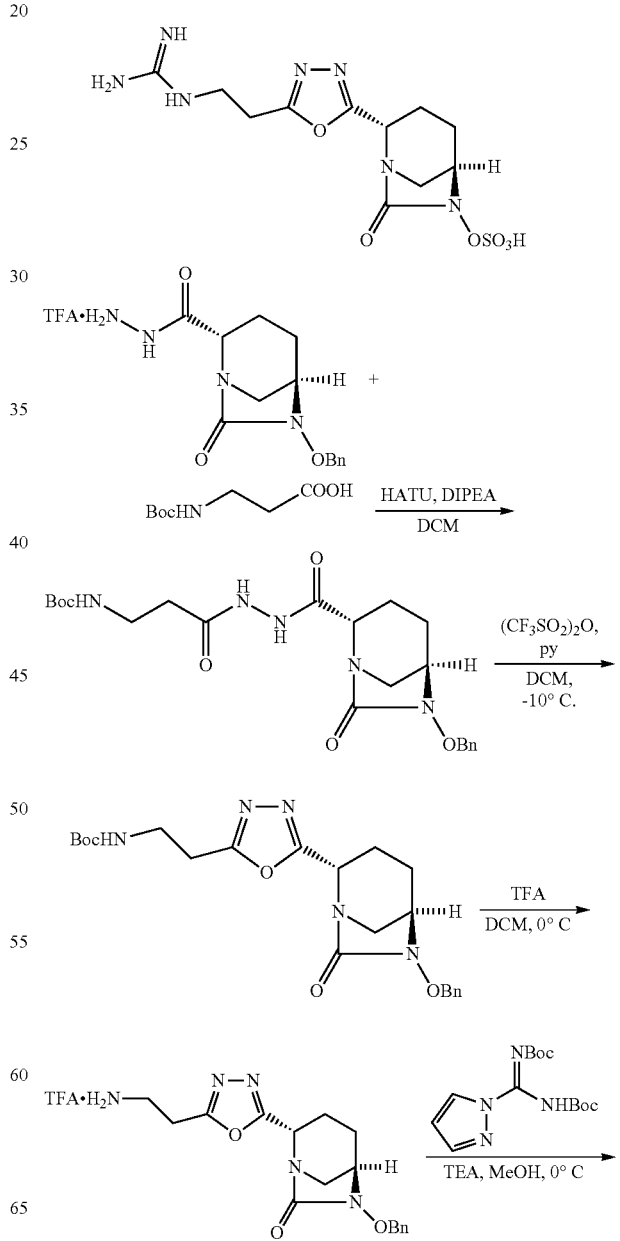

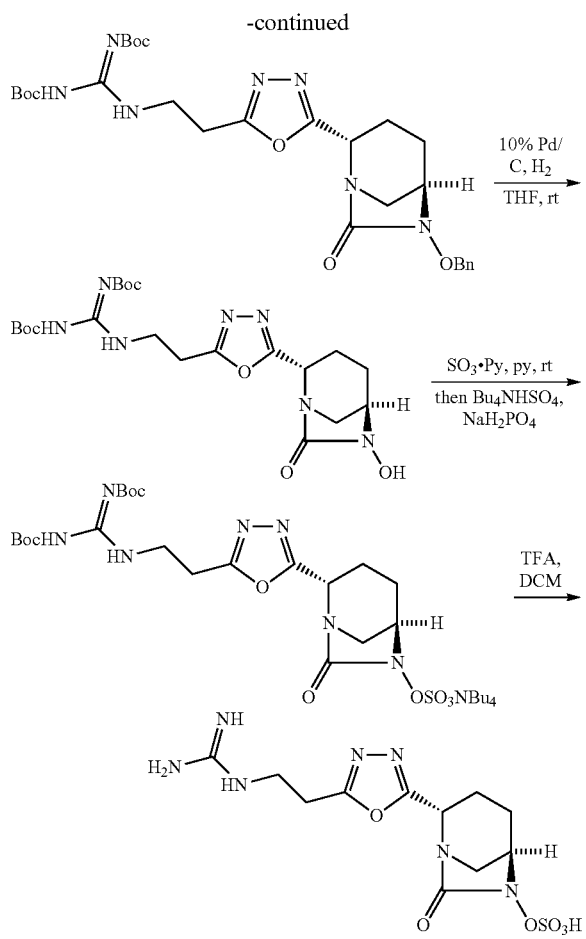

Step 1

DIPEA (1.1 g, 8.3 mmol) was added to a 0° C. solution of (2S,5R)-6-(benzyloxy)-7-oxo-1,6-diaza-bicyclo[3.2.1]octane-2-carbohydrazide (1.0 g, 2.48 mmol) in DMF (10 mL). 3-((tert-Butoxycarbonyl)amino)propanoic acid (0.39 g, 2.07 mmol) and HATU (0.90 g, 2.48 mmol) were then added. The reaction mixture was stirred at 0° C. for 1 h and then was quenched with saturated sodium chloride (50 mL). The organic layer was separated and the aqueous layer was exacted with EtOAc (3×). The combined organic layer was washed with saturated sodium chloride (2×), dried over $Na_2SO_4$, and concentrated. The residue was purified by silica gel column chromatography (gradient elution 10:1 to 2:1 hexanes/EtOAc) to afford tert-butyl (3-(2-((2S,5R)-6-(benzyloxy)-7-oxo-1,6-diazabicyclo[3.2.1]octane-2-carbonyl)hydrazinyl)-3-oxopropyl)carbamate (1.0 g, 87%). ESI-MS (EI$^+$, m/z): 462 [M+H]$^+$.

Step 2

$(CF_3SO_2)_2O$ (1.0 mL) was slowly added to a −10° C. solution of tert-butyl (3-(2-((2S,5R)-6-(benzyloxy)-7-oxo-1,6-diazabicyclo[3.2.1]octane-2-carbonyl)hydrazinyl)-3-oxopropyl)carbamate (1.0 g, 2.17 mmol) and pyridine (1.0 mL) in dry DCM (10 mL). The reaction mixture was allowed to warm to rt, was stirred at rt for 1 h then sat. $NaHCO_3$ was added at 0° C. very slowly. The organic layer was separated and the aqueous layer was exacted with EtOAc (3×). The combined organic layer was dried over $Na_2SO_4$ and concentrated. The residue was purified by silica gel column chromatography (gradient elution 10:1 to 4:1 petroleum ether/EtOAc) to give tert-butyl (2-(5-((2S,5R)-6-(benzyloxy)-7-oxo-1,6-diazabicyclo[3.2.1]octan-2-yl)-1,3,4-oxadiazol-2-yl)ethyl)carbamate (0.40 g, 42%) as a slight yellow solid. ESI-MS (EI$^+$, m/z): 444 [M+H]$^+$. $^1$H NMR (500 MHz, DMSO-$d_6$) δ 7.48-7.46 (m, 2H), 7.45-7.37 (m, 3H), 6.99 (t, J=5.5 Hz, 1H), 4.99-4.94 (m, 2H), 4.59 (d, J=7.0 Hz, 1H), 3.73 (br s, 1H), 3.32-3.26 (m, 2H), 2.96-2.92 (m, 2H), 2.85-2.81 (m, 2H), 2.19-2.15 (m, 1H), 2.05-1.99 (m, 2H), 1.86-1.83 (m, 1H), 1.34 (s, 9H).

Step 3

TFA (0.5 mL) was added to a 0° C. solution of tert-butyl 2-(5-((2S,5R)-6-(benzyloxy)-7-oxo-1,6-diaza-bicyclo[3.2.1]octan-2-yl)-1,3,4-oxadiazol-2-yl)ethylcarbamate (85 mg, 0.192 mmol) in $CH_2Cl_2$ (2.0 mL). The reaction mixture was stirred at 0° C. for 2 hrs and was then concentrated under vacuum to provide (2S,5R)-2-(5-(2-aminoethyl)-1,3,4-oxadiazol-2-yl)-6-(benzyloxy)-1,6-diazabicyclo[3.2.1]octan-7-one TFA salt as a sticky oil, which was used directly in the next step. ESI-MS (EI$^+$, m/z): 344.2 [M+H]$^+$.

Step 4

TEA (77 mg, 0.764 mmol) was added to a 0° C. solution of (2S,5R)-2-(5-(2-aminoethyl)-1,3,4-oxadiazol-2-yl)-6-(benzyloxy)-1,6-diaza-bicyclo[3.2.1]octan-7-one TFA salt from the previous step in MeOH (3.0 mL). Tert-Butyl (((tert-butoxycarbonyl)amino)(1H-pyrazol-1-yl)methylene)carbamate (65 mg, 0.209 mmol) was then added at 0° C. and the reaction mixture was stirred at 0° C. for 4 hrs. The reaction mixture was evaporated and the residue was purified by silica gel column chromatography (gradient elution 30%-50% EtOAc/petroleum ether) to give (2S,5R)-2-(5-((2,3-bis(tert-butoxycarbonyl)guanidino)ethyl)-1,3,4-oxadiazol-2-yl)-6-(benzyloxy)-1,6-diaza-bicyclo[3.2.1]octan-7-one (80 mg, 70% in 2 steps) as a colorless oil. ESI-MS (EI$^+$, m/z): 586.3 [M+H]$^+$.

Step 5

To a solution of (2S,5R)-2-(5-((2,3-bis(tert-butoxycarbonyl)guanidino)ethyl)-1,3,4-oxadiazol-2-yl)-6-(benzyloxy)-1,6-diaza-bicyclo[3.2.1]octan-7-one (80 mg, 0.136 mmol) in THF (15 mL) was added 10% Pd/C (45 mg) and the mixture was stirred under $H_2$ atmosphere at rt for 1 h. The reaction mixture was filtered and concentrated to afford (2S,5R)-6-hydroxy-2-(5-((2,3-bis(tert-butoxycarbonyl)guanidino)ethyl)-1,3,4-oxadiazol-2-yl)-1,6-diaza-bicyclo[3.2.1]octan-7-one, which was directly used in the next step. ESI-MS (EI$^+$, m/z): 496.2 [M+H]$^+$.

Step 6

To a solution of (2S,5R)-6-hydroxy-2-(5-((2,3-bis(tert-butoxycarbonyl)guanidino)ethyl)-1,3,4-oxadiazol-2-yl)-1,6-diaza-bicyclo[3.2.1]octan-7-one from the previous step in dry pyridine (2.0 mL) was added $SO_3$·Py (152 mg, 0.962 mmol). The mixture was stirred at rt for 3 hrs and then concentrated under vacuum. The residue was re-dissolved in aqueous $NaH_2PO_4$ (1.5 M, 15 mL) then tetrabutylammonium hydrogensulphate (50 mg, 0.15 mmol) was added. The mixture was stirred at rt for 20 minutes, then extracted with EtOAc (4×). The combined organic layer was dried and concentrated and the residue was purified by silica gel column chromatography (gradient elution 10:1 to 3:1 DCM/acetone) to afford tetrabutylammonium (2S,5R)-2-(5-(2-(2,3-bis(tert-butoxycarbonyl)guanidino)ethyl)-1,3,4-oxadiazol-2-yl)-7-oxo-1,6-diaza-bicyclo[3.2.1]octan-6-yl sulfate (60 mg, 53%) as a white solid. ESI-MS (E⁻, m/z): 574.1 [M–H]⁻.

Step 7

TFA (0.23 mL) was added to a 0° C. solution of tetrabutylammonium (2S,5R)-2-(5-(2-(2,3-bis(tert-butoxycarbonyl)guanidino)ethyl)-1,3,4-oxadiazol-2-yl)-7-oxo-1,6-diaza-bicyclo[3.2.1]octan-6-yl sulfate (50 mg, 0.06 mmol) in dry DCM (0.68 mL). The reaction mixture was stirred at 0° C. for 2 h and then diluted with ether. The precipitate was collected via centrifugation, washed with ether (3×) and further dried under high vacuum to provide (2S,5R)-2-(5-(2-guanidinoethyl)-1,3,4-oxadiazol-2-yl)-7-oxo-1,6-diazabicyclo[3.2.1]octan-6-yl hydrogen sulfate as TFA salt (~12 mg). ESI-MS (EI⁺, m/z): 376.18. ¹H NMR (300 MHz, D₂O) 4.77 (d, J=6.7 Hz, 1H), 4.19 (br s, 1H), 3.62 (t, J=6.4 Hz, 2H), 3.21-3.18 (m, 1H), 3.18 (t, J=6.4 Hz, 2H), 2.89 (d, J=12.3 Hz, 1H), 2.32-2.20 (m, 1H), 2.20-2.11 (m, 2H), 1.98-1.86 (m, 1H).

Example 6

Synthesis of (2S,5R)-7-oxo-2-(5-(piperidin-4-yl)-1,3,4-oxadiazol-2-yl)-1,6-diazabicyclo[3.2.1]octan-6-yl hydrogen sulfate (Compound 711)

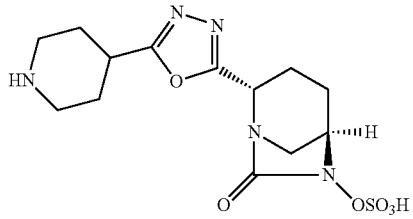

Following Steps 1-5 in Example 4, replacing 3-((tert-butoxycarbonyl)amino)propanoic acid in Step 1 with 1-(tert-butoxycarbonyl)piperidine-4-carboxylic acid, (2S,5R)-7-oxo-2-(5-(piperidin-4-yl)-1,3,4-oxadiazol-2-yl)-1,6-diazabicyclo[3.2.1]octan-6-yl hydrogen sulfate (89 mg) was obtained as a light yellow solid after prep-HPLC purification using ammonium formate buffer. ESI-MS (EI⁺, m/z): 374.26 ¹H NMR (300 MHz, D₂O) δ 4.77 (d, J=5.9 Hz, 1H), 4.20 (br s, 1H), 3.52-3.33 (m, 3H), 3.25-3.09 (m, 3H), 2.92 (d, J=12.3 Hz, 1H), 2.40-2.23 (m, 3H), 2.22-2.10 (m, 2H), 2.09-1.88 (m, 3H).

Example 7

Synthesis of (2S,5R)-2-(5-(1-carbamimidoylpiperidin-4-yl)-1,3,4-oxadiazol-2-yl)-7-oxo-1,6-diazabicyclo[3.2.1]octan-6-yl hydrogen sulfate (Compound 712)

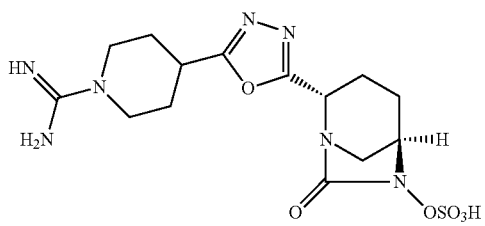

Following Steps 1-7 in Example 5, replacing 3-((tert-butoxycarbonyl)amino)propanoic acid in Step 1 with 1-(tert-butoxycarbonyl)piperidine-4-carboxylic acid, (2S,5R)-2-(5-(1-carbamimidoylpiperidin-4-yl)-1,3,4-oxadiazol-2-yl)-7-oxo-1,6-diazabicyclo[3.2.1]octan-6-yl hydrogen sulfate (35 mg) was obtained as a light yellow solid after prep-HPLC purification using ammonium formate buffer. ESI-MS (EI⁺, m/z): 416.24. ¹H NMR (300 MHz, D₂O) δ 4.77 (d, J=5.9 Hz, 1H), 4.19 (br s, 1H), 3.84-3.79 (m, 2H), 3.42-3.14 (m, 4H), 2.91 (d, J=12.0 Hz, 1H), 2.36-2.07 (m, 5H), 2.05-1.75 (m, 3H).

Example 8

Synthesis of (2S,5R)-2-(5-(azetidin-3-yl)-1,3,4-oxadiazol-2-yl)-7-oxo-1,6-diazabicyclo[3.2.1]octan-6-yl hydrogen sulfate (Compound 708)

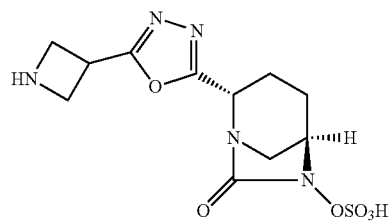

Following Steps 1-5 in Example 4, replacing 3-((tert-butoxycarbonyl)amino)propanoic acid in Step 1 with 1-(tert-butoxycarbonyl)azetidine-3-carboxylic acid, (2S,5R)-2-(5-(azetidin-3-yl)-1,3,4-oxadiazol-2-yl)-7-oxo-1,6-diazabicyclo[3.2.1]octan-6-yl hydrogen sulfate (18 mg) was obtained as a light yellow solid after prep-HPLC purification using ammonium formate buffer. ESI-MS (EI⁺, m/z): 346.17. ¹H NMR (300 MHz, D₂O) δ 4.81 (d, J=6.6 Hz, 1H), 4.58-4.32 (m, 4H), 4.20 (s, 1H), 3.21 (br d, J=12.1 Hz, 1H), 2.95 (d, J=12.3 Hz, 1H), 2.30 (dt, J=13.9, 6.8 Hz, 1H), 2.35-2.25 (m, 1H), 2.20-2.10 (m, 2H), 2.01-1.91 (m, 1H).

Example 9

Synthesis of (2S,5R)-2-(5-(1-carbamimidoylazetidin-3-yl)-1,3,4-oxadiazol-2-yl)-7-oxo-1,6-diazabicyclo[3.2.1]octan-6-yl hydrogen sulfate (Compound 709)

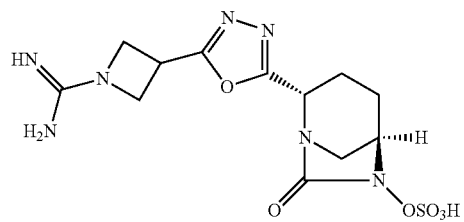

Following Steps 1-7 in Example 5, replacing 3-((tert-butoxycarbonyl)amino)propanoic acid in Step 1 with 1-(tert-butoxycarbonyl)azetidine-3-carboxylic acid, (2S,5R)-2-(5-(1-carbamimidoylazetidin-3-yl)-1,3,4-oxadiazol-2-yl)-7-oxo-1,6-diazabicyclo[3.2.1]octan-6-yl hydrogen sulfate (280 mg) was obtained as a light yellow solid after prep-HPLC purification using ammonium formate buffer. ESI-MS (EI$^+$, m/z): 388.12. $^1$H NMR (300 MHz, D$_2$O) δ 4.77 (br d, J=6.2 Hz, 1H), 4.57-4.44 (m, 2H), 4.39-4.22 (m, 3H), 4.17 (br s, 1H), 3.18 (br d, J=12.1 Hz, 1H), 2.91 (d, J=12.3 Hz, 1H), 2.31-2.19 (m, 1H), 2.19-2.06 (m, 2H), 2.00-1.84 (m, 1H).

Example 10

Synthesis of (2S,5R)-2-(5-(aminomethyl)-1,3,4-oxadiazol-2-yl)-7-oxo-1,6-diazabicyclo[3.2.1]octan-6-yl hydrogen sulfate (Compound 702)

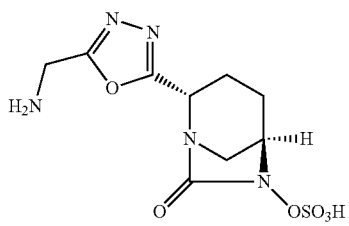

Following Steps 1-5 in Example 4, replacing 3-((tert-butoxycarbonyl)amino)propanoic acid in Step 1 with 2-((tert-butoxycarbonyl)amino)acetic acid, (2S,5R)-2-(5-(aminomethyl)-1,3,4-oxadiazol-2-yl)-7-oxo-1,6-diazabicyclo[3.2.1]octan-6-yl hydrogen sulfate (34 mg) as TFA salt. ESI-MS (EI$^+$, m/z): 320.16.

Example 11

Synthesis of (2S,5R)-2-(5-(guanidinomethyl)-1,3,4-oxadiazol-2-yl)-7-oxo-1,6-diazabicyclo[3.2.1]octan-6-yl hydrogen sulfate (Compound 704)

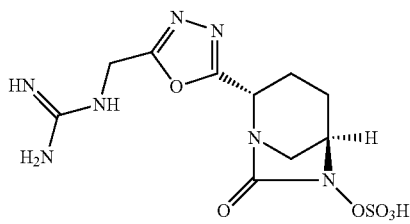

Following Steps 1-7 in Example 5, replacing 3-((tert-butoxycarbonyl)amino)propanoic acid in Step 1 with 2-((tert-butoxycarbonyl)amino)acetic acid, (2S,5R)-2-(5-(guanidinomethyl)-1,3,4-oxadiazol-2-yl)-7-oxo-1,6-diazabicyclo[3.2.1]octan-6-yl hydrogen sulfate (745 mg) was obtained as a light yellow solid after prep-HPLC purification using ammonium formate buffer. ESI-MS (EI$^+$, m/z): 362.2.

Example 12

Synthesis of (2S,5R)-2-(5-(3-aminopropyl)-1,3,4-oxadiazol-2-yl)-7-oxo-1,6-diazabicyclo[3.2.1]octan-6-yl hydrogen sulfate (Compound 720)

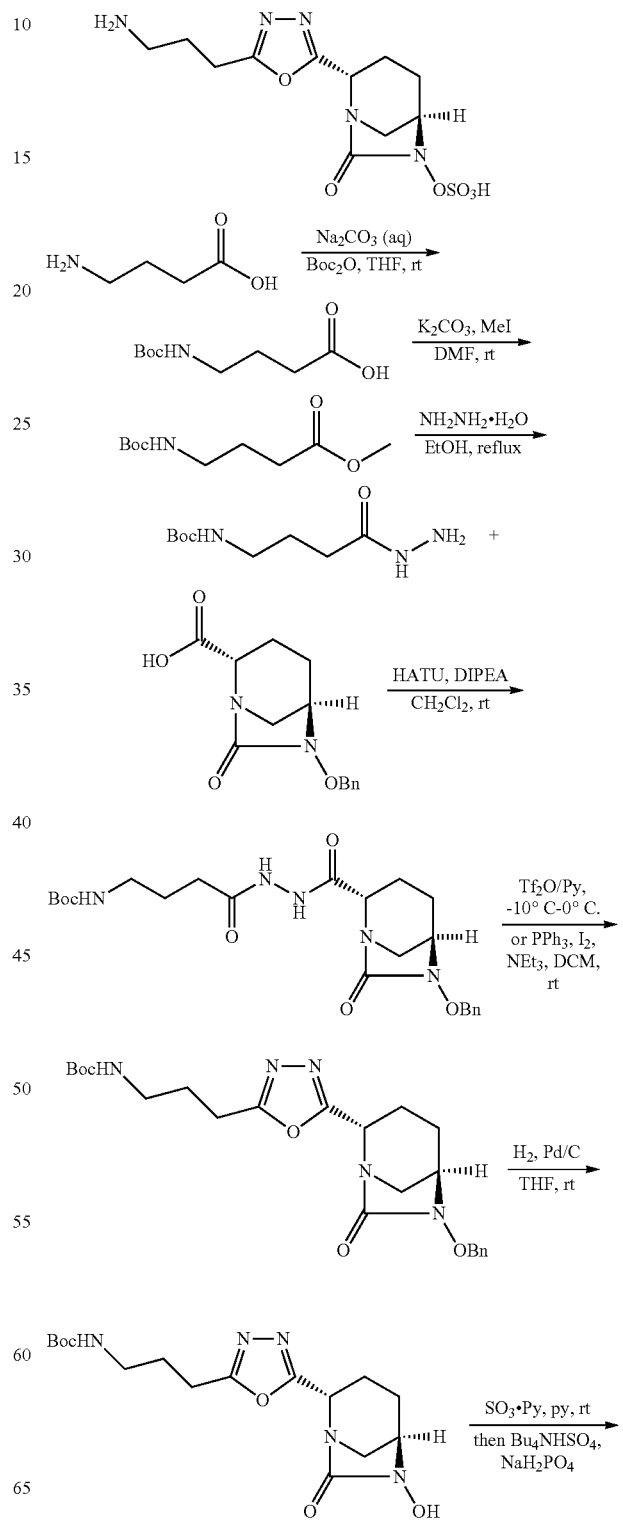

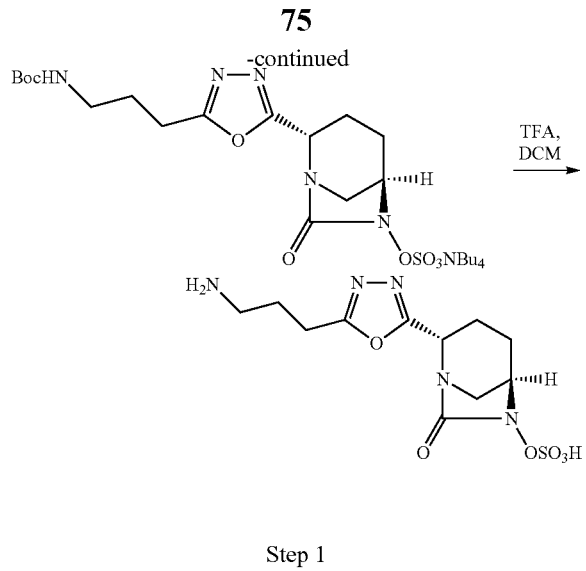

Step 1

Synthesis of 4-(tert-butoxycarbonylamino)butanoic acid

To an aqueous solution of 4-aminobutanoic acid (25 g, 242 mmol) in H₂O (500 mL) at rt was added Na₂CO₃ (75 g, 726 mmol), followed by Boc₂O (95 g, 435 mmol) in THF (200 mL). The reaction mixture was stirred at rt for 12 hrs then concentrated under reduced pressure. The aqueous residue was extracted with Et₂O, then the aqueous layer was acidified to pH 4-5 with citric acid and extracted with EtOAc. The combined organic layer was dried over Na₂SO₄, and concentrated to afford 4-(tert-butoxycarbonylamino)butanoic acid (45 g, 90%) as a colorless oil. ESI-MS (EI⁺, m/z): 226 [M+Na]⁺.

Step 2

Synthesis of methyl 4-(tert-butoxycarbonylamino)butanoate

To a solution of 4-(tert-butoxycarbonylamino)butanoic acid (7.0 g, 34.5 mmol) and K₂CO₃ (9.5 g, 68.9 mmol) in acetone (70 mL) was added MeI (7.5 g, 51.8 mmol) at rt. The reaction solution was stirred at 45° C. for 12 hrs. The mixture was washed with water and saturated sodium chloride, dried over Na₂SO₄, and concentrated to afford methyl 4-(tert-butoxycarbonylamino)butanoate (6.2 g, 83%) as a yellow oil. ESI-MS (EI⁺, m/z): 240 [M+Na]⁺.

Step 3

Synthesis of tert-butyl 4-hydrazinyl-4-oxobutylcarbamate

To a solution of methyl 4-(tert-butoxycarbonylamino)butanoate (21.0 g, 96.8 mmol) in MeOH (180 mL) was added NH₂NH₂·H₂O (28.0 g, 483 mmol) at rt. The mixture was stirred at 65° C. for 12 hrs then concentrated under reduced pressure. The crude material was dissolved in DCM (400 mL). The organic layer was washed with water (2×), and saturated sodium chloride (2×), dried over Na₂SO₄, and concentrated to afford tert-butyl 4-hydrazinyl-4-oxobutylcarbamate (18.9 g, 90%) as a white solid. ESI-MS (EI⁺, m/z): 240 [M+Na]⁺.

Step 4

Synthesis of tert-butyl4-(2-((2S,5R)-6-(benzyloxy)-7-oxo-1,6-diaza-bicyclo[3.2.1]octane-2-carbonyl)hydrazinyl)-4-oxobutylcarbamate To a 0° C. solution of (2S,5R)-6-(benzyloxy)-7-oxo-1,6-diaza-bicyclo[3.2.1]octane-2-carboxylic acid (12.0 g, 43.5 mmol) and tert-butyl 4-hydrazinyl-4-oxobutylcarbamate (10.5 g, 47.8 mmol) in CH₂Cl₂ (360 mL) was added HATU (19.6 g, 52.2 mmol) and DIPEA (16.6 g, 130.5 mmol). The mixture was allowed to warm to rt, was stirred at rt for 12 hrs then diluted with CH₂Cl₂ (300 mL), washed with water (2×) and saturated sodium chloride (2×), dried over Na₂SO₄, and concentrated. The residue was purified by silica gel column chromatography (gradient elution 50~80% EtOAc/petroleum ether) to afford tert-butyl 4-(2-((2S,5R)-6-(benzyloxy)-7-oxo-1,6-diaza-bicyclo[3.2.1]octane-2-carbonyl)hydrazinyl)-4-oxobutylcarbamate (19.3 g, 93%) as a white solid. ESI-MS (EI⁺, m/z): 476 [M+H]⁺.

Step 5

Synthesis of tert-butyl 3-(5-((2S,5R)-6-(benzyloxy)-7-oxo-1,6-diaza-bicyclo[3.2.1]octan-2-yl)-1,3,4-oxadiazol-2-yl)propylcarbamate:

Method A

Tf₂O (8.0 mL, 0.0474 mol) was added dropwise to a –78° C. solution of tert-butyl 4-(2-((2S,5R)-6-(benzyloxy)-7-oxo-1,6-diaza-bicyclo[3.2.1]octane-2-carbonyl)hydrazinyl)-4-oxobutylcarbamate (7.5 g, 0.0158 mol) and Py (10.2 mL, 0.126 mol) in dry DCM (120 mL). The reaction mixture was allowed to warm to 0° C. then the reaction mixture was stirred at 0° C. for 3 hrs. Sat. NaHCO₃ was added at 0° C. very slowly. The organic layer was separated and the water layer was exacted with DCM (3×). The combined organic layer was washed with water, saturated sodium chloride, dried over Na₂SO₄, and concentrated. The residue was purified by silica gel column (gradient elution 0-25% EtOAc/petroleum ether) to afford tert-butyl 3-(5-((2S,5R)-6-(benzyloxy)-7-oxo-1,6-diaza-bicyclo[3.2.1]octan-2-yl)-1,3,4-oxadiazol-2-yl)propylcarbamate (3.9 g, 54%) as a yellow solid. ESI-MS (EI⁺, m/z): 458 [M+H]⁺. ¹H NMR (500 MHz, CDCl₃) δ 7.45-7.37 (m, 5H), 5.08 (d, J=14.5 Hz, 1H), 4.93 (d, J=14.5 Hz, 1H), 4.70-4.66 (m, 1H), 3.37 (br s, 1H), 3.23-3.21 (m, 2H), 2.94-2.88 (m, 3H), 2.79 (d, J=14.5 Hz, 1H), 2.30-2.28 (m, 2H), 2.11-1.97 (m, 4H), 1.45 (s, 9H).

Method B

To s solution of PPh₃ (2.6 g, 10.0 mmol) in dry DCM (60 mL) was added I₂ (2.6 g, 10.0 mmol). After I₂ was dissolved completely, TEA (3.5 mL, 25.0 mmol) was added quickly at rt. The mixture was stirred for 15 mins. Tert-butyl 4-(2-((2S,5R)-6-(benzyloxy)-7-oxo-1,6-diaza-bicyclo[3.2.1]octane-2-carbonyl)hydrazinyl)-4-oxobutylcarbamate (2.4 g, 5.0 mmol) was added. The mixture was stirred at rt for 1 hr. The solvent was concentrated. EtOAc (250 mL) was added, and the solution was filtrated to remove POPh₃. The filtrate was concentrated. The resulting residue was purified by silica gel column chromatography (gradient elution 0~40% EtOAc/petroleum ether) to afford tert-butyl 3-(5-((2S,5R)-6-(benzyloxy)-7-oxo-1,6-diaza-bicyclo[3.2.1]octan-2-yl)-1,3,4-oxadiazol-2-yl)propylcarbamate (2.0 g, 86%) as a white solid. ESI-MS (EI+, m/z): 458 [M+H]+.

Step 6-8

Following Steps 3-5 in Example 4, replacing tert-butyl (2-(5-((2S,5R)-6-(benzyloxy)-7-oxo-1,6-diazabicyclo [3.2.1]octan-2-yl)-1,3,4-oxadiazol-2-yl)ethyl)carbamate in Step 3 with tert-butyl (3-(5-((2S,5R)-6-(benzyloxy)-7-oxo-1, 6-diazabicyclo[3.2.1]octan-2-yl)-1,3,4-oxadiazol-2-yl)propyl)carbamate; (2S,5R)-2-(5-(3-aminopropyl)-1,3,4-oxadiazol-2-yl)-7-oxo-1,6-diazabicyclo[3.2.1]octan-6-yl hydrogen sulfate (1.48 g) was obtained as a white solid after prep-HPLC purification using ammonium formate buffer. ESI-MS (EI+, m/z): 348.1. $^1$H NMR (300 MHz, D$_2$O) δ 4.74 (d, J=6.2 Hz, 1H), 4.17 (br s, 1H), 3.17 (br d, J=12.1 Hz, 1H), 3.05-2.95 (m, 4H), 2.89 (d, J=12.3 Hz, 1H), 2.31-2.20 (m, 1H), 2.20-2.02 (m, 4H), 2.00-1.82 (m, 1H).

Example 13

Synthesis of (2S,5R)-2-(5-(3-guanidinopropyl)-1,3, 4-oxadiazol-2-yl)-7-oxo-1,6-diazabicyclo[3.2.1]octan-6-yl hydrogen sulfate (Compound 714)

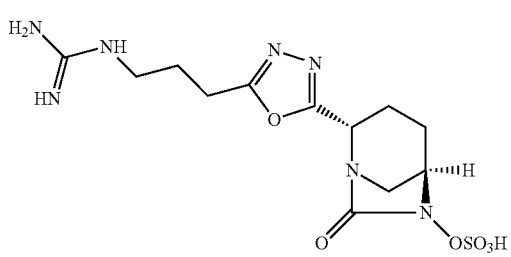

Following Steps 1-7 in Example 5, replacing 3-((tert-butoxycarbonyl)amino)propanoic acid in Step 1 with 4-((tert-butoxycarbonyl)amino)butanoic acid, (2S,5R)-2-(5-(3-guanidinopropyl)-1,3,4-oxadiazol-2-yl)-7-oxo-1,6-diazabicyclo[3.2.1]octan-6-yl hydrogen sulfate (42 mg) was obtained as a light yellow solid after prep-HPLC purification using ammonium formate buffer. ESI-MS (EI+, m/z): 390.13.

Example 14

Synthesis of (2S,5R)-7-oxo-2-(5-(pyrrolidin-3-yl)-1, 3,4-oxadiazol-2-yl)-1,6-diazabicyclo[3.2.1]octan-6-yl hydrogen sulfate (Compound 710)

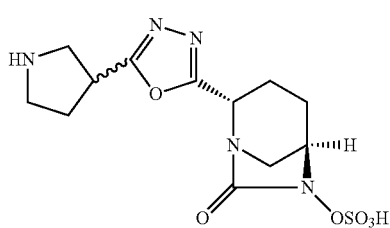

Following Steps 1-5 in Example 4, replacing 3-((tert-butoxycarbonyl)amino)propanoic acid in Step 1 with 1-(tert-butoxycarbonyl)pyrrolidine-3-carboxylic acid, (2S,5R)-7-oxo-2-(5-(pyrrolidin-3-yl)-1,3,4-oxadiazol-2-yl)-1,6-diazabicyclo[3.2.1]octan-6-yl hydrogen sulfate (20 mg) was obtained as TFA salt. ESI-MS (EI+, m/z): 360.20. $^1$H NMR (300 MHz, D$_2$O) δ 4.78 (d, J=6.5 Hz, 1H), 4.20 (br s, 1H), 4.05-3.94 (m, 1H), 3.80-3.73 (m, 1H), 3.66-3.60 (m, 1H), 3.53-3.38 (m, 2H), 3.20 (br d, J=12.5 Hz, 1H), 2.94 (d, J=12.3 Hz, 1H), 2.59-2.48 (m, 1H), 2.40-2.26 (m, 2H), 2.23-2.08 (m, 2H), 2.00-1.90 (m, 1H).

Example 15

Synthesis of (2S,5R)-7-oxo-2-(5-(piperazin-1-yl)-1, 3,4-oxadiazol-2-yl)-1,6-diazabicyclo[3.2.1]octan-6-yl hydrogen sulfate (Compound 713)

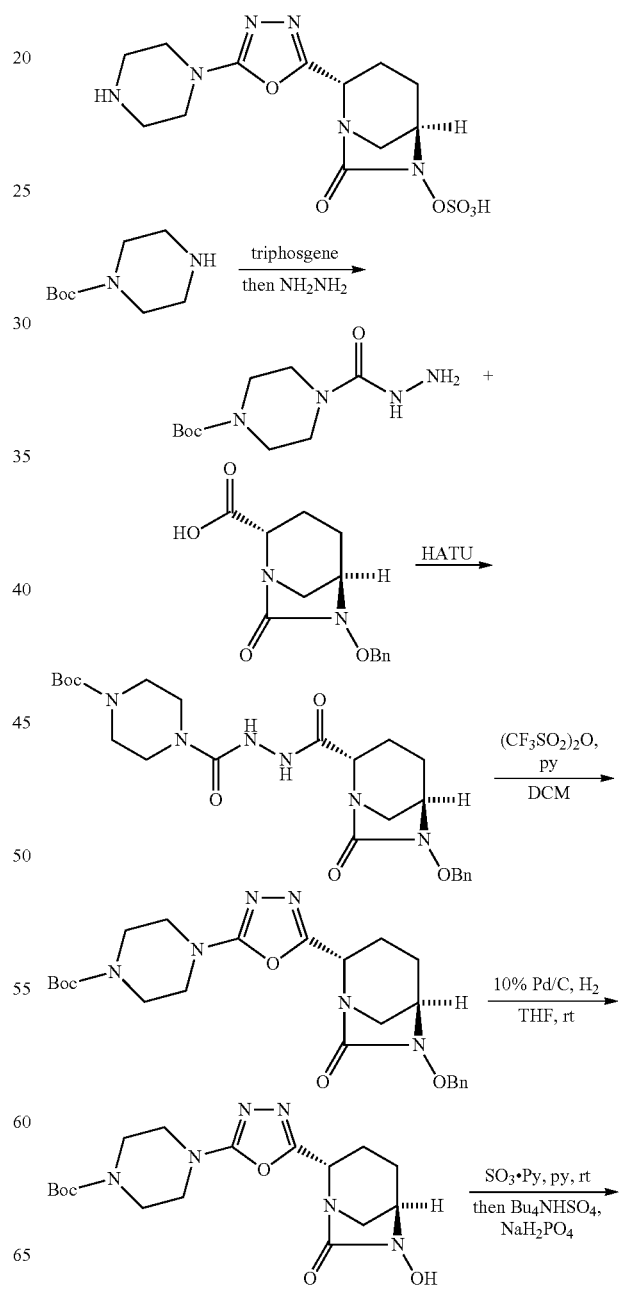

-continued

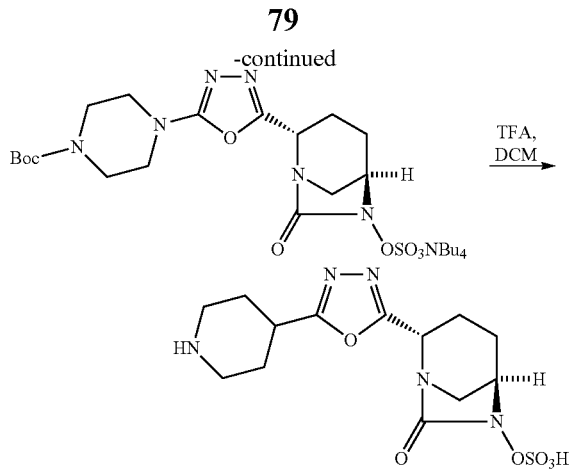

Step 1

DIPEA (105 g, 0.81 mol) was added to a 0° C. solution of tert-butyl piperazine-1-carboxylate (25.0 g, 0.134 mol) in DCM (250 mL), followed by the addition of triphosgene (92 g, 0.27 mol) in portions over a 40 minute time period. The reaction mixture was allowed to warm to rt then was stirred at rt for 3 hrs, filtered and concentrated to afford 1-tert-butyl 4-trichloromethyl piperazine-1,4-dicarboxylate (50 g) as an oil.

A solution of 1-tert-butyl 4-trichloromethyl piperazine-1, 4-dicarboxylate (50 g, 0.145 mol) in THF (50 mL) was added dropwise over a 30 minute time period to a solution of hydrazine hydrate (18 mL, 0.434 mol) in THF (150 mL). The reaction mixture was stirred at rt for 2 hrs then diluted with saturated sodium chloride (50 mL) and exacted with EtOAc (3x). The combined organic layer was washed with saturated sodium chloride (2x), dried over $Na_2SO_4$, and concentrated. The residue was purified by crystallization (3:1 petroleum ether/EtOAc) to provide tert-butyl 4-(hydrazinecarbonyl)piperazine-1-carboxylate (13 g, 40% for two steps). ESI-MS (EI$^+$, m/z): 245 [M+H]$^+$. $^1$H-NMR (500 MHz, CDCl$_3$): δ 5.92 (s, 1H), 3.45-3.35 (m, 8H), 1.41 (s, 9H).

Step 2

DIPEA (3.7 g, 10 mmol) was added to a 0° C. solution of (2S,5R)-6-(benzyloxy)-7-oxo-1,6-diaza-bicyclo[3.2.1]octane-2-carboxylic acid (1.45 g, 5.3 mmol, 0.8 eq.) and tert-butyl 4-(hydrazinecarbonyl)piperazine-1-carboxylate (1.6 g, 6.6 mmol) in dry DMF (50 mL), followed by the addition of HATU (1.45 g, 5.3 mmol). The reaction mixture was allowed to warm to rt then was stirred at rt overnight. The mixture was then diluted with water (200 mL) and the resulting precipitated material was collected by filtration, rinsed with water, and then recrystallized (3:1 petroleum ether/EtOAc) to afford tert-butyl 4-(2-((2S,5R)-6-(benzyloxy)-7-oxo-1,6-diazabicyclo[3.2.1]octane-2-carbonyl)hydrazinecarbonyl)piperazine-1-carboxylate (1.4 g, 54%), ESI-MS (EI$^+$, m/z): 503 [M+H]$^+$.

Step 3

To a solution of tert-butyl 4-(2-((2S,5R)-6-(benzyloxy)-7-oxo-1,6-diaza-bicyclo[3.2.1]octane-2-carbonyl)hydrazinecarbonyl)piperazine-1-carboxylate (903 mg, 1.8 mmol) in DCM (200 mL) was added pyridine (2.8 mL, 36.0 mmol). $(CF_3SO_2)_2O$ (2.8 ml, 9.0 mmol) was then slowly added at −10° C. The reaction mixture was stirred at rt for 3 hrs. Sat. NaHCO$_3$ was added at −10° C. very slowly. The organic layer was separated and the aqueous layer was exacted with EtOAc (3x). The combined organic layer was dried over $Na_2SO_4$ and concentrated. The crude product was purified by silica gel column chromatography (2:1 EtOAc/hexanes) to give tert-butyl 4-(5-(2S,5R)-6-(benzyloxy)-7-oxo-1,6-diaza-bicyclo[3.2.1]octan-2-yl)-1,3,4-oxadiazol-2-yl)piperazine-1-carboxylate (723 mg, 83%) as a slight yellow solid. ESI-MS (EI$^+$, m/z): 485.2 [M+H]$^+$.

Step 4

To a solution of tert-butyl 4-(5-((2S,5R)-6-hydroxy-7-oxo-1,6-diaza-bicyclo[3.2.1]octan-2-yl)-1,3,4-oxadiazol-2-yl)piperazine-1-carboxylate (50 mg, 0.1 mmol) in THF (5.0 mL) was added 10% Pd/C (20 mg). The mixture was stirred under $H_2$ atmosphere at rt for 3 hrs then filtered and concentrated to afford tert-butyl 4-(5-((2S,5R)-6-hydroxy-7-oxo-1,6-diazabicyclo[3.2.1]octan-2-yl)-1,3,4-oxadiazol-2-yl)piperazine-1-carboxylate (30 mg, 75%), which was used directly in the next step. ESI-MS (EI$^+$, m/z): 385 [M+H]$^+$.

Step 5

To a solution of tert-butyl 4-(5-((2S,5R)-6-hydroxy-7-oxo-1,6-diaza-bicyclo[3.2.1]octan-2-yl)-1,3,4-oxadiazol-2-yl)piperazine-1-carboxylate (30 mg, 0.077 mmol) in dry pyridine (3 ml) was added SO$_3$.Py (97 mg, 0.61 mmol). The mixture was stirred at rt for 3 hrs. The pyridine was evaporated under vacuum at 25° C. The residue was re-dissolved in aqueous NaH$_2$PO$_4$ (1.5 M, 20 mL) and tetrabutylammonium hydrogensulphate (300 mg) was added. The mixture was stirred at rt for 20 minutes, then extracted with EtOAc (4x). The combined organic layer was dried and concentrated and the residue was purified by silica gel column chromatography (gradient elution 10:1 to 1:1 DCM/acetone) to give tetrabutylammonium (2S,5R)-2-(5-(4-(tert-butoxycarbonyl)piperazin-1-yl)-1,3,4-oxadiazol-2-yl)-7-oxo-1,6-diazabicyclo[3.2.1]octan-6-yl sulfate (20 mg, 20%). ESI-MS (EI$^+$, m/z): 473 [M−H]$^-$.

Step 6

TFA (0.30 mL) was added to a 0° C. mixture of tetrabutylammonium tert-butyl 4-(5-((2S,5R)-7-oxo-6-(sulfooxy)-1,6-diazabicyclo[3.2.1]octan-2-yl)-1,3,4-oxadiazol-2-yl)piperazine-1-carboxylate (21 mg, 0.03 mmol) in dry DCM (0.80 mL). The reaction mixture was stirred at 0° C. for 2-3 hrs then diluted with ether (~15 mL). The precipitate was collected via centrifugation, washed with ether (3x) and dried under high vacuum to afford (2S,5R)-7-oxo-2-(5-(piperazin-1-yl)-1,3,4-oxadiazol-2-yl)-1,6-diazabicyclo[3.2.1]octan-6-yl hydrogen sulfate (4 mg, 35%) as a light yellow solid after prep-HPLC purification using ammonium formate buffer. ESI-MS (EI$^+$, m/z): 375.2. $^1$H NMR (300 MHz, D$_2$O) δ 4.65 (d, J=6.6 Hz, 1H), 4.19 (br s, 1H), 3.80-3.65 (m, 2H), 3.38-3.28 (m, 2H), 3.20-3.16 (m, 1H), 2.99-2.95 (m, 1H), 2.32-1.88 (m, 4H).

Example 16

Synthesis of (2S,5R)-2-(5-amino-1,3,4-oxadiazol-2-yl)-7-oxo-1,6-diazabicyclo[3.2.1]octan-6-yl hydrogen sulfate (Compound 707)

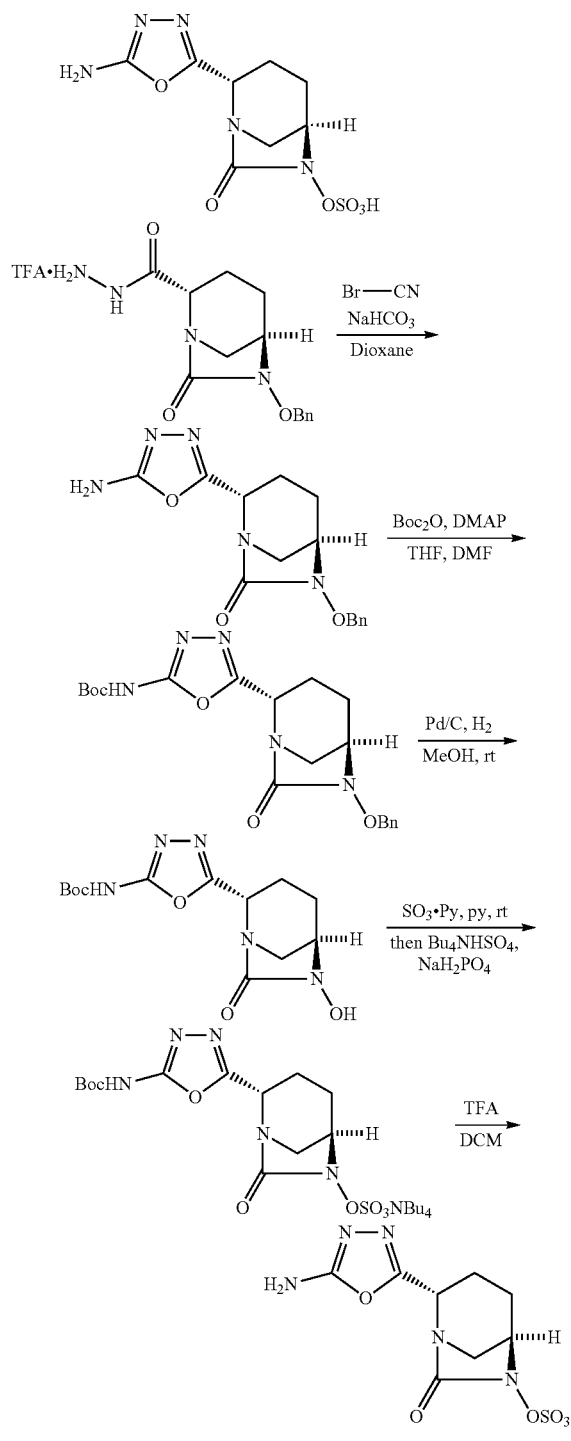

Step 1

Saturated NaHCO₃ (7.0 mL, 6.26 mmol) was added to a solution of (2S,5R)-6-(benzyloxy)-7-oxo-1,6-diazabicyclo[3.2.1]octane-2-carbohydrazide TFA salt (2.3 g, 5.69 mmol) in dioxane (11.4 mL) and the reaction mixture was stirred at rt for 5 minutes. Cyanic bromide (3 M solution, 2.3 mL, 6.90 mmol) was added and the reaction mixture was stirred at rt for 30 minutes. The reaction mixture was then loaded on a silica gel cartridge and purified by silica gel column chromatography (gradient elution 0-10% MeOH/DCM) to give (2S,5R)-2-(5-amino-1,3,4-oxadiazol-2-yl)-6-(benzyloxy)-1,6-diazabicyclo[3.2.1]octan-7-one (0.57 g, 32%). ESI-MS (EI⁺, m/z): 316.4 [M+H]⁺.

Step 2

N,N-Dimethylpyridin-4-amine (155 mg, 1.27 mmol) was added to a 0° C. solution of (2S,5R)-2-(5-amino-1,3,4-oxadiazol-2-yl)-6-(benzyloxy)-1,6-diazabicyclo[3.2.1]octan-7-one (0.20 g, 0.63 mmol), Boc₂O (0.27 g, 1.27 mmol), and triethylamine (0.18 mL, 1.27 mmol) in DMF. The reaction mixture was allowed to warm to rt and was stirred for 2-3 hrs. The reaction mixture was then concentrated, re-dissolved in DCM (50 mL), washed with water (50 mL), dried over Na₂SO₄, and concentrated. The residue was purified by silica gel column chromatography (gradient elution 0-50% EtOAc/hexane) to give tert-butyl (5-((2S,5R)-6-(benzyloxy)-7-oxo-1,6-diazabicyclo[3.2.1]octan-2-yl)-1,3,4-oxadiazol-2-yl)carbamate (0.16 g, 60.7%). ESI-MS (EI⁺, m/z): 416.4 [M+H]⁺.

Step 3-5

Following Steps 3-5 in Example 4, replacing tert-butyl (2-(5-((2S,5R)-6-(benzyloxy)-7-oxo-1,6-diazabicyclo[3.2.1]octan-2-yl)-1,3,4-oxadiazol-2-yl)ethyl)carbamate in Step 3 with tert-butyl (5-((2S,5R)-6-(benzyloxy)-7-oxo-1,6-diazabicyclo[3.2.1]octan-2-yl)-1,3,4-oxadiazol-2-yl)carbamate, (2S,5R)-2-(5-amino-1,3,4-oxadiazol-2-yl)-7-oxo-1,6-diazabicyclo[3.2.1]octan-6-yl hydrogen sulfate was obtained (64 mg) after prep-HPLC using ammonium formate buffer. ESI-MS (EI⁺, m/z): 306.25 [M+H]⁺. ¹H NMR (300 MHz, D₂O) δ 4.61 (d, J=6.6 Hz, 1H), 4.19 (br s, 1H), 3.17 (br d, J=12.2 Hz, 1H), 2.98 (d, J=12.3 Hz, 1H), 2.27-1.81 (m, 4H).

Example 17

Synthesis of (2S,5R)-2-(5-carbamoyl-1,3,4-oxadiazol-2-yl)-7-oxo-1,6-diaza-bicyclo[3.2.1]octan-6-yl hydrogen sulfate (Compound 706)

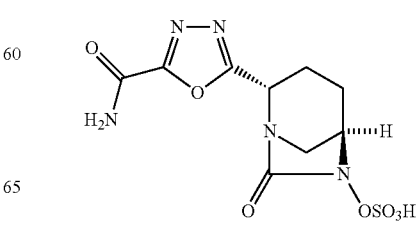

83

-continued

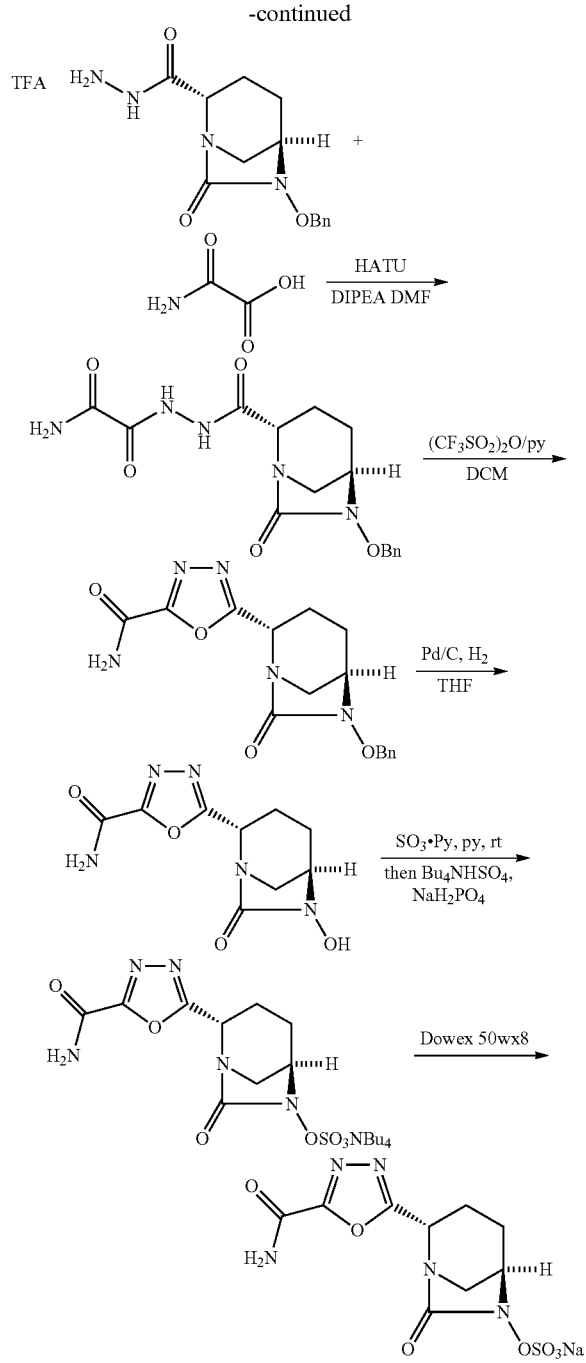

Step 1

HATU (0.95 g, 2.5 mmol) was added to a 0° C. solution of (2S,5R)-6-(benzyloxy)-7-oxo-1,6-diazabicyclo[3.2.1]octane-2-carbohydrazide (1.00 g, 2.5 mmol), 2-amino-2-oxoacetic acid (0.18 g, 2.1 mmol) and DIPEA (1.08 g, 8.4 mmol) in DMF (10 mL). The reaction mixture was stirred at 0° C. for 1 h then quenched with saturated sodium chloride (50 mL) and the organic layer was separated. The aqueous layer was exacted with EtOAc (3×). The combined organic layer was washed with saturated sodium chloride (2×), dried over $Na_2SO_4$, and concentrated. The residue was purified by silica gel column chromatography (1:1 EtOAc/hexane) to give 2-(2-((2S,5R)-6-(benzyloxy)-7-oxo-1,6-diazabicyclo[3.2.1]octane-2-carbonyl)hydrazinyl)-2-oxoacetamide (0.57 g, 64%). ESI-MS (EI+, m/z): 362 [M+H]+.

Step 2

$(CF_3SO_2)_2O$ (0.58 g, 2.08 mmol) was slowly added to a −10° C. solution of 2-(2-((2S,5R)-6-(benzyloxy)-7-oxo-1,6-diazabicyclo[3.2.1]octane-2-carbonyl)hydrazinyl)-2-oxoacetamide (0.30 g, 0.83 mmol) and pyridine (0.6 mL) in dry DCM (5 mL). The reaction mixture was allowed to warm to rt. The reaction mixture was stirred at rt for 1 h then quenched with sat. $NaHCO_3$ very slowly. The organic layer was separated and the aqueous layer was exacted with EtOAc (3×). The combined organic layer was dried over $Na_2SO_4$, and concentrated. The residue was purified by silica gel column chromatography (gradient elution 1:10 to 2:1 EtOAc/hexane followed by 10:1 to 2:1 petroleum ether/EtOAC) to give 5-((2S,5R)-6-(benzyloxy)-7-oxo-1,6-diazabicyclo[3.2.1]octan-2-yl)-1,3,4-oxadiazole-2-carboxamide (0.18 g, 47%) as a slight yellow solid. ESI-MS (EI+, m/z): 344.0 [M+H]+.

Step 3

To a solution of 5-((2S,5R)-6-(benzyloxy)-7-oxo-1,6-diazabicyclo[3.2.1]octan-2-yl)-1,3,4-oxadiazole-2-carboxamide (0.14 g, 0.41 mmol) in THF (10 mL) was added 10% Pd/C (0.14 g). The mixture was stirred under $H_2$ atmosphere at rt for 3 hrs then filtered and concentrated to provide 5-((2S,5R)-6-hydroxy-7-oxo-1,6-diazabicyclo[3.2.1]octan-2-yl)-1,3,4-oxadiazole-2-carboxamide (103 mg, 100%), which was directly used in the next step. ESI-MS (EI+, m/z): 254 [M+H]+.

Step 4

To a solution of 5-((2S,5R)-6-hydroxy-7-oxo-1,6-diazabicyclo[3.2.1]octan-2-yl)-1,3,4-oxadiazole-2-carboxamide (103 mg, 0.41 mmol) in dry pyridine (2.0 mL) was added $SO_3$.Py (323 mg, 2.03 mmol). The mixture was stirred at rt for 3 hrs and then concentrated under vacuum. The residue was re-dissolved in aqueous $NaH_2PO_4$ (1.5 M, 10 mL) then tetrabutylammonium hydrogen sulphate (166 mg, 0.49 mmol) was added. The mixture was stirred at rt for 20 minutes, then extracted with EtOAc (4×). The combined organic layer was dried and concentrated and the residue was purified by silica gel column chromatography (gradient elution 10:1 to 8:1 DCM/acetone) to afford tetrabutylammonium (2S,5R)-2-(1,3,4-oxadiazol-2-yl)-7-oxo-1,6-diazabicyclo[3.2.1]octan-6-yl sulfate (110 mg, 36%). ESI-MS (EI+, m/z): 333.0 [M+H]−.

Step 5 Sodium Resin Exchange tetrabutylammonium (2S,5R)-2-(1,3,4-oxadiazol-2-yl)-7-oxo-1,6-diazabicyclo[3.2.1]octan-6-yl sulfate (110 mg) was dissolved in a minimum amount of HPLC grade water (~80 mL) and passed through a column of 20 g of DOWEX 50WX 8 Na+ resin (the resin was pre-washed with >5 L of HPLC grade water) and eluted with HPLC grade water to provide sodium (2S,5R)-2-(1,3,4-oxadiazol-2-yl)-7-oxo-1,6-diazabicyclo[3.2.1]octan-6-yl sulfate (55 mg, 80%) as a white solid after lyophilization. ESI-MS (EI+, m/z): 332.0 [M−H]−.
1H NMR (500 MHz, $D_2O$): δ 4.97-4.93 (m, 1H), 4.27 (br s, 1H), 3.29 (d, J=11.0 Hz, 1H), 3.04 (d, J=12.0 Hz, 1H), 2.43-2.39 (m, 1H), 2.31-2.23 (m, 2H), 2.04-1.98 (m, 1H).

Example 18

Synthesis of (2S,5R)-7-oxo-2-(5-(piperidin-4-yl)-1,3,4-thiadiazol-2-yl)-1,6-diazabicyclo[3.2.1]octan-6-yl hydrogen sulfate (Compound 719)

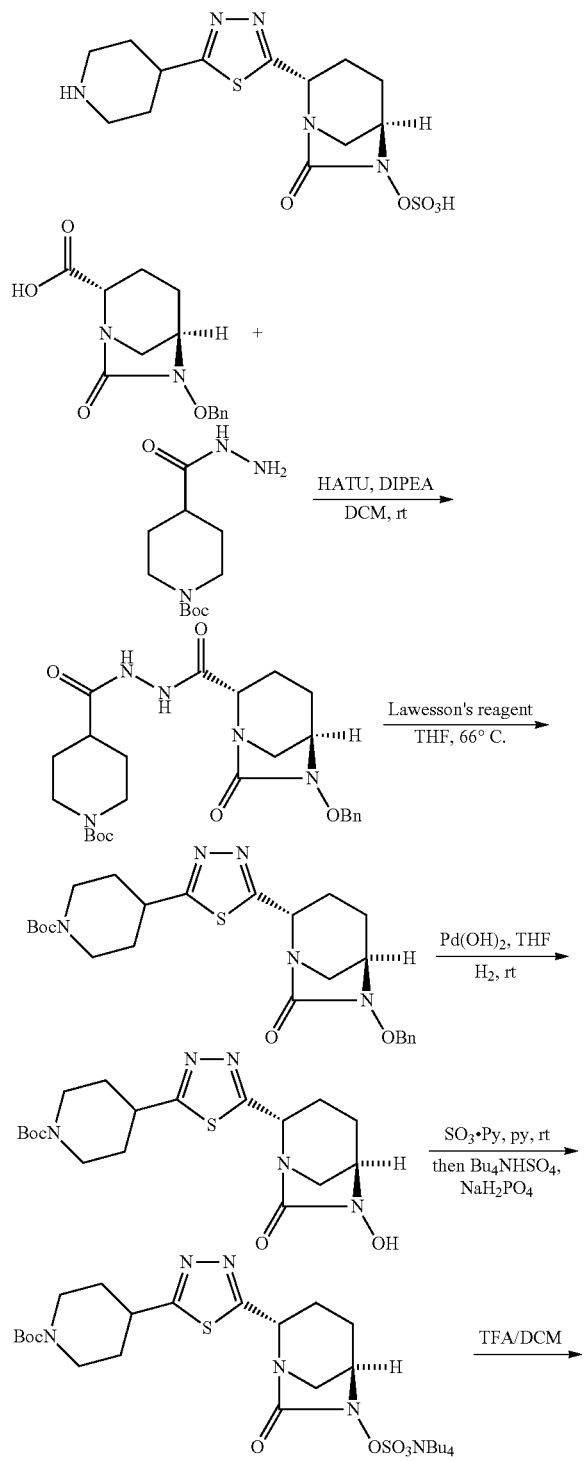

-continued

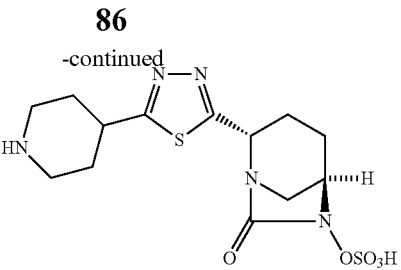

Step 1

HATU (3.3 g, 8.7 mmol) and tert-butyl 4-(hydrazinecarbonyl)piperidine-1-carboxylate (2.29 g, 9.42 mmol) were added to a 0° C. solution of (2S,5R)-6-(benzyloxy)-7-oxo-1,6-diaza-bicyclo[3.2.1]octane-2-carboxylic acid (2 g, 7.25 mmol) in $CH_2Cl_2$ (50 mL), followed by the addition of DIPEA (2.8 g, 21.8 mmol). The reaction mixture was stirred at 0° C. for 12 hrs then washed with water and saturated sodium chloride, dried over $Na_2SO_4$, and concentrated. The residue was purified by silica gel column chromatography (gradient elution 1%-10% $MeOH/CH_2Cl_2$) to give tert-butyl 4-(2-((2S,5R)-6-(benzyloxy)-7-oxo-1,6-diaza-bicyclo[3.2.1]octane-2-carbonyl)hydrazinecarbonyl)piperidine-1-carboxylate as a white solid. (2.2 g, 62%). ESI-MS (EI+, m/z): 502.2 [M+H]+.

Step 2

Lawesson's reagent (0.16 g, 6 mol) was added to a solution of tert-butyl 4-(2-((2S,5R)-6-(benzyloxy)-7-oxo-1,6-diaza-bicyclo[3.2.1]octane-2-carbonyl)hydrazinecarbonyl)piperidine-1-carboxylate (0.16 g, 0.319 mmol) in THF (20 mL). The reaction mixture was stirred at 70° C. for 0.5 h. The solution was cooled to room temperature and sat. $NaHCO_3$ was added. The organic layer was separated and the aqueous layer was exacted with EtOAc (2x). The combined organic layer was dried over $Na_2SO_4$ and concentrated. The residue was purified by silica gel column chromatography (gradient elution 20%-50% EtOAc/petroleum ether) to give tert-butyl 4-(5-((2S,5R)-6-(benzyloxy)-7-oxo-1,6-diaza-bicyclo[3.2.1]octan-2-yl)-1,3,4-thiadiazol-2-yl)piperidine-1-carboxylate (90 mg, 50%) as a white solid. ESI-MS (EI+, m/z): 500.2 [M+H]+. 1H NMR (500 MHz, DMSO-$d_6$): δ 7.48-7.37 (m, 5H), 4.99-4.94 (m, 2H), 4.77 (d, J=7.0 Hz, 1H), 3.99 (d, J=11 Hz, 2H), 3.69 (s, 1H), 3.39-3.35 (m, 1H), 2.88-2.85 (m, 3H), 2.68 (d, J=12 Hz, 1H), 2.44 (dd, J=7.5, 5.5 Hz, 1H), 2.05-1.96 (m, 4H), 1.79-1.77 (m, 1H), 1.62-1.55 (m, 2H), 1.40 (s, 9H).

Step 3

To a solution of tert-butyl 4-(5-((2S,5R)-6-(benzyloxy)-7-oxo-1,6-diaza-bicyclo[3.2.1]octan-2-yl)-1,3,4-thiadiazol-2-yl)piperidine-1-carboxylate (120 mg, 0.24 mmol) in THF (30 mL) was added 10% $Pd(OH)_2/C$ (200 mg). The mixture was stirred under $H_2$ atmosphere at rt for 3 h, filtered and concentrated to afford tert-butyl 4-(5-((2S,5R)-6-hydroxy-7-oxo-1,6-diaza-bicyclo[3.2.1]octan-2-yl)-1,3,4-thiadiazol-2-yl)piperidine-1-carboxylate as a yellow solid, which was directly used in the next step. ESI-MS (EI+, m/z): 410.2 [M+H]+.

Step 4

To a solution of tert-butyl 4-(5-((2S,5R)-6-hydroxy-7-oxo-1,6-diaza-bicyclo[3.2.1]octan-2-yl)-1,3,4-thiadiazol-2-yl)

piperidine-1-carboxylate from the former step in dry pyridine (3 mL) was added SO₃.Py (266 mg, 1.1 mmol). The mixture was stirred at rt for 3 hrs and then concentrated under vacuum. The residue was re-dissolved in aqueous NaH₂PO₄ (1.5 M, 20 mL) then tetrabutylammonium hydrogensulphate (150 mg, 0.44 mmol) was added. The mixture was stirred at rt for 20 minutes, then extracted with EtOAc (4×). The combined organic layer was dried and concentrated and the residue was purified by silica gel column chromatography (gradient elution 10:1 to 1:1 DCM/acetone) to afford tetrabutylammonium tert-butyl 4-(5-((2S,5R)-7-oxo-6-(sulfooxy)-1,6-diaza-bicyclo[3.2.1]octan-2-yl)-1,3,4-thiadiazol-2-yl)piperidine-1-carboxylate as a white solid (110 mg, 62%). ESI-MS (EI⁺, m/z): 488.1 [M−H]⁻.

Step 5

Tetrabutylammonium tert-butyl 4-(5-((2S,5R)-7-oxo-6-(sulfooxy)-1,6-diaza-bicyclo[3.2.1]octan-2-yl)-1,3,4-thiadiazol-2-yl)piperidine-1-carboxylate (110 mg, 0.15 mmol) was dissolved in a minimum amount of HPLC grade water (~15 mL) and passed through a column of 16 g of DOWEX 50WX 8 Na⁺ resin (the resin was pre-washed with >0.5 L of HPLC grade water) and eluted with HPLC grade water to afford sodium (2S,5R)-2-(5-(1-(tert-butoxycarbonyl)piperidin-4-yl)-1,3,4-thiadiazol-2-yl)-7-oxo-1,6-diaza-bicyclo [3.2.1]octan-6-yl sulfate after lyophilization as a white solid (50 mg, 65%). ESI-MS (EI⁺, m/z): 488.0 [M−H]⁻. ¹H NMR (500 MHz, D₂O) δ 4.88 (d, J=7.0 Hz, 1H), 4.15 (s, 1H), 4.06 (d, J=10.5 Hz, 2H), 3.39-3.35 (m, 1H), 3.13 (d, J=2 Hz, 1H), 2.94-2.87 (m, 3H), 2.45-2.41 (m, 1H), 2.17-2.04 (m, 4H), 1.89-1.86 (m, 1H), 1.67-1.62 (m, 2H), 1.36 (s, 9H).

Step 6

TFA (0.20 mL) was added to a 0° C. mixture of sodium (2S,5R)-2-(5-(1-(tert-butoxycarbonyl)piperidin-4-yl)-1,3,4-thiadiazol-2-yl)-7-oxo-1,6-diaza-bicyclo[3.2.1]octan-6-yl sulfate (50 mg, 0.10 mmol) in dry DCM (0.60 mL). The reaction mixture was stirred at 0° C. for 2-3 hrs and then diluted with ether (~10 mL). The precipitate was collected via centrifugation, washed with ether (3×) and dried under high vacuum to afford (2S,5R)-7-oxo-2-(5-(piperidin-4-yl)-1,3,4-thiadiazol-2-yl)-1,6-diazabicyclo[3.2.1]octan-6-yl hydrogen sulfate (10 mg, 25%) after prep-HPLC using ammonium formate buffer. ESI-MS (EI⁺, m/z): 390.12.

Example 19

Synthesis of (2S,5R)-2-(5-(2-(methylamino)ethyl)-1,3,4-oxadiazol-2-yl)-7-oxo-1,6-diazabicyclo[3.2.1]octan-6-yl hydrogen sulfate (Compound 722)

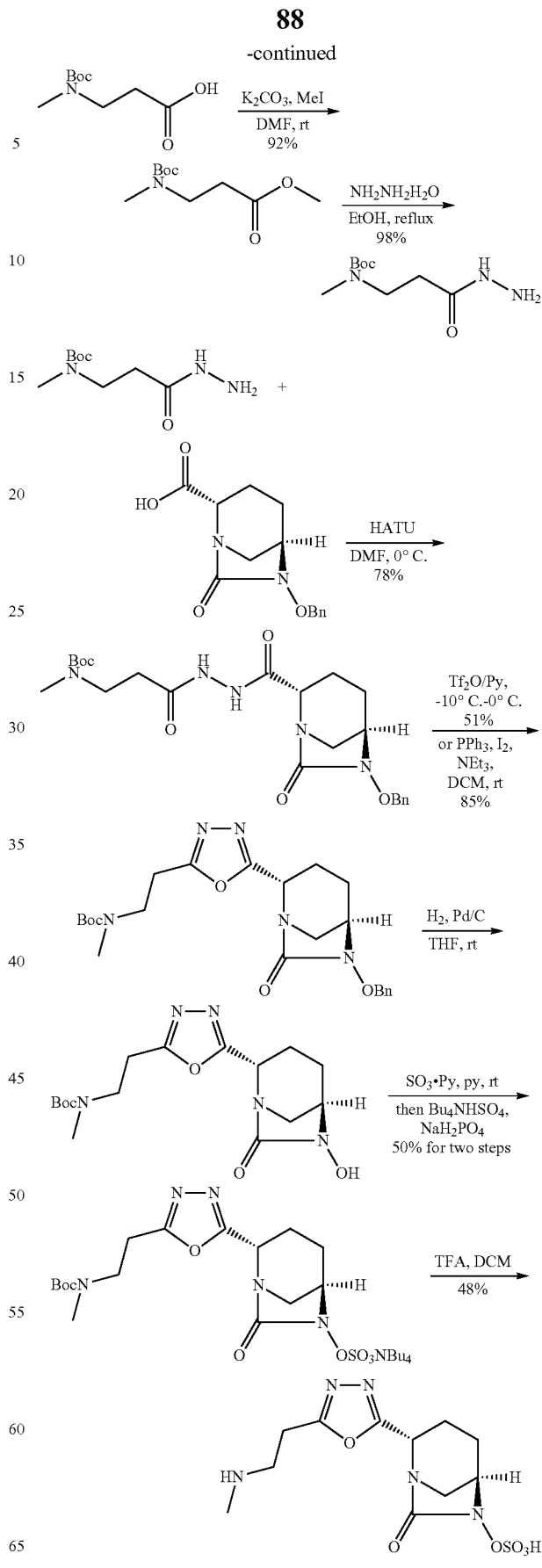

Step 1

Synthesis of methyl 3-(tert-butoxycarbonyl(methyl)amino)propanoate

To a solution of 3-(tert-butoxycarbonyl(methyl)amino) propanoic acid (7.0 g, 0.032 mol) and $K_2CO_3$ (13.3 g, 0.096 mol) in DMF (100 mL) was added MeI (9.0 g, 0.064 mol) at rt. The resultant solution was stirred at rt for 3 hrs. The reaction mixture was quenched with ice water and extracted with ethyl acetate (2×). The combined organic layer was dried over $Na_2SO_4$, and concentrated under reduced pressure. The residue was purified by silica gel column chromatography (gradient elution 0%~10% EtOAc/petroleum ether) to afford methyl 3-(tert-butoxycarbonyl(methyl)amino)propanoate (6.9 g, 92%) as a white solid. ESI-MS (EI+, m/z): 118 [M−100+H]+.

Step 2

Synthesis of tert-butyl 3-hydrazinyl-3-oxopropyl(methyl)carbamate

To a solution of methyl 3-(tert-butoxycarbonyl(methyl) amino)propanoate (6.9 g, 0.0317 mol) in EtOH (15 mL) was added hydrazine monohydrate (7.7 mL, 0.158 mol) at rt. The reaction mixture was heated to 80° C. and stirred at 80° C. overnight. The reaction mixture was concentrated, and then DCM (300 mL) was added. The organic layer was washed with water and saturated sodium chloride, dried over $Na_2SO_4$, and concentrated to afford tert-butyl 3-hydrazinyl-3-oxopropyl(methyl)carbamate (6.8 g, 98%) as sticky oil, which was used directly in the next step. ESI-MS (EI+, m/z): 118 [M−100+H]+.

Step 3

Synthesis of tert-butyl 3-(2-((2S,5R)-6-(benzyloxy)-7-oxo-1,6-diaza-bicyclo[3.2.1]octane-2-carbonyl) hydrazinyl)-3-oxopropyl(methyl)carbamate To a 0° C. solution of tert-butyl 3-hydrazinyl-3-oxopropyl (methyl)carbamate (4.3 g, 19.8 mmol) and (2S,5R)-6-(benzyloxy)-7-oxo-1,6-diazabicyclo[3.2.1]octane-2-carboxylic acid (4.9 g, 0.0178 mol) in DMF (100 mL) was added HATU (8.2 g, 0.0218 mol), followed by dropwise addition of DIPEA (9.6 mL, 0.0594 mol) slowly. The mixture was stirred at 0° C. for 1 h, and then quenched with ice water. The aqueous layer was extracted with EtOAc (2×). The combined organic layer was dried over $Na_2SO_4$, filtered and concentrated. The residue was purified by silica gel column chromatography (gradient elution 20-60% EtOAc/petroleum ether) to afford tert-butyl 3-(2-((2S,5R)-6-(benzyloxy)-7-oxo-1,6-diaza-bicyclo [3.2.1]octane-2-carbonyl)hydrazinyl)-3-oxopropyl(methyl) carbamate (6.7 g, 78%) as a white solid. ESI-MS (EI+, m/z): 476 [M+H]+.

Step 4

Synthesis of tert-butyl 2-(5-((2S,5R)-6-(benzyloxy)-7-oxo-1,6-diaza-bicyclo[3.2.1]octan-2-yl)-1,3,4-oxadiazol-2-yl)ethyl(methyl)carbamate

Method A $Tf_2O$ (7.2 mL, 0.0423 mol) was added slowly, drop-wise to a −78° C. solution of tert-butyl 3-(2-((2S,5R)-6-(benzyloxy)-7-oxo-1,6-diaza-bicyclo[3.2.1]octane-2-carbonyl)hydrazinyl)-3-oxopropyl(methyl)carbamate (6.7 g, 14.1 mmol) and pyridine (9.1 mL, 0.113 mol) in dry DCM (110 mL). The reaction mixture was allowed to warm to 0° C. then was stirred at 0° C. for 3 hrs. Aqueous $NaHCO_3$ was added at 0° C. very slowly. The organic layer was separated and the water layer was washed with DCM (3×). The combined organic layer was dried over $Na_2SO_4$, and concentrated. The crude product was purified by reverse-phase biotage (water/acetonitrile gradient) to afford tert-butyl 2-(5-((2S,5R)-6-(benzyloxy)-7-oxo-1,6-diaza-bicyclo[3.2.1]octan-2-yl)-1,3,4-oxadiazol-2-yl)ethyl(methyl)carbamate (3.3 g, 51%) as a light yellow solid. ESI-MS (EI+, m/z): 458.0 [M+H]+; 1H NMR (500 MHz, $CDCl_3$): δ 7.45-7.36 (m, 5H), 5.09 (d, J=11.5 Hz, 1H), 4.94 (d, J=11.5 Hz, 1H), 4.71 (t, J=4.5 Hz, 1H), 3.67-3.59 (m, 2H), 3.37 (s, 1H), 3.31 (t, J=6.5 Hz, 2H), 2.94-2.86 (m, 2H), 2.82 (s, 3H), 2.32-2.28 (m, 2H), 2.15-2.12 (m, 1H), 2.00-1.95 (m, 1H), 1.45 (s, 9H).

Method B

To a solution of $PPh_3$ (5.3 g, 20.0 mmol) in $CH_2Cl_2$ (250 mL) at rt was added $I_2$(5.2 g, 20.0 mmol). After $I_2$ was dissolved completely, the solution was cooled to 0° C. and TEA (7.0 mL, 50.0 mmol) was added. Tert-butyl3-(2-((2S,5R)-6-(benzyloxy)-7-oxo-1,6-diaza-bicyclo[3.2.1]octane-2-carbonyl)hydrazinyl)-3-oxopropyl(methyl)carbamate (4.8 g, 10.0 mol) was added and the mixture was stirred at rt for 1 hr. The mixture was concentrated, EtOAc (250 mL) was added, and the solution was filtered to remove $POPh_3$. The filtrate was concentrated and the residue was purified by silica gel column chromatography (gradient elution 30 to 50% EtOAc/petroleum ether) to afford tert-butyl 2-(5-((2S,5R)-6-(benzyloxy)-7-oxo-1,6-diaza-bicyclo[3.2.1]octan-2-yl)-1,3,4-oxadiazol-2-yl)ethyl(methyl)carbamate (4.1 g, 85%) as a white solid. ESI-MS (EI+, m/z): 458 [M+H]+.

Step 5-7

Following Steps 3-5 in Example 4, replacing tert-butyl (2-(5-((2S,5R)-6-(benzyloxy)-7-oxo-1,6-diazabicyclo [3.2.1]octan-2-yl)-1,3,4-oxadiazol-2-yl)ethyl)carbamate in Step 3 with tert-butyl (2-(5-((2S,5R)-6-(benzyloxy)-7-oxo-1, 6-diazabicyclo[3.2.1]octan-2-yl)-1,3,4-oxadiazol-2-yl) ethyl)(methyl)carbamate; (2S,5R)-2-(5-(2-(methylamino) ethyl)-1,3,4-oxadiazol-2-yl)-7-oxo-1,6-diazabicyclo[3.2.1] octan-6-yl hydrogen sulfate (1.2 g) was obtained as a white solid after prep-HPLC purification using ammonium formate buffer. ESI-MS (EI+, m/z): 348.2. 1H NMR (300 MHz, $D_2O$) δ 4.76 (d, J=6.3 Hz, 1H), 4.18 (br s, 1H), 3.44 (t, J=7.1 Hz, 2H), 3.32 (t, J=6.6 Hz, 2H), 3.18 (br d, J=12.0 Hz, 1H), 2.93 (d, J=12.3 Hz, 1H), 2.68 (s, 3H), 2.33-2.06 (m, 3H), 1.98-1.86 (m, 1H).

Example 20

Synthesis of (2S,5R)-2-(5-((azetidin-3-ylamino)methyl)-1,3,4-oxadiazol-2-yl)-7-oxo-1,6-diazabicyclo[3.2.1]octan-6-yl hydrogen sulfate (Compound 726)

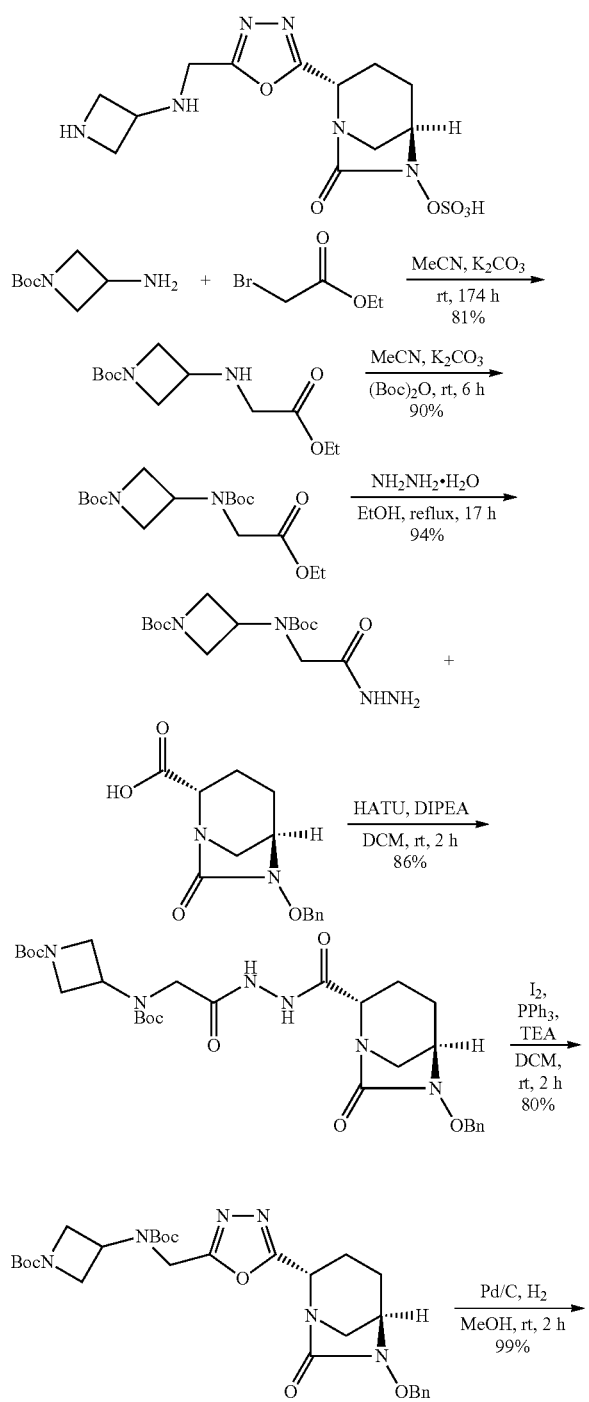

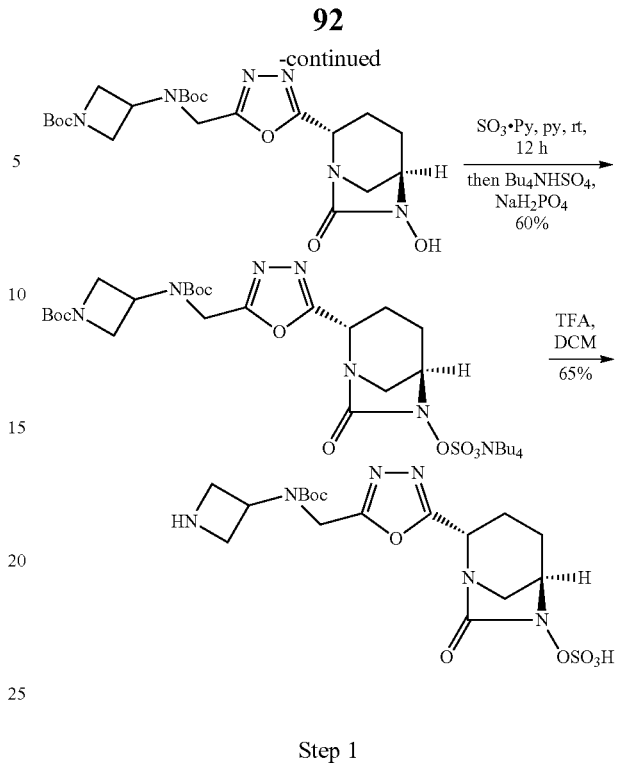

Step 1

Synthesis of tert-butyl 3-(2-ethoxy-2-oxoethylamino)azetidine-1-carboxylate

A mixture of tert-butyl 3-aminoazetidine-1-carboxylate (10.0 g, 58 mmol), ethyl 2-bromoacetate (10.7 g, 64 mmol) and potassium carbonate (24.0 g, 174 mmol) in MeCN (200 mL) was stirred at rt for 13 hrs. The reaction mixture was filtered and concentrated. The crude material was purified by silica gel column chromatography (gradient elution 0~66% EtOAc/petroleum ether) to afford tert-butyl 3-(2-ethoxy-2-oxoethylamino)azetidine-1-carboxylate (12.1 g, 81%) as a white solid. ESI-MS (EI$^+$, m/z): 259.0 [M+H]$^+$.

Step 2

Synthesis of tert-butyl 3-(tert-butoxycarbonyl(2-ethoxy-2-oxoethyl)amino)azetidine-1-carboxylate A mixture of tert-butyl 3-(2-ethoxy-2-oxoethylamino)azetidine-1-carboxylate (10.3 g, 40 mmol), di-tert-butyl dicarbonate (10.4 g, 48 mmol) and potassium carbonate (16.6 g, 120 mmol) in MeCN (200 mL) was stirred at rt for 6 hrs. The reaction mixture was then filtered and concentrated. The crude product was purified by silica gel column chromatography (gradient elution 0~80% EtOAc/petroleum ether) to afford tert-butyl 3-(tert-butoxycarbonyl(2-ethoxy-2-oxoethyl)amino)azetidine-1-carboxylate (13.0 g, 90%) as a white solid. ESI-MS (EI$^+$, m/z): 359.0 [M+H]$^+$.

Step 3

Synthesis of tert-butyl 3-(tert-butoxycarbonyl(2-hydrazinyl-2-oxoethyl)amino)azetidine-1-carboxylate A mixture of tert-butyl 3-(tert-butoxycarbonyl(2-ethoxy-2-oxoethyl)amino)azetidine-1-carboxylate (7.2 g, 20 mmol), hydrazine (5.0 g, 100 mmol) and ethanol (50 mL) was stirred at 80° C. for 17 hrs. The reaction mixture was then concentrated to afford the crude tert-butyl 3-(tert-butoxycarbonyl(2-hydrazinyl-2-oxoethyl)amino)azetidine-1-carboxylate (6.4 g, 94%) as a white solid, which was used directly in the next step. ESI-MS (EI$^+$, m/z): 345.0 [M+H]$^+$.

Step 4

Synthesis of tert-butyl 3-((2-(2-((2S,5R)-6-(benzyloxy)-7-oxo-1,6-diaza-bicyclo[3.2.1]octane-2-carbonyl)hydrazinyl)-2-oxoethyl)(tert-butoxycarbonyl) amino)azetidine-1-carboxylate DIPEA (14 g, 0.11 mol) was added to a 0° C. solution of tert-butyl 3-(tert-butoxycarbonyl(2-hydrazinyl-2-oxoethyl)amino)azetidine-1-carboxylate (15 g, 0.044 mol), (5R)-6-(benzyloxy)-7-oxo-1,6-diaza-bicyclo[3.2.1]octane-2-carboxylic acid (10 g, 0.036 mol) and HATU (15 g, 0.04 mol) in CH$_2$Cl$_2$ (250 mL). The mixture was allowed to warm to rt then was stirred at rt for 2 hrs. The mixture was quenched with saturated sodium chloride (50 mL) and the organic layer was separated. The water layer was extracted with EtOAc (3×). The combined organic layer was washed with saturated sodium chloride (2×), dried over Na$_2$SO$_4$, and concentrated. The residue was purified by silica gel column chromatography (gradient elution 0~50% EtOAc/petroleum ether) to afford tert-butyl 3-((2-(2-((2S,5R)-6-(benzyloxy)-7-oxo-1,6-diaza-bicyclo[3.2.1]octane-2-carbonyl)hydrazinyl)-2-oxoethyl)(tert-butoxycarbonyl)amino)azetidine-1-carboxylate (18.5 g, 86%). ESI-MS (EI$^+$, m/z): 603.3 [M+H]$^+$.

Step 5

Synthesis of tert-butyl 3-(((5-((2S,5R)-6-(benzyloxy)-7-oxo-1,6-diaza-bicyclo[3.2.1]octan-2-yl)-1,3,4-oxadiazol-2-yl)methyl)(tert-butoxycarbonyl) amino)azetidine-1-carboxylate Et$_3$N (8.3 g, 0.082 mol) was added to a 0° C. solution of I$_2$ (10.43 g, 0.041 mol) and PPh$_3$ (10.76 g, 0.041 mol) in CH$_2$Cl$_2$ (250 mL). After the mixture was stirred at rt for 0.5 hr, tert-butyl 3-((2-(2-((2S,5R)-6-(benzyloxy)-7-oxo-1,6-diaza-bicyclo[3.2.1]octane-2-carbonyl)hydrazinyl)-2-oxoethyl)(tert-butoxycarbonyl)amino)azetidine-1-carboxylate (12.34 g, 0.0205 mol) was added. The mixture was stirred for another 1 hr. The mixture was then concentrated and EtOAc (250 mL) was added to the resulting residue. The residue, was stirred and then filtrated to remove Ph$_3$PO. The filtrate was concentrated and purified by silica gel column chromatography (gradient elution 33~50% EtOAc/petroleum ether) to afford tert-butyl 3-(((5-((2S,5R)-6-(benzyloxy)-7-oxo-1,6-diaza-bicyclo[3.2.1]octan-2-yl)-1,3,4-oxadiazol-2-yl)methyl)(tert-butoxycarbonyl)amino) azetidine-1-carboxylate (9.6 g, 80%). ESI-MS (EI$^+$, m/z): 585.3 [M+H]$^+$.

Step 6-8

Following Steps 3-5 in Example 4, replacing tert-butyl (2-(5-((2S,5R)-6-(benzyloxy)-7-oxo-1,6-diazabicyclo[3.2.1]octan-2-yl)-1,3,4-oxadiazol-2-yl)ethyl)carbamate in Step 3 with tert-butyl 3-(((5-((2S,5R)-6-(benzyloxy)-7-oxo-1,6-diazabicyclo[3.2.1]octan-2-yl)-1,3,4-oxadiazol-2-yl)methyl)(tert-butoxycarbonyl)amino)azetidine-1-carboxylate; (2S,5R)-2-(5-((azetidin-3-ylamino)methyl)-1,3,4-oxadiazol-2-yl)-7-oxo-1,6-diazabicyclo[3.2.1]octan-6-yl hydrogen sulfate (1.5 g) was obtained as a white solid after prep-HPLC purification using ammonium formate buffer. ESI-MS (EI$^+$, m/z): 375.1. $^1$H NMR (300 MHz, D$_2$O) δ 5.00 (d, J=5.4 Hz, 1H), 4.39-4.34 (m, 3H), 4.25 (s, 2H), 4.21-4.08 (m, 3H), 3.41 (br d, J=13.1 Hz, 1H), 3.11 (d, J=12.3 Hz, 1H), 2.57-2.28 (m, 3H), 2.19-2.08 (m, 1H).

Example 21

Synthesis of (2S,5R)-2-(5-((1r,3S)-3-aminocyclobutyl)-1,3,4-oxadiazol-2-yl)-7-oxo-1,6-diazabicyclo[3.2.1]octan-6-yl hydrogen sulfate (Compound 727)

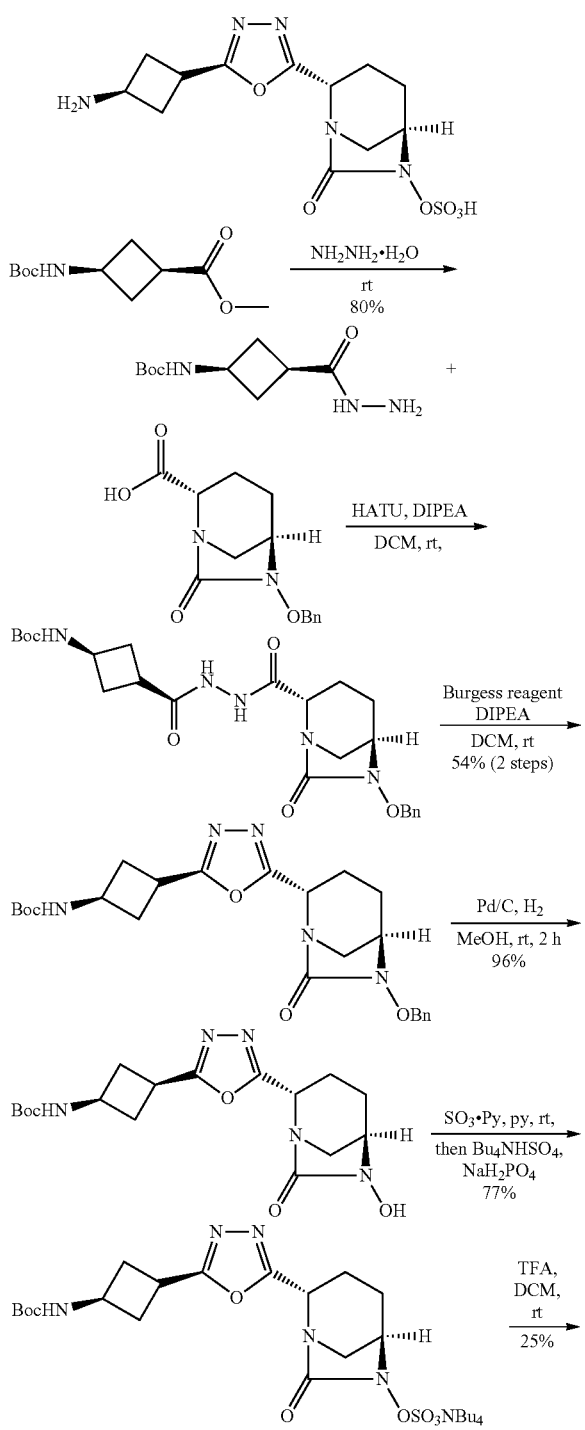

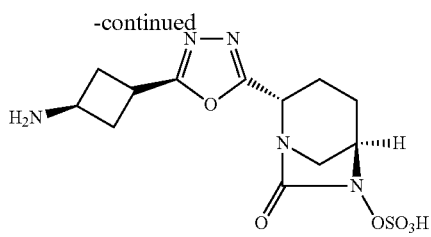

Step 1

Synthesis of tert-butyl ((1s,3s)-3-(hydrazinecarbonyl)cyclobutyl)carbamate

A solution of (1s,3s)-methyl 3-((tert-butoxycarbonyl)amino)cyclobutanecarboxylate (1.0 g, 4.36 mmol) in $NH_2NH_2 \cdot H_2O$ (2 mL, 65.4 mmol) was stirred at rt for 12 hrs. $Et_2O$ (20 mL) was then added to the mixture and the product was obtain by filtration. The solid material was dried under vacuum to give tert-butyl ((1s,3s)-3-(hydrazinecarbonyl)cyclobutyl)carbamate (0.8 g, 80%) as a white solid. ESI-MS (EI$^+$, m/z): 230.4.

Step 2: Synthesis of tert-butyl((1S,3r)-3-(2-((2S,5R)-6-(benzyloxy)-7-oxo-1,6-diazabicyclo[3.2.1]octane-2-carbonyl)hydrazinecarbonyl)cyclobutyl)carbamate HATU (56.4 g, 148 mmol), and DIPEA (27.8 mL, 160 mmol) were added to a solution of (2S,5R)-6-(benzyloxy)-7-oxo-1,6-diaza-bicyclo[3.2.1]octane-2-carboxylic acid (31.6 g, 114 mmol) and tert-butyl 4-hydrazinyl-4-oxobutylcarbamate (28.8 g, 126 mmol) in $CH_2Cl_2$ (460 mL). The mixture was stirred at rt for 4 hrs then diluted with $CH_2Cl_2$ (300 mL), washed with water (2×) and saturated sodium chloride (2×), dried over $Na_2SO_4$, and concentrated to give a slightly yellow solid that was used in the next step without further purification. ESI-MS (EI$^+$, m/z): 488.5.

Step 3: Synthesis of tert-butyl((1S,3r)-3-(5-((2S,5R)-6-(benzyloxy)-7-oxo-1,6-diazabicycl[3.2.1]octan-2-yl)-1,3,4-oxadiazol-2-yl)cyclobutyl)carbamate To a solution of tert-butyl((1S,3r)-3-(2-((2S,5R)-6-(benzyloxy)-7-oxo-1,6-diazabicyclo[3.2.1]octane-2-carbonyl)hydrazinecarbonyl)cyclobutyl)carbamate (65 g, 133 mmol) in DCM (445 mL) was added DIPEA (45 mL, 267 mmol), followed by and Burgess reagent (63.5 g, 267 mmol). The reaction mixture was stirred at rt 12 hrs and then diluted with $CH_2Cl_2$ (300 mL), washed with water (2×) and saturated sodium chloride (2×), dried over $Na_2SO_4$, and concentrated. The residue was purified by silica gel column chromatography (gradient elution 0~50% DCM/acetone) to afford tert-butyl((1S,3r)-3-(5-((2S,5R)-6-(benzyloxy)-7-oxo-1,6-diazabicycl[3.2.1]octan-2-yl)-1,3,4-oxadiazol-2-yl)cyclobutyl)carbamate as a slightly pink solid (29 g, 62 mmol, 54% over 2 steps). ESI-MS (EI$^+$, m/z): 470.5.

Step 4-6

Following Steps 3-5 in Example 4, replacing tert-butyl (2-(5-((2S,5R)-6-(benzyloxy)-7-oxo-1,6-diazabicyclo[3.2.1]octan-2-yl)-1,3,4-oxadiazol-2-yl)ethyl)carbamate in Step 3 with tert-butyl ((1S,3r)-3-(5-((2S,5R)-6-(benzyloxy)-7-oxo-1,6-diazabicyclo[3.2.1]octan-2-yl)-1,3,4-oxadiazol-2-yl)cyclobutyl)carbamate; (2S,5R)-2-(5-((1r,3S)-3-aminocyclobutyl)-1,3,4-oxadiazol-2-yl)-7-oxo-1,6-diazabicyclo[3.2.1]octan-6-yl hydrogen sulfate (3.3 g) was obtained as a white solid after prep-HPLC purification using ammonium formate buffer. ESI-MS (EI$^+$, m/z): 360.2. $^1$H NMR (300 MHz, $D_2O$) δ 4.74 (d, J=7.6 Hz, 1H), 4.17 (br s, 1H), 3.96-3.80 (m, 1H), 3.72-3.55 (m, 1H), 3.17 (br d, J=13.1 Hz, 1H), 2.90 (d, J=12.3 Hz, 1H), 2.82-2.73 (m, 2H), 2.53-2.43 (m, 2H), 2.30-2.08 (m, 3H), 2.00-1.83 (m, 1H).

Example 22

Synthesis of (2S,5R)-2-(5-(1-(guanidinomethyl)cyclopropyl)-1,3,4-oxadiazol-2-yl)-7-oxo-1,6-diazabicyclo[3.2.1]octan-6-yl hydrogen sulfate (Compound 723)

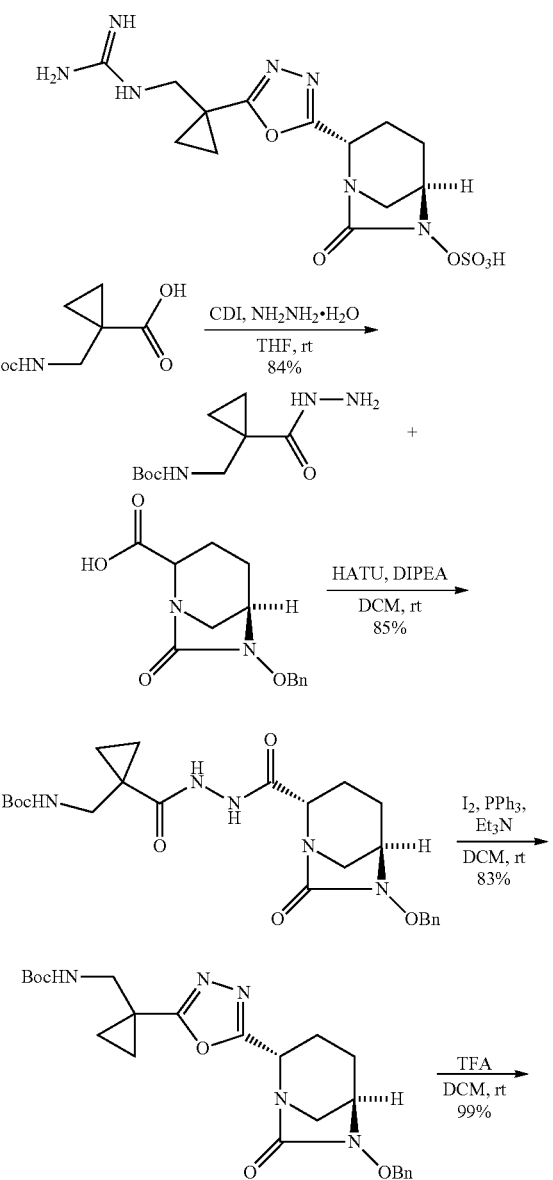

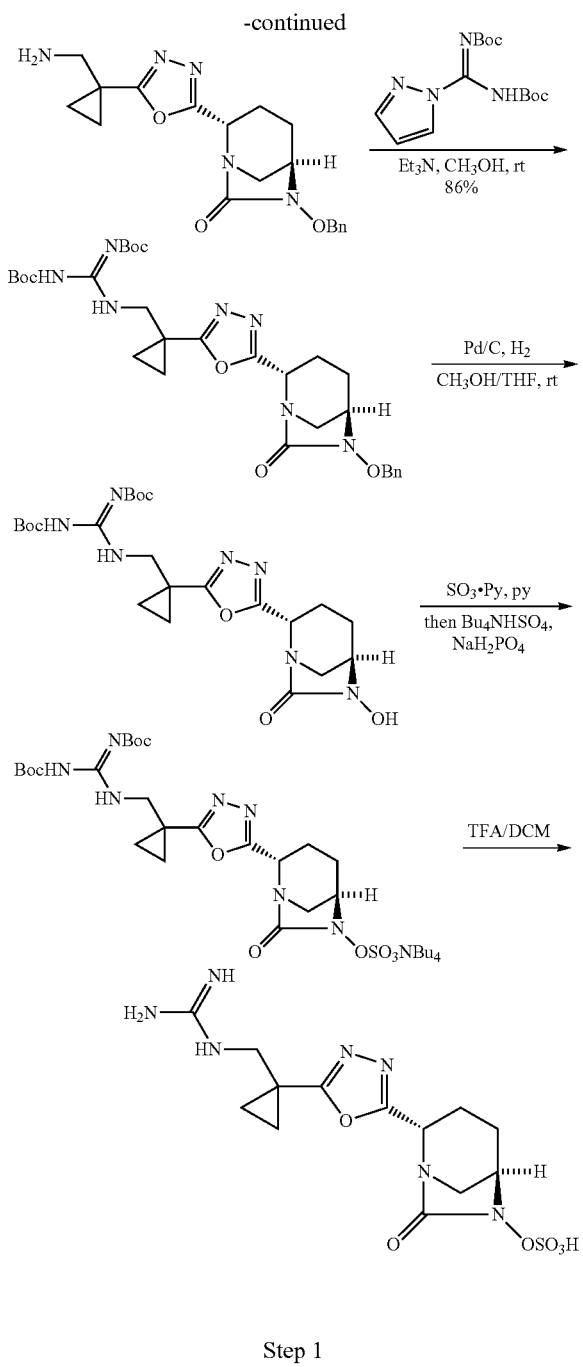

Step 1

Synthesis of tert-butyl(1-(hydrazinecarbonyl)cyclopropyl)methylcarbamate

CDI (12.5 g, 0.077 mol) was added to a 0° C. solution of 1-((tert-butoxycarbonylamino)methyl)cyclopropanecarboxylic acid (15.0 g, 0.07 mol) in THF (250 mL). The mixture was allowed to warm to rt, and stirred at rt. for 2 hrs, and then $NH_2NH_2 \cdot H_2O$ (10.5 g, 0.21 mol) was added rapidly. The mixture was stirred for another 1 hr. The reaction mixture was concentrated, and then $CH_2Cl_2$ (500 mL) was added. The combined organic layer was washed with $H_2O$ (100 mL), dried over $Na_2SO_4$, and concentrated to afford tert-butyl(1-(hydrazinecarbonyl)cyclopropyl)methylcarbamate (13.5 g, 84%). ESI-MS (EI$^+$, m/z): 230.2 [M+H]$^+$.

Step 2: Synthesis of tert-butyl(1-(2-((5R)-6-(benzyloxy)-7-oxo-1,6-diaza-bicyclo[3.2.1]octane-2-carbonyl)hydrazinecarbonyl)cyclopropyl)methylcarbamate DIPEA (14 g, 0.11 mol) was added to a solution of tert-butyl (1-(hydrazinecarbonyl)cyclopropyl)methylcarbamate (10.0 g, 0.044 mol), (5R)-6-(benzyloxy)-7-oxo-1,6-diaza-bicyclo[3.2.1]octane-2-carboxylic acid (10 g, 0.036 mol), and HATU (15 g, 0.04 mol) in $CH_2Cl_2$ (250 mL). The mixture was stirred at rt for 2 hrs. The mixture was diluted with $CH_2Cl_2$ (500 mL), washed with $H_2O$ (300 mL), dried over $Na_2SO_4$, and concentrated. The crude product was washed with EtOAc (200 mL), and filtrated to afford tert-butyl(1-(2-((5R)-6-(benzyloxy)-7-oxo-1,6-diaza-bicyclo[3.2.1]octane-2-carbonyl)hydrazinecarbonyl)cyclopropyl)methylcarbamate (15 g, 85%) as a white solid. ESI-MS (EI$^+$, m/z): 488.3 [M+H]$^+$.

Step 3: Synthesis of tert-butyl(1-(5-((5R)-6-(benzyloxy)-7-oxo-1,6-diaza-bicyclo[3.2.1]octan-2-yl)-1,3,4-oxadiazol-2-yl)cyclopropyl)methylcarbamate $Et_3N$ (8.3 g, 0.082 mol) was added to a 0° C. solution of $I_2$ (10.43 g, 0.041 mol), $PPh_3$ (10.76 g, 0.041 mol) in $CH_2Cl_2$ (250 mL). The mixture was allowed to warm to rt. After stirring at rt for 0.5 hr, tert-butyl(1-(2-((5R)-6-(benzyloxy)-7-oxo-1,6-diaza-bicyclo[3.2.1]octane-2-carbonyl)hydrazinecarbonyl)cyclopropyl)methylcarbamate (10 g, 0.0205 mol) was added. The mixture was stirred at rt for another 1 hr. The mixture was concentrated, EtOAc (250 mL) was added, and the mixture was filtered to remove $Ph_3PO$. The filtrate was concentrated and the residue was purified by silica gel column chromatography (gradient elution 33~50% EtOAc/petroleum ether) to afford tert-butyl (1-(5-((5R)-6-(benzyloxy)-7-oxo-1,6-diaza-bicyclo[3.2.1]octan-2-yl)-1,3,4-oxadiazol-2-yl)cyclopropyl)methylcarbamate (8 g, 83%) as a white solid. ESI-MS (EI$^+$, m/z): 470.3 [M+H]$^+$.

Step 4

Synthesis of (5R)-2-(5-(1-(aminomethyl)cyclopropyl)-1,3,4-oxadiazol-2-yl)-6-(benzyloxy)-1,6-diaza-bicyclo[3.2.1]octan-7-one TFA (30 mL) was added to a 0° C. solution of tert-butyl(1-(5-((5R)-6-(benzyloxy)-7-oxo-1,6-diaza-bicyclo[3.2.1]octan-2-yl)-1,3,4-oxadiazol-2-yl)cyclopropyl)methylcarbamate (8 g, 0.017 mol) in DCM (100 mL). The mixture was allowed to warm to rt and was stirred at rt for 1 h. The mixture was concentrated and the residue was washed with $Et_2O$ (50 mL), and then filtrated to afford (5R)-2-(5-(1-(aminomethyl)cyclopropyl)-1,3,4-oxadiazol-2-yl)-6-(benzyloxy)-1,6-diaza-bicyclo[3.2.1]octan-7-one (7 g, 99%), which was used directly in the next step. ESI-MS (EI$^+$, m/z): 370.2 [M+H]$^+$.

Step 5: Synthesis of (5R)-2-(5-(1-(2,3-bis-(tert-butoxycarbonyl)-guanidinomethyl)cyclopropyl)-1,3,4-oxadiazol-2-yl)-6-(benzyloxy)-1,6-diaza-bicyclo[3.2.1]octan-7-one $Et_3N$ (5 g, 0.05 mol) and tert-butyl (((tert-butoxycarbonyl)amino)(1H-pyrazol-1-yl)methylene)carbamate (5.5 g, 17.5 mmol) were added to a solution of (5R)-2-(5-(1-(aminomethyl)cyclopropyl)-1,3,4-oxadiazol-2-yl)-6-(benzyloxy)-1,6-diaza-bicyclo[3.2.1]octan-7-one (7 g, 0.017 mol) in $CH_3OH$ (500 mL). The mixture was stirred at rt for 4 hrs and then concentrated. The residue was purified by silica gel column chromatography (gradient elution 50 to 66% EtOAc/ petroleum ether) to afford (5R)-2-(5-(1-(2,3-bis-(tert-butoxycarbonyl)-guanidinomethyl)cyclopropyl)-1,3,4-oxadiazol-2-yl)-6-(benzyloxy)-1,6-diaza-bicyclo[3.2.1]octan-7-one (9 g, 86%) as a white solid. ESI-MS (EI+, m/z): 612.3 [M+H]+.

Step 6-8

Following Steps 3-5 in Example 4, replacing tert-butyl (2-(5-((2S,5R)-6-(benzyloxy)-7-oxo-1,6-diazabicyclo[3.2.1]octan-2-yl)-1,3,4-oxadiazol-2-yl)ethyl)carbamate in Step 3 with (5R)-2-(5-(1-(2,3-bis-(tert-butoxycarbonyl)-guanidinomethyl)cyclopropyl)-1,3,4-oxadiazol-2-yl)-6-(benzyloxy)-1,6-diaza-bicyclo[3.2.1]octan-7-one; (2S,5R)-2-(5-(1-(guanidinomethyl)cyclopropyl)-1,3,4-oxadiazol-2-yl)-7-oxo-1,6-diazabicyclo[3.2.1]octan-6-yl hydrogen sulfate (0.74 g) was obtained as a white solid after prep-HPLC purification using ammonium formate buffer. ESI-MS (EI+, m/z): 402.1. ¹H NMR (300 MHz, D₂O) δ 4.74 (d, J=7.9 Hz, 1H), 4.17 (s, 1H), 3.57 (s, 2H), 3.17 (br d, J=12.9 Hz, 1H), 2.88 (d, J=12.3 Hz, 1H), 2.32-2.05 (m, 3H), 1.98-1.82 (m, 1H), 1.38 (br s, 2H), 1.23 (br s, 2H).

Example 23

Synthesis of (2S,5R)-2-(5-((1-aminocyclopropyl)methyl)-1,3,4-oxadiazol-2-yl)-7-oxo-1,6-diazabicyclo[3.2.1]octan-6-yl hydrogen sulfate (Compound 724)

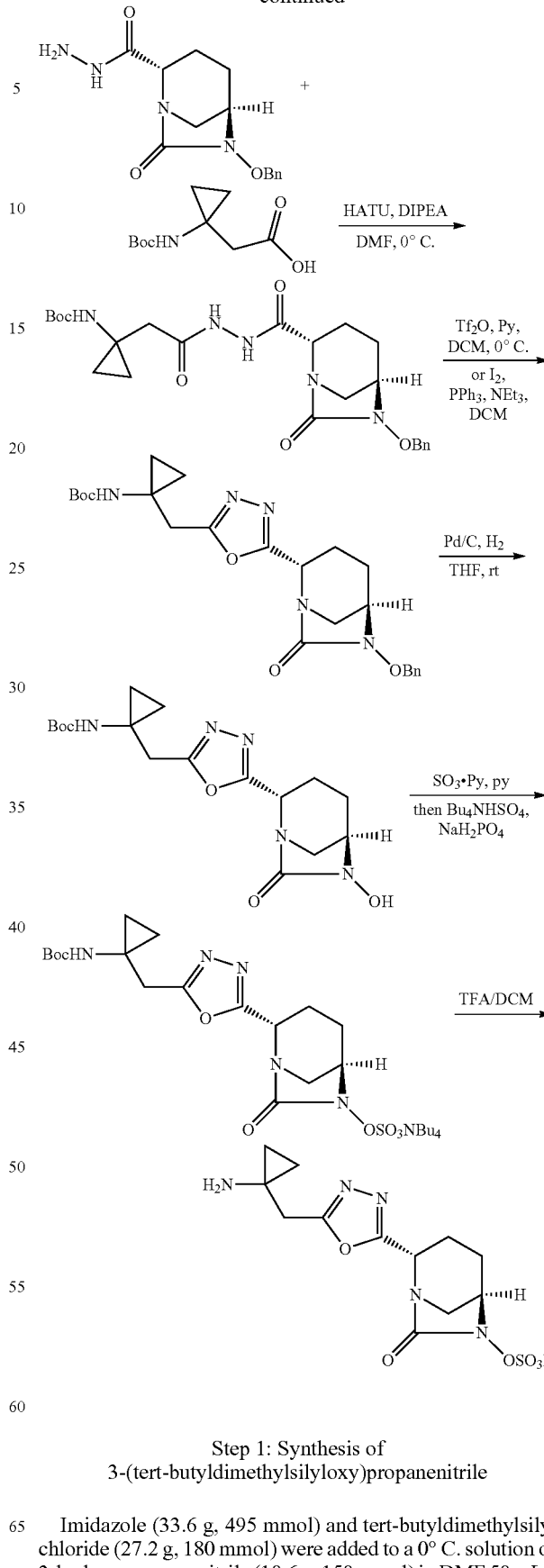

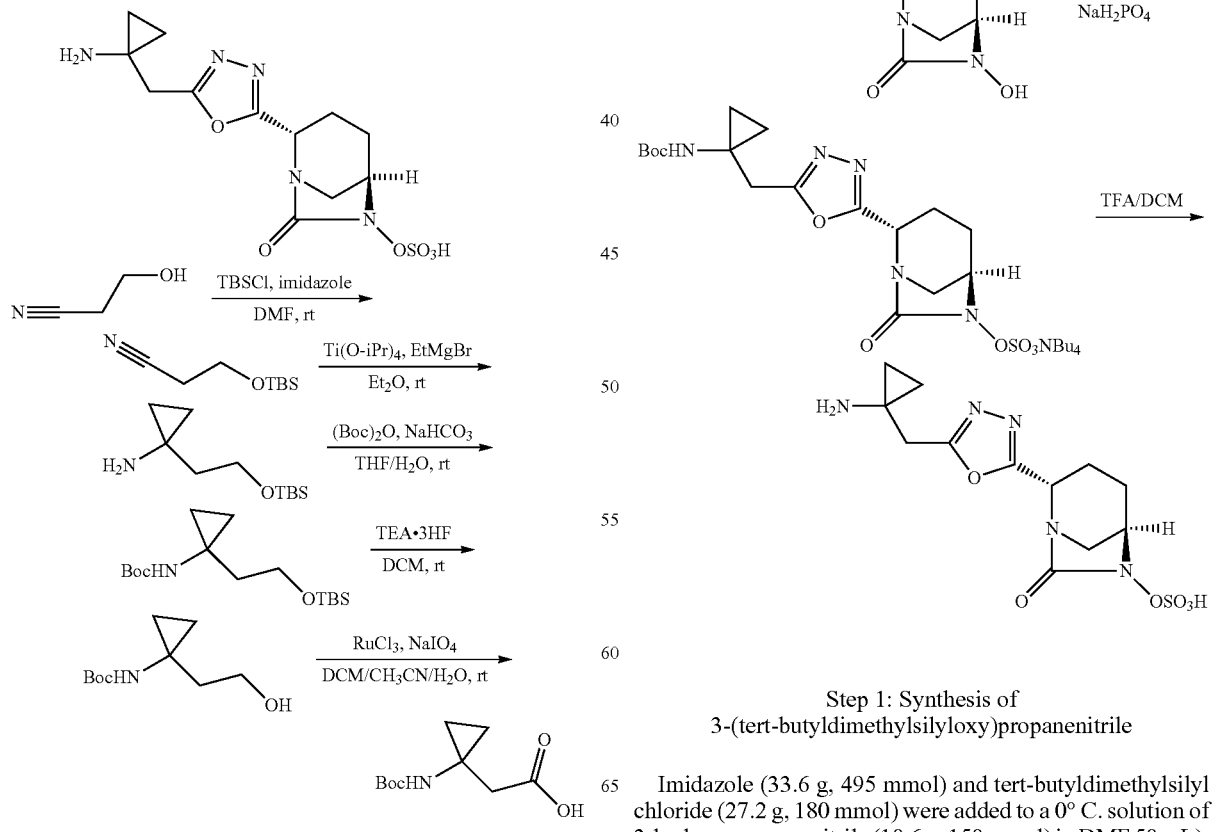

Step 1: Synthesis of 3-(tert-butyldimethylsilyloxy)propanenitrile

Imidazole (33.6 g, 495 mmol) and tert-butyldimethylsilyl chloride (27.2 g, 180 mmol) were added to a 0° C. solution of 3-hydroxypropanenitrile (10.6 g, 150 mmol) in DMF 50 mL).

The mixture was allowed to warm to rt, then was stirred at rt for 12 hrs. The mixture was quenched with water (500 mL), and then extracted with EtOAc (3×). The combined organic layer was dried over $Na_2SO_4$ and concentrated. The residue was purified by silica gel column chromatography (gradient elution 0-5% EtOAc/petroleum ether) to give 3-(tert-butyldimethylsilyloxy) propanenitrile (18 g, 75%) as a colorless oil. $^1$H NMR (400 MHz, $CDCl_3$): δ 3.74 (t, J=6.0 Hz, 2H), 2.43 (t, J=6.0 Hz, 2H), 0.81 (s, 9H), 0.00 (s, 6H).

Step 2: Synthesis of 1-(2-(tert-butyldimethylsilyloxy)ethyl)cyclopropanamine

To a solution of 3-(tert-butyldimethylsilyloxy)propanenitrile (11.1 g, 60 mmol) in $Et_2O$ (400 mL) was added titanium tetraisopropanolate (28.9 g, 102 mmol) under $N_2$ atmosphere. Ethylmagnesium bromide (3M in $Et_2O$, 50 mL) was slowly added drop-wise at 0° C. The mixture was stirred at rt for 1 hr. Boron trifluoride etherate (17.0 g, 120 mmol) was slowly added at 0° C. The mixture was stirred at rt for 1 hr. The mixture was quenched with 10% aq. NaOH (300 mL) and then extracted with DCM (3×). The combined organic layer was dried over $Na_2SO_4$ and concentrated. The residue was purified by silica gel column chromatography (gradient elution 5~50% EtOAc/petroleum ether) to afford 1-(2-(tert-butyldimethylsilyloxy)ethyl)cyclopropanamine (3.9 g, 30%) as a colorless oil. ESI-MS ($EI^+$, m/z): 216.2 $[M+H]^+$.

Step 3: Synthesis of tert-butyl 1-(2-(tert-butyldimethylsilyloxy)ethyl)cyclopropyl-carbamate A solution of 1-(2-(tert-butyldimethylsilyloxy)ethyl)cyclopropanamine (1.9 g, 8.8 mmol), $(Boc)_2O$ (2.9 g, 13.2 mmol), $NaHCO_3$ (1.5 g, 17.6 mmol) in $THF/H_2O$ (20 mL/20 mL) was stirred at rt for 17 hrs. The mixture was extracted with EtOAc (3×). The combined organic layer was dried over $Na_2SO_4$ and concentrated. The residue was purified by silica gel column chromatography (0~15% gradient elution EtOAc/petroleum ether) to afford tert-butyl 1-(2-(tert-butyldimethylsilyloxy)ethyl)cyclopropylcarbamate (2.5 g, 90%) as a colorless oil. ESI-MS ($EI^+$, m/z): 316 $[M+H]^+$.

Step 4: Synthesis of tert-butyl 1-(2-hydroxyethyl)cyclopropylcarbamate

A solution of tert-butyl 1-(2-(tert-butyldimethylsilyloxy)ethyl)cyclopropylcarbamate (11.9 g, 37.8 mmol) and 3HF.TEA (22.0 g) in DCM (50 mL) was stirred at rt for 17 hrs. The mixture was concentrated and the residue was purified by silica gel column chromatography (0~20% gradient elution EtOAc/petroleum ether) to afford tert-butyl 1-(2-hydroxyethyl)cyclopropylcarbamate (4.6 g, 60%) as a white solid.

Step 5: Synthesis of 2-(1-(tert-butoxycarbonylamino)cyclopropyl)acetic acid $RuCl_3.H_2O$ (124 mg, 0.6 mmol) was added to a solution of tert-butyl 1-(2-hydroxyethyl)cyclopropylcarbamate (6.1 g, 30 mmol), and $NaIO_4$ (19.0 g, 90 mmol) in $DCM/H_2O/CH_3CN$ (20 mL/40 mL/20 mL). The mixture was stirred at rt for 3 hrs. The mixture was then diluted with $H_2O$ (100 mL), and extracted with DCM (3×). The combined organic layer was dried over $Na_2SO_4$ and concentrated. The residue was purified by silica gel column chromatography (0~30% gradient elution EtOAc/petroleum ether) to afford 2-(1-(tert-butoxycarbonylamino)cyclopropyl)acetic acid (6.0 g, 90%) as a white solid. ESI-MS ($EI^+$, m/z): 238 $[M+Na]^+$.

Step 6: Synthesis of tert-butyl 1-(2-(2-((2S,5R)-6-(benzyloxy)-7-oxo-1,6-diaza-bicyclo[3.2.1]octane-2-carbonyl)hydrazinyl)-2-oxoethyl)cyclopropylcarbamate A solution of 2-(1-(tert-butoxycarbonylamino)cyclopropyl)acetic acid (1.5 g, 6.9 mmol), (2S,5R)-6-(benzyloxy)-7-oxo-1,6-diaza-bicyclo[3.2.1]octane-2-carbohydrazide (3.1 g, 7.6 mmol), DIPEA (2.7 g, 21.0 mmol), and HATU (3.9 g, 10.45 mmol) in DMF (20 mL) was stirred at 0° C. for 1 hr. The mixture was quenched with saturated sodium chloride (150 mL) and EtOAc (150 mL). The organic layer was separated and washed with saturated sodium chloride (2×), dried over $Na_2SO_4$, and concentrated. The residue was purified by silica gel column chromatography (0~80% gradient elution EtOAc/petroleum ether) to afford tert-butyl 1-(2-(2-((2S,5R)-6-(benzyloxy)-7-oxo-1,6-diaza-bicyclo[3.2.1]octane-2-carbonyl)hydrazinyl)-2-oxoethyl)cyclopropylcarbamate (2.4 g, 70%) as a white solid. ESI-MS ($EI^+$, m/z): 488 $[M+H]^+$.

Step 7: Synthesis of tert-butyl 1-((5-((2S,5R)-6-(benzyloxy)-7-oxo-1,6-diaza-bicyclo[3.2.1]octan-2-yl)-1,3,4-oxadiazol-2-yl)methyl)cyclopropylcarbamate Method A Pyridine (5.2 g, 65.6 mmol) was added to a 0° C. solution of tert-butyl 1-(2-(2-((2S,5R)-6-(benzyloxy)-7-oxo-1,6-diaza-bicyclo[3.2.1]octane-2-carbonyl)hydrazinyl)-2-oxoethyl)cyclopropylcarbamate (4.0 g, 8.2 mmol) in DCM (40 mL). $Tf_2O$ (5.7 g, 20.5 mmol) was added slowly at 0° C. The reaction mixture was stirred at 0° C. for 3.5 hrs. Sat. $NaHCO_3$ was added very slowly at 0° C. The organic layer was separated and washed with saturated sodium chloride (2×), dried over $Na_2SO_4$, and concentrated. The residue was purified by silica gel column chromatography (0~70% gradient elution EtOAc/petroleum ether) to afford tert-butyl 1-((5-((2S,5R)-6-(benzyloxy)-7-oxo-1,6-diaza-bicyclo[3.2.1]octan-2-yl)-1,3,4-oxadiazol-2-yl)methyl)cyclopropylcarbamate (2.6 g, 65%) as a yellow solid. ESI-MS ($EI^+$, m/z): 470 $[M+H]^+$.

Method B

To s solution of $PPh_3$ (5.2 g, 20.0 mmol) in dry DCM (60 mL) was added $I_2$ (5.1 g, 20.0 mmol). After $I_2$ was dissolved completely, TEA (7.0 mL, 50.0 mmol) was added quickly at rt. The mixture was stirred for 15 mins. Tert-butyl 1-(2-(2-((2S,5R)-6-(benzyloxy)-7-oxo-1,6-diaza-bicyclo[3.2.1]octane-2-carbonyl)hydrazinyl)-2-oxoethyl)cyclopropyl-carbamate (4.9 g, 10.0 mmol) was added and the mixture was stirred at rt for 1 hr. The solvent was concentrated. EtOAc (250 mL) was added, and the solution was filtered to remove $PPh_3O$. The filtrate was concentrated and the residue was purified by silica gel column chromatography (0~60% gradient elution EtOAc/petroleum ether) to afford tert-butyl 1-((5-((2S,5R)-6-(benzyloxy)-7-oxo-1,6-diaza-bicyclo[3.2.1]octan-2-yl)-1,3,4-oxadiazol-2-yl)methyl)cyclopropyl-carbamate (4.1 g, 87%) as a white solid. ESI-MS ($EI^+$, m/z): 470 $[M+H]^+$.

Step 8-10

Following Steps 3-5 in Example 4, replacing tert-butyl (2-(5-((2S,5R)-6-(benzyloxy)-7-oxo-1,6-diazabicyclo

[3.2.1]octan-2-yl)-1,3,4-oxadiazol-2-yl)ethyl)carbamate in Step 3 with tert-butyl (1-((5-((2S,5R)-6-(benzyloxy)-7-oxo-1,6-diazabicyclo[3.2.1]octan-2-yl)-1,3,4-oxadiazol-2-yl)methyl)cyclopropyl)carbamate; (2S,5R)-2-(5-((1-aminocyclopropyl)methyl)-1,3,4-oxadiazol-2-yl)-7-oxo-1,6-diazabicyclo[3.2.1]octan-6-yl hydrogen sulfate (0.78 g) was obtained as a white solid after prep-HPLC purification using ammonium formate buffer. ESI-MS (EI+, m/z): 360.1. 1H NMR (300 MHz, D2O) δ 4.75 (d, J=6.4 Hz, 1H), 4.16 (br s, 1H), 3.25 (s, 2H), 3.17 (br d, J=12.7 Hz, 1H), 2.95 (d, J=12.4 Hz, 1H), 2.34-2.03 (m, 3H), 2.00-1.82 (m, 1H), 1.08-0.86 (m, 4H).

Example 24

Synthesis of (2S,5R)-2-(5-(azetidin-3-ylmethyl)-1,3,4-oxadiazol-2-yl)-7-oxo-1,6-diazabicyclo[3.2.1]octan-6-yl hydrogen sulfate (Compound 725)

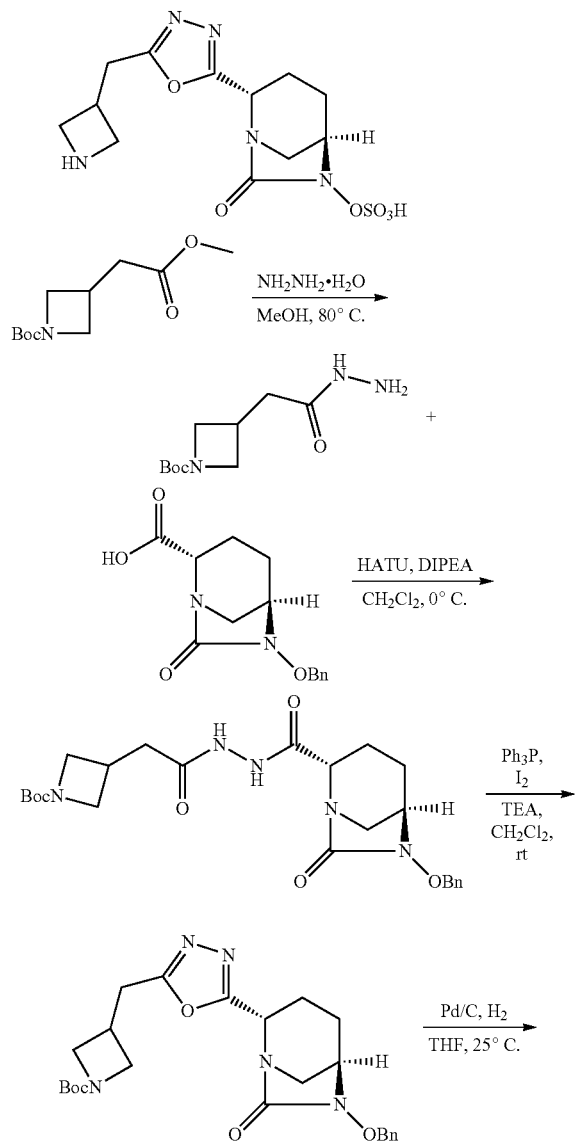

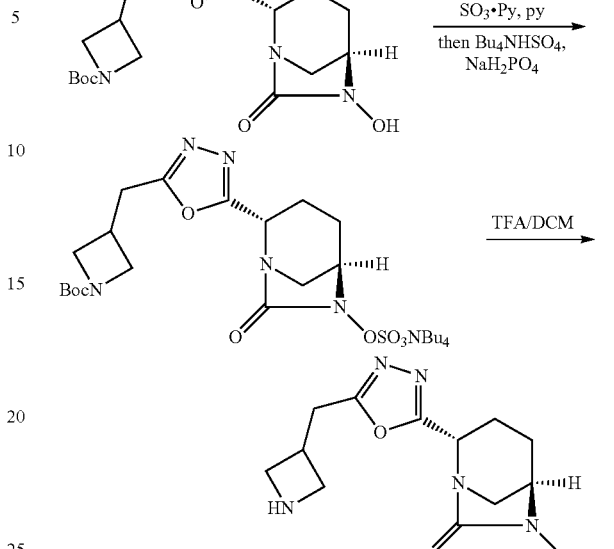

Step 1: Synthesis of tert-butyl 3-(2-hydrazinyl-2-oxoethyl)azetidine-1-carboxylate To a solution of tert-butyl 3-(2-methoxy-2-oxoethyl)azetidine-1-carboxylate (25.0 g, 109 mmol) in MeOH (150 mL) was added NH2NH2.H2O (27.3 g, 546 mmol) at rt. The mixture was heated at 65° C. for 12 hrs and then concentrated. The residue was diluted with DCM (400 mL), washed with water (2×) and saturated sodium chloride (2×), dried over Na2SO4, and concentrated to give tert-butyl 3-(2-hydrazinyl-2-oxoethyl)azetidine-1-carboxylate (24.0 g, 96%) as a yellow gum. ESI-MS (EI+, m/z): 252 [M+Na]+.

Step 2: Synthesis of tert-butyl 3-(2-(2-((2S,5R)-6-(benzyloxy)-7-oxo-1,6-diaza bicyclo[3.2.1]octane-2-carbonyl)hydrazinyl)-2-oxoethyl)azetidine-1-carboxylate HATU (19.6 g, 52.2 mmol) and DIPEA (16.6 g, 130.5 mmol) were added to a 0° C. solution of (2S,5R)-6-(benzyloxy)-7-oxo-1,6-diaza-bicyclo[3.2.1]octane-2-carboxylic acid (12.0 g, 43.5 mmol), tert-butyl 3-(2-hydrazinyl-2-oxoethyl)azetidine-1-carboxylate (11.3 g, 49.8 mmol) in CH2Cl2 (360 mL). The mixture was allowed to warm to rt then the mixture was stirred at rt for 12 hrs. The mixture was then diluted with CH2Cl2 (300 mL), washed with water (2×) and saturated sodium chloride (2×), dried and concentrated. The residue was purified by silica gel column chromatography (0-20% gradient elution EtOAc/petroleum ether) to afford tert-butyl 3-(2-(2-((2S,5R)-6-(benzyloxy)-7-oxo-1,6-diaza bicyclo[3.2.1]octane-2-carbonyl)hydrazinyl)-2-oxoethyl)azetidine-1-carboxylate (19.3 g, 93%) as a white solid. ESI-MS (EI+, m/z): 488 [M+H]+.

Step 3: Synthesis of tert-butyl 3-((5-((2S,5R)-6-(benzyloxy)-7-oxo-1,6-diaza-bicyclo[3.2.1]octan-2-yl)-1,3,4-oxadiazol-2-yl)methyl)azetidine-1-carboxylate To s solution of PPh3 (2.2 g, 8.2 mmol) in dry DCM (60 mL) was added I2 (2.1 g, 8.2 mmol). After I2 was dissolved completely, TEA (1.7 g, 16.4 mmol) was added quickly at rt. The mixture was stirred for 15 mins. Tert-butyl 3-(2-(2-((2S,5R)-6-(benzyloxy)-7-oxo-1,6-diaza bicyclo[3.2.1]octane-2-carbonyl)hydrazinyl)-2-oxoethyl)azetidine-1-carboxylate (2.0 g, 4.1 mmol) was added. The mixture was stirred at rt for 1 h. The reaction mixture was concentrated and the residue was purified by silica gel column chromatography (gradient elution 0~40% EtOAc/petroleum ether) to afford tert-butyl 3-((5-((2S,5R)-6-(benzyloxy)-7-oxo-1,6-diaza-bicyclo[3.2.1]octan-2-yl)-1,3,4-oxadiazol-2-yl)methyl)azetidine-1-carboxylate (1.3 g, 66%) as a white solid. ESI-MS (EI$^+$, m/z): 470 [M+H]$^+$.

Step 4-6

Following Steps 3-5 in Example 4, replacing tert-butyl (2-(5-((2S,5R)-6-(benzyloxy)-7-oxo-1,6-diazabicyclo[3.2.1]octan-2-yl)-1,3,4-oxadiazol-2-yl)ethyl)carbamate in Step 3 with tert-butyl 3-((5-((2S,5R)-6-(benzyloxy)-7-oxo-1,6-diazabicyclo[3.2.1]octan-2-yl)-1,3,4-oxadiazol-2-yl)methyl)azetidine-1-carboxylate, (2S,5R)-2-(5-(azetidin-3-ylmethyl)-1,3,4-oxadiazol-2-yl)-7-oxo-1,6-diazabicyclo[3.2.1]octan-6-yl hydrogen sulfate was obtained as a white solid after prep-HPLC purification using ammonium formate buffer. ESI-MS (EI$^+$, m/z): 360.2. $^1$H NMR (300 MHz, D$_2$O) 4.74 (d, J=6.4 Hz, 1H), δ 4.23-4.15 (m, 3H), 3.95 (dd, J=11.5, 7.5 Hz, 2H), 3.50-3.30 (m, 1H), 3.25 (d, J=6.0 Hz, 2H), 3.17-3.14 (m, 1H), 2.88 (d, J=12.0 Hz, 1H), 2.27-2.05 (m, 3H), 1.95-1.85 (m, 1H).

Example 25

Synthesis of (2S,5R)-2-(5-(((1s,3R)-3-aminocyclobutyl)methyl)-1,3,4-oxadiazol-2-yl)-7-oxo-1,6-diazabicyclo[3.2.1]octan-6-yl hydrogen sulfate (Compound 728) and (2S,5R)-2-(5-(((1r,3S)-3-aminocyclobutyl)methyl)-1,3,4-oxadiazol-2-yl)-7-oxo-1,6-diazabicyclo[3.2.1]octan-6-yl hydrogen sulfate (Compound 751)

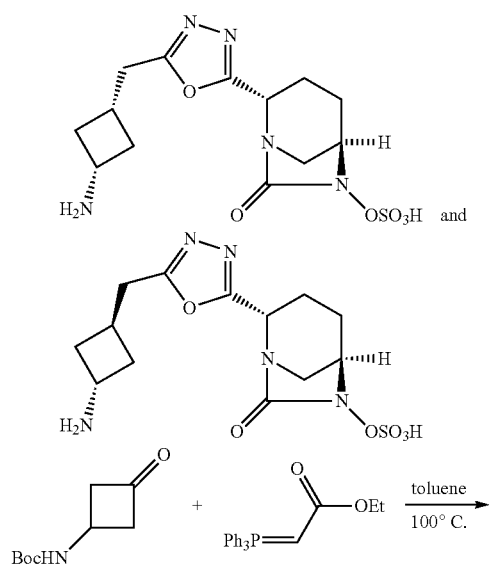

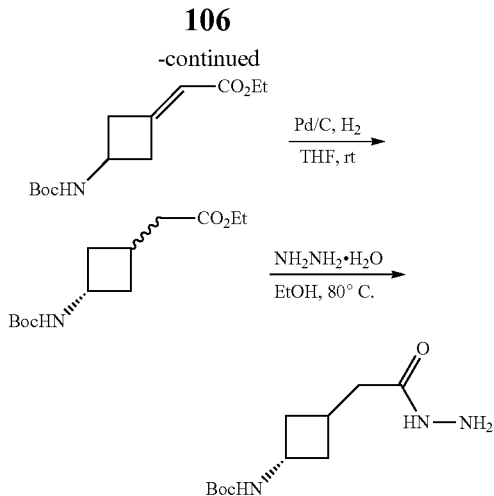

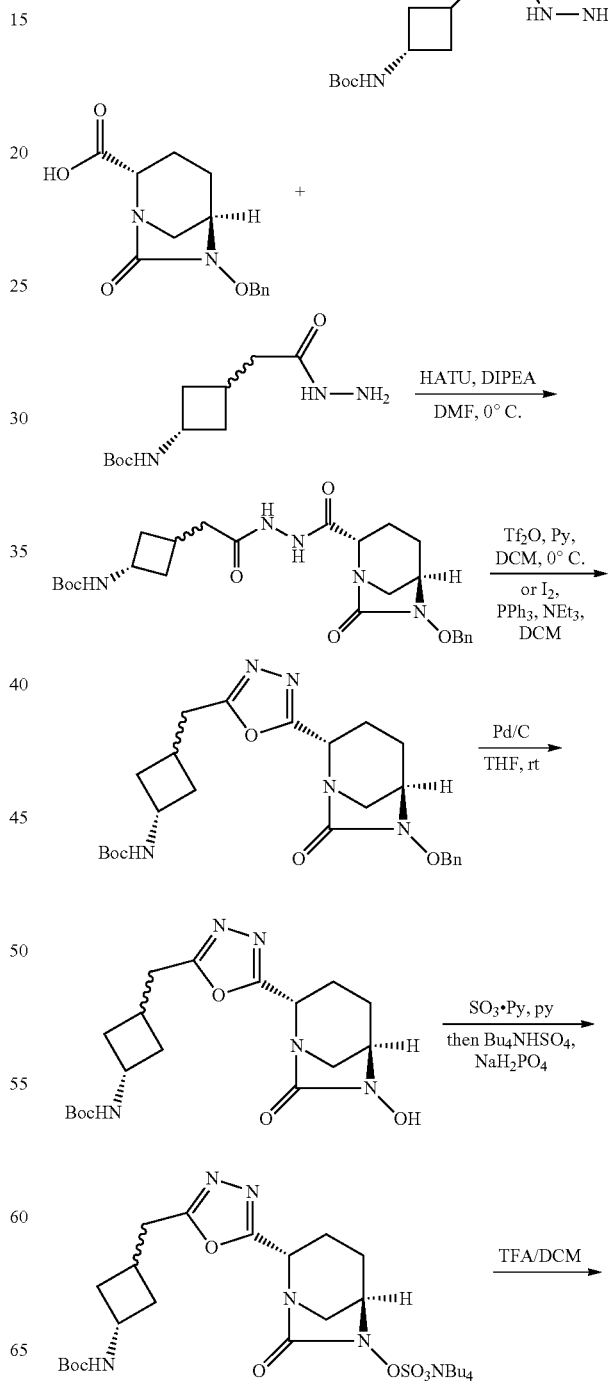

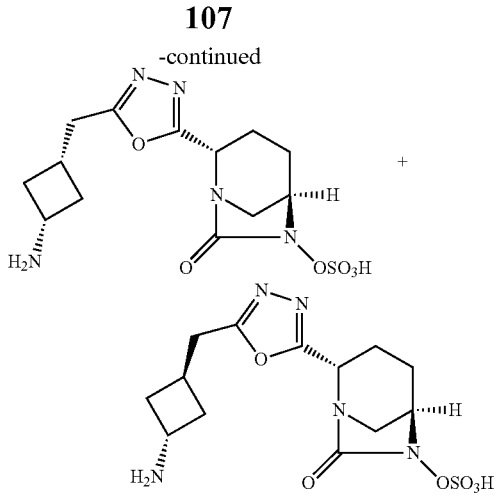

Step 1: Synthesis of ethyl 2-(3-(tert-butoxycarbonylamino)cyclobutylidene)acetate To a solution of tert-butyl 3-oxocyclobutylcarbamate (1.0 g, 5.4 mmol) in toluene (10 mL) was added ethyl 2-(triphenylphosphoranylidene)acetate (2.1 g, 5.9 mmol). The reaction mixture was heated at 100° C. for 2 hrs, and then concentrated. The residue was purified by silica gel column chromatography (10% EtOAc/petroleum ether) to afford ethyl 2-(3-(tert-butoxycarbonylamino)cyclobutylidene)acetate (1.2 g, 89%). ESI-MS (EI+, m/z): 256 [M+H]+.

Step 2: Synthesis of ethyl 2-(3-(tert-butoxycarbonylamino)cyclobutyl)acetate 10% Pd/C (360 mg) was added to a solution of ethyl 2-(3-(tert-butoxycarbonylamino)cyclobutylidene) acetate (1.2 g, 4.8 mmol) in MeOH (10 mL) at 23° C. The reaction mixture was stirred under a H₂ balloon at rt for 1.5 hrs. The mixture was filtered and concentrated. The residue was purified by silica gel column (10% EtOAc/petroleum ether) to afford ethyl 2-(3-(tert-butoxycarbonylamino)cyclobutyl)-acetate (1.2 g, 96%). ESI-MS (EI+, m/z): 258 [M+H]+.

Step 3: Synthesis of tert-butyl 3-(2-hydrazinyl-2-oxoethyl)cyclobutylcarbamate A solution of ethyl 2-(3-(tert-butoxycarbonylamino)cyclobutyl)acetate (1.2 g, 4.7 mmol) and hydrazine hydrate (1.4 g, 23.5 mmol) in EtOH (8 mL) was heated at 80° C. for 17 hrs. The reaction mixture was concentrated and the residue was dissolved in DCM (20 mL). The organic phase was washed with saturated sodium chloride (10 mL) and water (10 mL). The water layer was exacted with EtOAc (3×). The combined organic layer was dried over Na₂SO₄ and concentrated to afford tert-butyl 3-(2-hydrazinyl-2-oxoethyl)cyclobutylcarbamate (1.1 g, 97%). ESI-MS (EI+, m/z): 244 [M+H]+.

Step 4: Synthesis of tert-butyl 3-(2-(2-((2S,5R)-6-(benzyloxy)-7-oxo-1,6-diaza-bicyclo[3.2.1]octane-2-carbonyl)hydrazinyl)-2-oxoethyl)cyclobutylcarbamate HATU (1.6 g, 4.3 mmol) and DIPEA (0.93 g, 7.2 mmol) were added to a 0° C. solution of (2S,5R)-6-(benzyloxy)-7-oxo-1,6-diaza-bicyclo[3.2.1]octane-2-carboxylic acid (1.0 g, 3.6 mmol), tert-butyl 3-(2-hydrazinyl-2-oxoethyl)cyclobutylcarbamate (0.97 g, 3.9 mmol) in DMF (10 mL) at. The reaction mixture was stirred at 0° C. for 1 hr. The mixture was quenched with saturated sodium chloride (50 mL) and the organic layer was separated. The water layer was exacted with EtOAc (3×). The combined organic layer was washed with saturated sodium chloride (2×), dried over Na₂SO₄, and concentrated. The residue was purified by silica gel column chromatography (50% EtOAc/petroleum ether) to afford tert-butyl 3-(2-(2-((2S,5R)-6-(benzyloxy)-7-oxo-1,6-diaza-bicyclo[3.2.1]octane-2-carbonyl)hydrazinyl)-2-oxoethyl)cyclobutylcarbamate (1.5 g, 88%). ESI-MS (EI+, m/z): 502 [M+H]+.

Step 5: Synthesis of tert-butyl 3-((5-((2S,5R)-6-(benzyloxy)-7-oxo-1,6-diaza-bicyclo[3.2.1]octan-2-yl)-1,3,4-oxadiazol-2-yl)methyl)cyclobutylcarbamate

Method A

To a solution of tert-butyl 3-(2-(2-((2S,5R)-6-(benzyloxy)-7-oxo-1,6-diaza-bicyclo[3.2.1]octane-2-carbonyl)hydrazinyl)-2-oxoethyl)cyclobutylcarbamate (1.0 g, 1.99 mmol) in DCM (20 mL) was added pyridine (1.5 mL). (CF₃SO₂)₂O (1.4 g, 4.97 mmol) was added slowly at −10° C. The reaction mixture was stirred at 0° C. for 1 h. Sat. NaHCO₃ was added at 0° C. very slowly. The organic layer was separated and the water layer was exacted with EtOAc (3×). The combined organic layer was dried over Na₂SO₄ and concentrated. The residue was purified by silica gel column chromatography (gradient elution 10~50% EtOAc/petroleum ether) to afford tert-butyl 3-((5-((2S,5R)-6-(benzyloxy)-7-oxo-1,6-diaza-bicyclo[3.2.1]octan-2-yl)-1,3,4-oxadiazol-2-yl)methyl)cyclobutylcarbamate (0.7 g, 48%) as a slight yellow solid. ESI-MS (EI+, m/z): 484.0 [M+H]+.

Method B

To a solution of PPh₃ (7.9 g, 30.0 mmol) in dry DCM (60 mL) was added I₂ (7.8 g, 30.0 mmol). After I₂ was dissolved completely, TEA (10.5 mL, 75.0 mmol) was added quickly at rt. The mixture was stirred for 15 mins. Tert-butyl 3-(2-(2-((2S,5R)-6-(benzyloxy)-7-oxo-1,6-diaza-bicyclo[3.2.1]octane-2-carbonyl)hydrazinyl)-2-oxoethyl)cyclobutyl-carbamate (4.9 g, 15.0 mmol) was added. The mixture was stirred at rt for 1 hr. The solvent was concentrated. EtOAc (300 mL) was added, and the solution was filtered to remove PPh₃O. The filtrate was concentrated. The residue was purified by silica gel column chromatography (gradient elution 0~50% EtOAc/petroleum ether) to afford tert-butyl 3-((5-((2S,5R)-6-(benzyloxy)-7-oxo-1,6-diaza-bicyclo[3.2.1]octan-2-yl)-1,3,4-oxadiazol-2-yl)methyl)cyclobutyl-carbamate (6.2 g, 85%) as a white solid. ESI-MS (EI+, m/z): 484.0 [M+H]+.

Step 6-8

Following Steps 3-5 in Example 4, replacing tert-butyl (2-(5-((2S,5R)-6-(benzyloxy)-7-oxo-1,6-diazabicyclo[3.2.1]octan-2-yl)-1,3,4-oxadiazol-2-yl)ethyl)carbamate in Step 3 with tert-butyl (3-((5-((2S,5R)-6-(benzyloxy)-7-oxo-1,6-diazabicyclo[3.2.1]octan-2-yl)-1,3,4-oxadiazol-2-yl)methyl)cyclobutyl)carbamate, (2S,5R)-2-(5-(((1s,3R)-3-aminocyclobutyl)methyl)-1,3,4-oxadiazol-2-yl)-7-oxo-1,6-diazabicyclo[3.2.1]octan-6-yl hydrogen sulfate (245 mg) and (2S,5R)-2-(5-(((1r,3S)-3-aminocyclobutyl)methyl)-1,3,4-oxadiazol-2-yl)-7-oxo-1,6-diazabicyclo[3.2.1]octan-6-yl hydrogen sulfate (178 mg) were obtained as white solids after prep-HPLC purification using ammonium formate buffer.

(2S,5R)-2-(5-(((1s,3R)-3-aminocyclobutyl)methyl)-1,3,4-oxadiazol-2-yl)-7-oxo-1,6-diazabicyclo[3.2.1]octan-6-yl hydrogen sulfate (Compound 728): ESI-MS (EI+, m/z): 374.3. $^1$H NMR (300 MHz, D$_2$O) δ 4.76 (d, J=6.5 Hz, 1H), 4.15 (br s, 1H), 3.71-3.55 (m, 1H), 3.16 (br d, J=11.5 Hz, 1H), 3.00 (d, J=6.7 Hz, 2H), 2.86 (d, J=12.3 Hz, 1H), 2.58-2.40 (m, 3H), 2.32-2.03 (m, 3H), 1.96-1.78 (m, 3H).

(2S,5R)-2-(5-(((1r,3S)-3-aminocyclobutyl)methyl)-1,3,4-oxadiazol-2-yl)-7-oxo-1,6-diazabicyclo[3.2.1]octan-6-yl hydrogen sulfate (Compound 751): ESI-MS (EI+, m/z): 374.0. $^1$H NMR (300 MHz, D$_2$O) δ 4.75 (d, J=6.5 Hz, 1H), 4.15 (br s, 1H), 3.89-3.79 (m, 1H), 3.16 (br d, J=12.0 Hz, 1H), 3.07 (d, J=6.0 Hz, 2H), 2.87 (d, J=8.0 Hz, 1H), 2.86-2.78 (m, 1H), 2.35-2.05 (m, 7H), 1.99-1.83 (m, 1H).

Example 26

Synthesis of (2S,5R)-2-(5-((1S,3R)-3-aminocyclopentyl)-1,3,4-oxadiazol-2-yl)-7-oxo-1,6-diazabicyclo[3.2.1]octan-6-yl hydrogen sulfate (Compound 729)

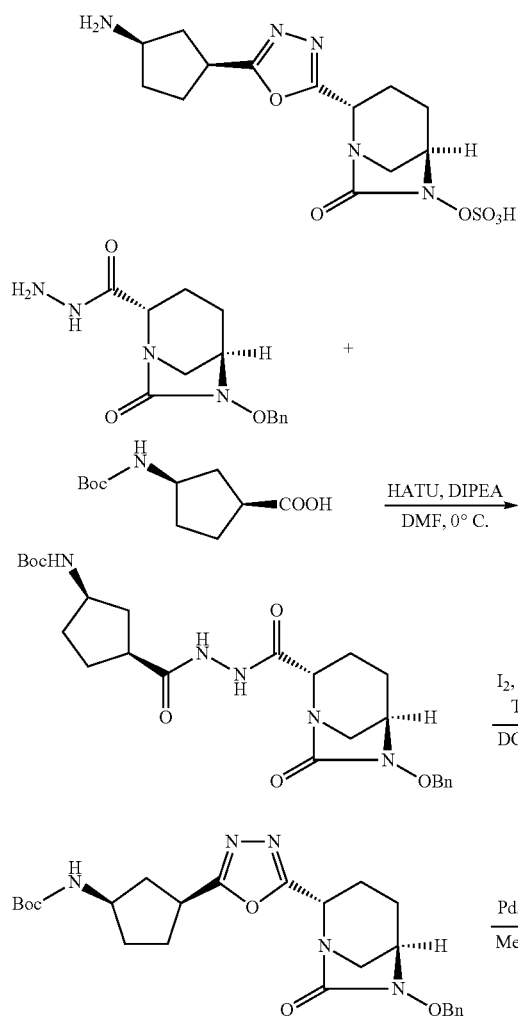

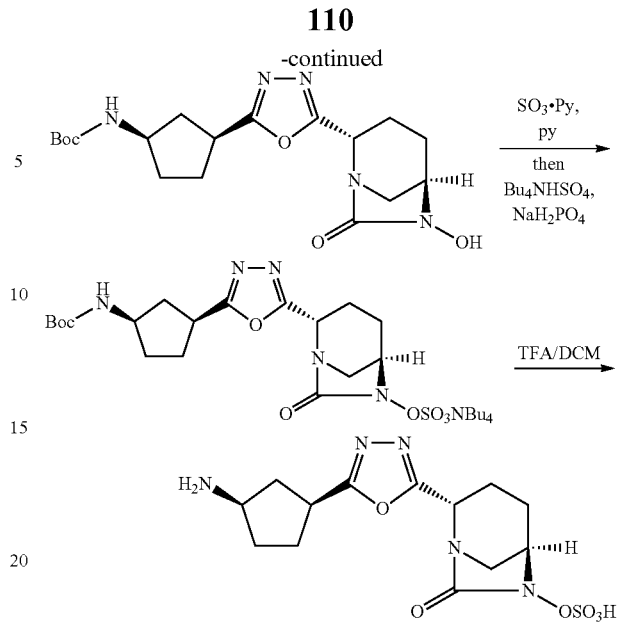

Step 1: Synthesis of tert-butyl(1R,3S)-3-(2-((2S,5R)-6-(benzyloxy)-7-oxo-1,6-diaza-bicyclo[3.2.1]octane-2-carbonyl)hydrazinecarbonyl)cyclopentylcarbamate To a 0° C. solution of (1S,3R)-3-(tert-butoxycarbonylamino)cyclopentanecarboxylic acid (3.8 g, 16.6 mmol) and (2S,5R)-6-(benzyloxy)-7-oxo-1,6-diaza-bicyclo[3.2.1]octane-2-carbohydrazide (5.3 g, 18.26 mmol) in DMF (30 mL) were added HATU (7.6 g, 19.92 mmol) and DIPEA (11.6 ml, 66.4 mmol). The reaction mixture was stirred at 0° C. for 1.5 hrs. The reaction mixture was diluted with water and extracted with EtOAc (2×). The combined organic layer was washed with saturated sodium chloride (4×) and citric acid (5% aq.), dried over Na$_2$SO$_4$, and concentrated. The residue was purified by silica gel column (gradient elution 50~80% EtOAc/petroleum ether) to afford tert-butyl (1R,3S)-3-(2-((2S,5R)-6-(benzyloxy)-7-oxo-1,6-diaza-bicyclo[3.2.1]octane-2-carbonyl) hydrazinecarbonyl)cyclopentylcarbamate (4.5 g, 55%) as a white solid. ESI-MS (EI+, m/z): 502.3 [M+H]+.

Step 2: Synthesis of tert-butyl(1R,3S)-3-(5-(2S,5R)-6-(benzyloxy)-7-oxo-1,6-diaza-bicyclo[3.2.1]octan-2-yl)-1,3,4-oxadiazol-2-yl)cyclopentylcarbamate To a 0° C. solution of PPh$_3$ (2.2 g 8.4 mmol) in dry DCM (20 mL) was added I$_2$(2.1 g, 8.4 mmol). After I$_2$ was dissolved, TEA (2.4 mL, 16.8 mmol) was added quickly at rt. The reaction mixture was stirred for 15 min. tert-Butyl (1R,3S)-3-(2-((2S,5R)-6-(benzyloxy)-7-oxo-1,6-diaza-bicyclo[3.2.1]octane-2-carbonyl)hydrazinecarbonyl)cyclopentylcarbamate (2.1 g, 4.2 mmol) was added. The reaction mixture was stirred at rt for 1 h. The reaction mixture was concentrated and the residue was purified by silica gel column (gradient elution 0~50% EtOAc/petroleum ether) to afford the crude tert-butyl (1R,3S)-3-(5-((2S,5R)-6-(benzyloxy)-7-oxo-1,6-diaza-bicyclo[3.2.1]octan-2-yl)-1,3,4-oxadiazol-2-yl)cyclopentylcarbamate (~1.7 g) as a white solid. ESI-MS (EI+, m/z): 484.1.

Step 3-5

Following Steps 3-5 in Example 4, replacing tert-butyl (2-(5-((2S,5R)-6-(benzyloxy)-7-oxo-1,6-diazabicyclo[3.2.1]octan-2-yl)-1,3,4-oxadiazol-2-yl)ethyl)carbamate in Step 3 with tert-butyl ((1R,3S)-3-(5-((2S,5R)-6-(benzyloxy)-7-oxo-1,6-diazabicyclo[3.2.1]octan-2-yl)-1,3,4-oxadiazol-2-yl)cyclopentyl)carbamate; (2S,5R)-2-(5-((1S,3R)-3-aminocyclopentyl)-1,3,4-oxadiazol-2-yl)-7-oxo-1,6-diazabicyclo[3.2.1]octan-6-yl hydrogen sulfate (286 mg) was obtained as a white solid after prep-HPLC purification using ammonium formate buffer. ESI-MS (EI+, m/z): 374.2. $^1$H NMR (300 MHz, D$_2$O) δ 4.74 (d, J=6.5 Hz, 1H), 4.16 (br s, 1H), 3.82-3.66 (m, 1H), 3.56-3.41 (m, 1H), 3.15 (br d, J=12.3 Hz, 1H), 2.89 (d, J=12.3 Hz, 1H), 2.67-2.51 (m, 1H), 2.30-1.69 (m, 9H).

The compounds described in Examples 27-87 were prepared as described in the reaction schemes following similar procedures of Examples 1-26.

Example 27

Synthesis of (2S,5R)-2-(5-(4-aminobutyl)-1,3,4-oxadiazol-2-yl)-7-oxo-1,6-diazabicyclo[3.2.1]octan-6-yl hydrogen sulfate (Compound 735)

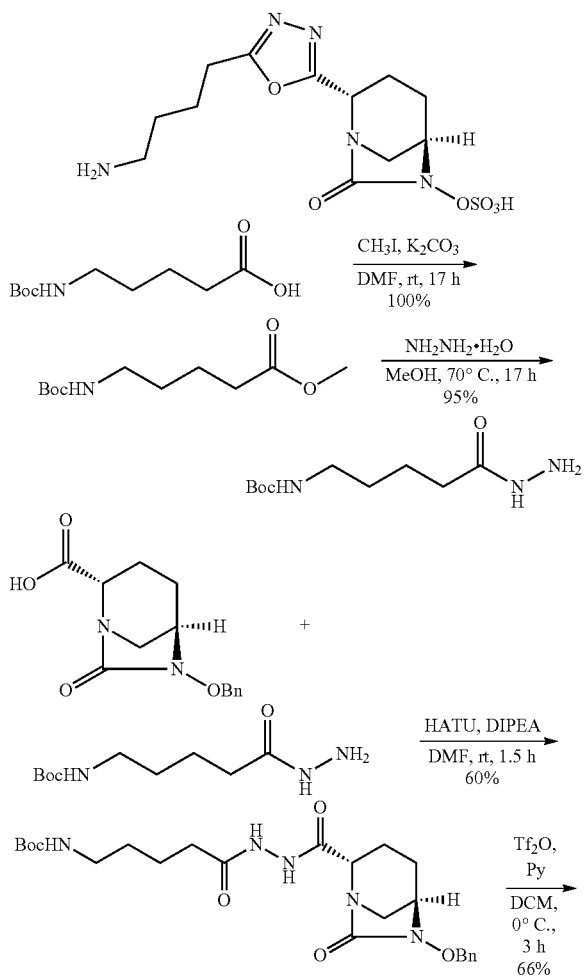

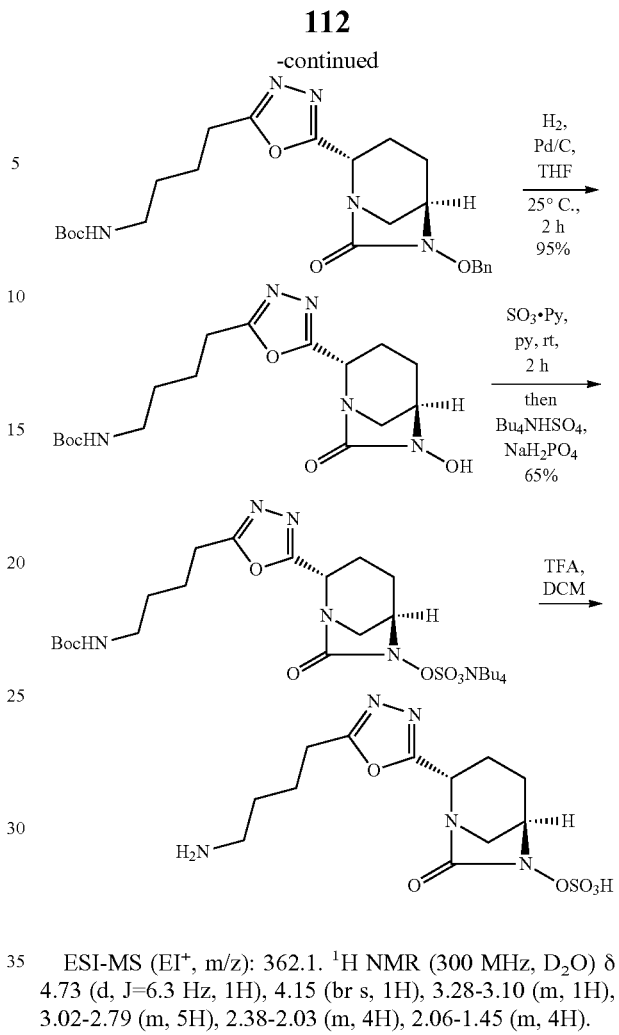

ESI-MS (EI+, m/z): 362.1. $^1$H NMR (300 MHz, D$_2$O) δ 4.73 (d, J=6.3 Hz, 1H), 4.15 (br s, 1H), 3.28-3.10 (m, 1H), 3.02-2.79 (m, 5H), 2.38-2.03 (m, 4H), 2.06-1.45 (m, 4H).

Example 28

Synthesis of (2S,5R)-2-(5-(2-iminoimidazolidin-4-yl)-1,3,4-oxadiazol-2-yl)-7-oxo-1,6-diazabicyclo[3.2.1]octan-6-yl hydrogen sulfate (Compound 767)

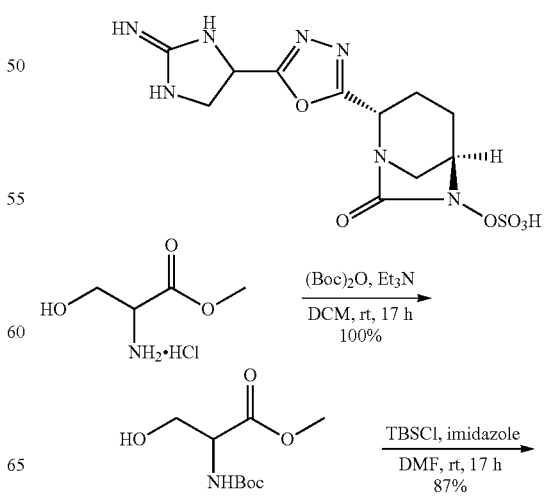

113
-continued
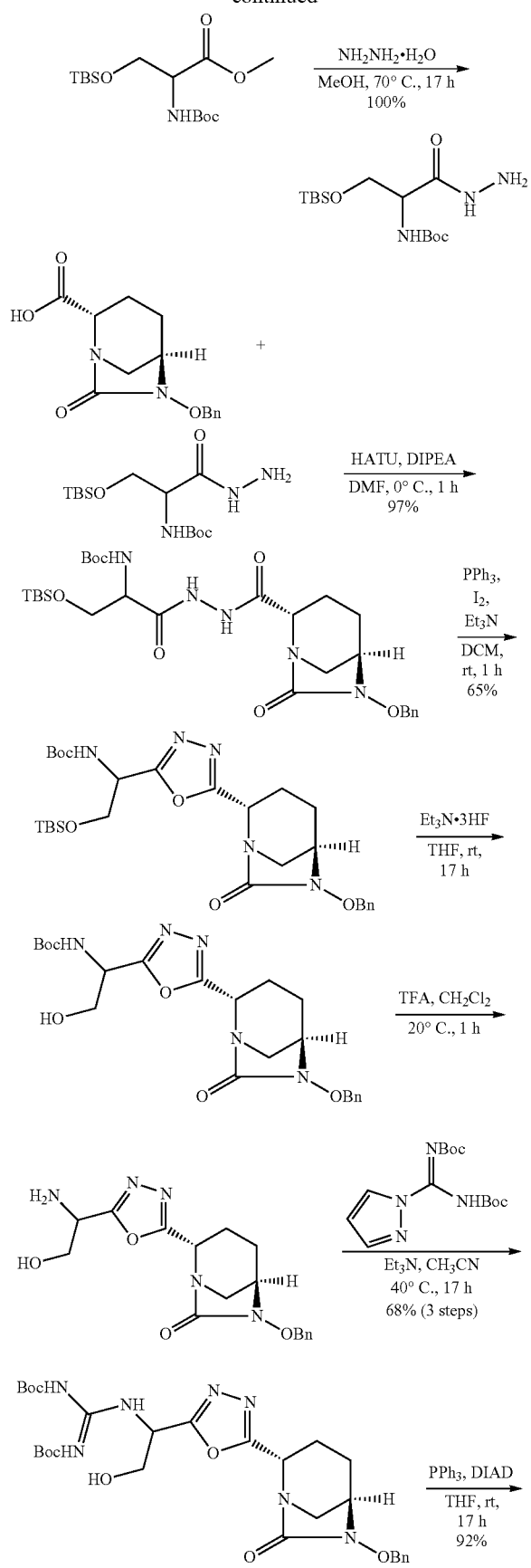
114
-continued
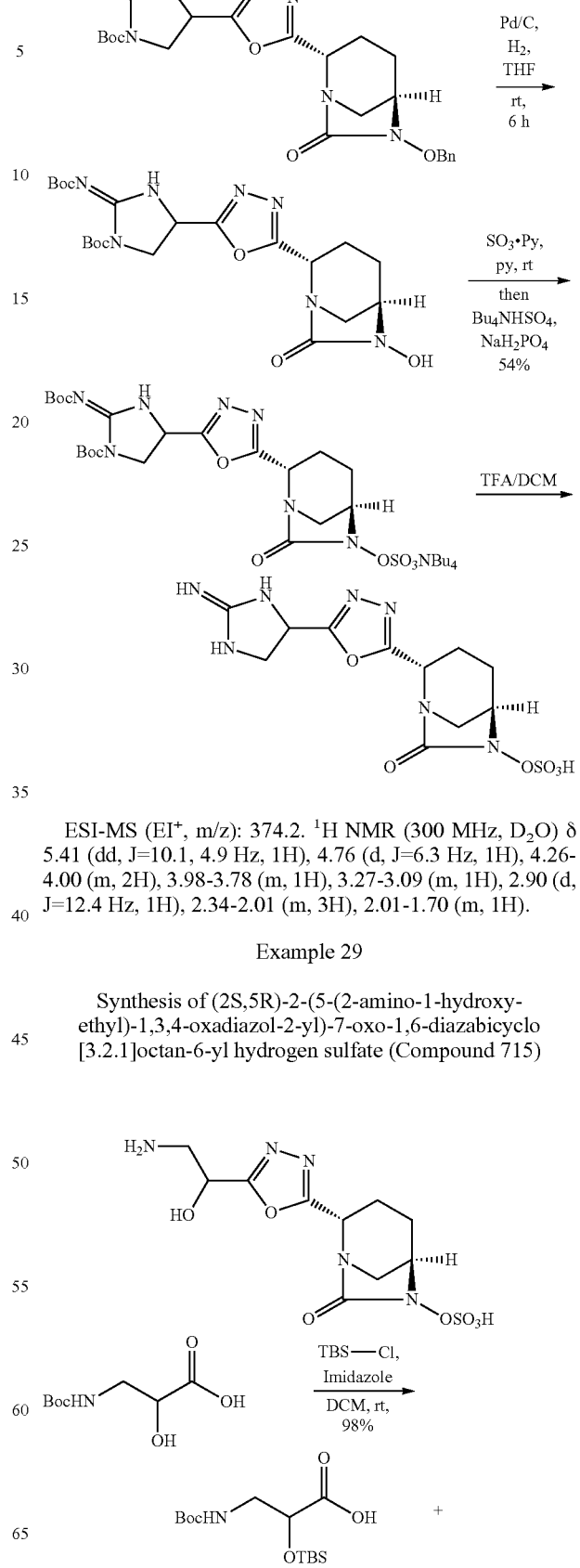
ESI-MS (EI+, m/z): 374.2. $^1$H NMR (300 MHz, $D_2O$) δ 5.41 (dd, J=10.1, 4.9 Hz, 1H), 4.76 (d, J=6.3 Hz, 1H), 4.26-4.00 (m, 2H), 3.98-3.78 (m, 1H), 3.27-3.09 (m, 1H), 2.90 (d, J=12.4 Hz, 1H), 2.34-2.01 (m, 3H), 2.01-1.70 (m, 1H).
Example 29
Synthesis of (2S,5R)-2-(5-(2-amino-1-hydroxy-ethyl)-1,3,4-oxadiazol-2-yl)-7-oxo-1,6-diazabicyclo[3.2.1]octan-6-yl hydrogen sulfate (Compound 715)

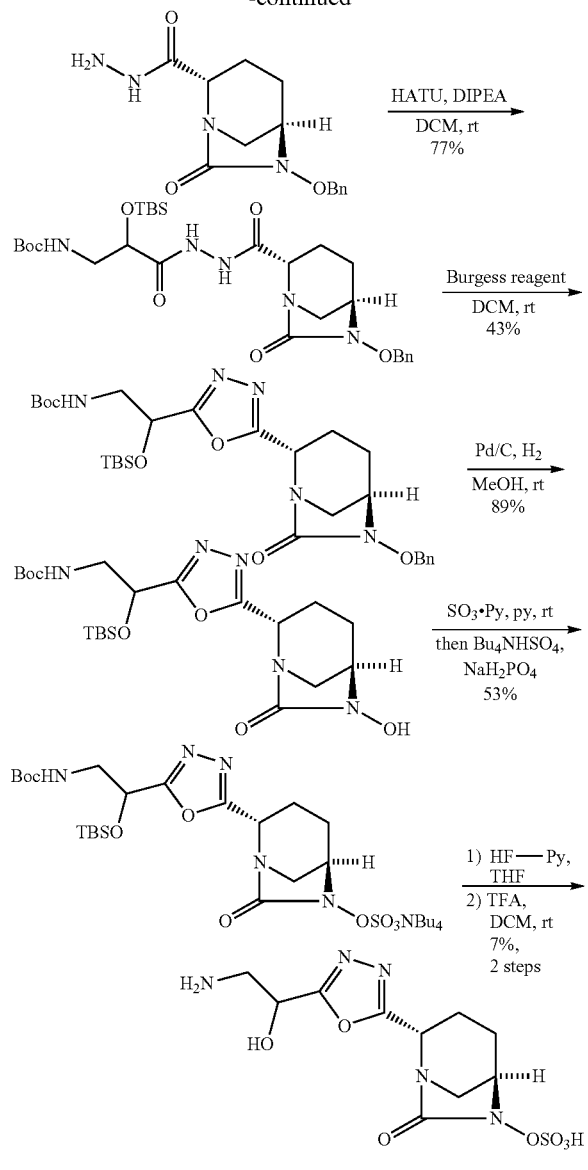
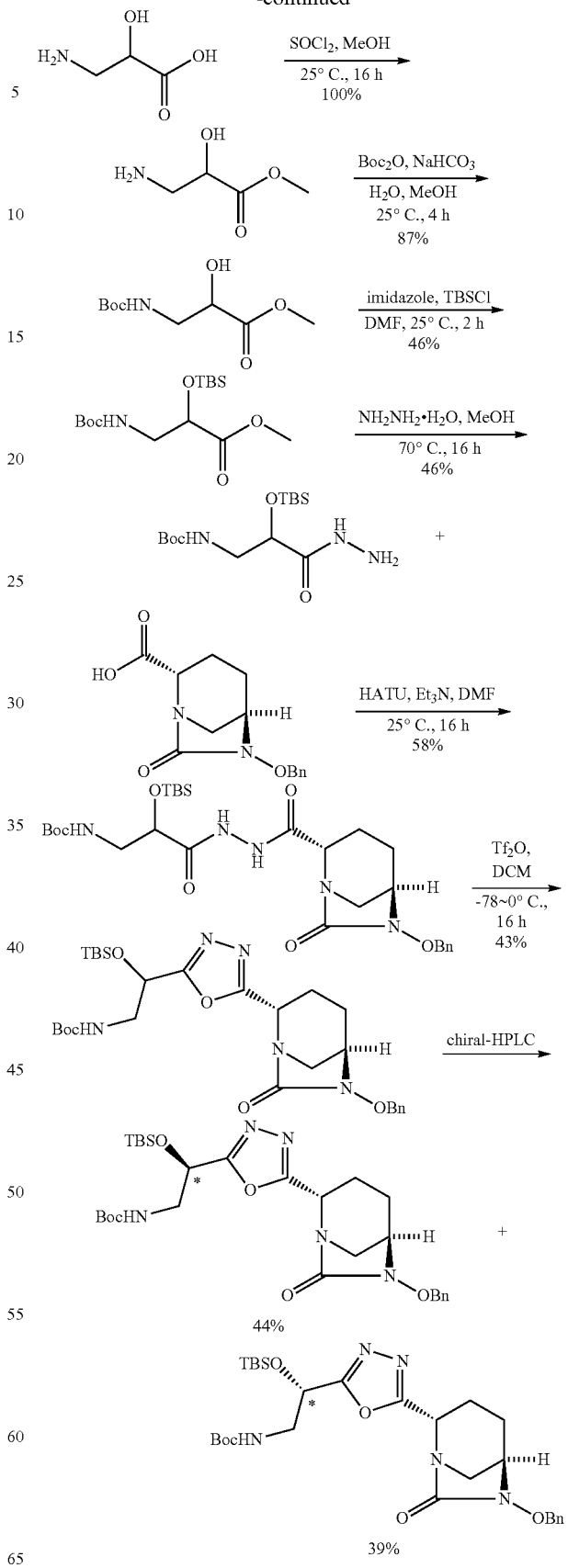
ESI-MS (EI+, m/z): 350.1. ¹H NMR (300 MHz, D₂O) δ 5.25 (dd, J=8.4, 3.9 Hz, 1H), 4.78 (d, J=6.7 Hz, 1H), 4.22-4.11 (m, 1H), 3.56-3.32 (m, 2H), 3.23-3.12 (m, 1H), 2.92 (dd, J=12.3, 1.4 Hz, 1H), 2.34-2.02 (m, 3H), 2.03-1.83 (m, 1H).
Example 30
Synthesis of (2S,5R)-2-(5-((R)-2-guanidino-1-hydroxyethyl)-1,3,4-oxadiazol-2-yl)-7-oxo-1,6-diazabicyclo[3.2.1]octan-6-yl hydrogen sulfate (Compound 731)
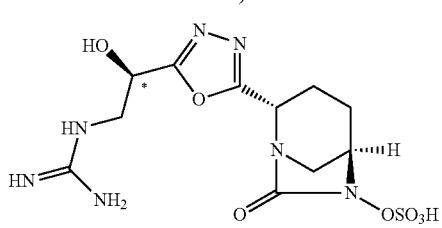
* Absolute stereochemistry of the OTBS group was arbitrarily assigned.

117
-continued

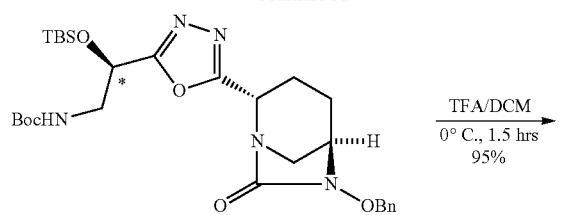

TFA/DCM
0° C., 1.5 hrs
95%

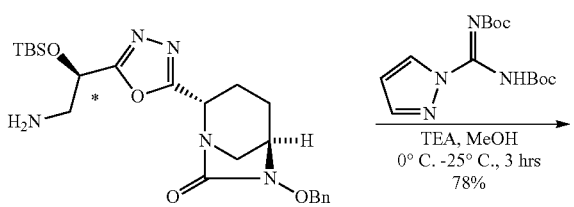

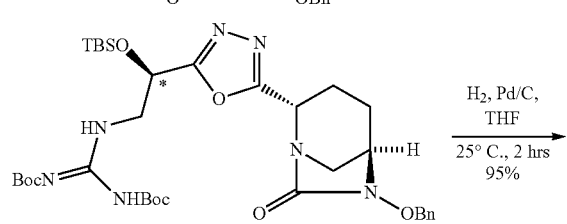

H₂, Pd/C, THF
25° C., 2 hrs
95%

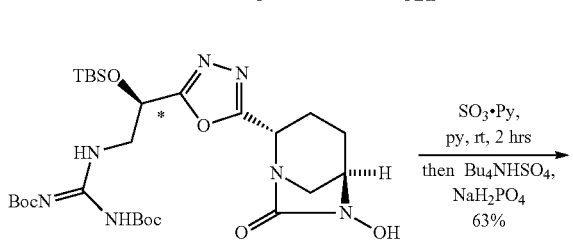

SO₃·Py, py, rt, 2 hrs
then Bu₄NHSO₄, NaH₂PO₄
63%

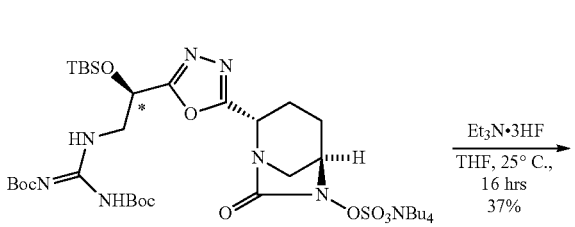

Et₃N·3HF
THF, 25° C., 16 hrs
37%

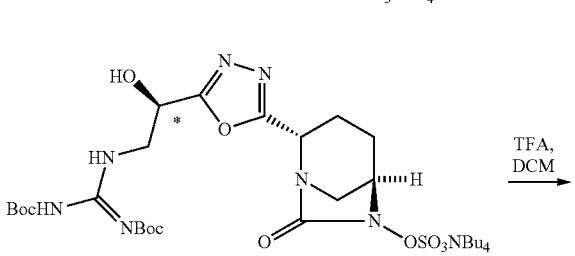

TFA, DCM

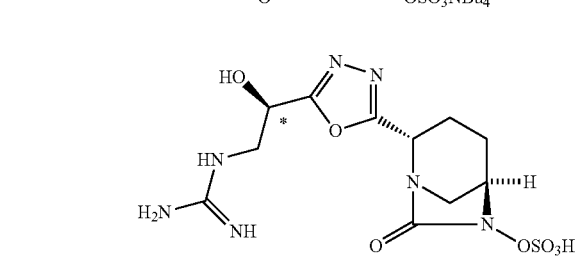

ESI-MS (EI⁺, m/z): 392.2. ¹H NMR (300 MHz, D₂O) δ 5.15 (t, J=4.9 Hz, 1H), 4.78 (d, J=6.5 Hz, 1H), 4.18 (s, 1H), 3.78-3.57 (m, 2H), 3.26-3.11 (m, 1H), 2.89 (d, J=12.1 Hz, 1H), 2.39-2.08 (m, 3H), 2.03-1.78 (m, 1H).

118
Example 31

Synthesis of (2S,5R)-2-(5-((S)-2-guanidino-1-hydroxyethyl)-1,3,4-oxadiazol-2-yl)-7-oxo-1,6-diazabicyclo[3.2.1]octan-6-yl hydrogen sulfate (Compound 732)

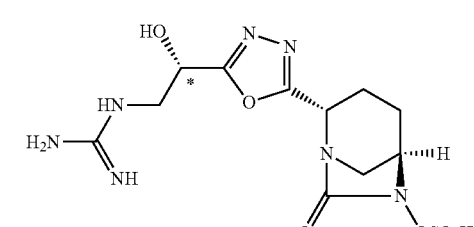

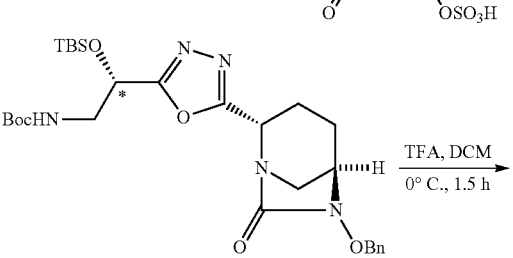

TFA, DCM
0° C., 1.5 h

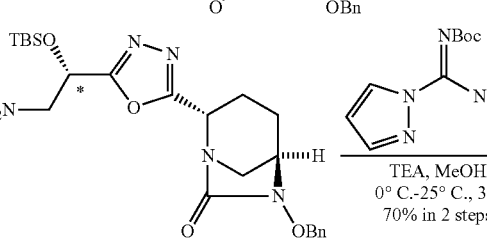

TEA, MeOH
0° C.-25° C., 3 h
70% in 2 steps

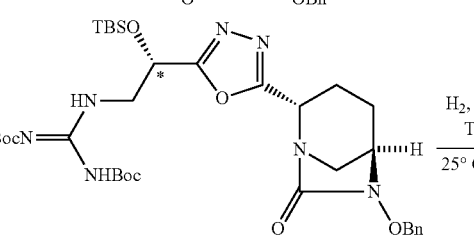

H₂, Pd/C, THF
25° C., 2 h

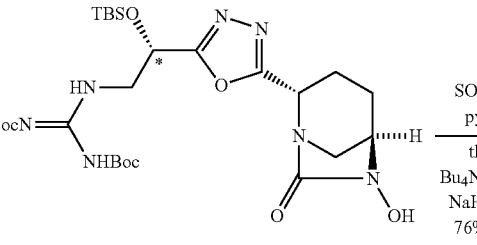

SO₃·Py, py, rt
then Bu₄NHSO₄, NaH₂PO₄
76% for 2 steps

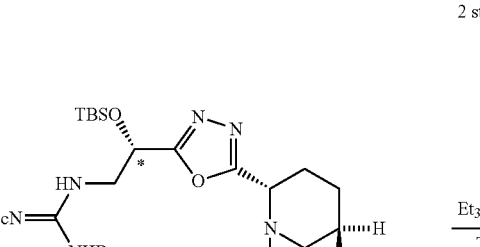

Et₃N·2HF
THF, 25° C., 16 h
70%

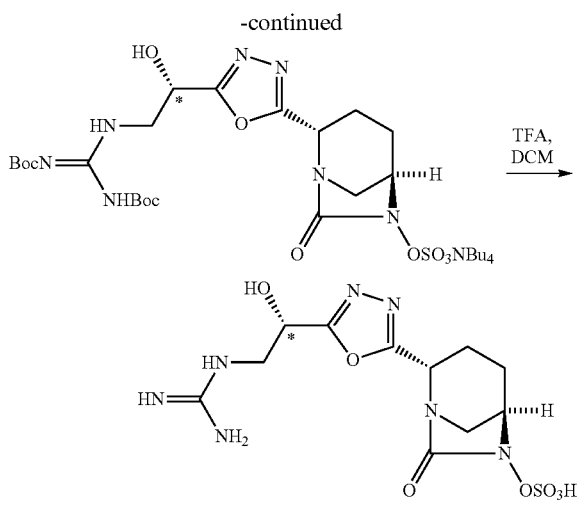
ESI-MS (EI+, m/z): 392.2. ¹H NMR (300 MHz, D₂O) δ 5.14 (t, J=4.9 Hz, 1H), 4.78 (d, J=6.5 Hz, 1H), 4.16 (s, 1H), 3.66 (dd, J=5.3, 3.2 Hz, 2H), 3.17 (br d, J=12.1 Hz, 1H), 2.87 (d, J=12.4 Hz, 1H), 2.35-2.00 (m, 3H), 1.97-1.85 (m, 1H).
Example 32
Synthesis of (2S,5R)-2-(5-(3-amino-2-hydroxypropyl)-1,3,4-oxadiazol-2-yl)-7-oxo-1,6-diazabicyclo[3.2.1]octan-6-yl hydrogen sulfate (Compound 733)
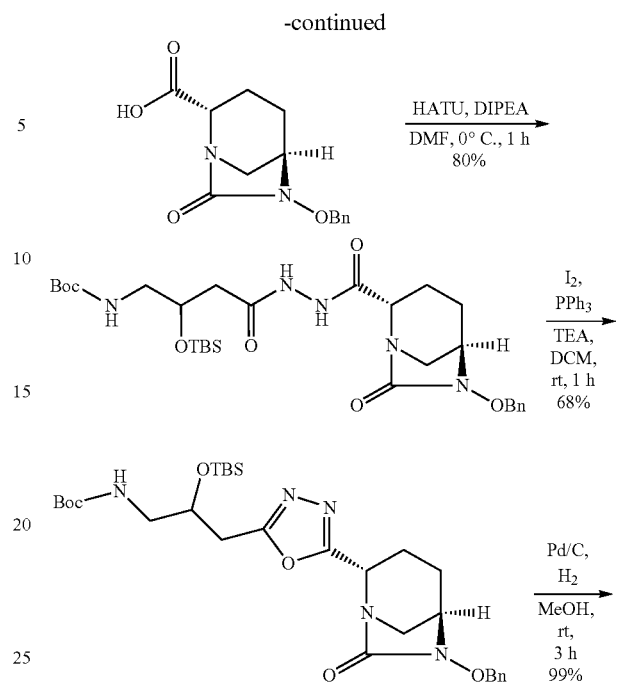
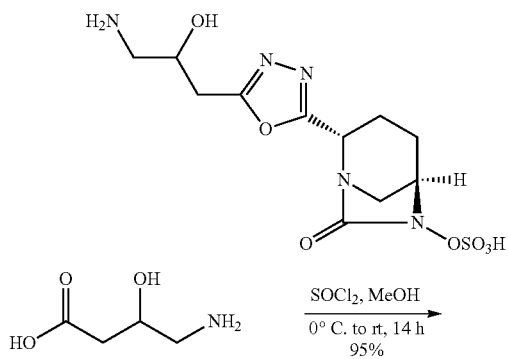
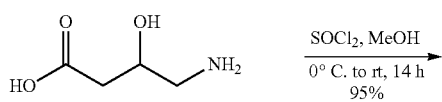
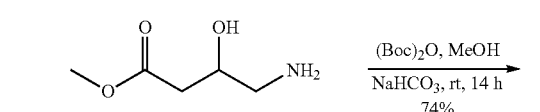
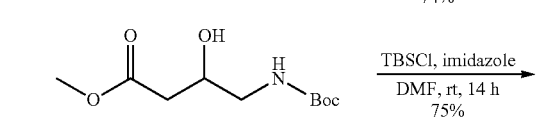
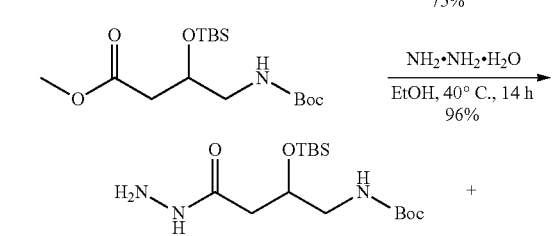

ESI-MS (EI+, m/z): 364.2. ¹H NMR (300 MHz, D₂O) δ 4.77 (d, J=6.5 Hz, 1H), 4.38-4.22 (m, 1H), 4.18 (br s, 1H), 3.46-2.84 (m, 6H), 2.36-2.03 (m, 3H), 2.05-1.74 (m, 1H).
Example 33
Synthesis of (2S,5R)-2-(5-(3-guanidino-2-hydroxypropyl)-1,3,4-oxadiazol-2-yl)-7-oxo-1,6-diazabicyclo[3.2.1]octan-6-yl hydrogen sulfate (Compound 730)
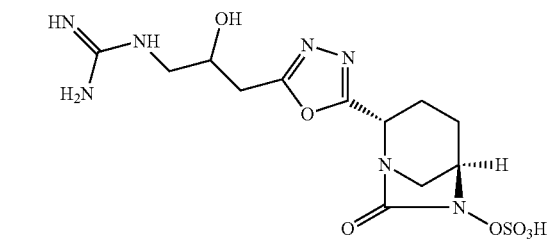
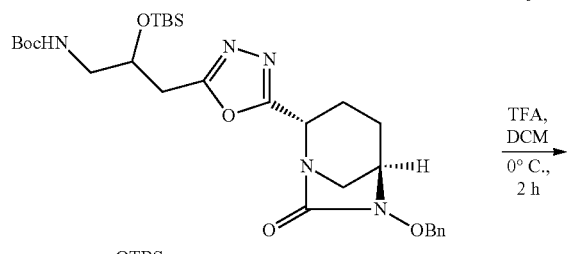
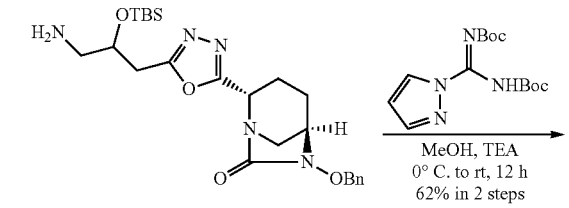
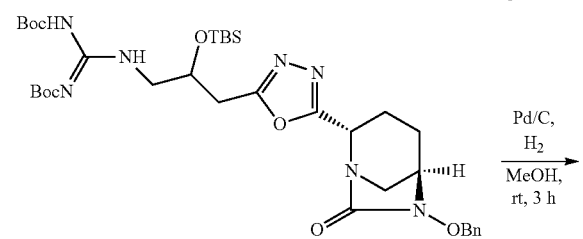
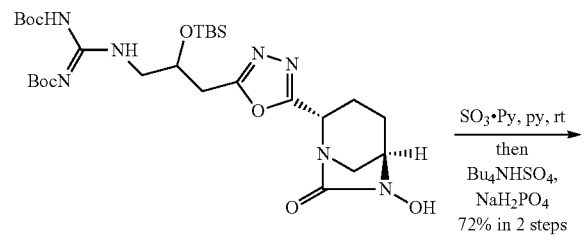
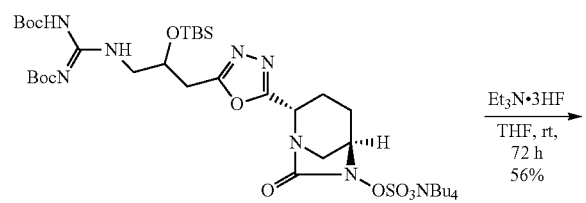
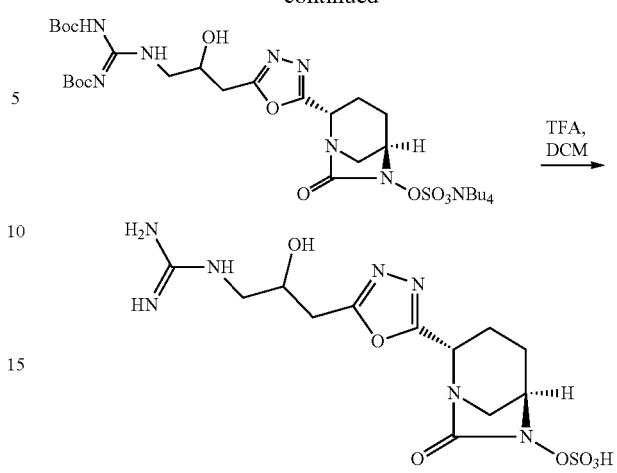
ESI-MS (EI+, m/z): 406.2. ¹H NMR (300 MHz, D₂O) δ 4.75 (d, J=6.5 Hz, 1H), 4.41-4.03 (m, 2H), 3.37 (d, J=10.8 Hz, 1H), 3.31-2.95 (m, 4H), 2.89 (d, J=12.1 Hz, 1H), 2.34-2.02 (m, 3H), 2.02-1.78 (m, 1H).
Example 34
Synthesis of (2S,5R)-2-(5-(2-((2-aminoethyl)amino)ethyl)-1,3,4-oxadiazol-2-yl)-7-oxo-1,6-diazabicyclo[3.2.1]octan-6-yl hydrogen sulfate (Compound 716)
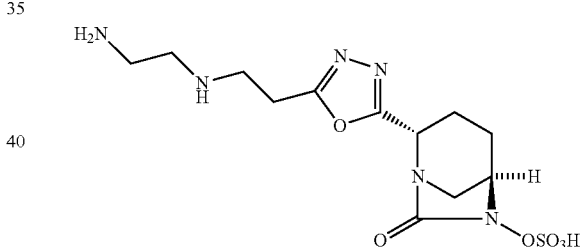
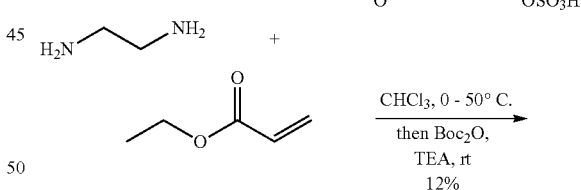
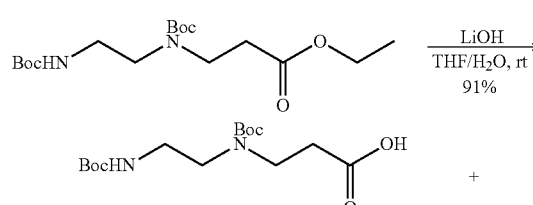
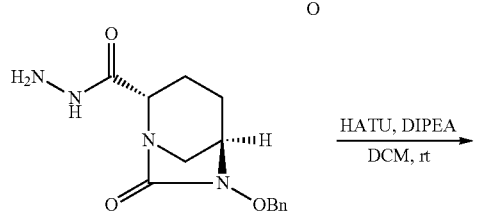

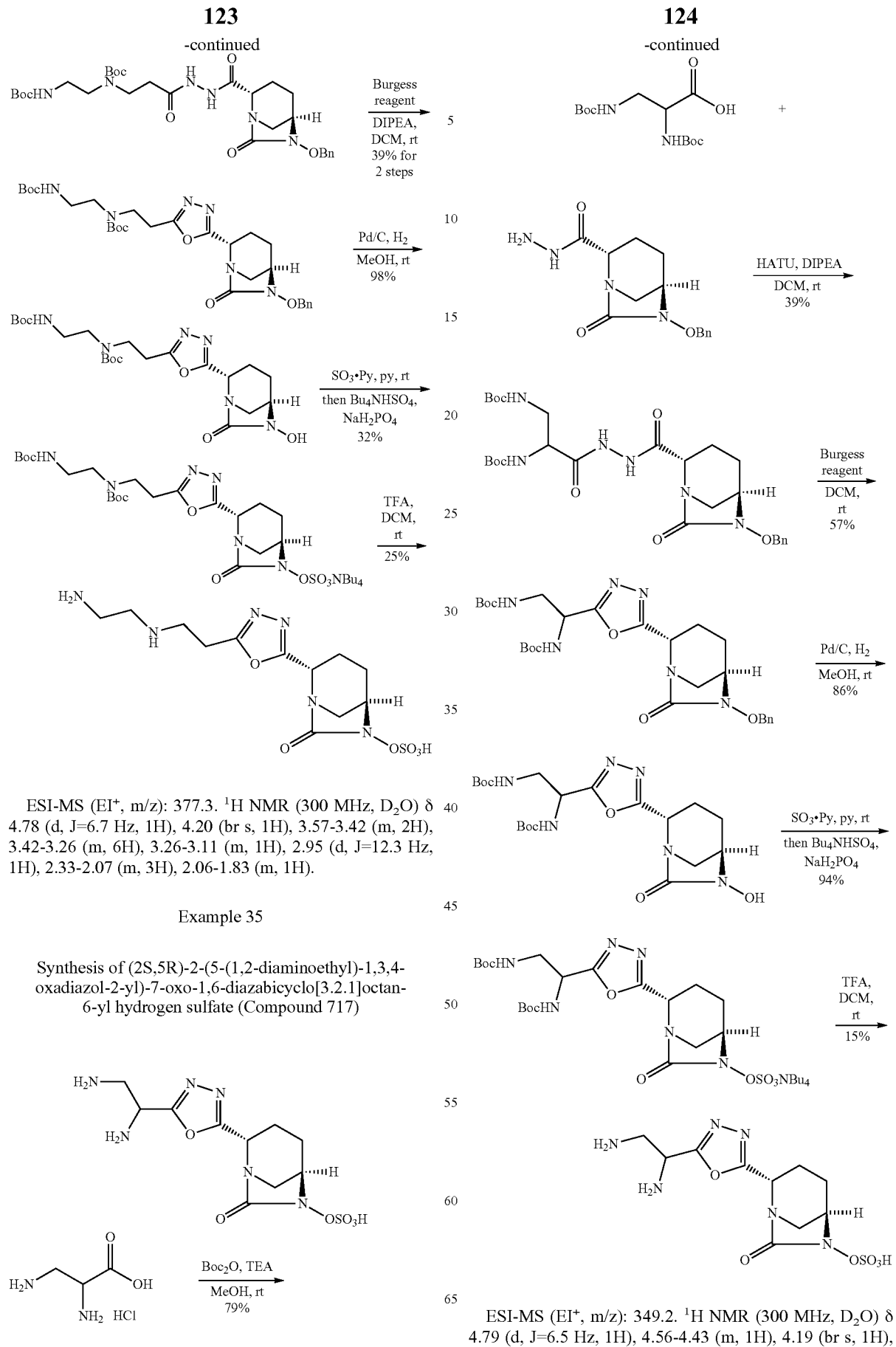
ESI-MS (EI+, m/z): 377.3. ¹H NMR (300 MHz, D₂O) δ 4.78 (d, J=6.7 Hz, 1H), 4.20 (br s, 1H), 3.57-3.42 (m, 2H), 3.42-3.26 (m, 6H), 3.26-3.11 (m, 1H), 2.95 (d, J=12.3 Hz, 1H), 2.33-2.07 (m, 3H), 2.06-1.83 (m, 1H).
Example 35
Synthesis of (2S,5R)-2-(5-(1,2-diaminoethyl)-1,3,4-oxadiazol-2-yl)-7-oxo-1,6-diazabicyclo[3.2.1]octan-6-yl hydrogen sulfate (Compound 717)
ESI-MS (EI+, m/z): 349.2. ¹H NMR (300 MHz, D₂O) δ 4.79 (d, J=6.5 Hz, 1H), 4.56-4.43 (m, 1H), 4.19 (br s, 1H), 3.52-3.41 (m, 1H), 3.35-3.13 (m, 2H), 2.97 (d, J=12.4 Hz, 1H), 2.35-2.09 (m, 3H), 2.09-1.81 (m, 1H).
Example 36
Synthesis of (2S,5R)-2-(5-(2-amino-2-methylpropyl)-1,3,4-oxadiazol-2-yl)-7-oxo-1,6-diazabicyclo[3.2.1]octan-6-yl hydrogen sulfate (Compound 737)
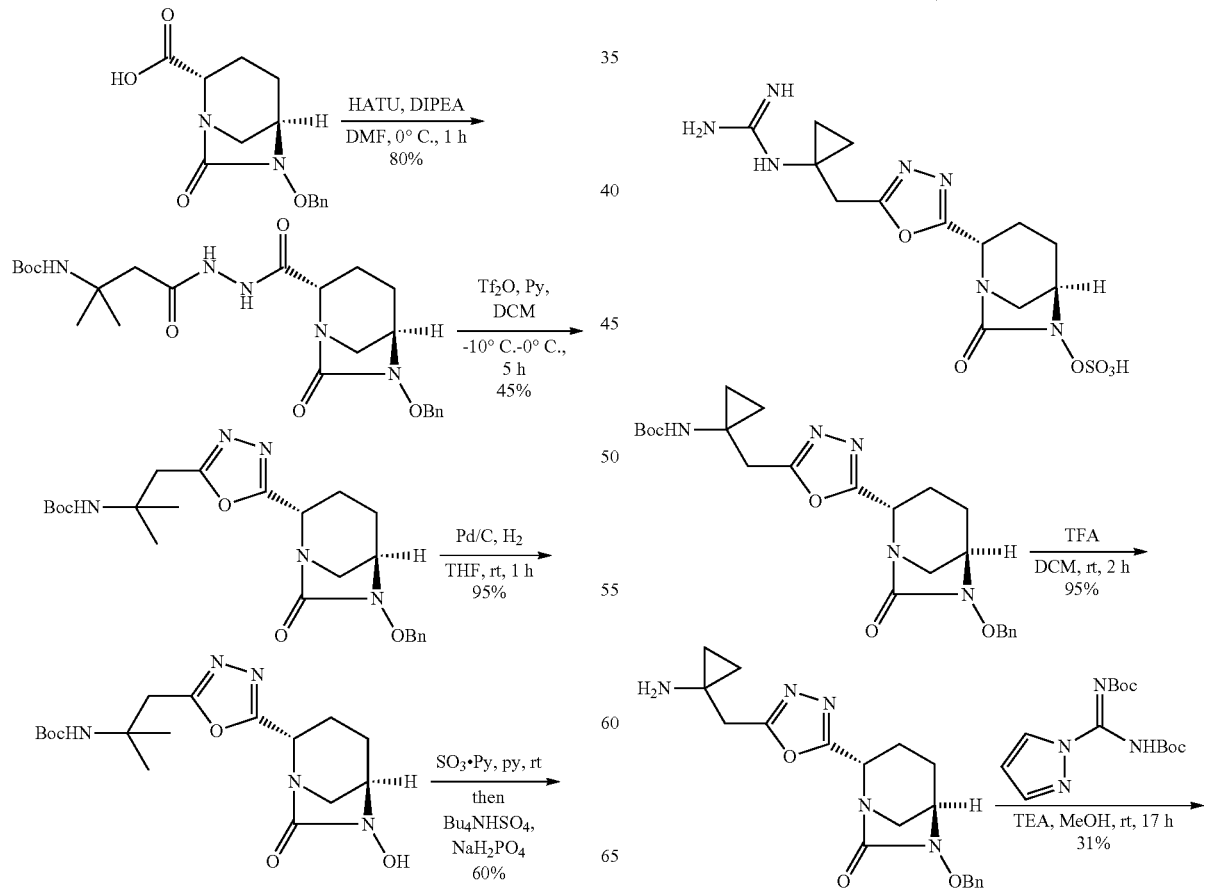
ESI-MS (EI+, m/z): 362.3. 1H NMR (300 MHz, D2O) δ 4.78 (d, J=7.3 Hz, 1H), 4.18 (br s, 1H), 3.28 (s, 2H), 3.20-3.06 (m, 1H), 2.94 (d, J=12.3 Hz, 1H), 2.34-2.07 (m, 3H), 2.01-1.87 (m, 1H), 1.41-1.33 (m, 6H).
Example 37
Synthesis of (2S,5R)-2-(5-((1-guanidinocyclopropyl)methyl)-1,3,4-oxadiazol-2-yl)-7-oxo-1,6-diazabicyclo[3.2.1]octan-6-yl hydrogen sulfate (Compound 739)

127
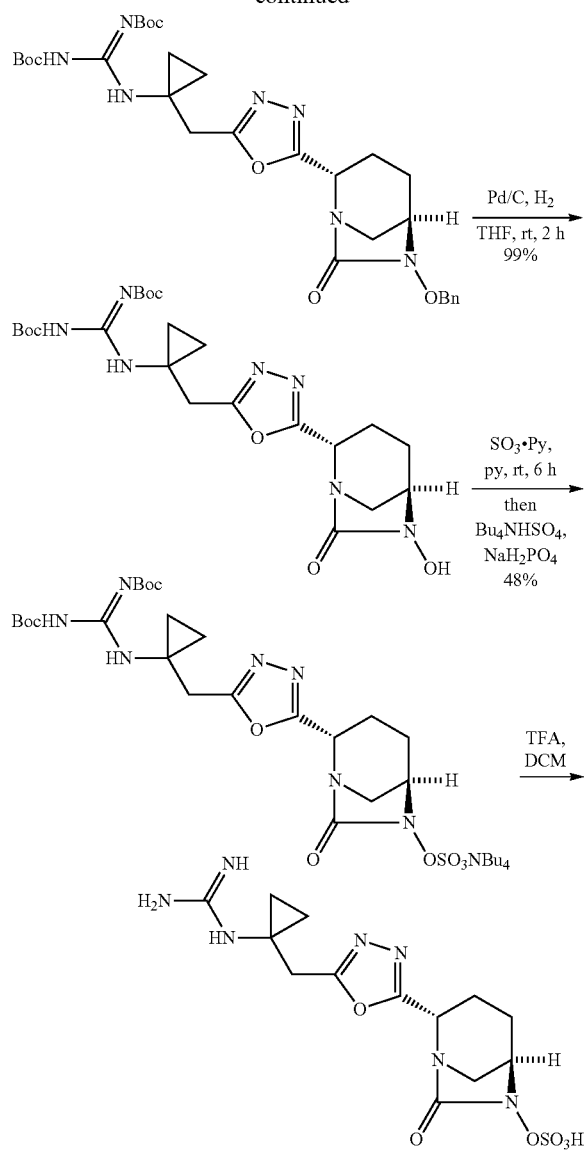
ESI-MS (EI+, m/z): 402.3. $^1$H NMR (300 MHz, D$_2$O) δ 4.75 (d, J=6.4 Hz, 1H), 4.17 (br s, 1H), 3.27-3.00 (m, 3H), 2.90 (d, J=12.3 Hz, 1H), 2.36-2.04 (m, 3H), 2.03-1.79 (m, 1H), 1.09-0.84 (m, 4H).
Example 38
Synthesis of (2S,5R)-7-oxo-2-(5-((R)-pyrrolidin-3-yl)-1,3,4-oxadiazol-2-yl)-1,6-diazabicyclo[3.2.1]octan-6-yl hydrogen sulfate (Compound 759)
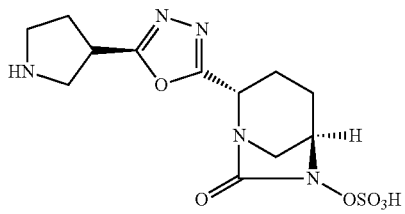
128
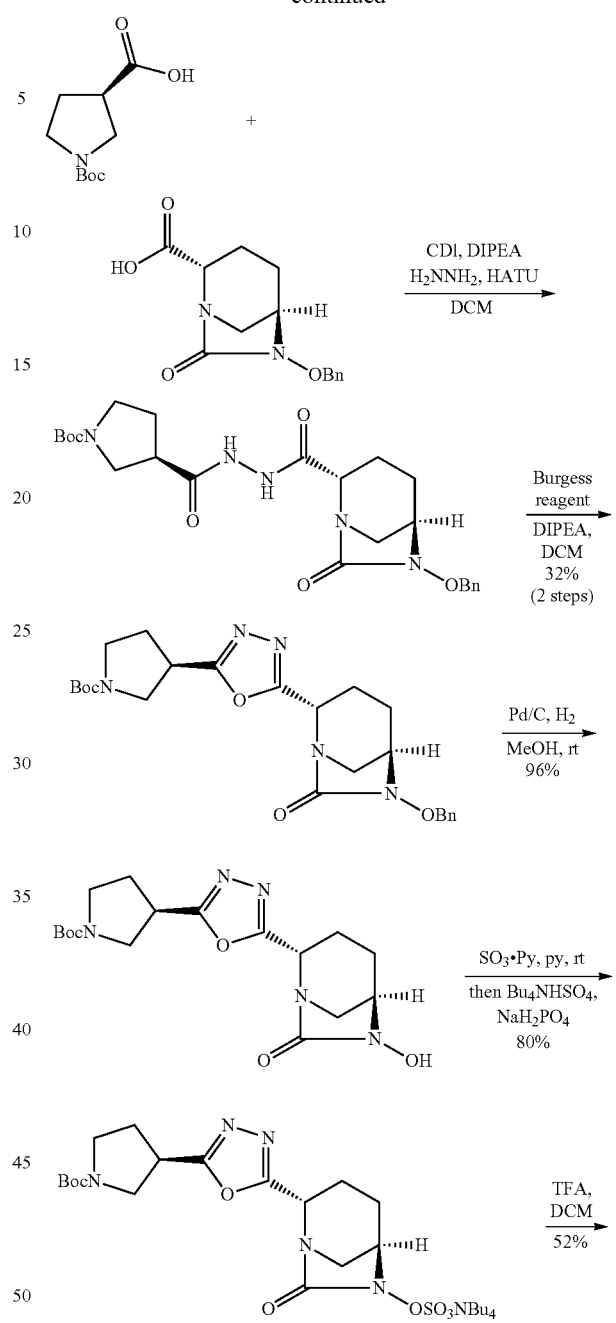
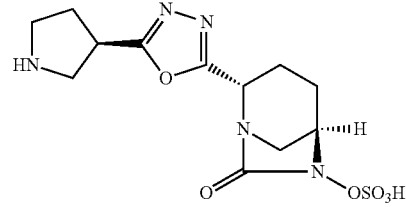
ESI-MS (EI+, m/z): 360.1. $^1$H NMR (300 MHz, D$_2$O) δ 4.78 (d, J=6.4 Hz, 1H), 4.20 (br s, 1H), 4.05-3.95 (m, 1H), 3.83-3.71 (m, 1H), 3.68-3.54 (m, 1H), 3.54-3.38 (m, 2H), 3.26-3.16 (m, 1H), 2.94 (d, J=12.3 Hz, 1H), 2.62-2.45 (m, 1H), 2.43-2.09 (m, 4H), 2.04-1.85 (m, 1H).

Example 39
Synthesis of (2S,5R)-7-oxo-2-(5-((S)-pyrrolidin-3-yl)-1,3,4-oxadiazol-2-yl)-1,6-diazabicyclo[3.2.1]octan-6-yl hydrogen sulfate (Compound 758)
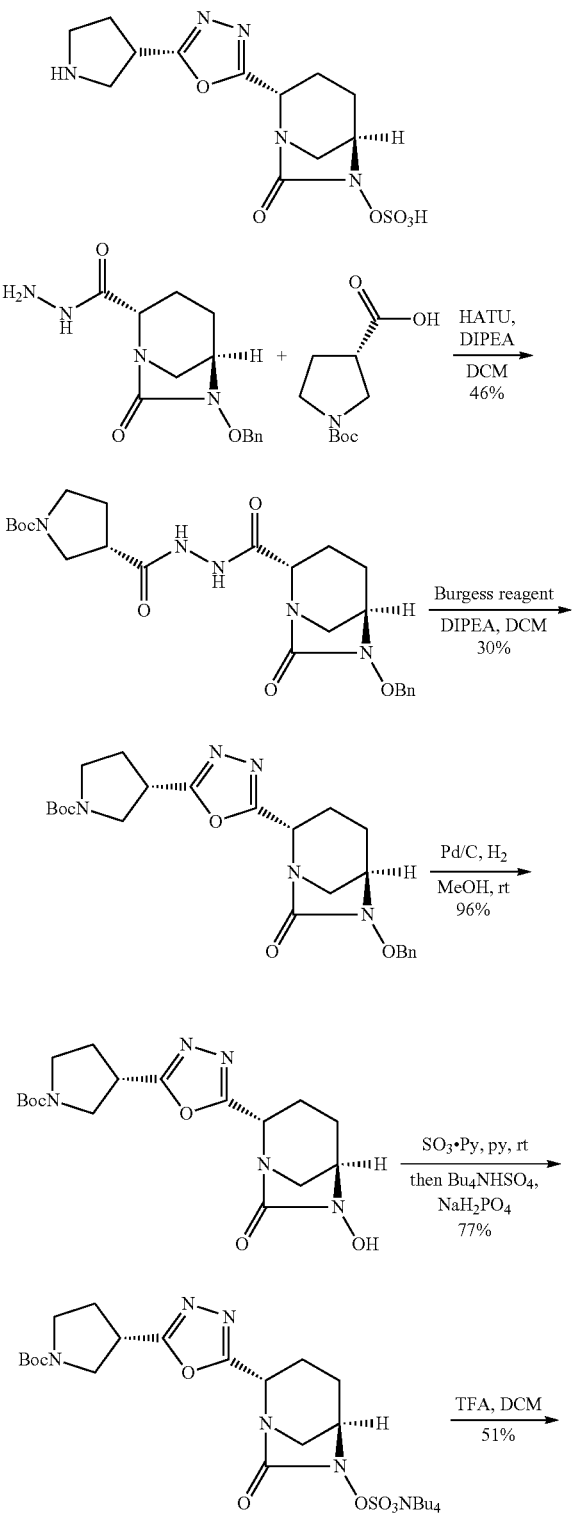
ESI-MS (EI+, m/z): 360.1.
Example 40
Synthesis of (2S,5R)-2-(5-(2-azaspiro[3.3]heptan-6-yl)-1,3,4-oxadiazol-2-yl)-7-oxo-1,6-diazabicyclo[3.2.1]octan-6-yl hydrogen sulfate (Compound 750)
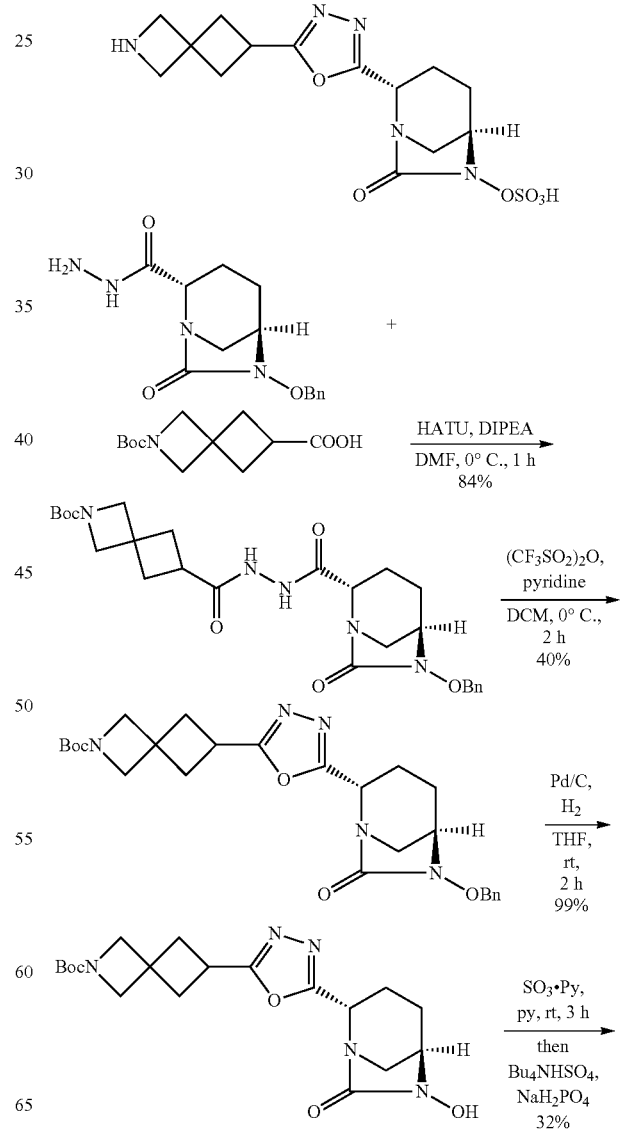

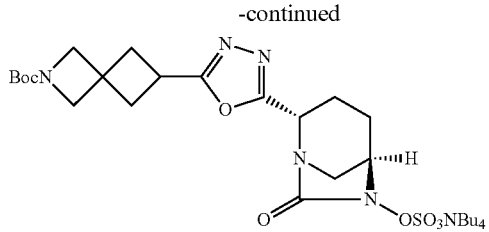
ESI-MS (EI+, m/z): 386.3.
Example 41
Synthesis of (2S,5R)-2-(5-((1-carbamimidoylazetidin-3-yl)methyl)-1,3,4-oxadiazol-2-yl)-7-oxo-1,6-diazabicyclo[3.2.1]octan-6-yl hydrogen sulfate (Compound 741)
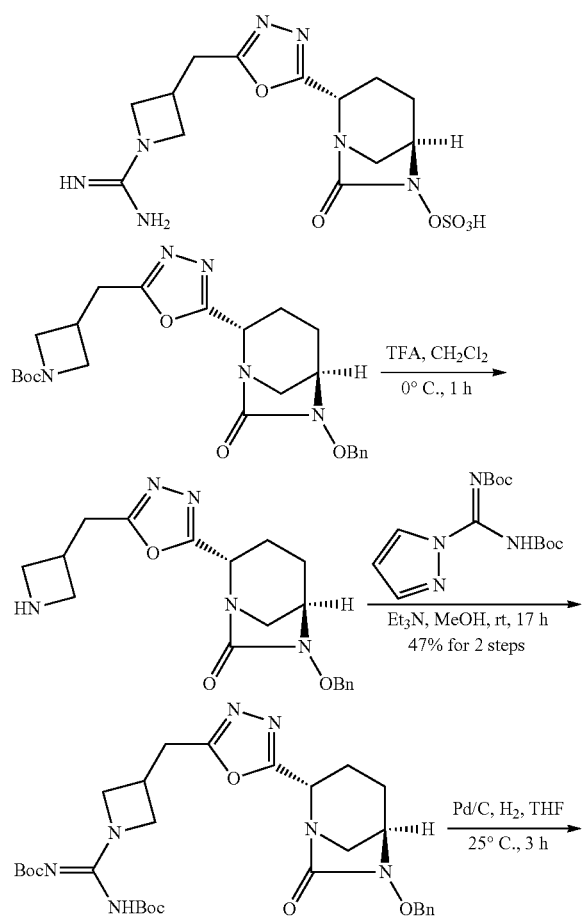
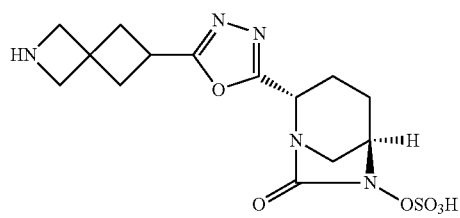
ESI-MS (EI+, m/z): 402.1. $^1$H NMR (300 MHz, DMSO-$d_6$) δ 4.63 (d, J=6.4 Hz, 1H), 4.27-4.12 (m, 2H), 4.07 (br s, 1H), 3.84 (dd, J=8.7, 4.8 Hz, 2H), 3.32-3.25 (m, 3H), 3.03-2.89 (m, 1H), 2.71 (d, J=11.9 Hz, 1H), 2.21-2.10 (m, 1H), 2.08-1.94 (m, 2H), 1.94-1.79 (m, 1H).
Example 42
Synthesis of (2S,5R)-2-(5-(2-(azetidin-3-yl)ethyl)-1,3,4-oxadiazol-2-yl)-7-oxo-1,6-diazabicyclo[3.2.1]octan-6-yl hydrogen sulfate (Compound 742)
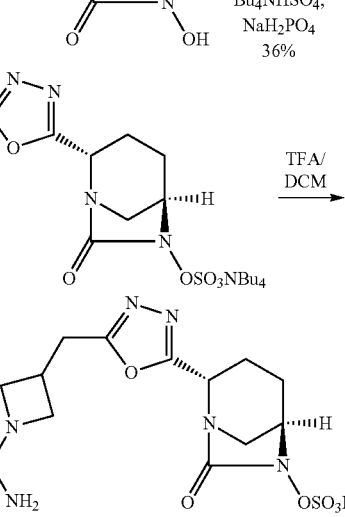
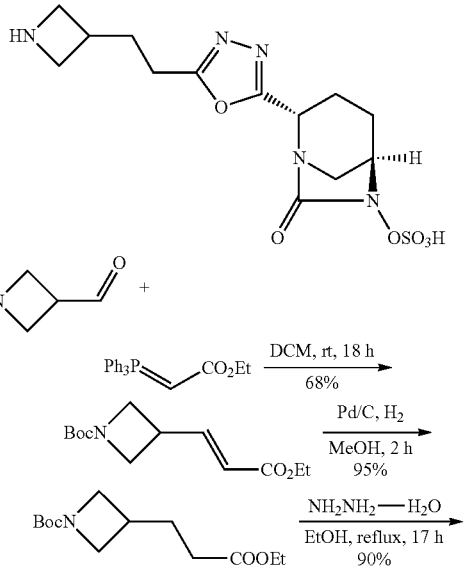

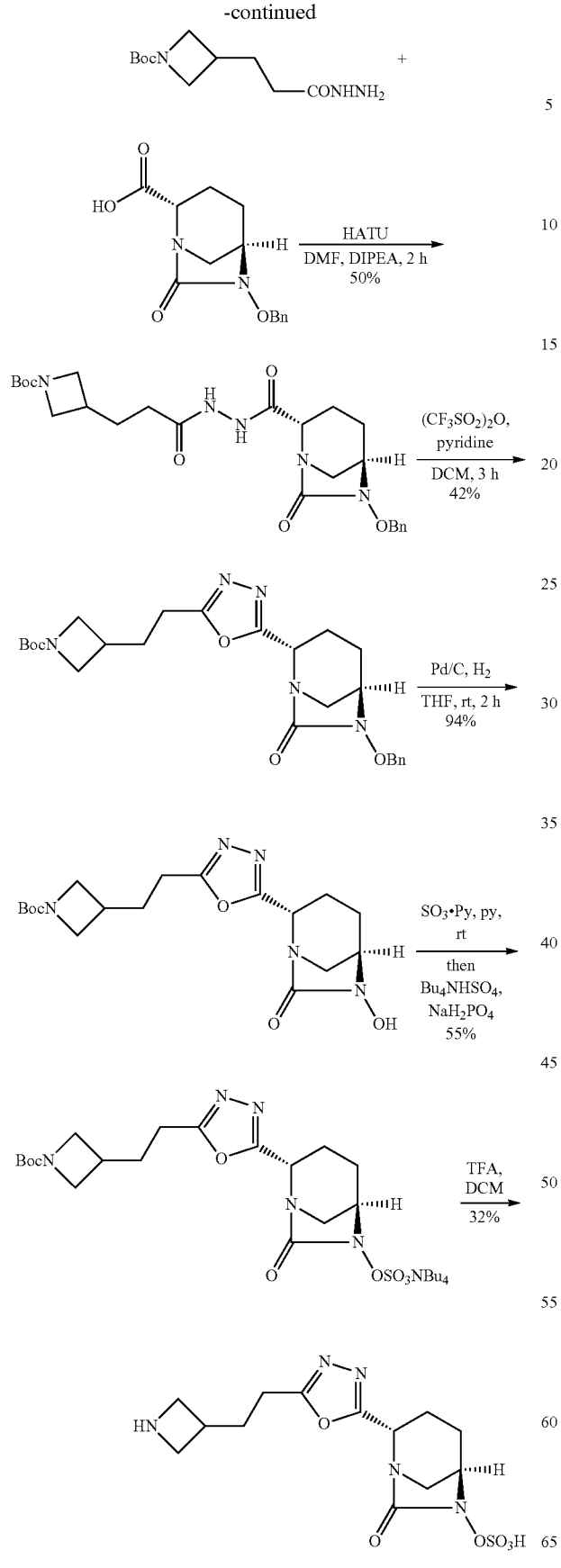
ESI-MS (EI+, m/z): 374.2. ¹H NMR (300 MHz, D₂O) δ 4.73 (d, J=6.4 Hz, 1H), 4.16 (brs, 1H), 4.12-4.00 (m, 2H), 3.81-3.71 (m, 2H), 3.22-3.09 (m, 1H), 3.02-2.74 (m, 4H), 2.32-1.76 (m, 6H).
Example 43
Synthesis of (2S,5R)-2-(5-((azetidin-3-yloxy)methyl)-1,3,4-oxadiazol-2-yl)-7-oxo-1,6-diazabicyclo[3.2.1]octan-6-yl hydrogen sulfate (Compound 744)
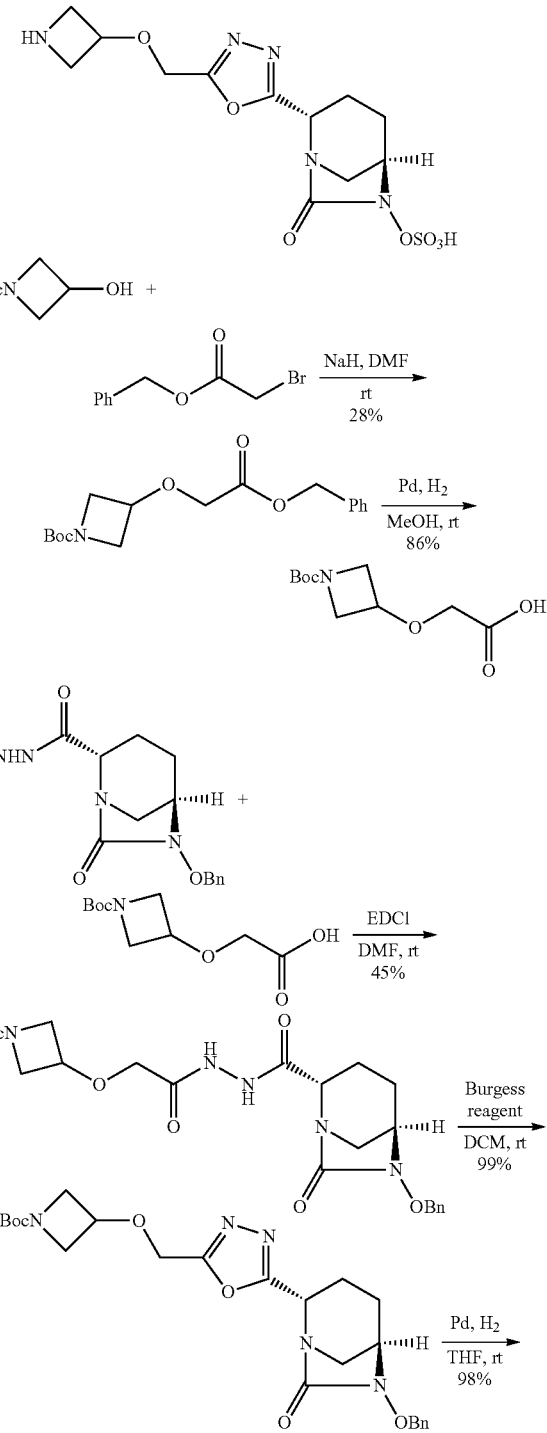

135
-continued
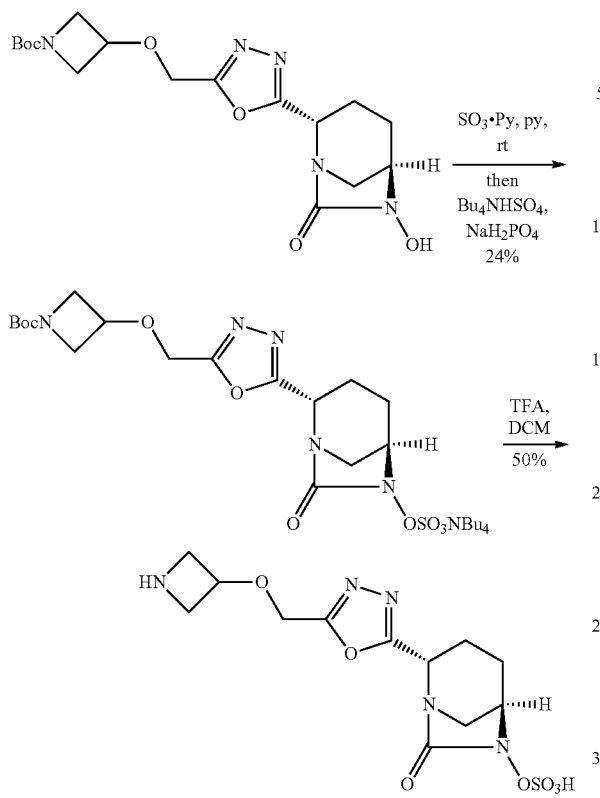
ESI-MS (EI+, m/z): 376.2. ¹H NMR (300 MHz, D₂O) δ 4.78 (s, 2H), 4.74 (d, J=6.4 Hz, 1H), 4.66-4.56 (m, 1H), 4.34-4.22 (m, 2H), 4.16 (br s, 1H), 4.06-3.91 (m, 2H), 3.23-3.04 (m, 1H), 2.88 (d, J=12.3 Hz, 1H), 2.35-2.00 (m, 3H), 2.00-1.80 (m, 1H).
Example 44
Synthesis of (2S,5R)-2-(5-(3-(azetidin-3-yl)propyl)-1,3,4-oxadiazol-2-yl)-7-oxo-1,6-diazabicyclo[3.2.1]octan-6-yl hydrogen sulfate (Compound 743)
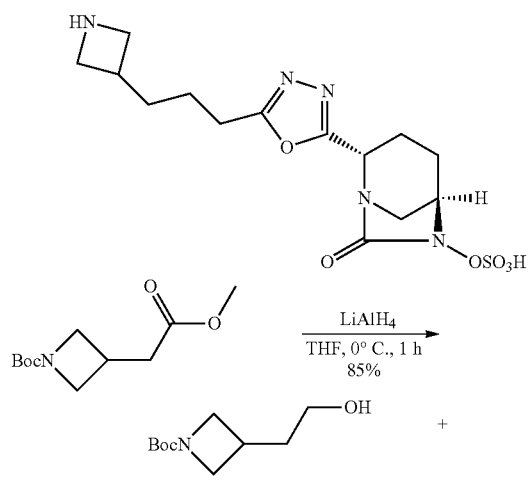
136
-continued
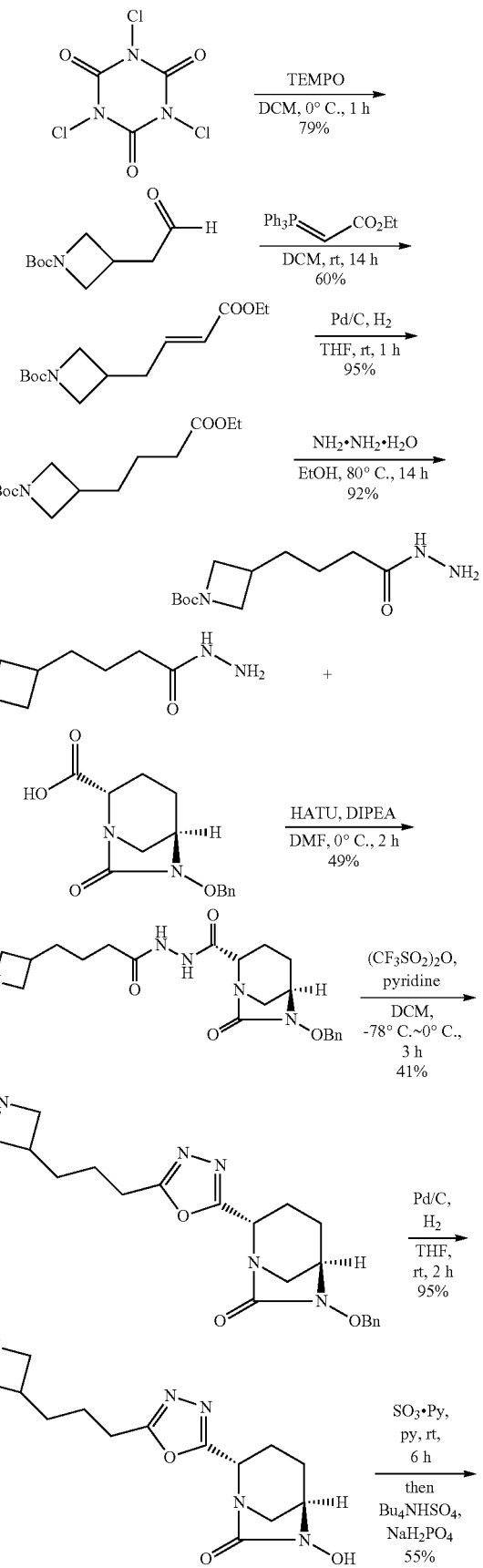

137
-continued

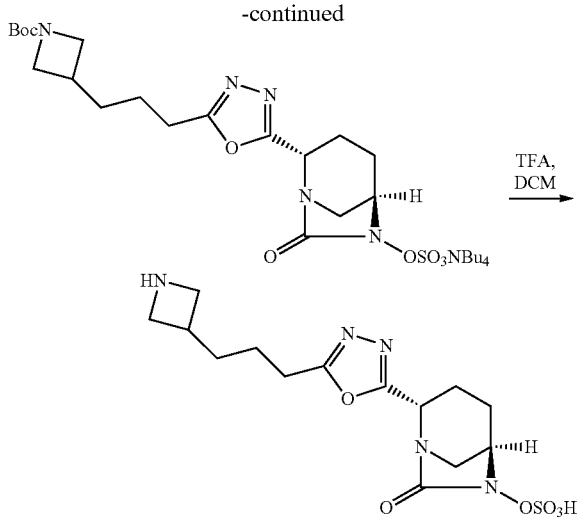

ESI-MS (EI+, m/z): 388.2. $^1$H NMR (300 MHz, D$_2$O) δ 4.75 (d, J=6.5 Hz, 1H), 4.16 (br s, 1H), 4.11-3.99 (m, 2H), 3.72 (dd, J=11.4, 7.6 Hz, 2H), 3.22-3.10 (m, 1H), 2.95-2.74 (m, 4H), 2.34-2.03 (m, 3H), 2.01-1.77 (m, 1H), 1.72-1.50 (m, 4H).

Example 45

Synthesis of (2S,5R)-7-oxo-2-(5-(pyrrolidin-3-ylmethyl)-1,3,4-oxadiazol-2-yl)-1,6-diazabicyclo[3.2.1]octan-6-yl hydrogen sulfate (Compound 764)

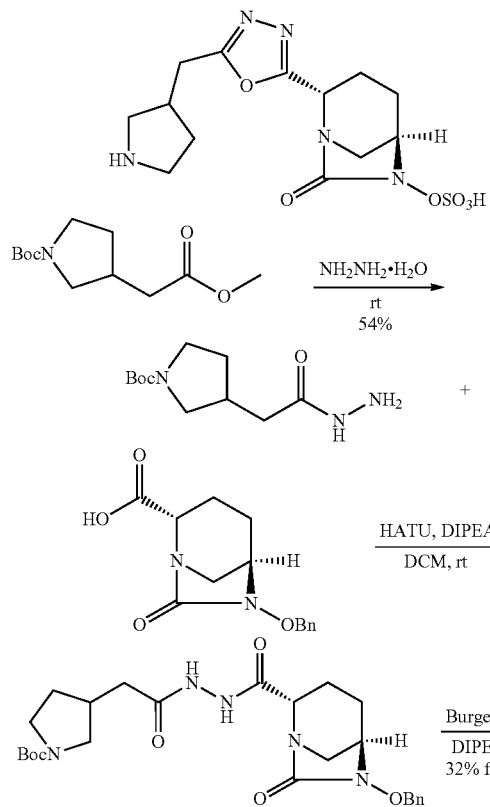

138
-continued

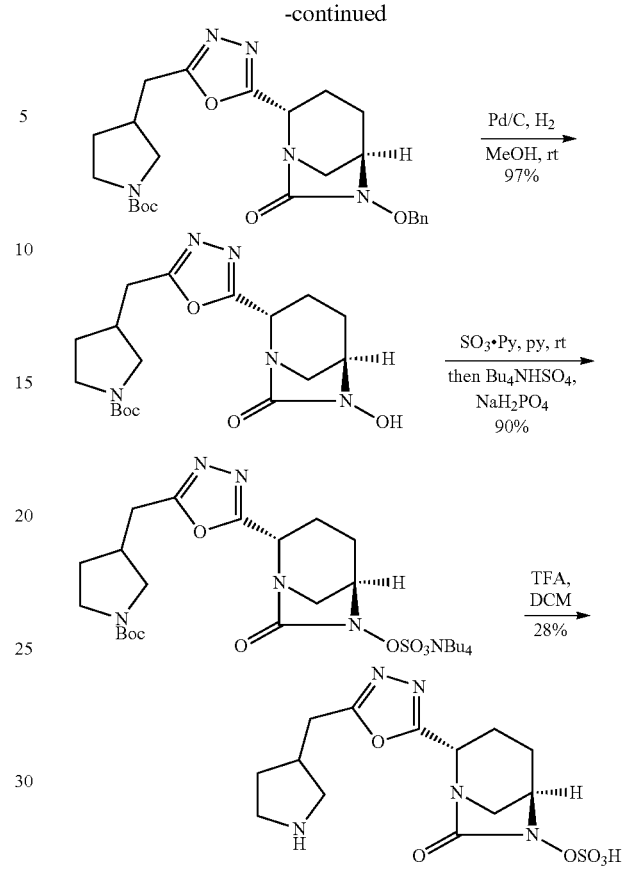

ESI-MS (EI+, m/z): 374.2. $^1$H NMR (300 MHz, D$_2$O) δ 4.74 (d, J=6.4 Hz, 1H), 4.16 (br s, 1H), 3.50 (dd, J=11.8, 7.7 Hz, 1H), 3.45-3.31 (m, 1H), 3.30-3.10 (m, 2H), 3.11-2.68 (m, 5H), 2.33-2.02 (m, 4H), 2.01-1.80 (m, 1H), 1.80-1.53 (m, 1H).

Example 46

Synthesis of (2S,5R)-2-(5-((1R,3S)-3-aminocyclopentyl)-1,3,4-oxadiazol-2-yl)-7-oxo-1,6-diazabicyclo[3.2.1]octan-6-yl hydrogen sulfate (Compound 768)

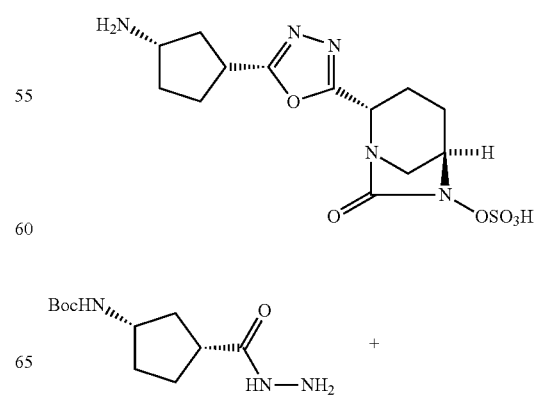

-continued
ESI-MS (EI+, m/z): 374.3.
Example 47
Synthesis of (2S,5R)-2-(5-(3-azabicyclo[3.1.0]hexan-6-yl)-1,3,4-oxadiazol-2-yl)-7-oxo-1,6-diazabicyclo[3.2.1]octan-6-yl hydrogen sulfate (Compound 740)
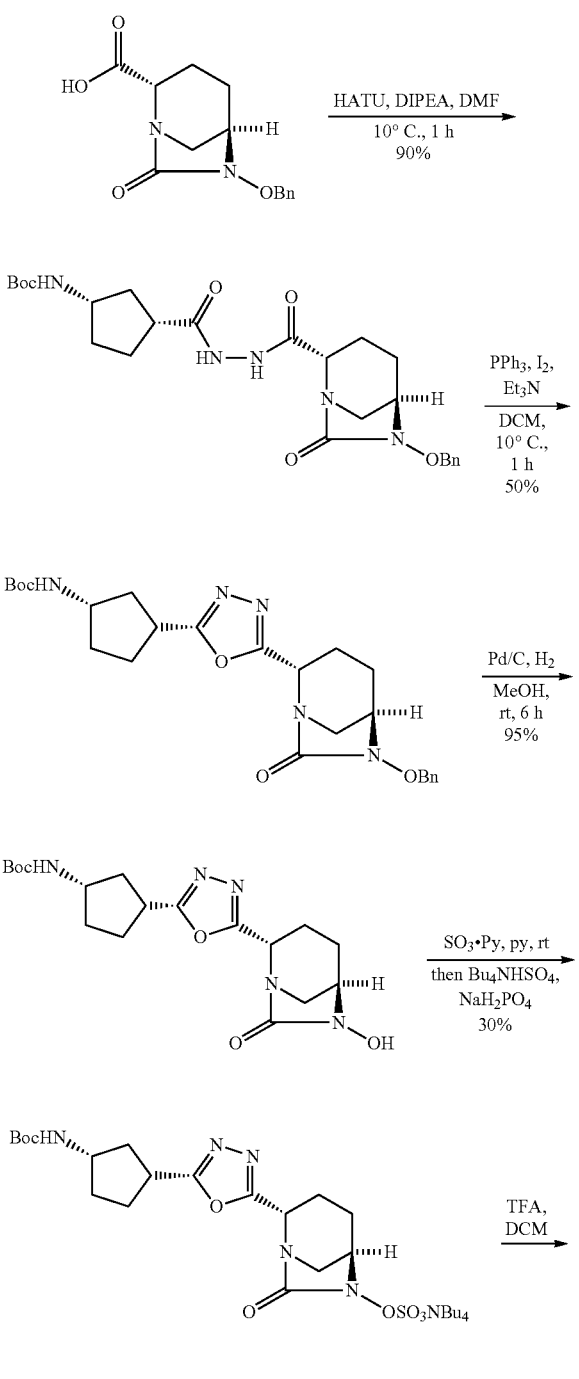

-continued
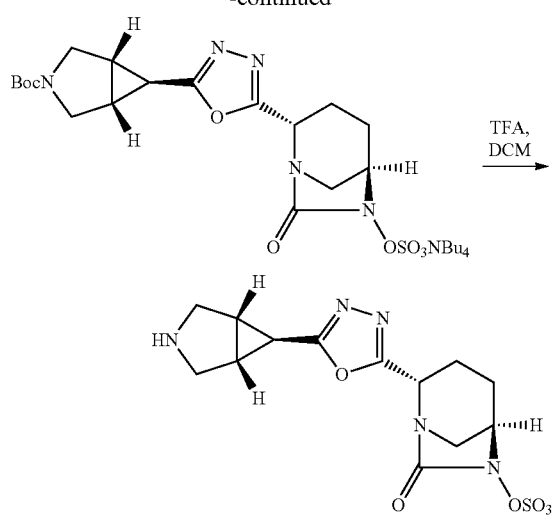
ESI-MS (EI⁺, m/z): 372.3.
Example 48
Synthesis of (2S,5R)-2-(5-(1-methylpyridin-1-ium-4-yl)-1,3,4-oxadiazol-2-yl)-7-oxo-1,6-diazabicyclo[3.2.1]octan-6-yl sulfate (Compound 782)
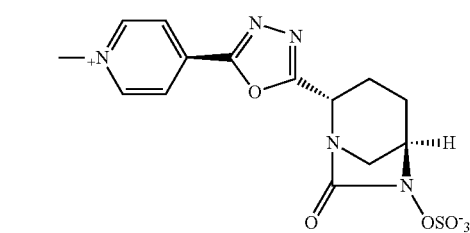
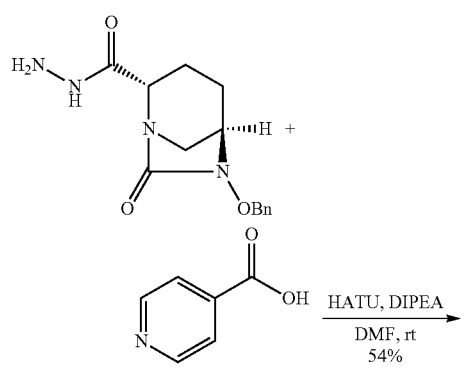
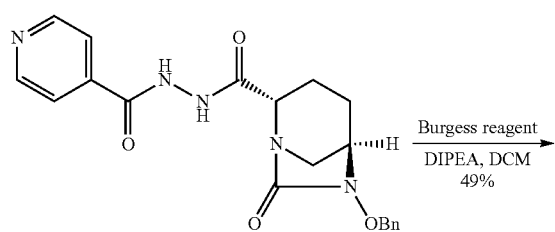
-continued
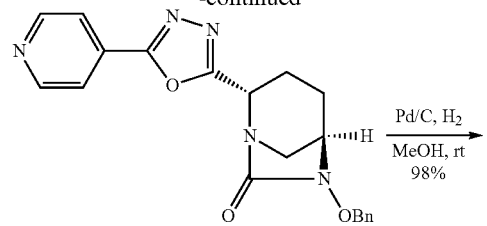
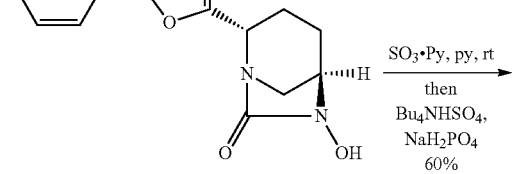
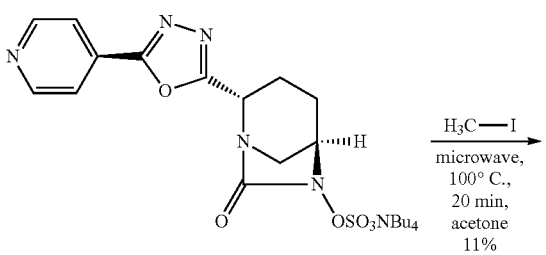
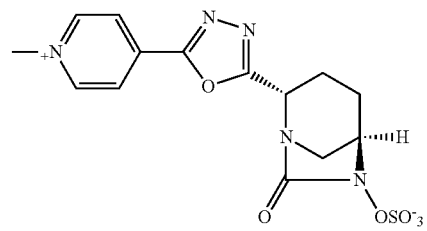
ESI-MS (EI⁺, m/z): 382.1. $^1$H NMR (300 MHz, D$_2$O) δ 8.95 (d, J=6.8 Hz, 2H), 8.53 (d, J=6.9 Hz, 2H), 4.92 (d, J=7.0 Hz, 1H), 4.38 (s, 3H), 4.20 (br s, 1H), 3.22 (br d, J=13.2 Hz, 1H), 2.98 (d, J=12.4 Hz, 1H), 2.42-2.33 (m, 1H), 2.31-2.10 (m, 2H), 2.03-1.90 (m, 1H).
Example 49
Synthesis of (2S,5R)-7-oxo-2-(5-(piperazin-1-ylmethyl)-1,3,4-oxadiazol-2-yl)-1,6-diazabicyclo[3.2.1]octan-6-yl hydrogen sulfate (Compound 777)
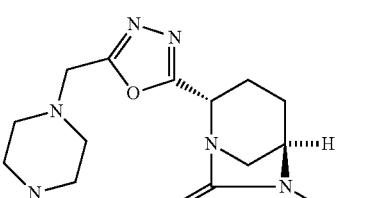
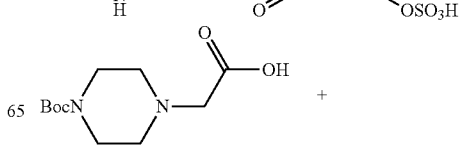

143
-continued
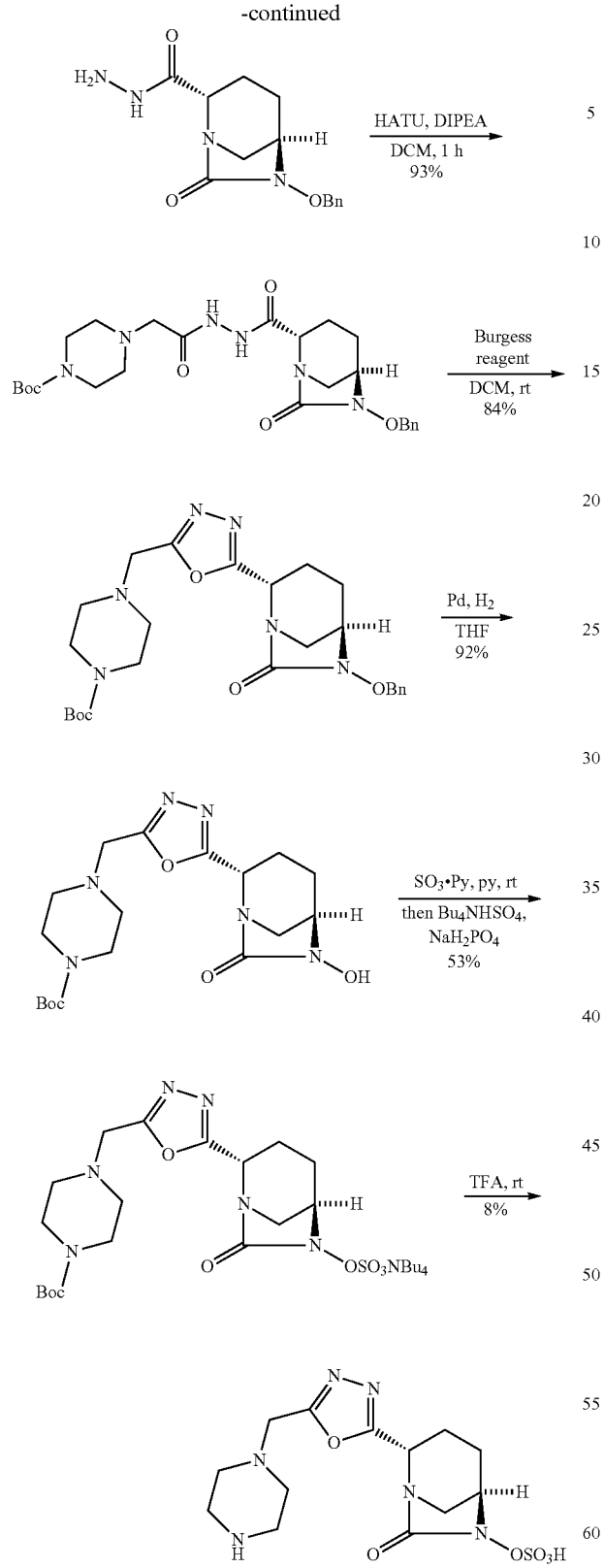
ESI-MS (EI+, m/z): 389.2. ¹H NMR (300 MHz, D₂O) δ 4.77 (d, J=6.4 Hz, 1H), 4.16 (br s, 1H), 3.96 (s, 2H), 3.22-3.11 (m, 5H), 2.88 (d, J=12.3 Hz, 1H), 2.85-2.76 (m, 4H), 2.31-2.02 (m, 3H), 1.98-1.78 (m, 1H).
144
Example 50
Synthesis of (2S,5R)-2-(5-((4-aminopiperidin-1-yl)methyl)-1,3,4-oxadiazol-2-yl)-7-oxo-1,6-diazabicyclo[3.2.1]octan-6-yl hydrogen sulfate (Compound 774)
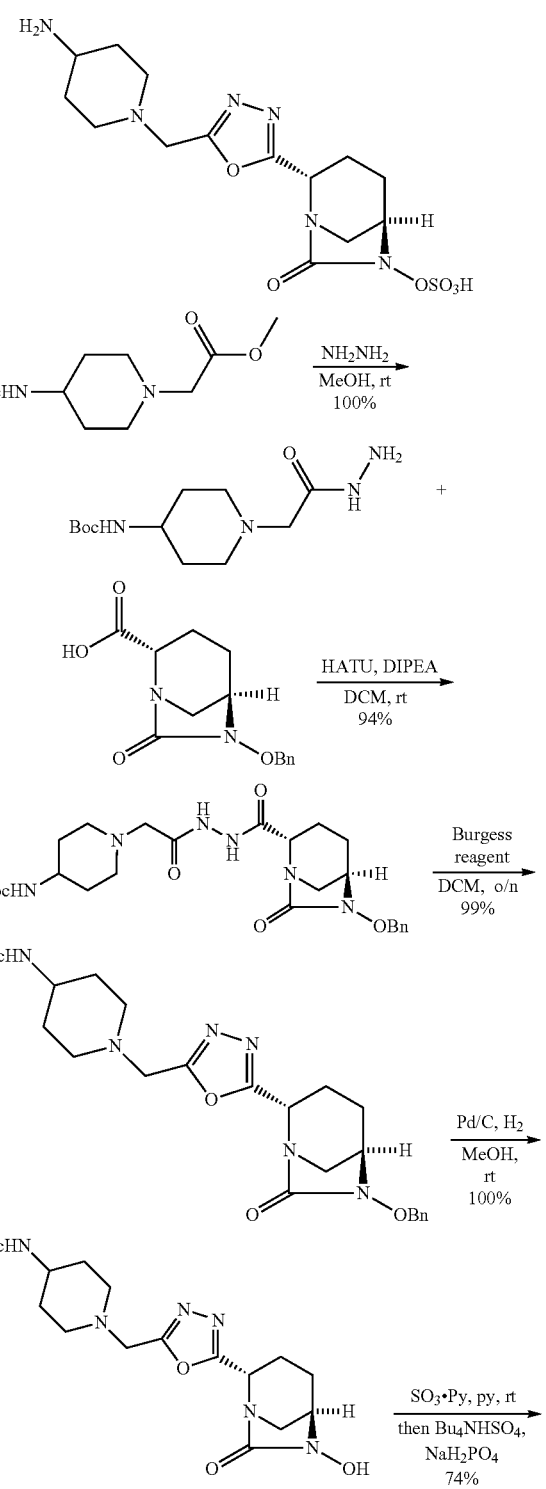

145
-continued
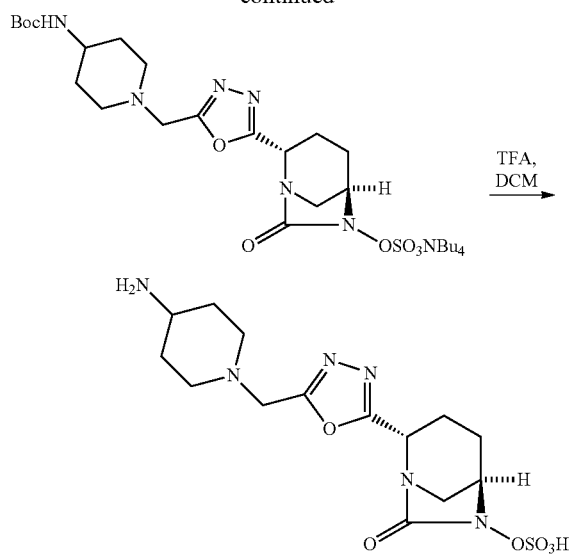
ESI-MS (EI⁺, m/z): 403.2. ¹H NMR (300 MHz, D₂O) δ 4.77 (d, J=6.5 Hz, 1H), 4.16 (br s, 1H), 3.87 (s, 2H), 3.20-3.05 (m, 2H), 3.00-2.91 (m, 2H), 2.87 (d, J=12.3 Hz, 1H), 2.32-2.04 (m, 5H), 2.03-1.85 (m, 3H), 1.57 (q, J=11.7 Hz, 2H).
Example 51
Synthesis of (2S,5R)-2-(5-((1r,3S)-3-aminocyclobutyl)-1,3,4-oxadiazol-2-yl)-7-oxo-1,6-diaza-bicyclo[3.2.1]octan-6-yl hydrogen sulfate (Compound 747)
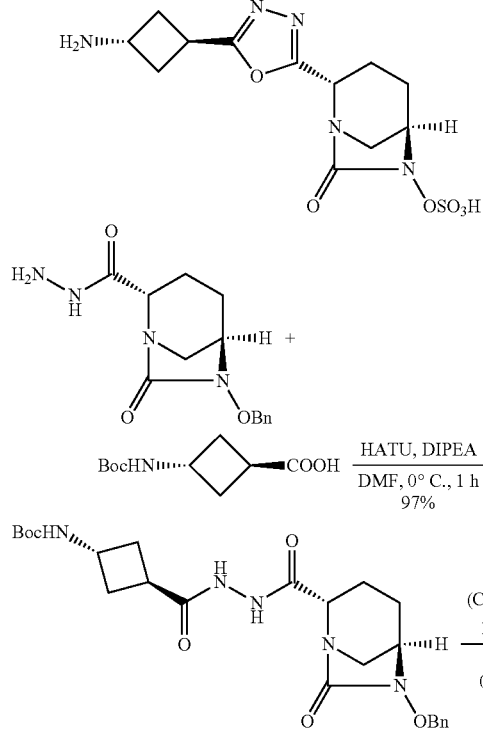
146
-continued
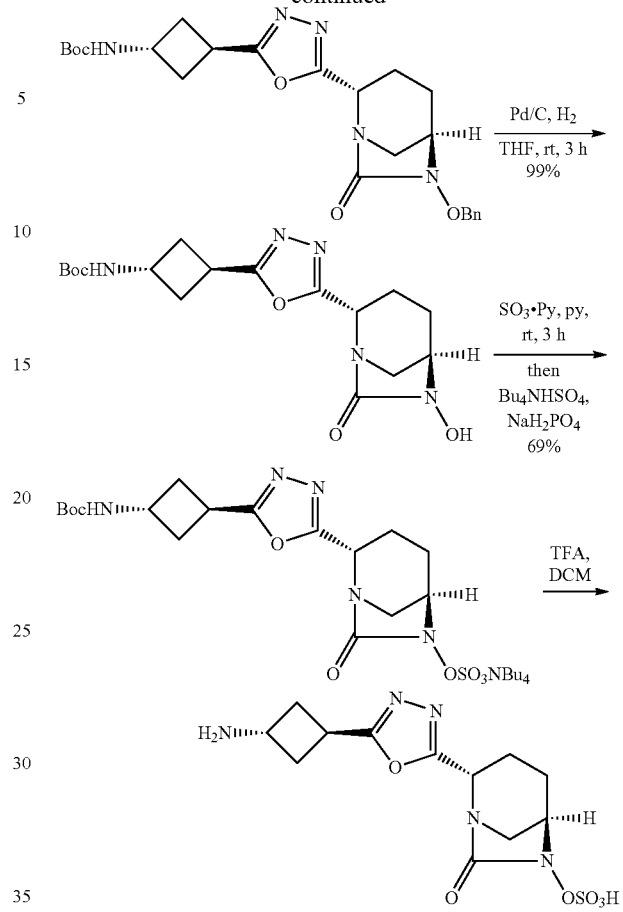
ESI-MS (EI⁺, m/z): 360.2.
Example 52
Synthesis of (2S,5R)-2-(5-((1r,3S)-3-guanidinocyclobutyl)-1,3,4-oxadiazol-2-yl)-7-oxo-1,6-diazabicyclo[3.2.1]octan-6-yl hydrogen sulfate (Compound 748)
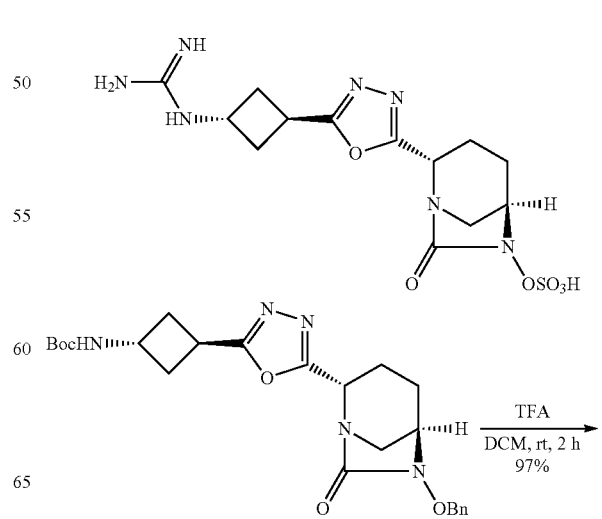

147
-continued
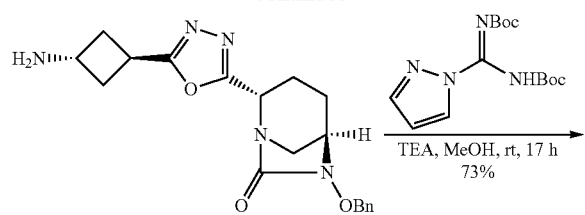
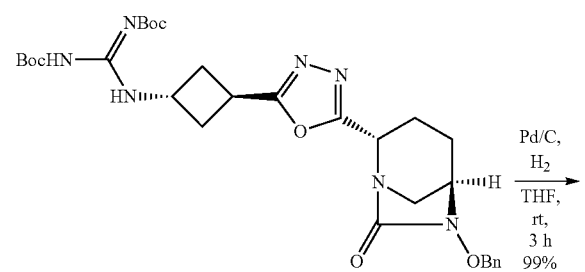
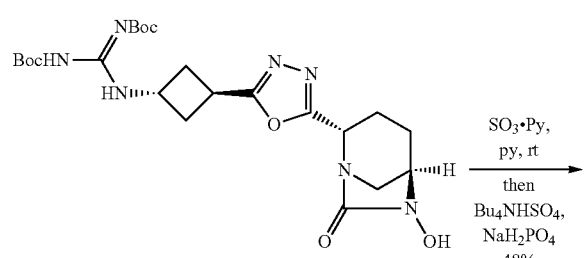
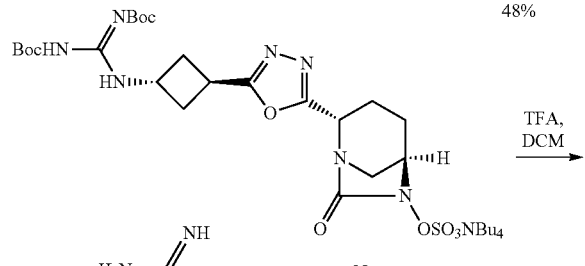
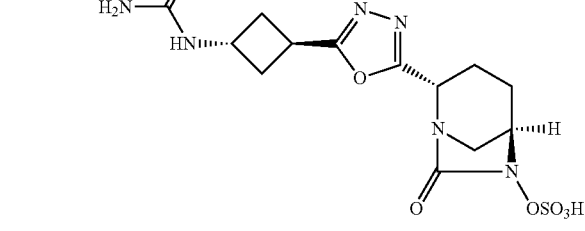
ESI-MS (EI+, m/z): 402.3.
Example 53
2S,5R)-2-(5-((1s,3R)-3-guanidinocyclobutyl)-1,3,4-oxadiazol-2-yl)-7-oxo-1,6-diazabicyclo[3.2.1]octan-6-yl hydrogen sulfate (Compound 749
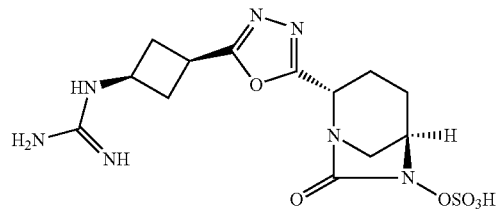
148
-continued
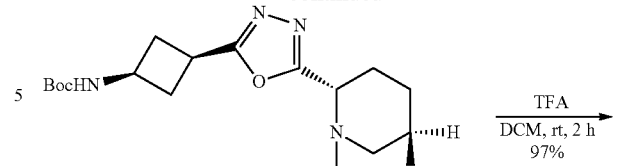
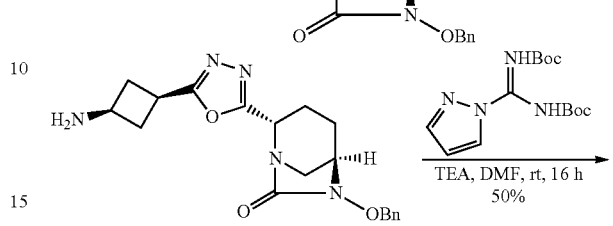
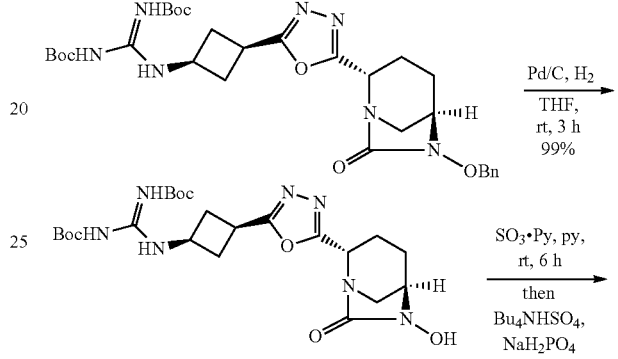
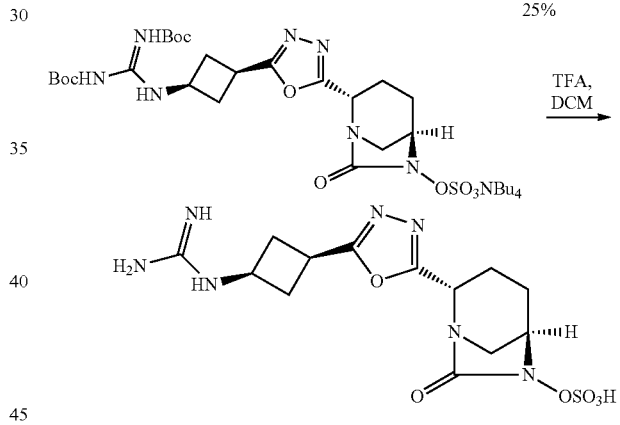
ESI-MS (EI+, m/z): 402.2.
Example 54
Synthesis of (2S,5R)-2-(5-(2-((1s,3S)-3-aminocyclobutyl)ethyl)-1,3,4-oxadiazol-2-yl)-7-oxo-1,6-diazabicyclo[3.2.1]octan-6-yl hydrogen sulfate (Compound 754)
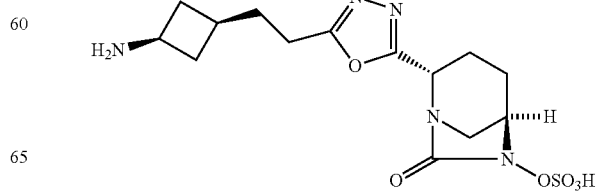

149
-continued
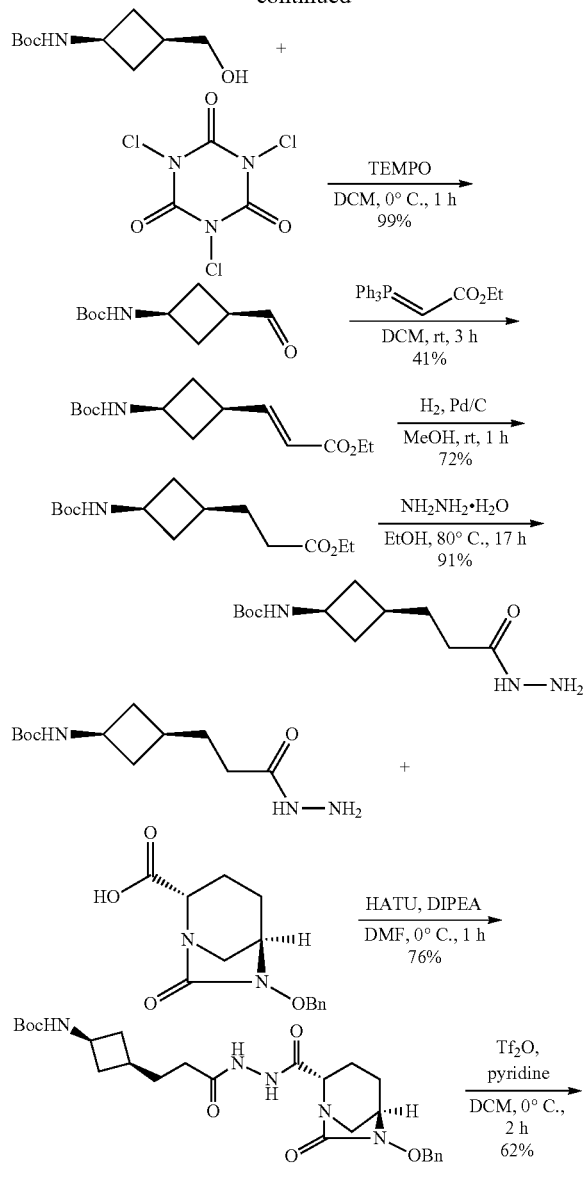
150
-continued
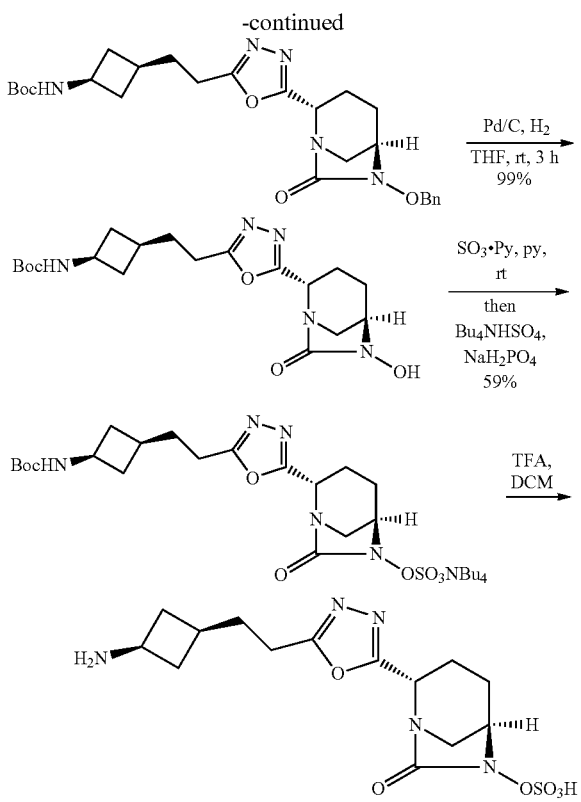
ESI-MS (EI+, m/z): 388.2. $^1$H NMR (300 MHz, D$_2$O) δ 4.68 (d, J=6.5 Hz, 1H), 4.11 (br s, 1H), 3.56-3.45 (m, 1H), 3.10 (br d, J=12.4 Hz, 1H), 2.86-2.67 (m, 3H), 2.38-1.94 (m, 6H), 1.95-1.70 (m, 3H), 1.66-1.52 (m, 2H).
Example 55
Synthesis of (2S,5R)-2-(5-(((1-carbamimidoylazetidin-3-yl)amino)methyl)-1,3,4-oxadiazol-2-yl)-7-oxo-1,6-diazabicyclo[3.2.1]octan-6-yl hydrogen sulfate (Compound 746)
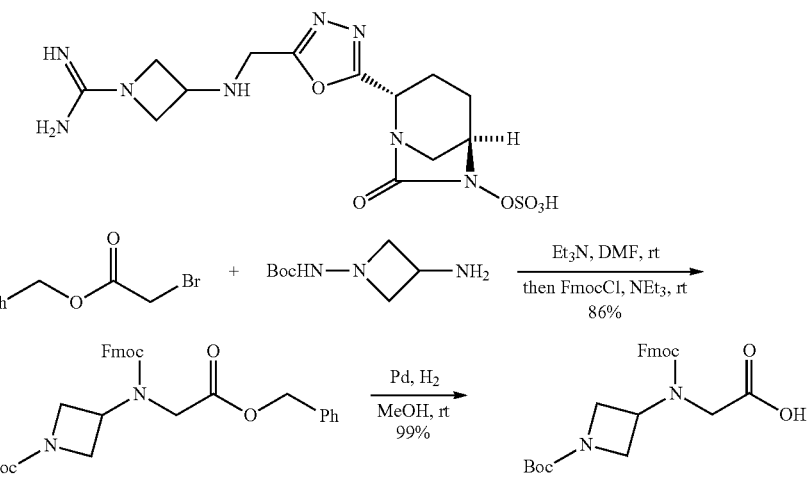

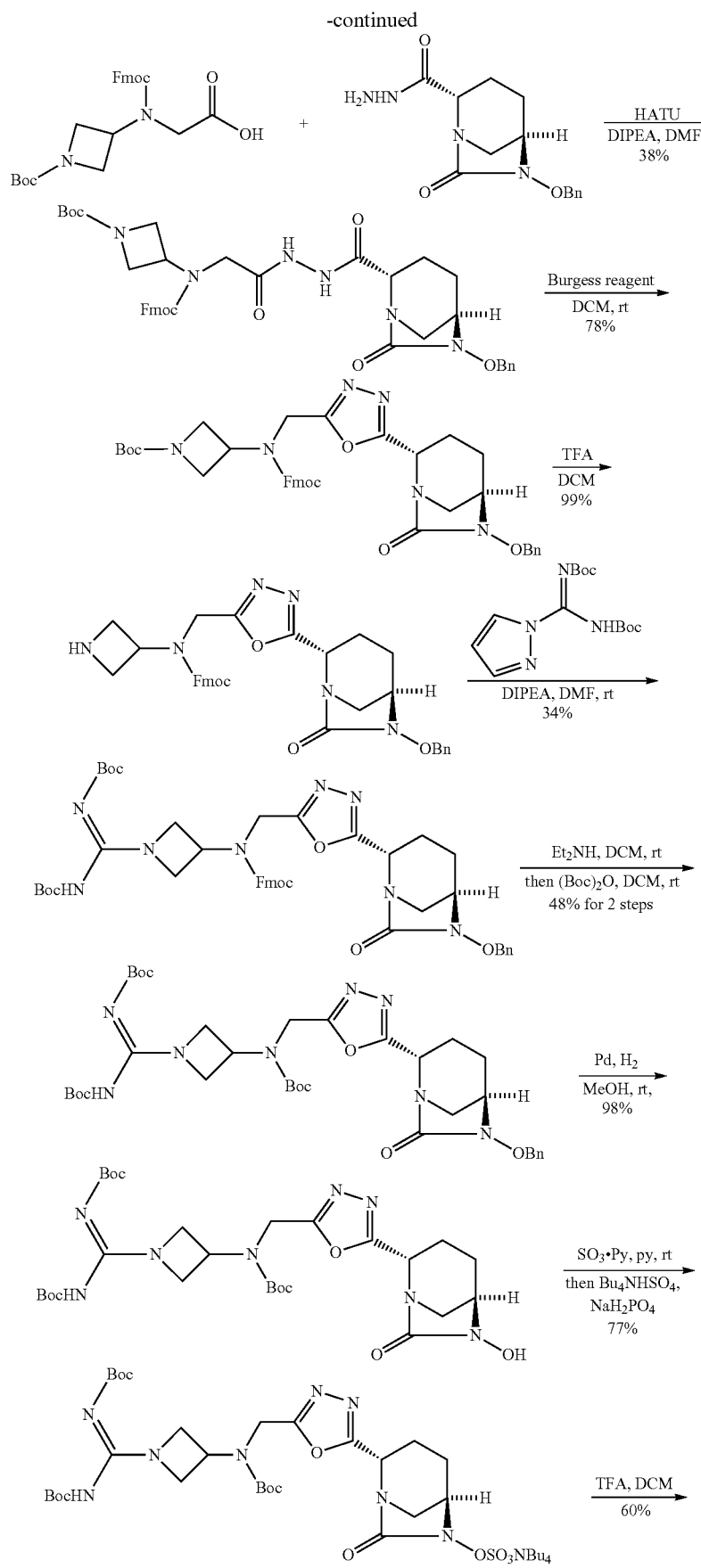

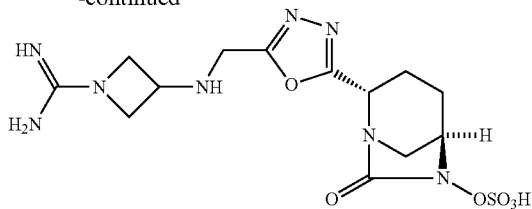
ESI-MS (EI+, m/z): 417.1. $^{1}$H NMR (300 MHz, D$_2$O) δ 4.75 (d, J=5.8 Hz, 1H), 4.26-4.15 (m, 3H), 4.00 (s, 2H), 3.82-3.72 (m, 3H), 3.21-3.12 (m, 1H), 2.88 (d, J=12.3 Hz, 1H), 2.32-2.02 (m, 3H), 1.99-1.84 (m, 1H).
Example 56
Synthesis of (2S,5R)-2-(5-(2-(azetidin-3-ylamino)ethyl)-1,3,4-oxadiazol-2-yl)-7-oxo-1,6-diazabicyclo[3.2.1]octan-6-yl hydrogen sulfate (Compound 745)
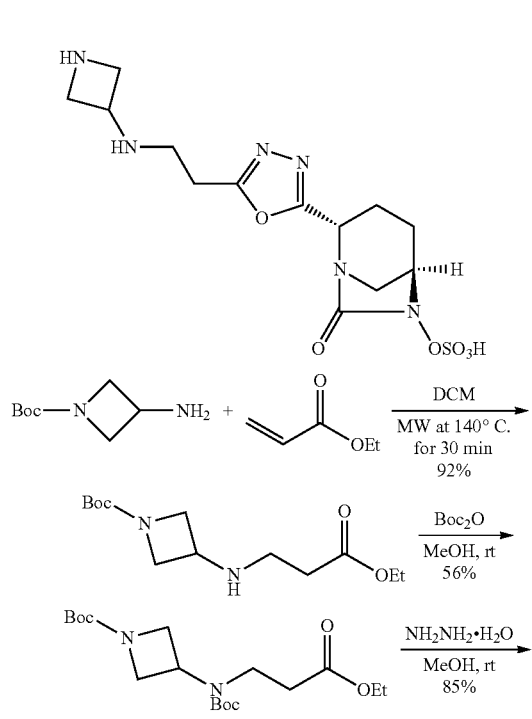
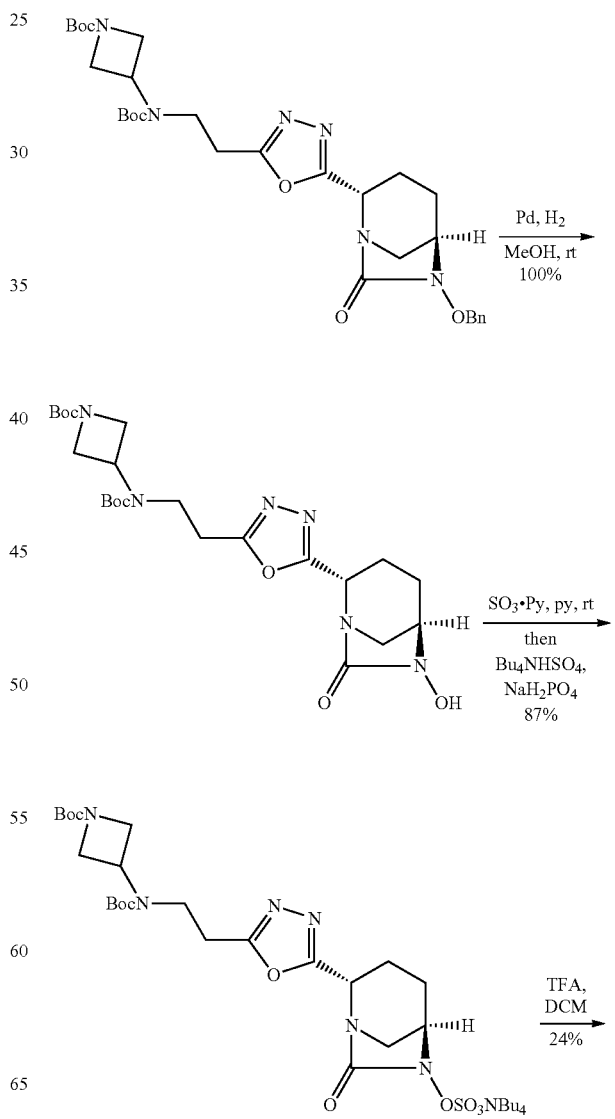

US 8,933,233 B2

155
-continued

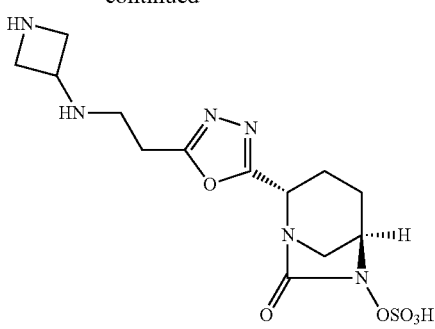

ESI-MS (EI+, m/z): 389.2.

Example 57

Synthesis of (2S,5R)-2-(5-((((1s,3R)-3-aminocyclobutyl)amino)methyl)-1,3,4-oxadiazol-2-yl)-7-oxo-1,6-diazabicyclo[3.2.1]octan-6-yl hydrogen sulfate (Compound 756) and (2S,5R)-2-(5-((((1r,3S)-3-aminocyclobutyl)amino)methyl)-1,3,4-oxadiazol-2-yl)-7-oxo-1,6-diazabicyclo[3.2.1]octan-6-yl hydrogen sulfate (Compound 757)

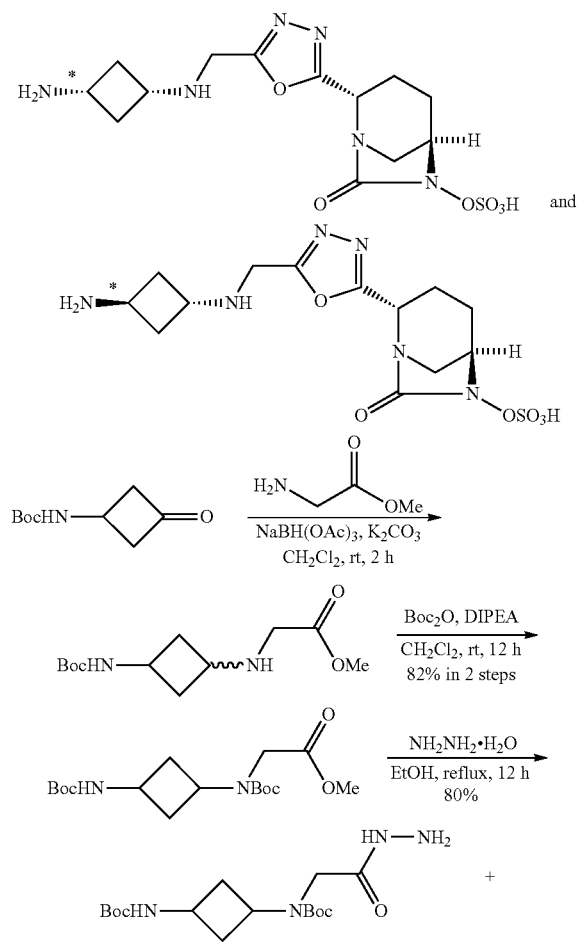

156
-continued

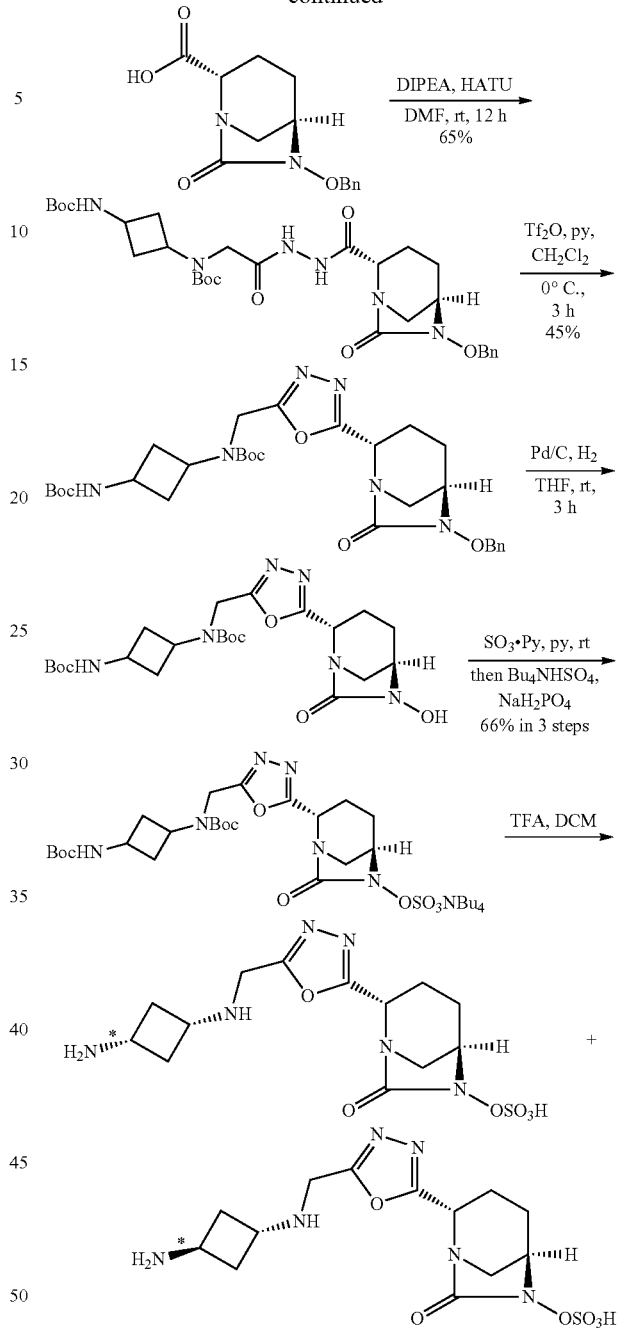

* The cyclobutane cis and trans isomers were seperated by prep-HPLC. The stereochemistry was arbitrarily assigned.

(2S,5R)-2-(5-((((1s,3R)-3-aminocyclobutyl)amino)methyl)-1,3,4-oxadiazol-2-yl)-7-oxo-1,6-diazabicyclo[3.2.1]octan-6-yl hydrogen sulfate (Compound 756): ESI-MS (EI+, m/z): 389.2. $^1$H NMR (300 MHz, D$_2$O) δ 4.75 (d, J=6.5 Hz, 1H), 4.15 (br s, 1H), 3.91 (s, 2H), 3.85-3.60 (m, 1H), 3.60-3.35 (m, 1H), 3.31-3.04 (m, 1H), 2.86 (d, J=12.2 Hz, 1H), 2.36-2.02 (m, 7H), 1.99-1.83 (m, 1H).

(2S,5R)-2-(5-((((1r,3 S)-3-aminocyclobutyl)amino)methyl)-1,3,4-oxadiazol-2-yl)-7-oxo-1,6-diazabicyclo[3.2.1]octan-6-yl hydrogen sulfate (Compound 757). ESI-MS (EI+, m/z): 389.2. $^1$H NMR (300 MHz, D$_2$O, as formate salt) δ 8.30 (s, 1H), 4.76 (d, J=6.5 Hz, 1H), 4.16 (br s, 1H), 4.01 (s, 2H), 3.44 (dt, J=16.1, 8.0 Hz, 1H), 3.23-3.07 (m, 2H), 2.86 (d, J=12.2 Hz, 1H), 2.65-2.47 (m, 2H), 2.33-2.03 (m, 3H), 1.98-1.76 (m, 3H)
Example 58
Synthesis of (2S,5R)-7-oxo-2-(5-(((R)-pyrrolidin-3-ylamino)methyl)-1,3,4-oxadiazol-2-yl)-1,6-diazabicyclo[3.2.1]octan-6-yl hydrogen sulfate (Compound 766)
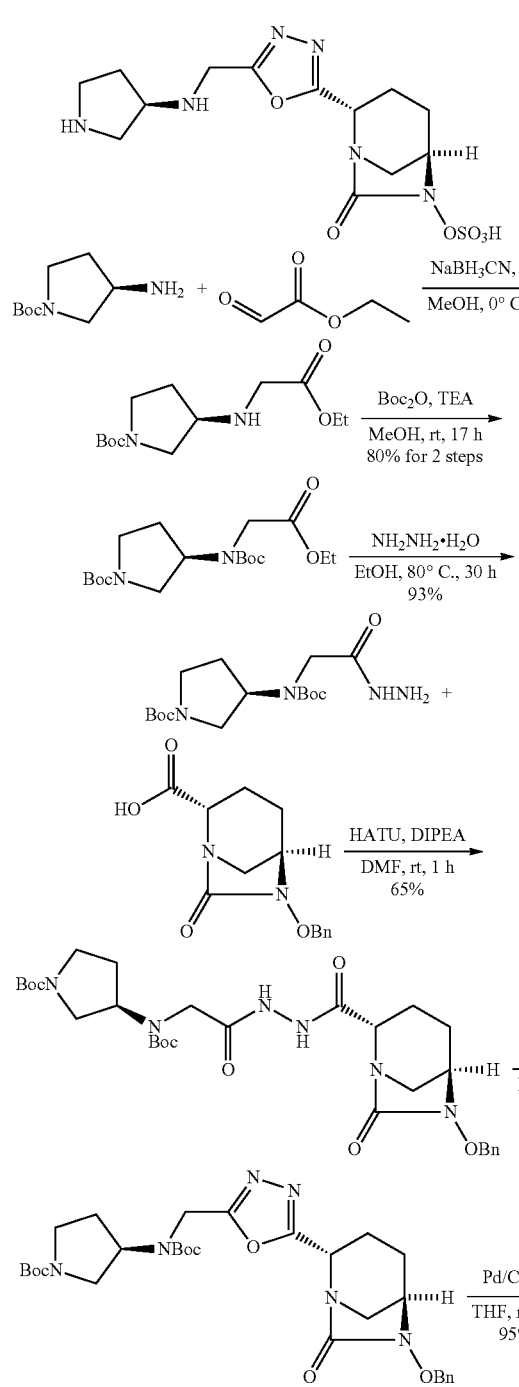
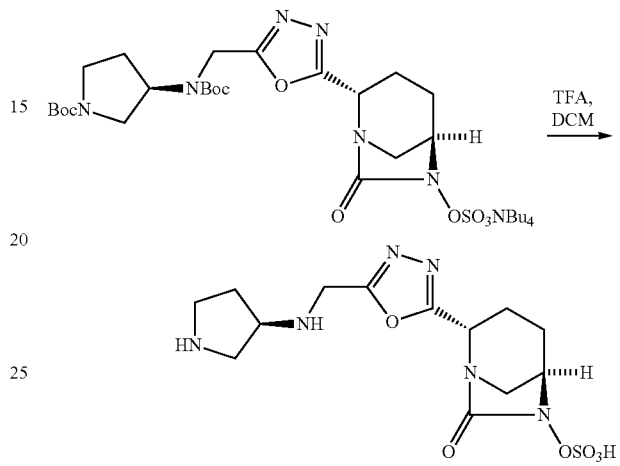
ESI-MS (EI+, m/z): 389.1. ¹H NMR (300 MHz, D₂O) δ 4.77 (d, J=6.5 Hz, 1H), 4.17 (br s, 1H), 4.03 (s, 2H), 3.60-3.45 (m, 1H), 3.36 (dd, J=12.5, 6.0 Hz, 2H), 3.29-3.12 (m, 2H), 3.06 (dd, J=12.2, 4.4 Hz, 1H), 2.89 (d, J=12.2 Hz, 1H), 2.32-2.07 (m, 5H), 1.99-1.75 (m, 1H).
Example 59
Synthesis of (2S,5R)-7-oxo-2-(5-(((S)-pyrrolidin-3-ylamino)methyl)-1,3,4-oxadiazol-2-yl)-1,6-diazabicyclo[3.2.1]octan-6-yl hydrogen sulfate (Compound 765)
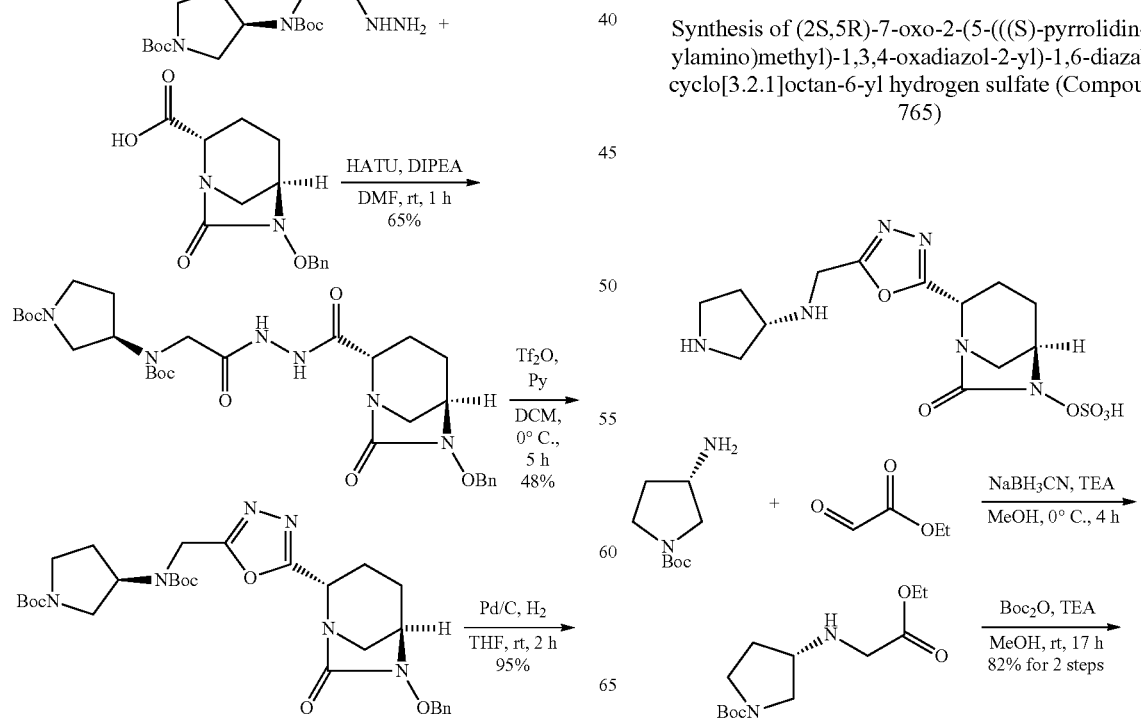

160
Example 60
Synthesis of (2S,5R)-2-(5-(((2S,4S)-4-aminopyrrolidin-2-yl)-1,3,4-oxadiazol-2-yl)-7-oxo-1,6-diazabicyclo[3.2.1]octan-6-yl hydrogen sulfate (Compound 760)
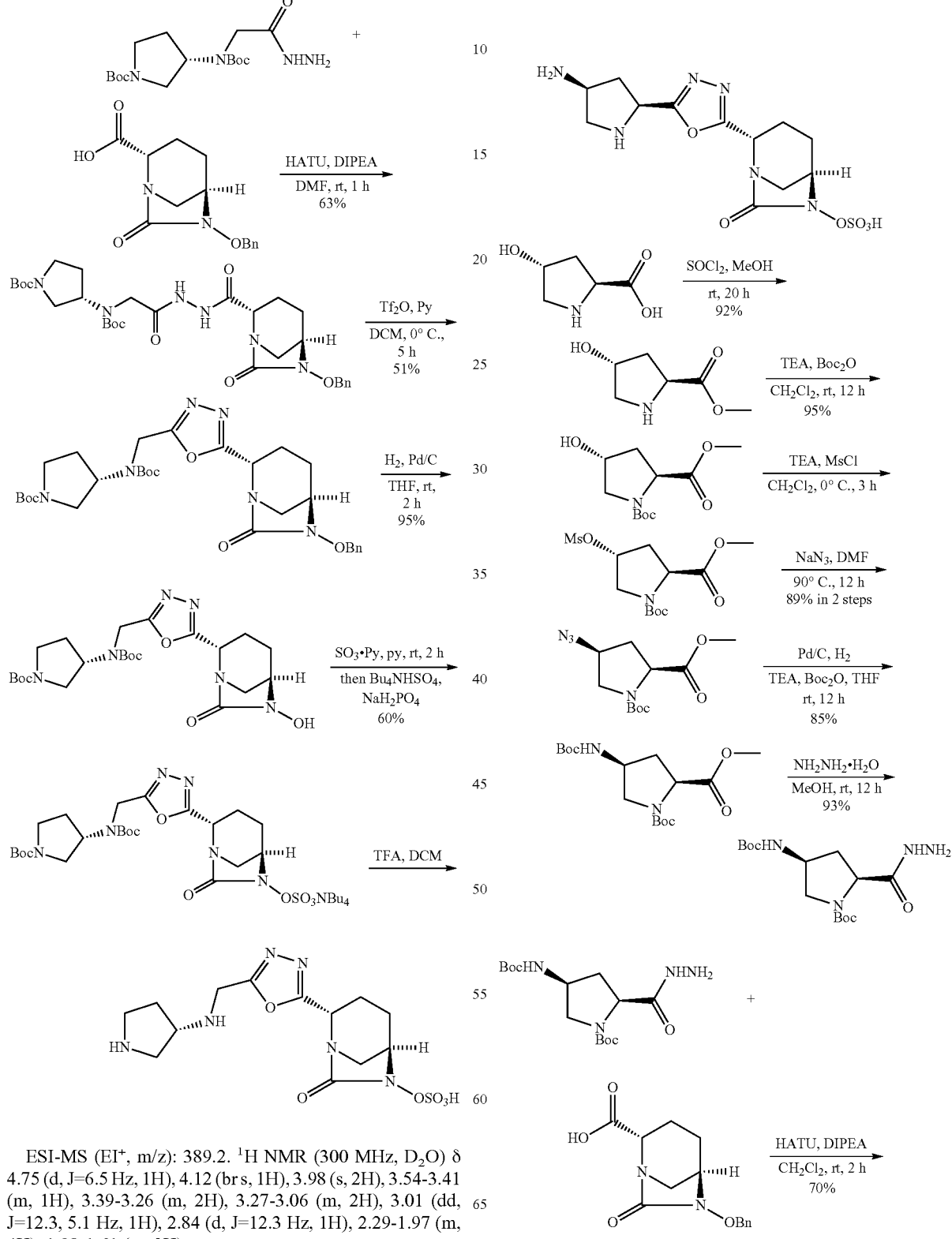
ESI-MS (EI+, m/z): 389.2. $^1$H NMR (300 MHz, D$_2$O) δ 4.75 (d, J=6.5 Hz, 1H), 4.12 (br s, 1H), 3.98 (s, 2H), 3.54-3.41 (m, 1H), 3.39-3.26 (m, 2H), 3.27-3.06 (m, 2H), 3.01 (dd, J=12.3, 5.1 Hz, 1H), 2.84 (d, J=12.3 Hz, 1H), 2.29-1.97 (m, 4H), 1.98-1.61 (m, 2H).
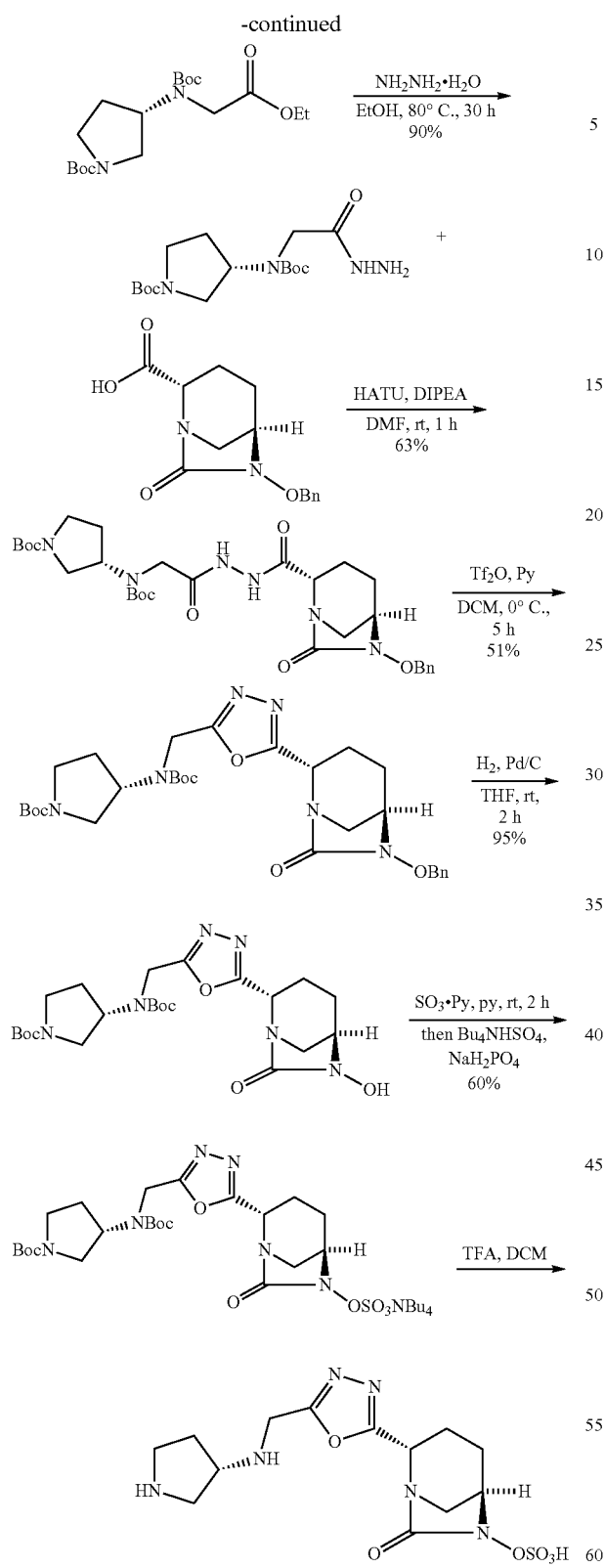

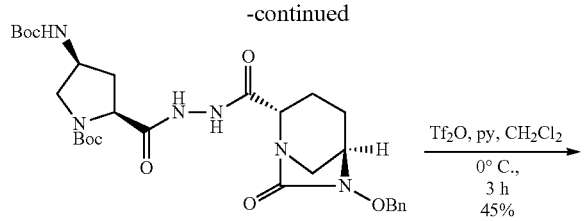
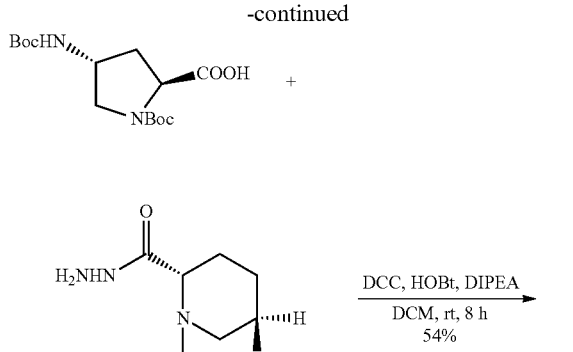
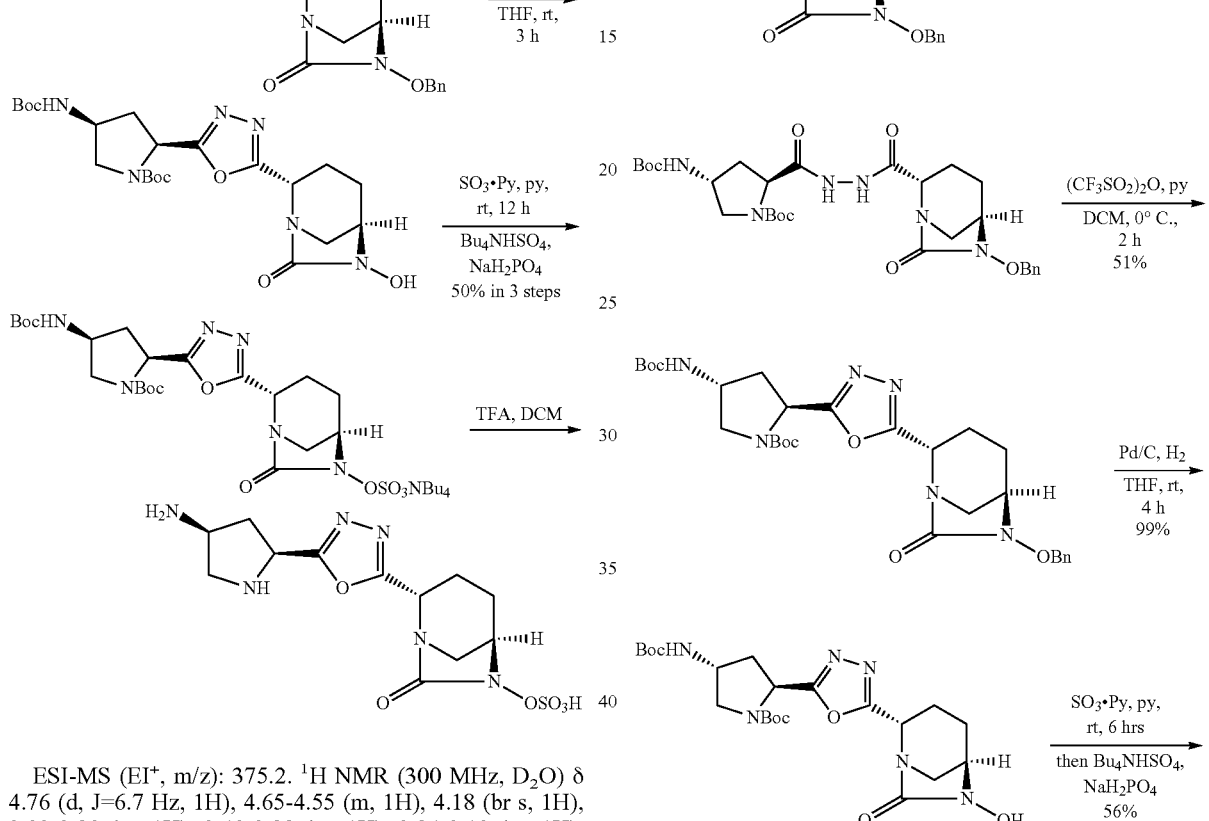
ESI-MS (EI+, m/z): 375.2. ¹H NMR (300 MHz, D₂O) δ 4.76 (d, J=6.7 Hz, 1H), 4.65-4.55 (m, 1H), 4.18 (br s, 1H), 3.93-3.80 (m, 1H), 3.40-3.28 (m, 1H), 3.24-3.13 (m, 1H), 2.96-2.83 (m, 2H), 2.75 (dd, J=14.6, 7.9 Hz, 1H), 2.34-1.82 (m, 5H).
Example 61
Synthesis of (2S,5R)-2-(5-((2S,4R)-4-aminopyrrolidin-2-yl)-1,3,4-oxadiazol-2-yl)-7-oxo-1,6-diazabicyclo[3.2.1]octan-6-yl hydrogen sulfate (Compound 762)
ESI-MS (EI+, m/z): 375.3.

Example 62
Synthesis of (2S,5R)-2-(5-((2R,4S)-4-aminopyrrolidin-2-yl)-1,3,4-oxadiazol-2-yl)-7-oxo-1,6-diazabicyclo[3.2.1]octan-6-yl hydrogen sulfate (Compound 763)
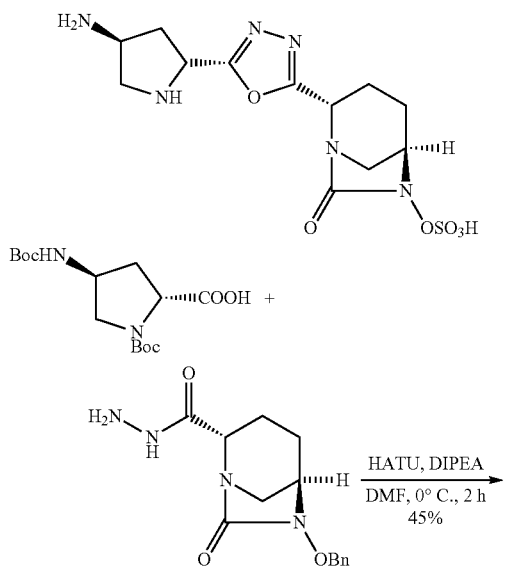
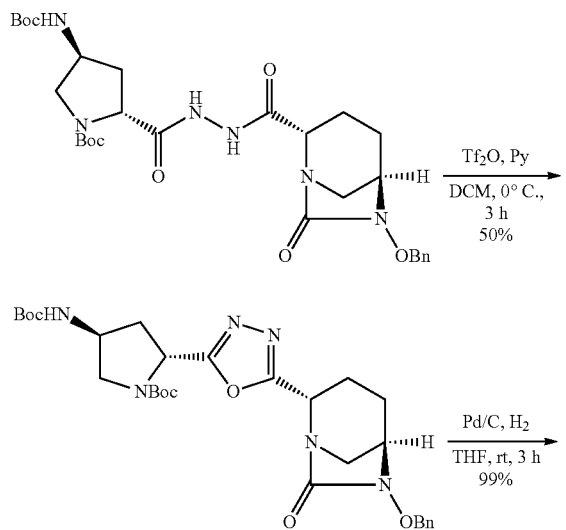
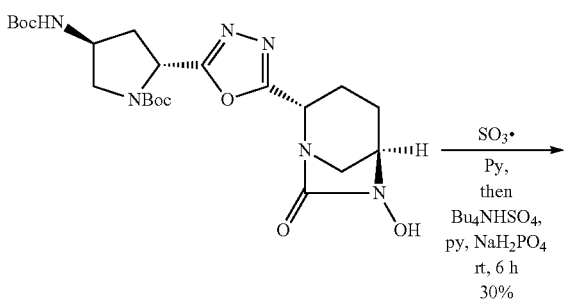
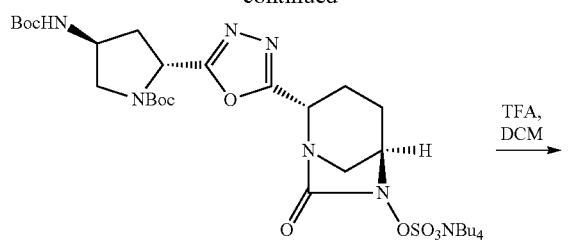
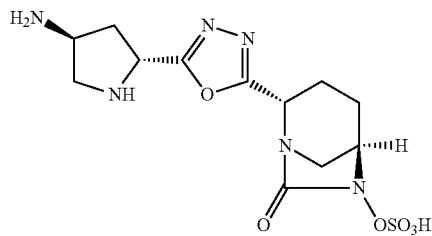
ESI-MS (EI+, m/z): 375.3.
Example 63
Synthesis of (2S,5R)-2-(5-((2R,4R)-4-aminopyrrolidin-2-yl)-1,3,4-oxadiazol-2-yl)-7-oxo-1,6-diazabicyclo[3.2.1]octan-6-yl hydrogen sulfate (Compound 761)
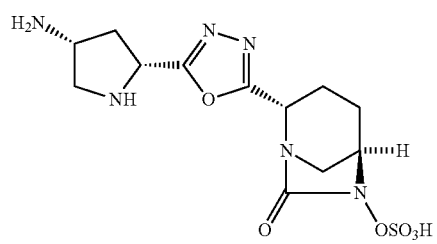
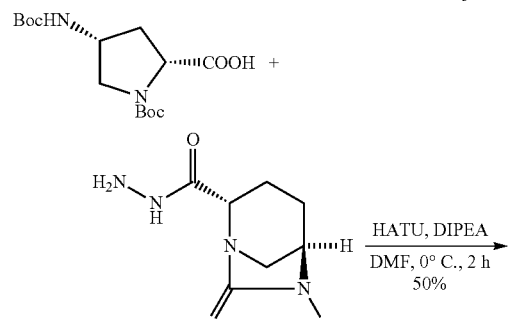
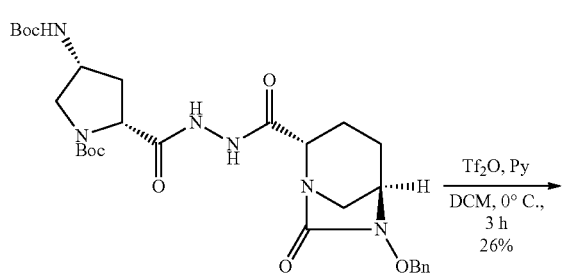

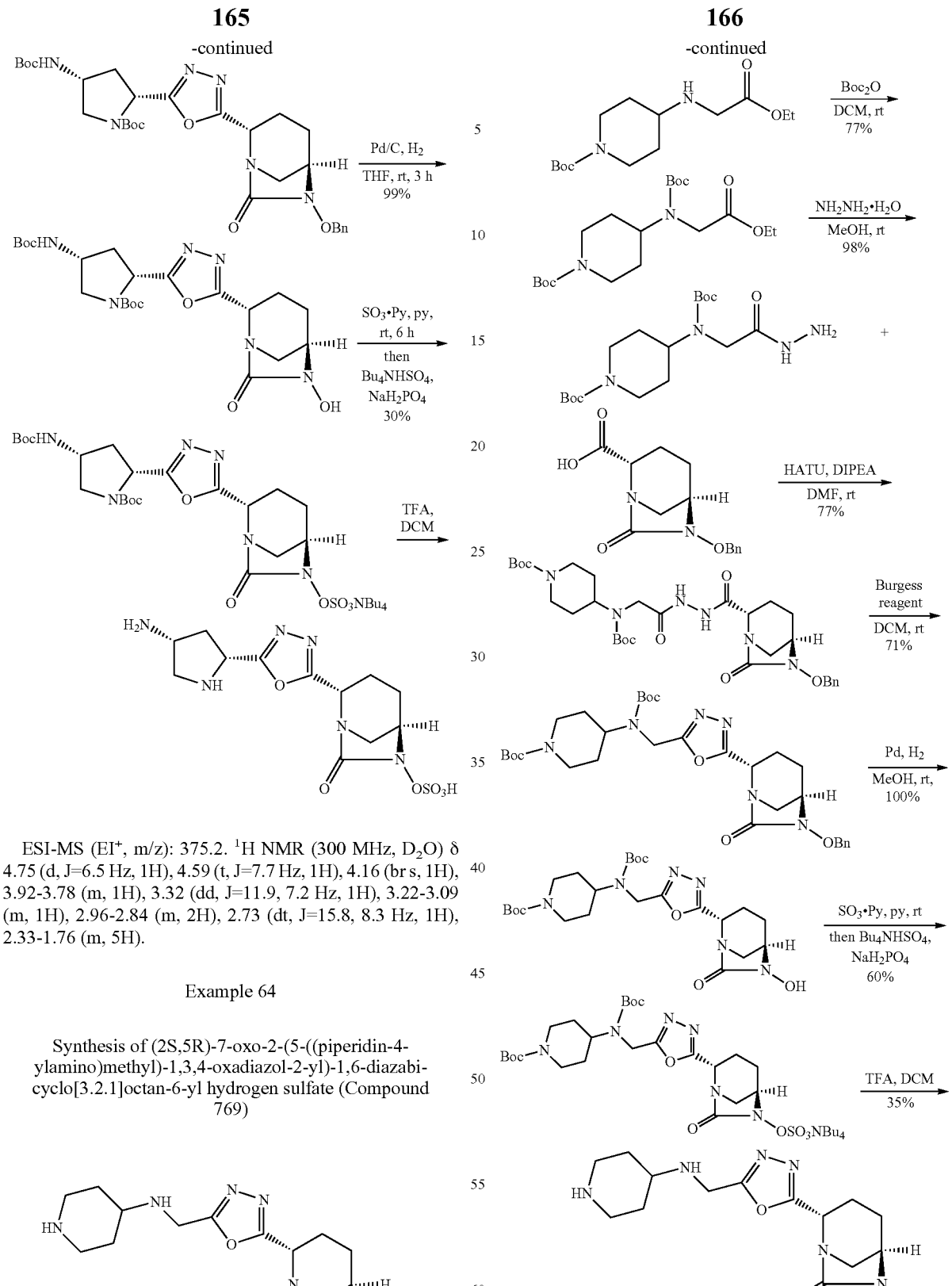
ESI-MS (EI+, m/z): 375.2. ¹H NMR (300 MHz, D₂O) δ 4.75 (d, J=6.5 Hz, 1H), 4.59 (t, J=7.7 Hz, 1H), 4.16 (br s, 1H), 3.92-3.78 (m, 1H), 3.32 (dd, J=11.9, 7.2 Hz, 1H), 3.22-3.09 (m, 1H), 2.96-2.84 (m, 2H), 2.73 (dt, J=15.8, 8.3 Hz, 1H), 2.33-1.76 (m, 5H).
Example 64
Synthesis of (2S,5R)-7-oxo-2-(5-((piperidin-4-ylamino)methyl)-1,3,4-oxadiazol-2-yl)-1,6-diazabicyclo[3.2.1]octan-6-yl hydrogen sulfate (Compound 769)
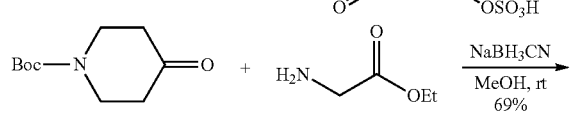
ESI-MS (EI+, m/z): 403.1. ¹H NMR (300 MHz, D₂O) δ 4.81 (d, J=6.5 Hz, 1H), 4.40 (s, 2H), 4.19 (br s, 1H), 3.55-3.41 (m, 2H), 3.34-3.23 (m, 1H), 3.20 (br d, J=13.2 Hz, 1H), 3.01-2.94 (m, 2H), 2.91 (d, J=12.3 Hz, 1H), 2.38-2.07 (m, 5H), 2.03-1.85 (m, 1H), 1.79-1.58 (m, 2H).

Example 65
Synthesis of (2S,5R)-7-oxo-2-(5-(2-(piperidin-4-ylamino)ethyl)-1,3,4-oxadiazol-2-yl)-1,6-diazabicyclo[3.2.1]octan-6-yl hydrogen sulfate (Compound 770)
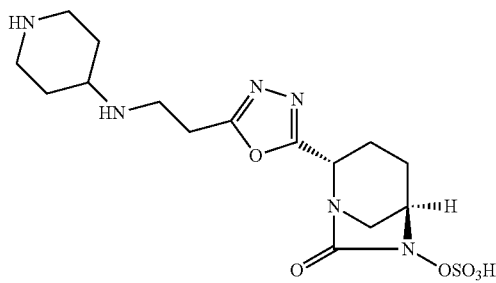
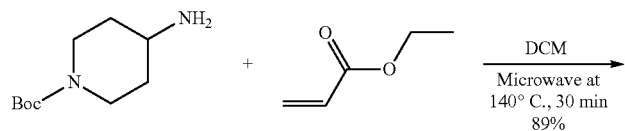
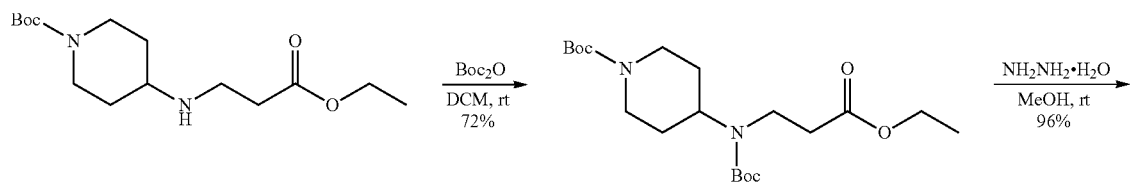
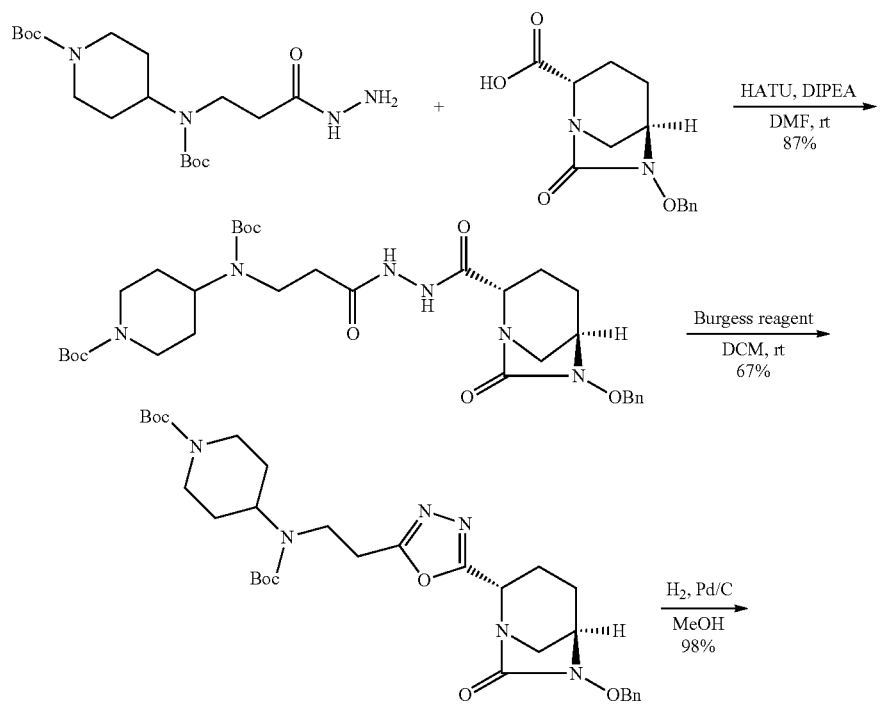

-continued
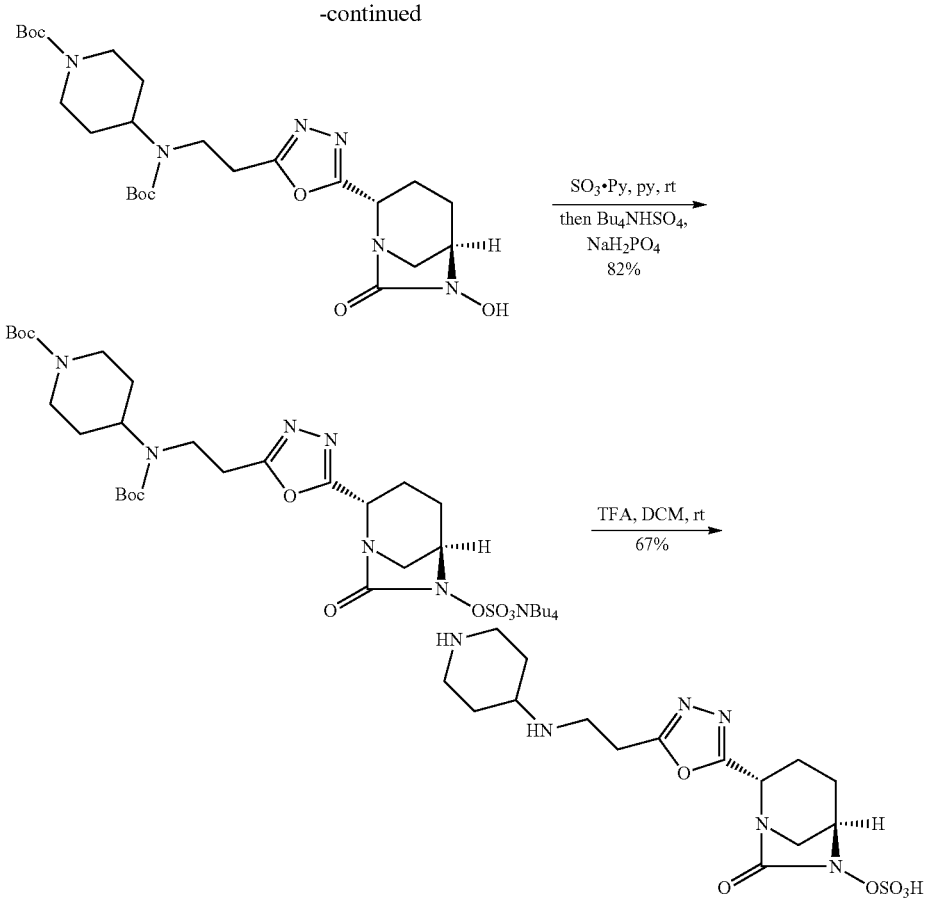
ESI-MS (EI+, m/z): 417.2. ¹H NMR (300 MHz, D₂O) δ 4.79 (d, J=6.9 Hz, 1H), 4.20 (br s, 1H), 3.61-3.51 (m, 5H), 3.38 (t, J=7.0 Hz, 2H), 3.21 (br d, J=12.4 Hz, 1H), 3.11-3.01 (m, 2H), 2.97 (d, J=12.3 Hz, 1H), 2.39-2.10 (m, 5H), 2.01-1.76 (m, 3H).
Example 66
Synthesis of (2S,5R)-7-oxo-2-(5-(3-(piperidin-4-ylamino)propyl)-1,3,4-oxadiazol-2-yl)-1,6-diazabicyclo[3.2.1]octan-6-yl hydrogen sulfate (Compound 771)
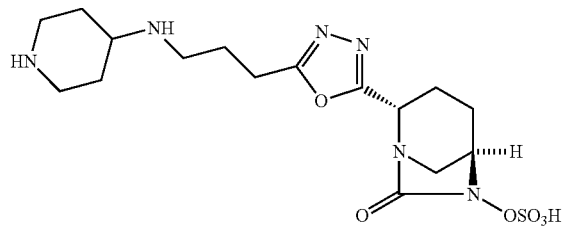
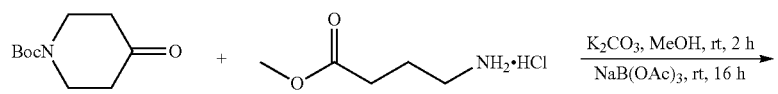

-continued
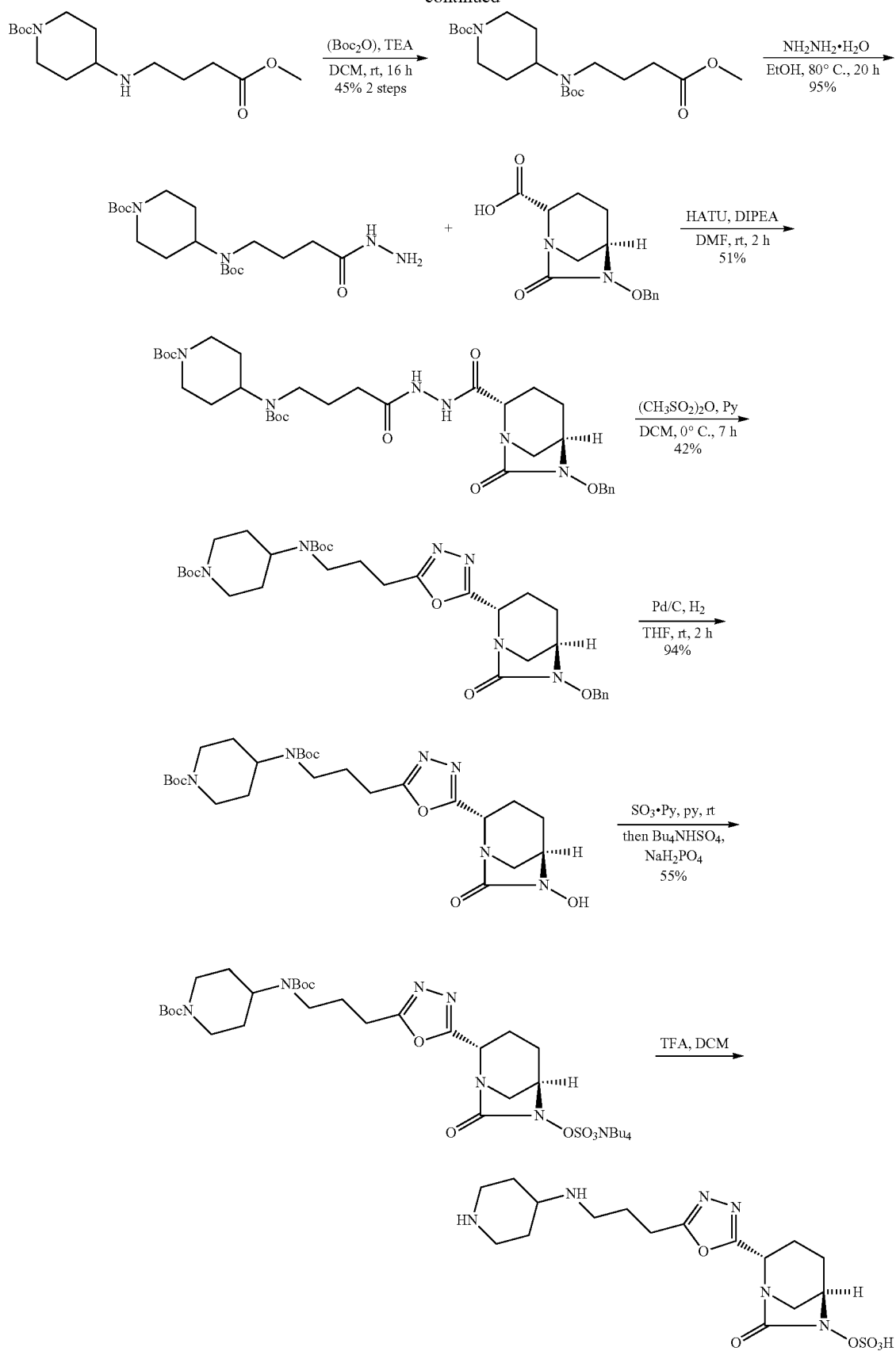

ESI-MS (EI+, m/z): 431.1. 1H NMR (300 MHz, D2O, as formate salt) δ 8.34 (s, 1H), 4.74 (d, J=6.5 Hz, 1H), 4.17 (br s, 1H), 3.71-3.21 (m, 3H), 3.23-2.69 (m, 8H), 2.34-2.06 (m, 7H), 2.02-1.59 (m, 3H).

Example 67

Synthesis of (2S,5R)-7-oxo-2-(5-(4-(piperidin-4-ylamino)butyl)-1,3,4-oxadiazol-2-yl)-1,6-diazabicyclo[3.2.1]octan-6-yl hydrogen sulfate (Compound 772)

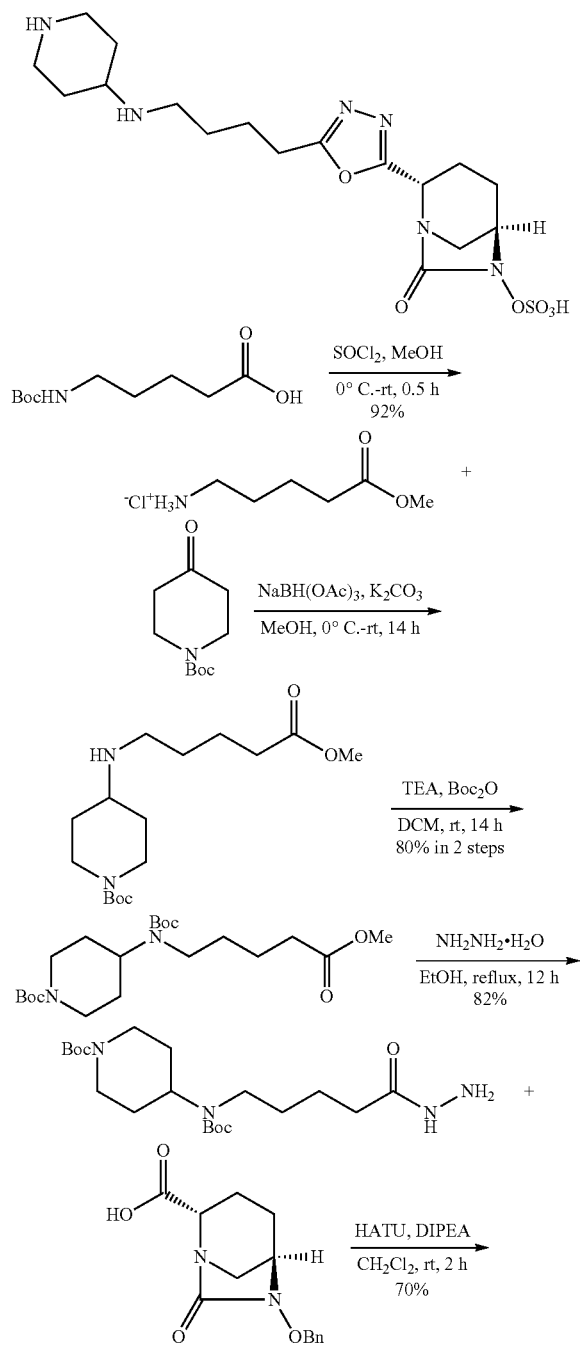

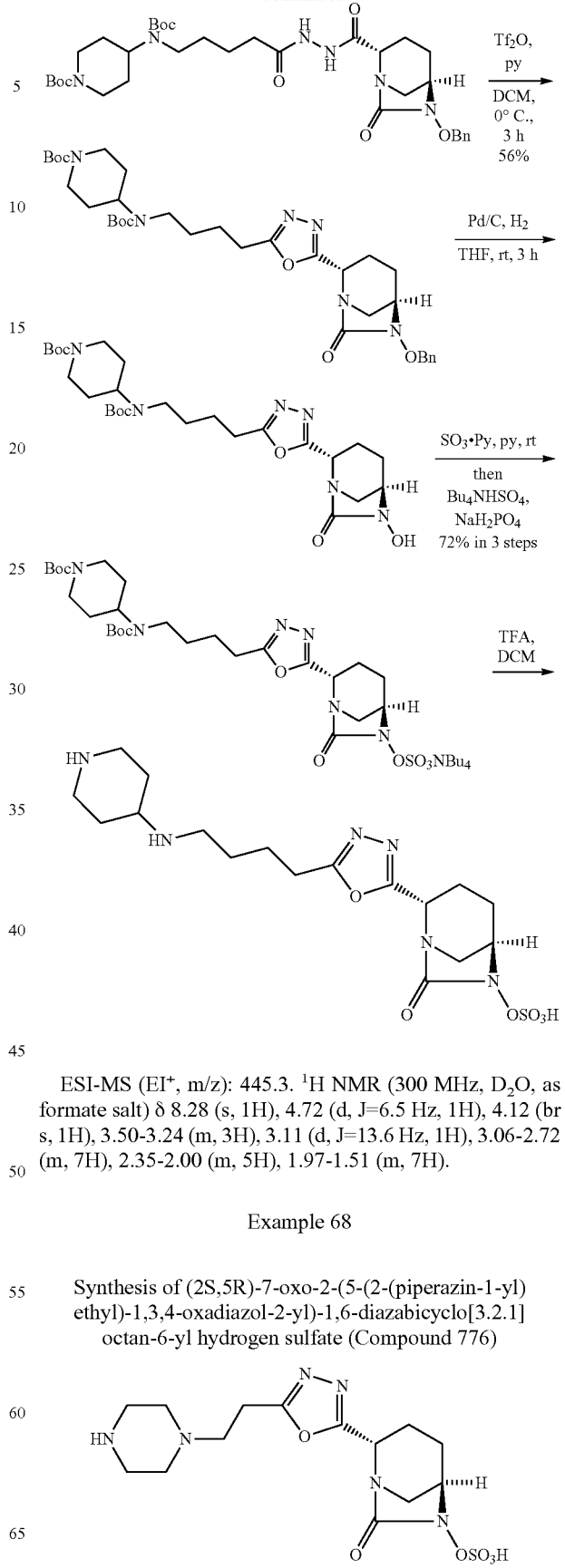

ESI-MS (EI+, m/z): 445.3. 1H NMR (300 MHz, D2O, as formate salt) δ 8.28 (s, 1H), 4.72 (d, J=6.5 Hz, 1H), 4.12 (br s, 1H), 3.50-3.24 (m, 3H), 3.11 (d, J=13.6 Hz, 1H), 3.06-2.72 (m, 7H), 2.35-2.00 (m, 5H), 1.97-1.51 (m, 7H).

Example 68

Synthesis of (2S,5R)-7-oxo-2-(5-(2-(piperazin-1-yl)ethyl)-1,3,4-oxadiazol-2-yl)-1,6-diazabicyclo[3.2.1]octan-6-yl hydrogen sulfate (Compound 776)

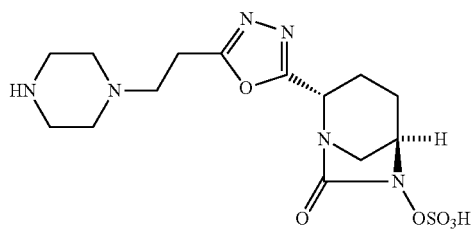

-continued
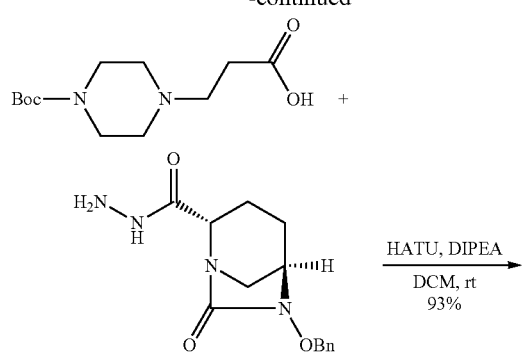
ESI-MS (EI+, m/z): 403.2. ¹H NMR (300 MHz, D₂O) δ 4.75 (d, J=6.4 Hz, 1H), 4.16 (br s, 1H), 3.21-3.02 (m, 6H), 2.96-2.83 (m, 4H), 2.71 (br s, 4H), 2.32-2.03 (m, 3H), 1.96-1.84 (m, 1H).
Example 69
Synthesis of (2S,5R)-7-oxo-2-(5-((R)-piperazin-2-yl)-1,3,4-oxadiazol-2-yl)-1,6-diazabicyclo[3.2.1]octan-6-yl hydrogen sulfate (Compound 779)
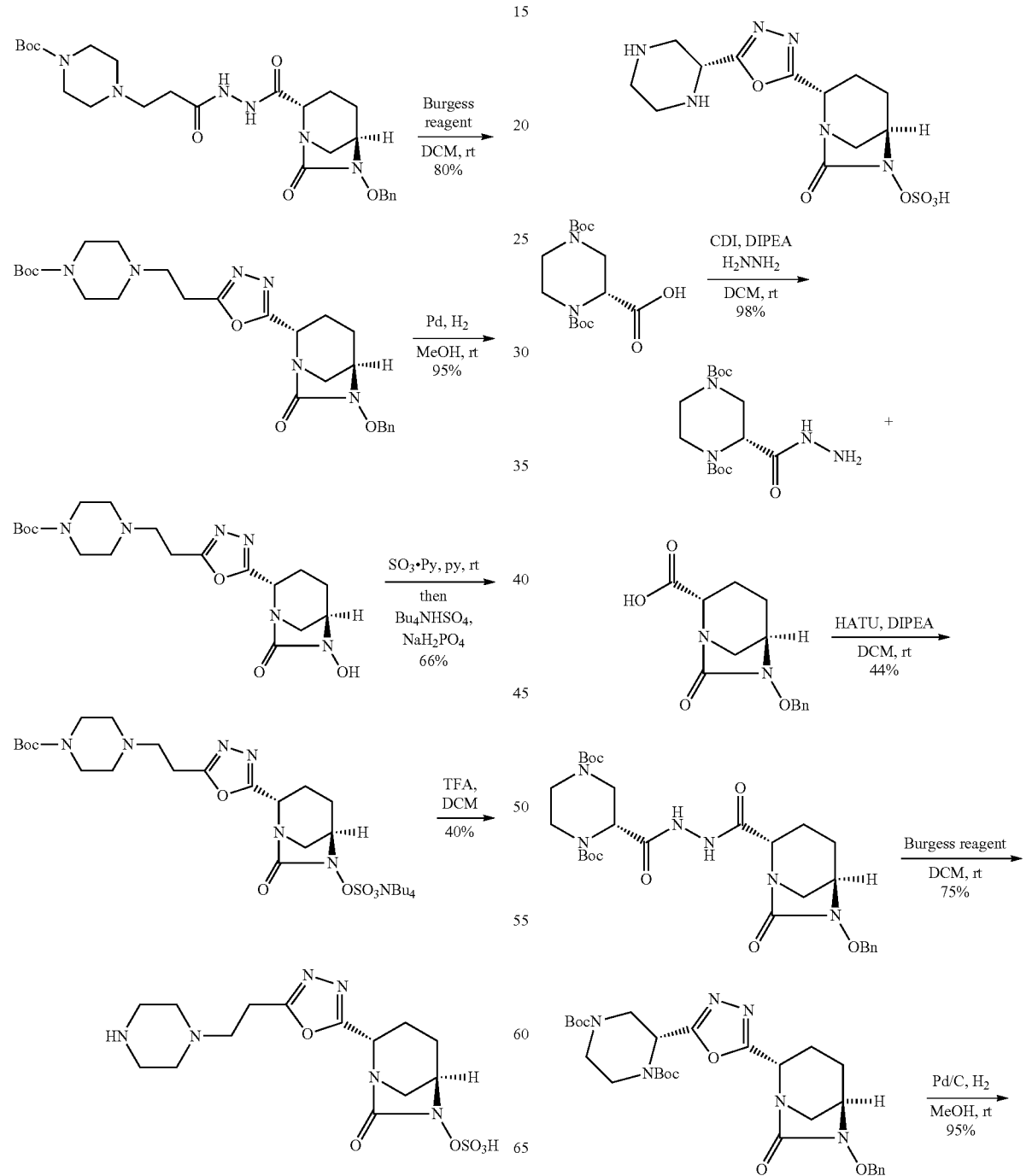

177
-continued
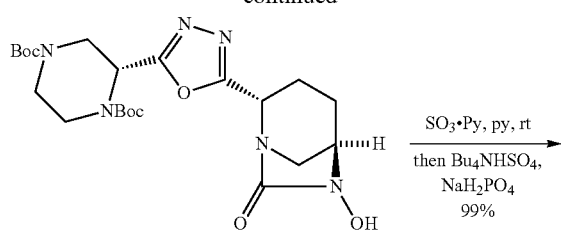
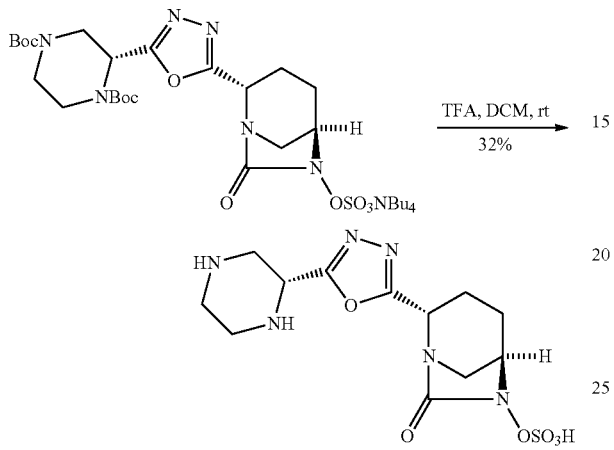
ESI-MS (EI⁺, m/z): 375.3. $^1$H NMR (300 MHz, D$_2$O) δ 4.81 (d, J=6.5 Hz, 1H), 4.57 (dd, J=8.8, 3.5 Hz, 1H), 4.19 (br s, 1H), 3.65 (dd, J=13.0, 3.4 Hz, 1H), 3.46-2.98 (m, 6H), 2.92 (d, J=12.4 Hz, 1H), 2.34-2.05 (m, 3H), 2.02-1.82 (m, 1H).
Example 70
Synthesis of (2S,5R)-7-oxo-2-(5-((S)-piperazin-2-yl)-1,3,4-oxadiazol-2-yl)-1,6-diazabicyclo[3.2.1]octan-6-yl hydrogen sulfate (Compound 778)
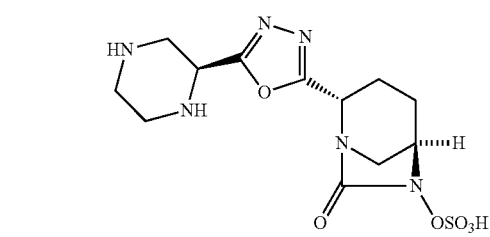
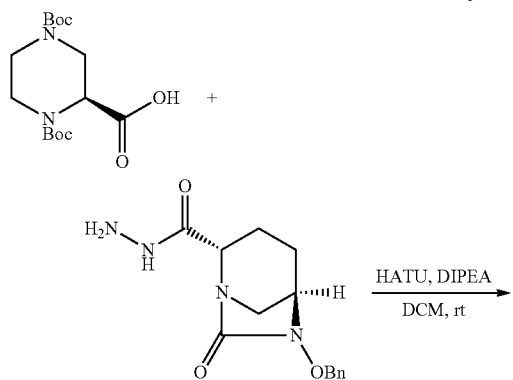
178
-continued
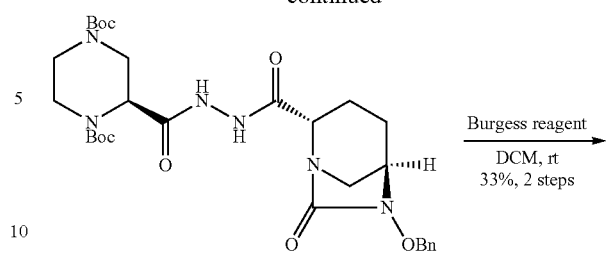
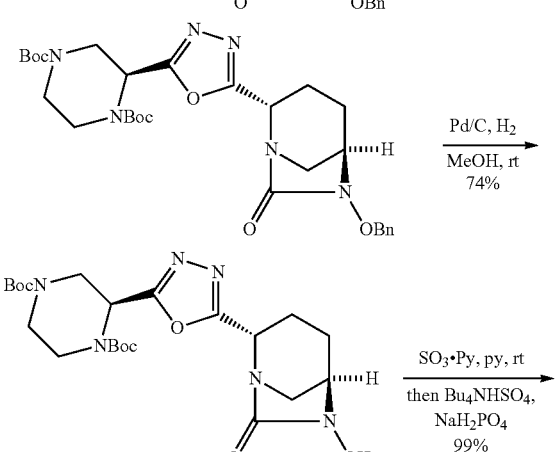
ESI-MS (EI⁺, m/z): 375.3.
Example 71
Synthesis of (2S,5R)-2-(5-(4-aminopiperidin-1-yl)-1,3,4-oxadiazol-2-yl)-7-oxo-1,6-diazabicyclo[3.2.1]octan-6-yl hydrogen sulfate (Compound 773)
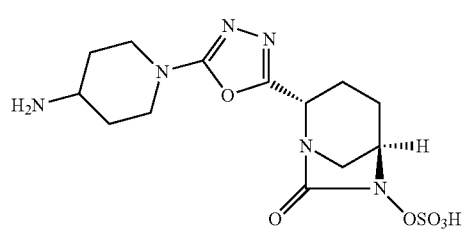

179
-continued
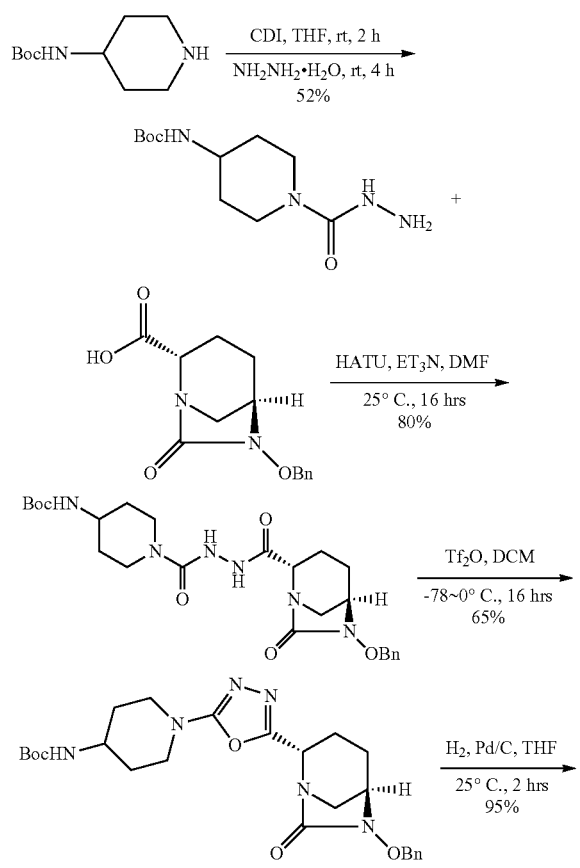
180
-continued
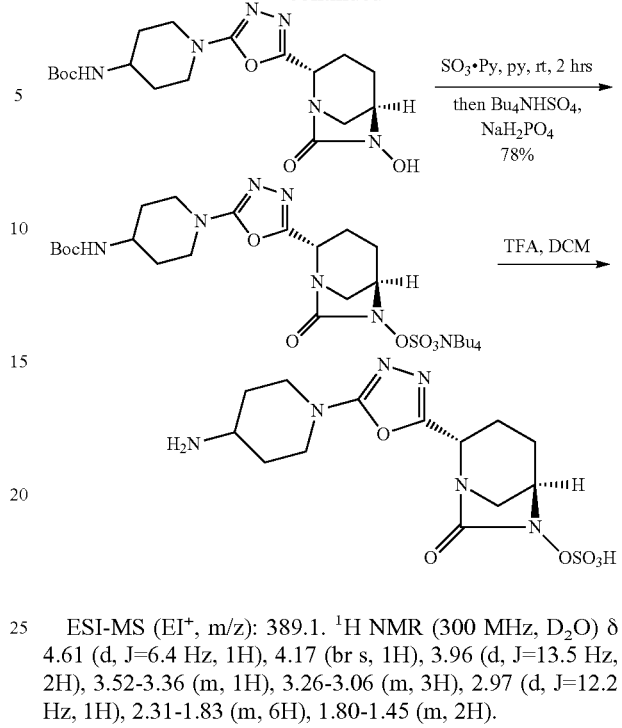
ESI-MS (EI+, m/z): 389.1. $^1$H NMR (300 MHz, D$_2$O) δ 4.61 (d, J=6.4 Hz, 1H), 4.17 (br s, 1H), 3.96 (d, J=13.5 Hz, 2H), 3.52-3.36 (m, 1H), 3.26-3.06 (m, 3H), 2.97 (d, J=12.2 Hz, 1H), 2.31-1.83 (m, 6H), 1.80-1.45 (m, 2H).
Example 72
Synthesis of (2S,5R)-2-(5-(2-(4-aminopiperidin-1-yl)ethyl)-1,3,4-oxadiazol-2-yl)-7-oxo-1,6-diazabicyclo[3.2.1]octan-6-yl hydrogen sulfate (Compound 775)
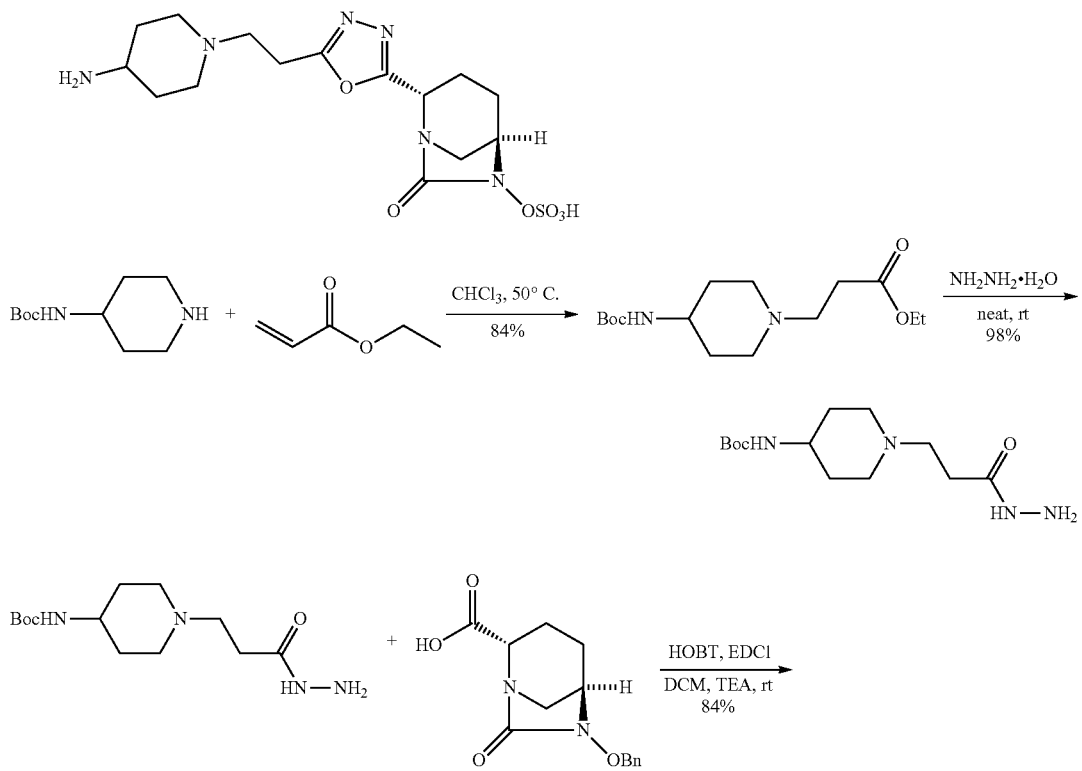

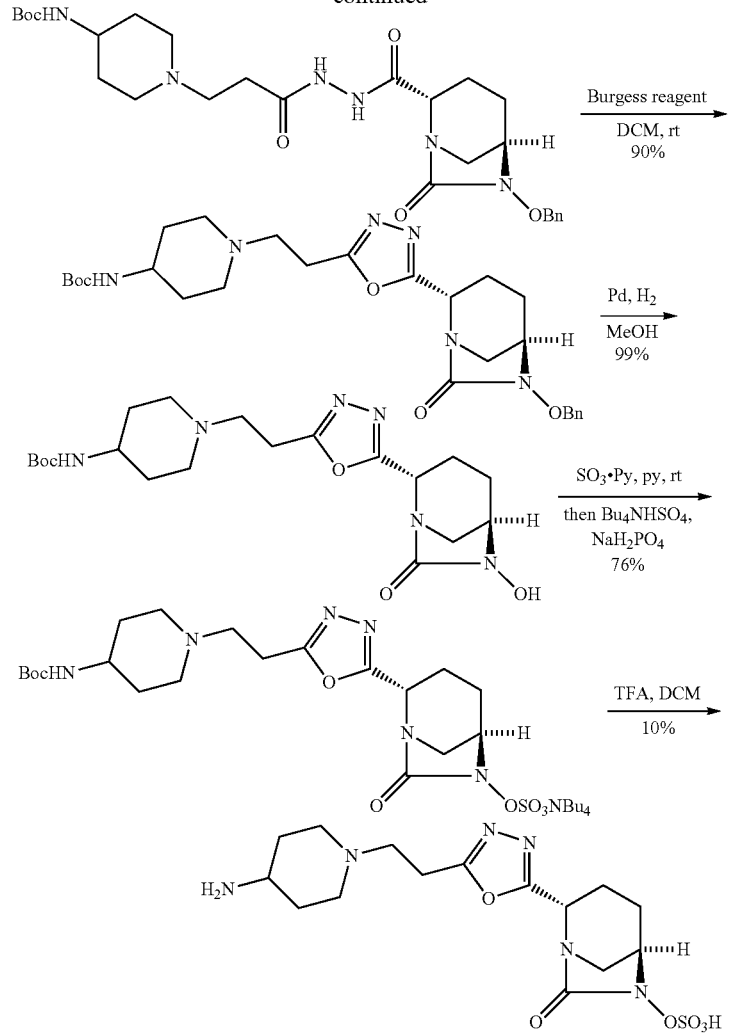
ESI-MS (EI⁺, m/z): 417.2. ¹H NMR (300 MHz, D₂O, as formate salt) δ 8.31 (s, 1H), 4.74 (d, J=6.1 Hz, 1H), 4.16 (br s, 1H), 3.78-3.55 (m, 4H), 3.55-3.32 (m, 3H), 3.25-3.04 (m, 3H), 2.90 (d, J=12.2 Hz, 1H), 2.32-2.04 (m, 5H), 1.97-1.75 (m, 3H).
Example 73
Synthesis of (2S,5R)-2-(5-((3-guanidinocyclobutyl)methyl)-1,3,4-oxadiazol-2-yl)-7-oxo-1,6-diazabicyclo[3.2.1]octan-6-yl hydrogen sulfate (Compound 752)
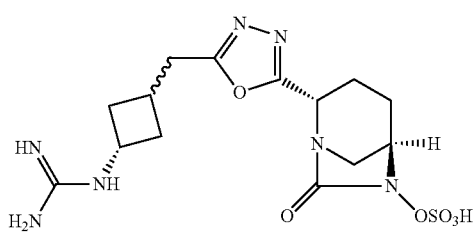
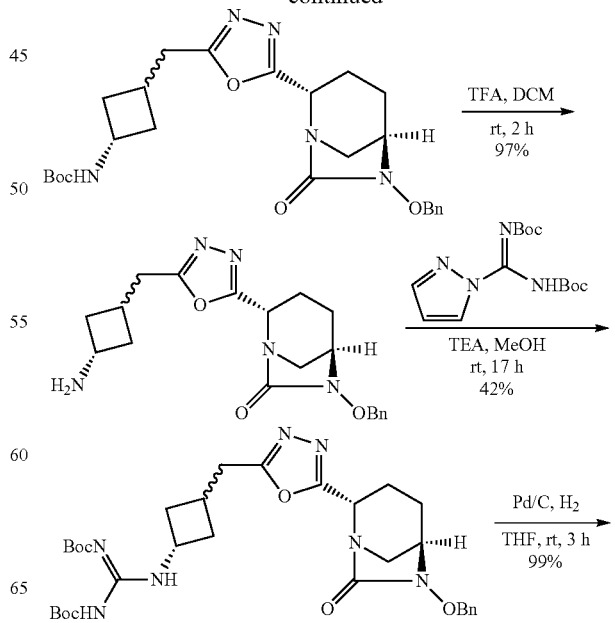

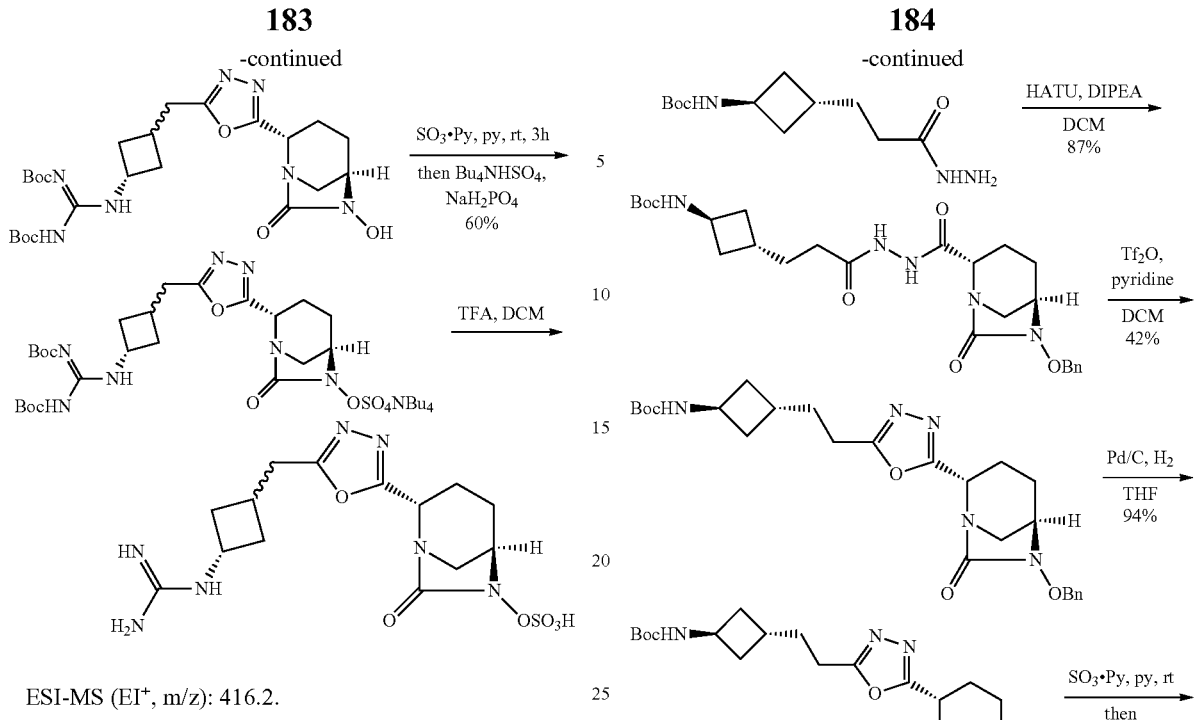
ESI-MS (EI+, m/z): 416.2.
Example 74
Synthesis of (2S,5R)-2-(5-(2-((1r,3R)-3-aminocyclobutyl)ethyl)-1,3,4-oxadiazol-2-yl)-7-oxo-1,6-diazabicyclo[3.2.1]octan-6-yl hydrogen sulfate (Compound 753)
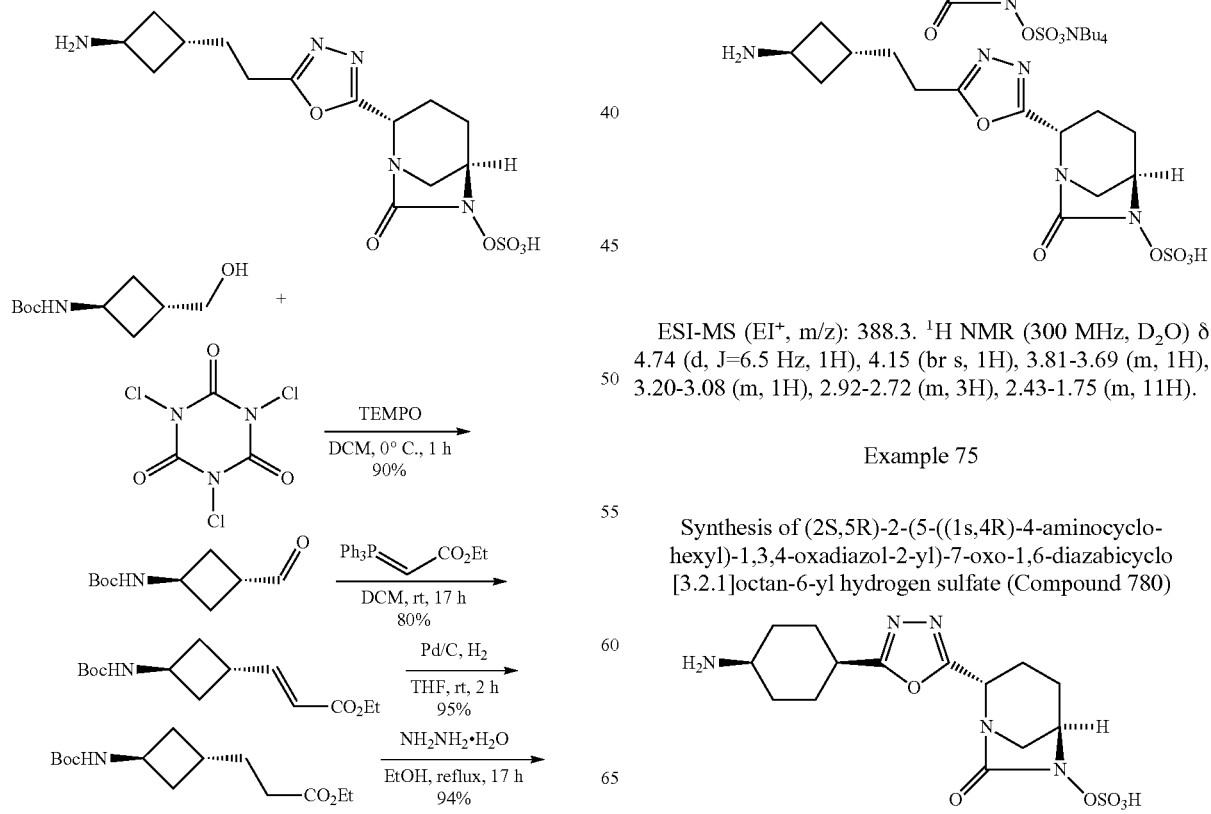
ESI-MS (EI+, m/z): 388.3. $^1$H NMR (300 MHz, D$_2$O) δ 4.74 (d, J=6.5 Hz, 1H), 4.15 (br s, 1H), 3.81-3.69 (m, 1H), 3.20-3.08 (m, 1H), 2.92-2.72 (m, 3H), 2.43-1.75 (m, 11H).
Example 75
Synthesis of (2S,5R)-2-(5-((1s,4R)-4-aminocyclohexyl)-1,3,4-oxadiazol-2-yl)-7-oxo-1,6-diazabicyclo[3.2.1]octan-6-yl hydrogen sulfate (Compound 780)
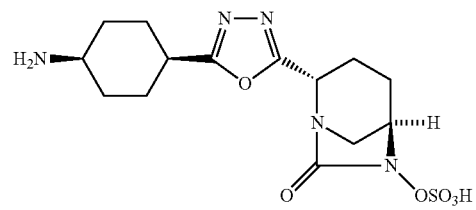

-continued
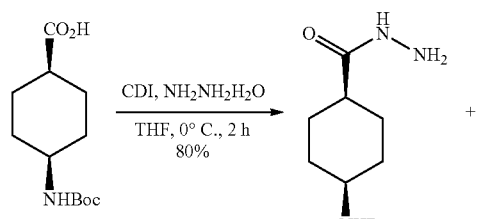
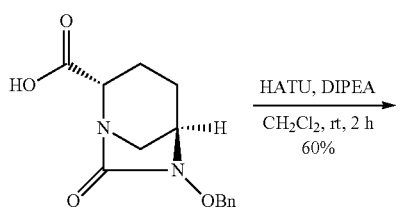
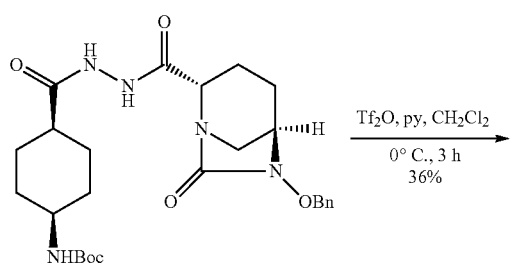
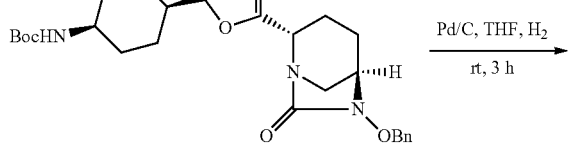
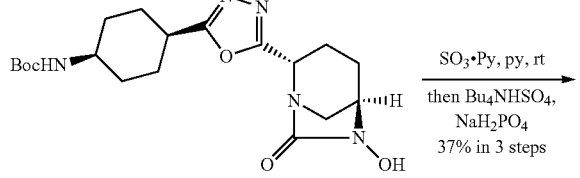
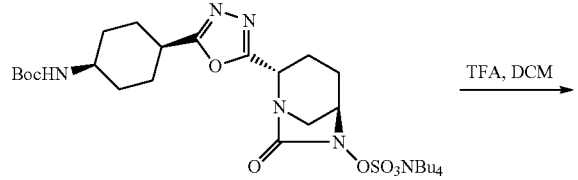
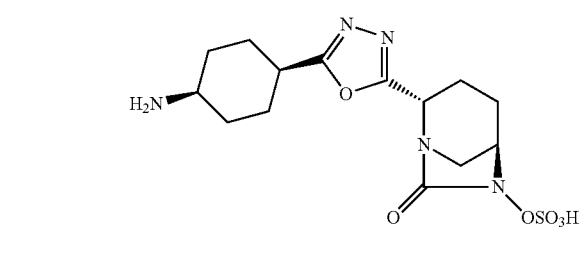
ESI-MS (EI+, m/z): 388.2.
Example 76
Synthesis of (2S,5R)-2-(5-((1r,4S)-4-aminocyclohexyl)-1,3,4-oxadiazol-2-yl)-7-oxo-1,6-diazabicyclo[3.2.1]octan-6-yl hydrogen sulfate (Compound 781)
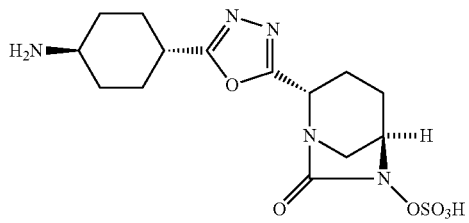
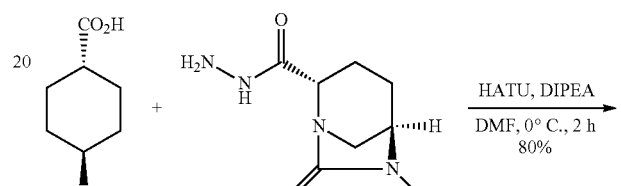
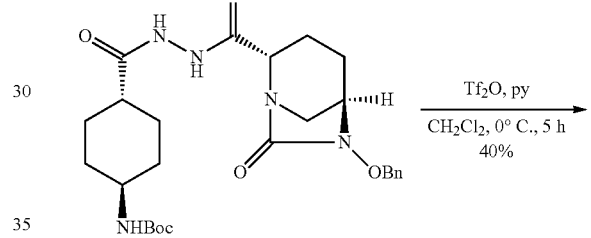
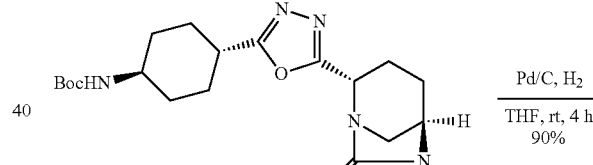
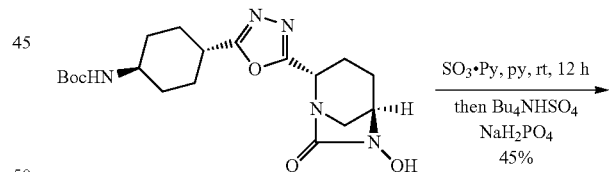
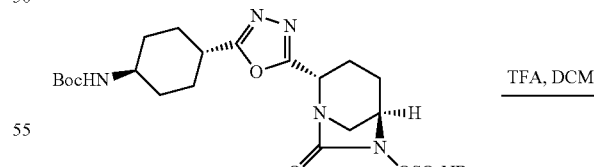
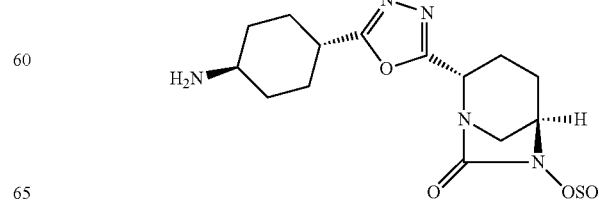

ESI-MS (EI⁺, m/z): 388.2. ¹H NMR (300 MHz, D₂O) δ 4.72 (d, J=6.6 Hz, 1H), 4.15 (br s, 1H), 3.24-3.03 (m, 3H), 3.01-2.89 (m, 1H), 2.86 (d, J=12.3 Hz, 1H), 2.30-1.98 (m, 4H), 1.98-1.79 (m, 1H), 1.69-1.37 (m, 4H), 1.32-1.10 (m, 2H).
Example 77
Synthesis of (2S,5R)-2-(5-guanidino-1,3,4-oxadiazol-2-yl)-7-oxo-1,6-diazabicyclo[3.2.1]octan-6-yl hydrogen sulfate (Compound 738)
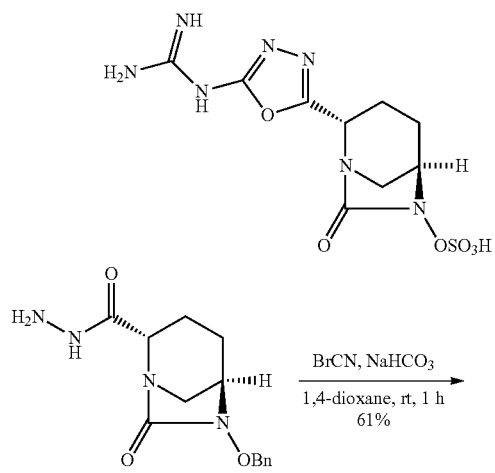
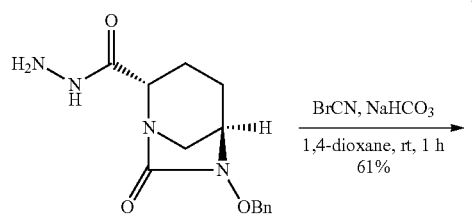
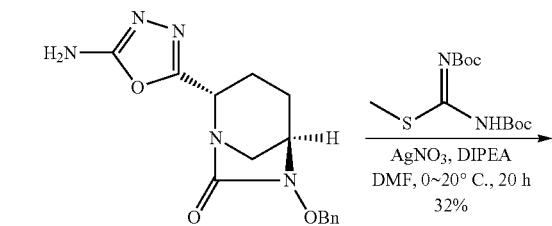
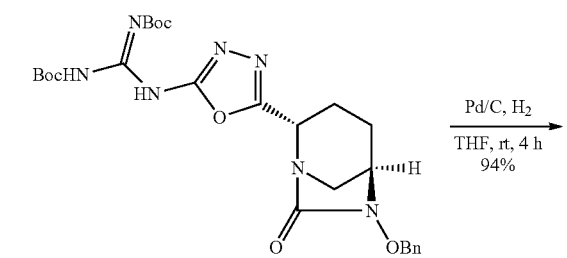
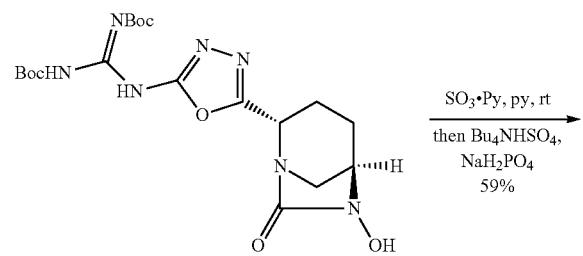
-continued
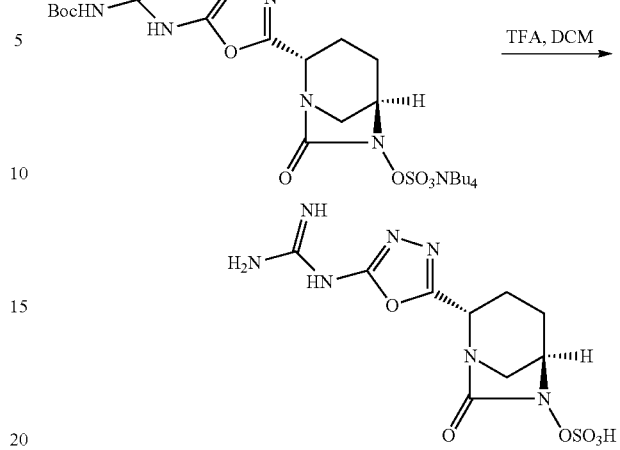
ESI-MS (EI⁺, m/z): 348.1. ¹H NMR (300 MHz, D₂O) δ 4.60 (d, J=6.6 Hz, 1H), 4.15 (br s, 1H), 3.20-3.10 (m, 1H), 2.97 (d, J=12.3 Hz, 1H), 2.27-1.85 (m, 4H).
Example 78
Synthesis of (2S,5R)-2-(5-(2-((2-hydroxyethyl)amino)ethyl)-1,3,4-oxadiazol-2-yl)-7-oxo-1,6-diazabicyclo[3.2.1]octan-6-yl hydrogen sulfate (Compound 736)
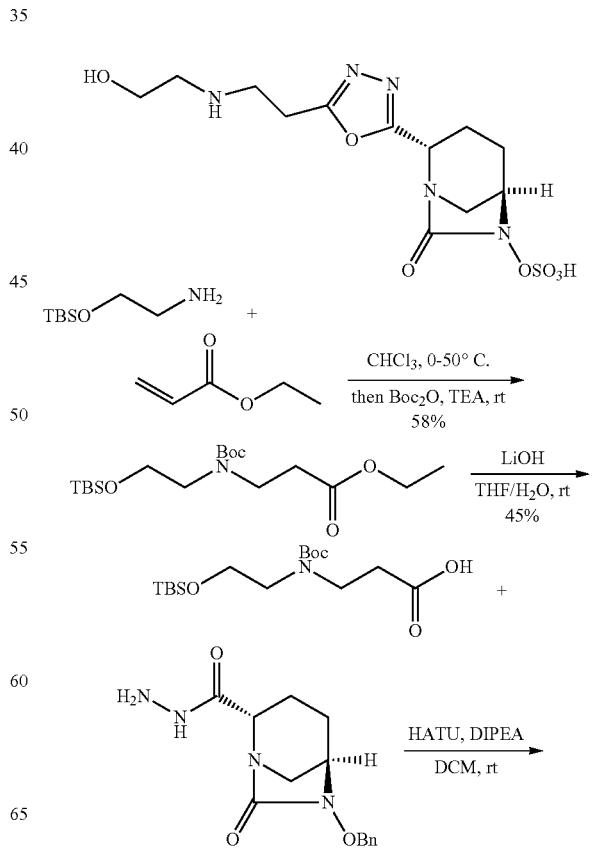

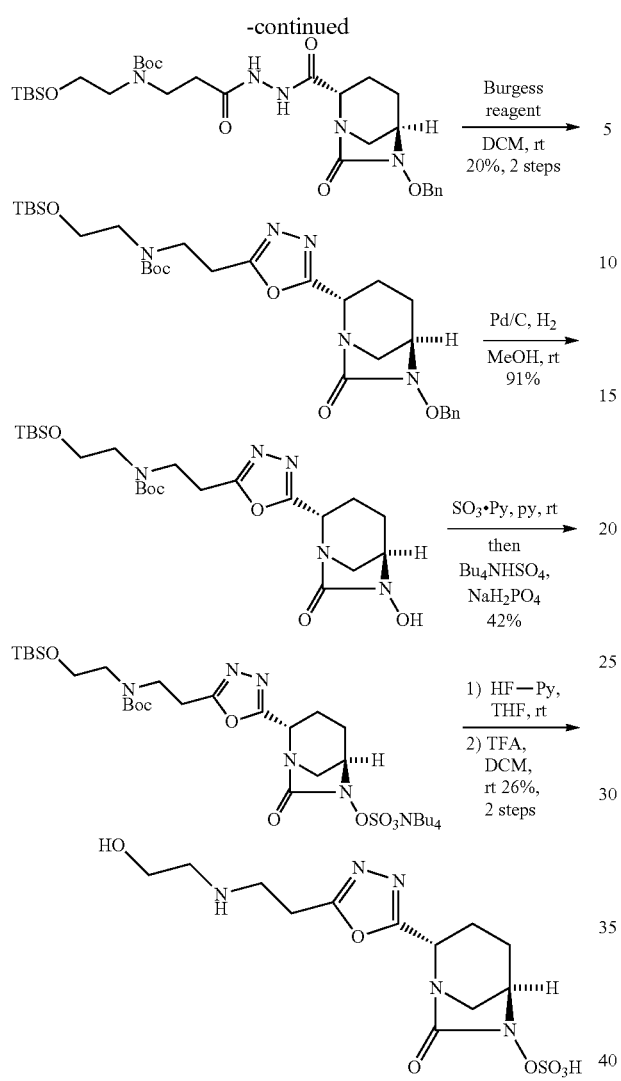
ESI-MS (EI⁺, m/z): 378.2.
Example 79
2S,5R)-2-(5-(3-(methylamino)propyl)-1,3,4-oxadiazol-2-yl)-7-oxo-1,6-diazabicyclo[3.2.1]octan-6-yl hydrogen sulfate (Compound 734
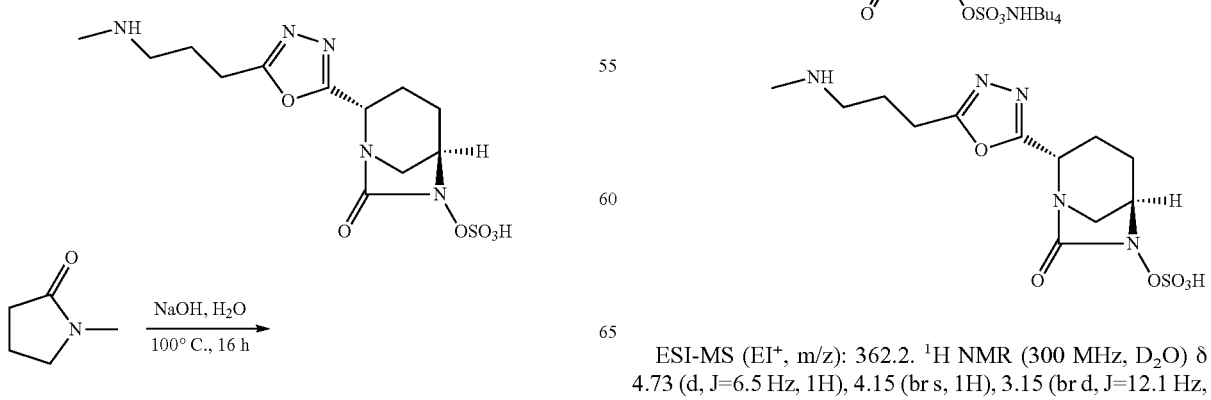
ESI-MS (EI⁺, m/z): 362.2. ¹H NMR (300 MHz, D₂O) δ 4.73 (d, J=6.5 Hz, 1H), 4.15 (br s, 1H), 3.15 (br d, J=12.1 Hz, 1H), 3.08-2.99 (m, 2H), 2.96 (t, J=7.5 Hz, 2H), 2.87 (d, J=12.3 Hz, 1H), 2.61 (s, 3H), 2.32-2.02 (m, 5H), 1.99-1.78 (m, 1H).
Example 80
Synthesis of (2S,5R)-2-(5-(guanidinomethyl)-1,3,4-thiadiazol-2-yl)-7-oxo-1,6-diazabicyclo[3.2.1]octan-6-yl hydrogen sulfate (Compound 721)
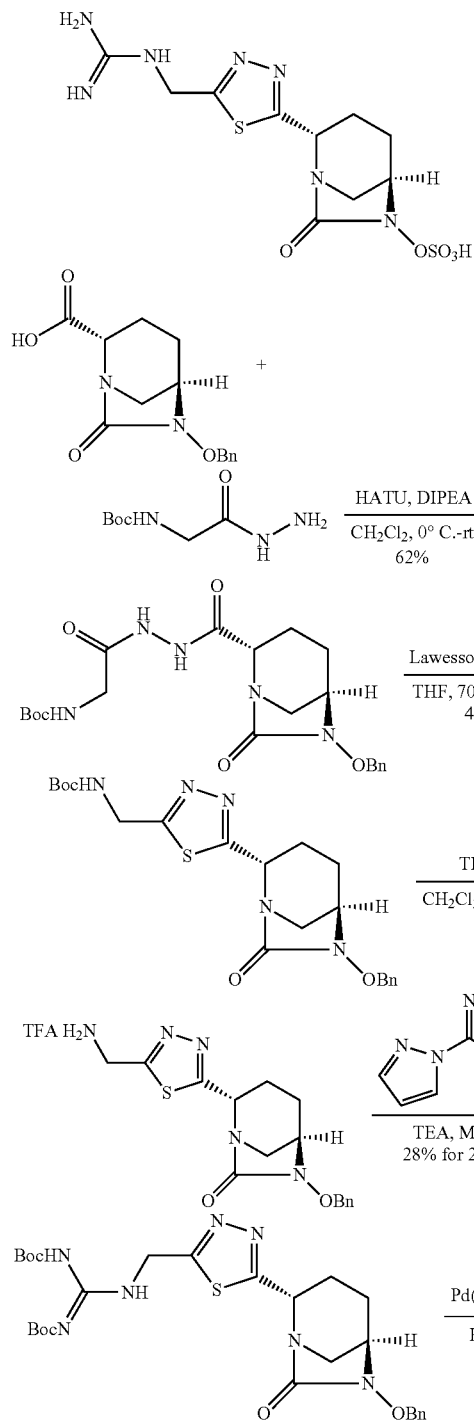
-continued
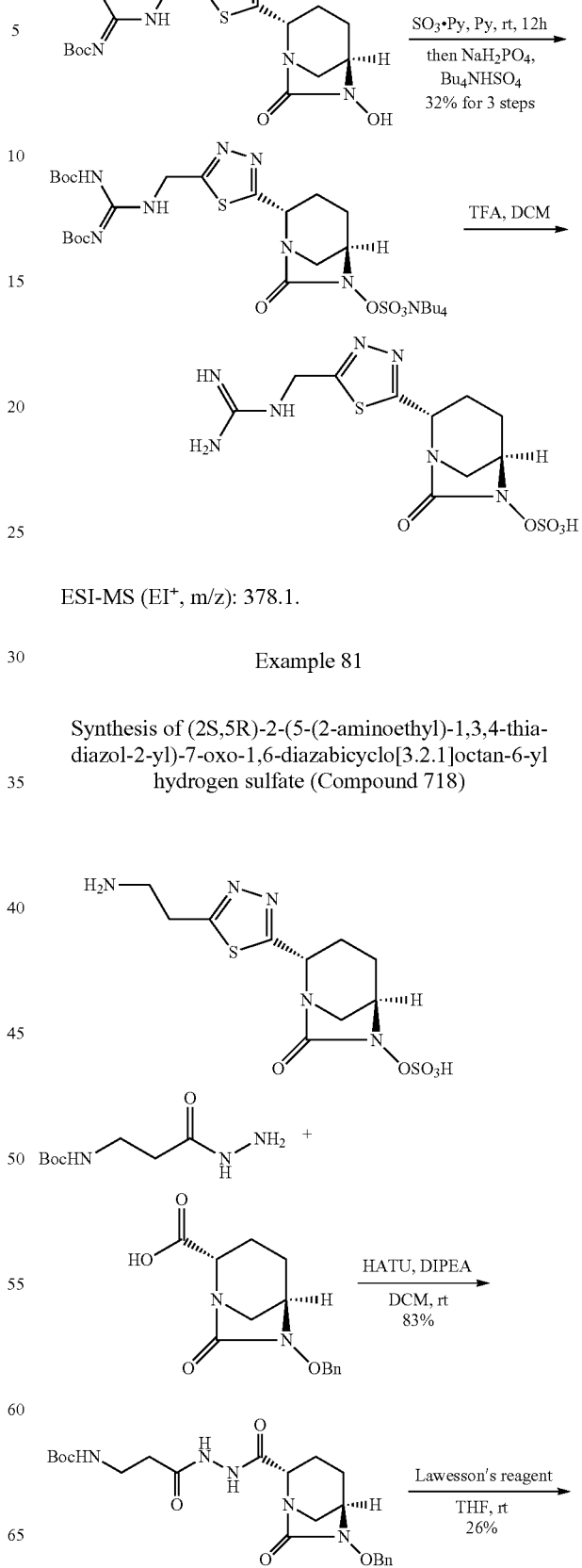
ESI-MS (EI⁺, m/z): 378.1.
Example 81
Synthesis of (2S,5R)-2-(5-(2-aminoethyl)-1,3,4-thiadiazol-2-yl)-7-oxo-1,6-diazabicyclo[3.2.1]octan-6-yl hydrogen sulfate (Compound 718)

193
-continued
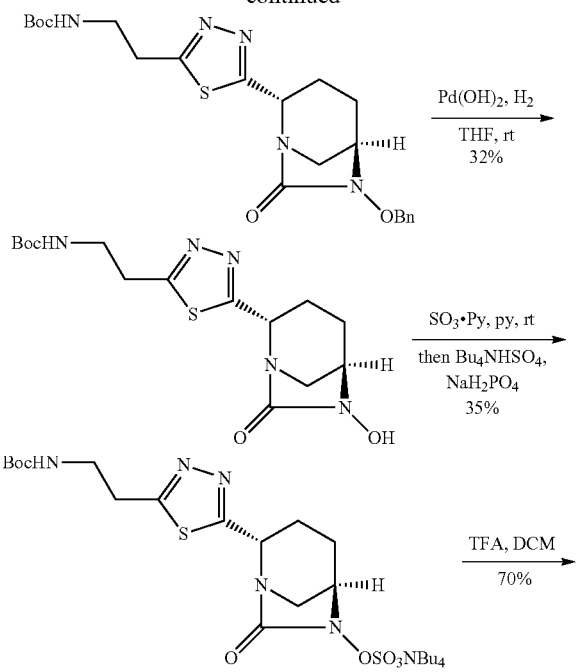
ESI-MS (EI⁺, m/z): 350.1. ¹H NMR (300 MHz, D₂O) δ 4.89 (d, J=6.3 Hz, 1H), 4.14 (br s, 1H), 3.50-3.35 (m, 4H), 3.14 (br d, J=12.2 Hz, 1H), 2.90 (d, J=12.2 Hz, 1H), 2.50-2.38 (m, 1H), 2.20-2.05 (m, 2H), 1.90-1.80 (m, 1H).
Example 82
Synthesis of (2S,5R)-2-(5-(2-guanidinoethyl)-1,3,4-thiadiazol-2-yl)-7-oxo-1,6-diazabicyclo[3.2.1]octan-6-yl hydrogen sulfate (Compound 794)
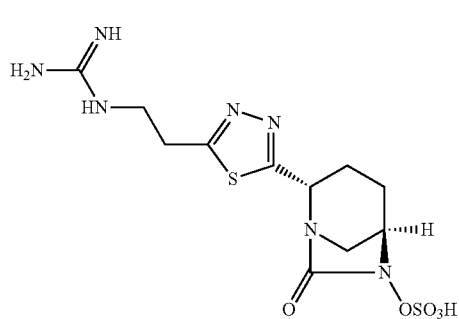
194
-continued
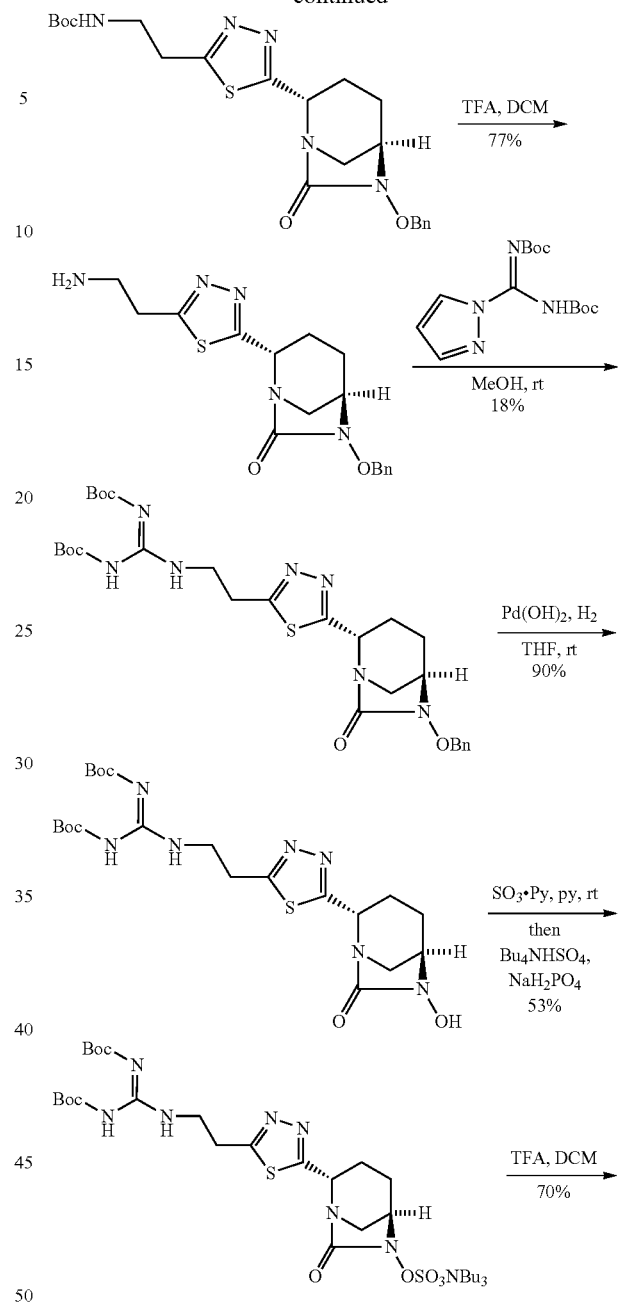
ESI-MS (EI⁺, m/z): 392.1. ¹H NMR (300 MHz, D₂O) δ 4.89 (d, J=6.7 Hz, 1H), 4.14 (br s, 1H), 3.57 (t, J=6.3 Hz, 2H), 3.34 (t, J=6.3 Hz, 2H), 3.14 (br d, J=12.2 Hz, 1H), 2.84 (d, J=12.2 Hz, 1H), 2.46-2.40 (m, 1H), 2.20-2.05 (m, 2H), 1.92-1.80 (m, 1H).
Example 83
Synthesis of (2S,5R)-2-(5-((1r,3S)-3-aminocyclobutyl)-1,3,4-thiadiazol-2-yl)-7-oxo-1,6-diazabicyclo[3.2.1]octan-6-yl hydrogen sulfate (Compound 783)
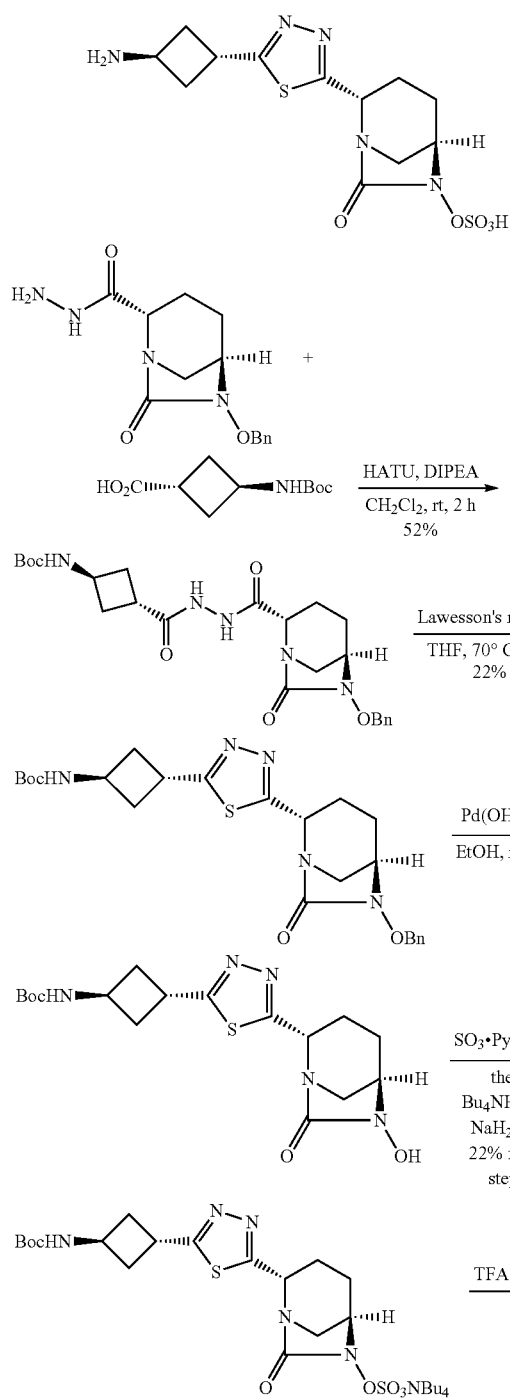
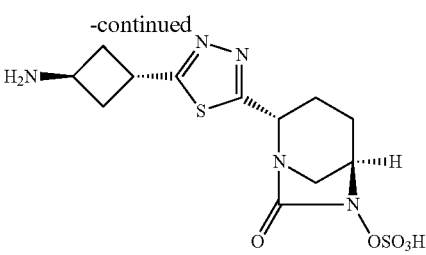
ESI-MS (EI+, m/z): 376.3. $^1$H NMR (300 MHz, D$_2$O) δ 4.90 (d, J=6.6 Hz, 1H), 4.15-4.00 (m, 3H), 3.15 (br d, J=12.2 Hz, 1H), 2.90 (d, J=12.4 Hz, 1H), 2.74-2.69 (m, 4H), 2.48-2.40 (m, 1H), 2.19-2.10 (m, 2H), 1.93-1.82 (m, 1H).
Example 84
Synthesis of (2S,5R)-2-(5-((1s,3R)-3-aminocyclobutyl)-1,3,4-thiadiazol-2-yl)-7-oxo-1,6-diazabicyclo[3.2.1]octan-6-yl hydrogen sulfate (Compound 795)
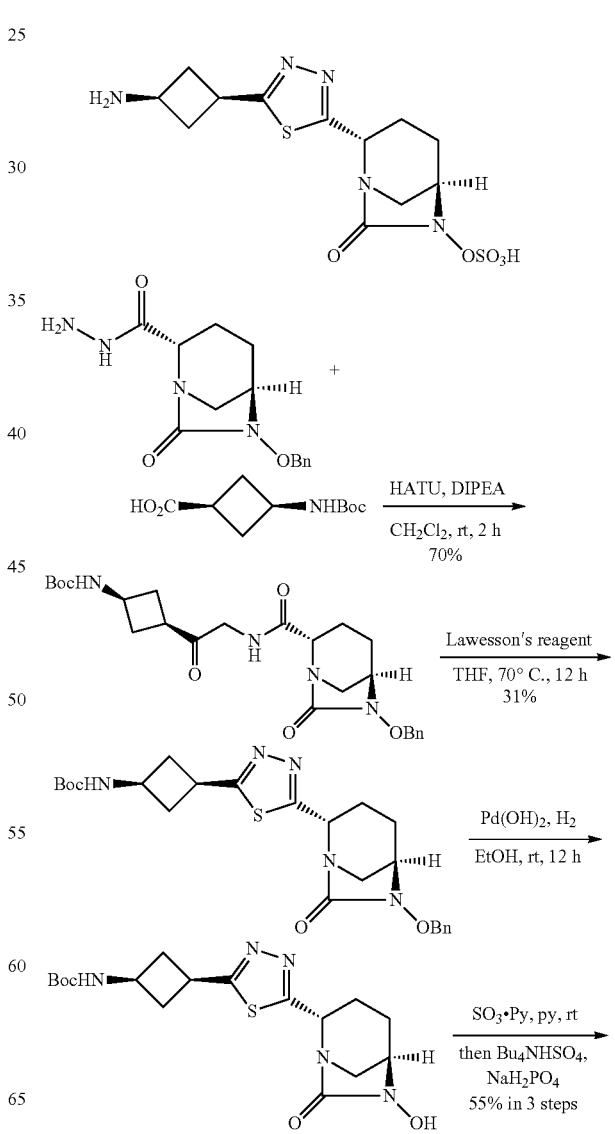

197

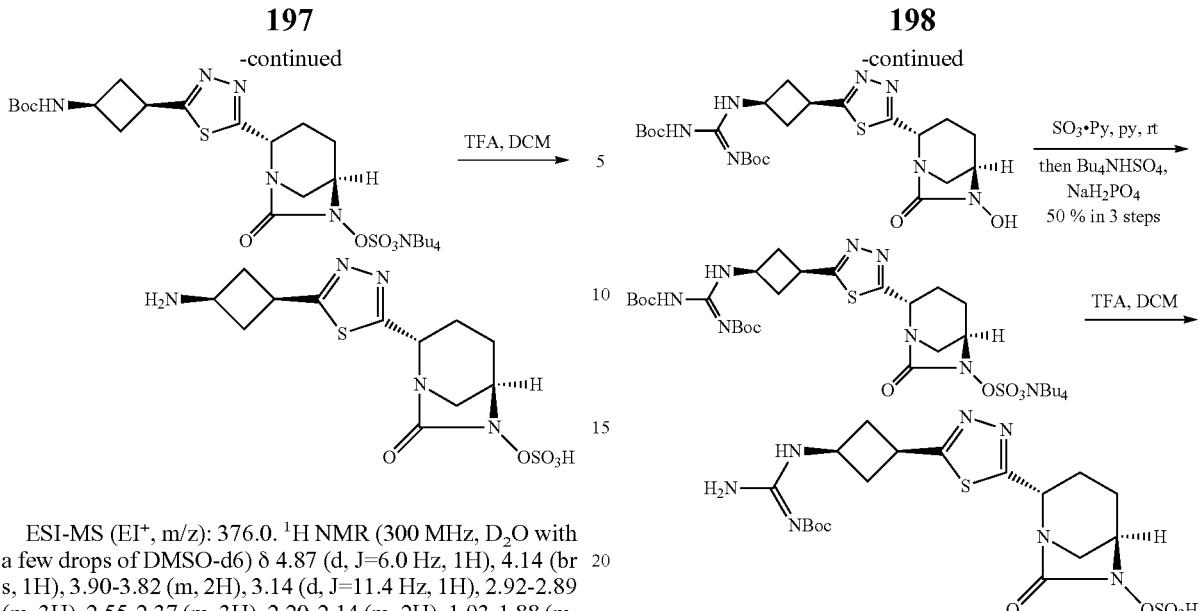

ESI-MS (EI⁺, m/z): 376.0. ¹H NMR (300 MHz, D₂O with a few drops of DMSO-d6) δ 4.87 (d, J=6.0 Hz, 1H), 4.14 (br s, 1H), 3.90-3.82 (m, 2H), 3.14 (d, J=11.4 Hz, 1H), 2.92-2.89 (m, 3H), 2.55-2.37 (m, 3H), 2.20-2.14 (m, 2H), 1.93-1.88 (m, 1H).

Example 85

Synthesis of (2S,5R)-2-(5-((1s,3R)-3-guanidinocyclobutyl)-1,3,4-thiadiazol-2-yl)-7-oxo-1,6-diazabicyclo[3.2.1]octan-6-yl hydrogen sulfate (Compound 784)

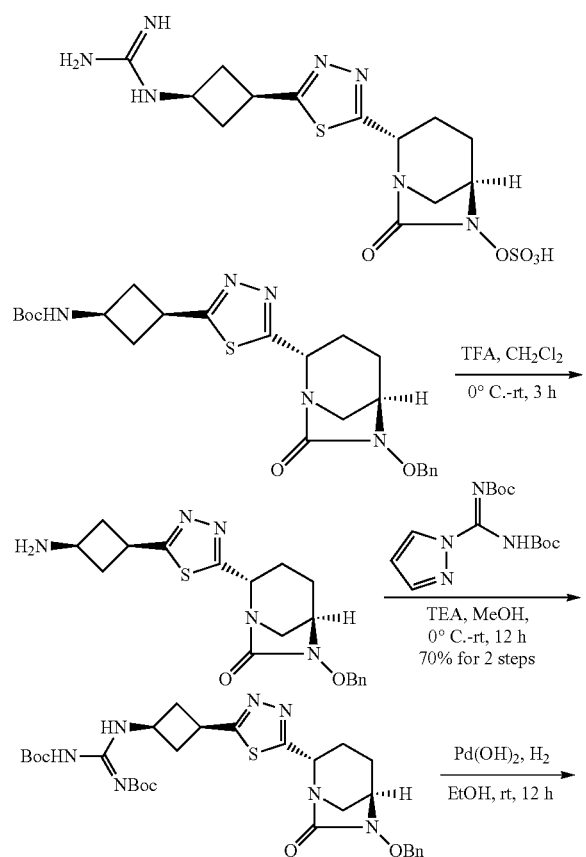

198

ESI-MS (EI⁺, m/z): 418. ¹H NMR (300 MHz, DMSO-d6) δ 8.08 (br s, 1H), 7.13 (br s, 4H), 4.78 (d, J=6.4 Hz, 1H), 4.09-4.01 (m, 2H), 3.70-3.62 (m, 1H), 2.95-2.88 (m, 2H), 2.70 (d, J=11.9 Hz, 1H), 2.58-2.40 (m, 2H), 2.37-2.26 (m, 2H), 2.10-1.90 (m, 2H), 1.82-1.70 (m, 1H).

Example 86

Synthesis of (2S,5R)-2-(5-((1r,3S)-3-guanidinocyclobutyl)-1,3,4-thiadiazol-2-yl)-7-oxo-1,6-diazabicyclo[3.2.1]octan-6-yl hydrogen sulfate (Compound 785)

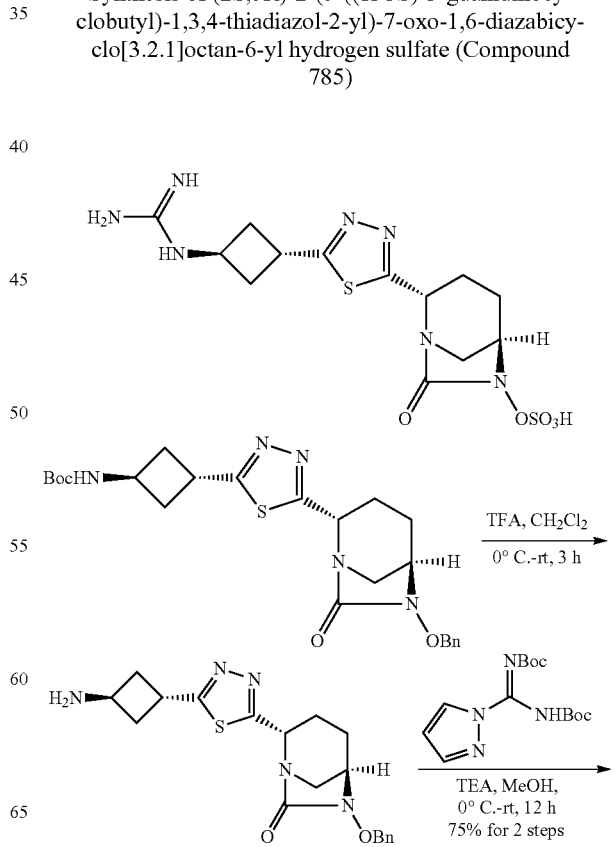

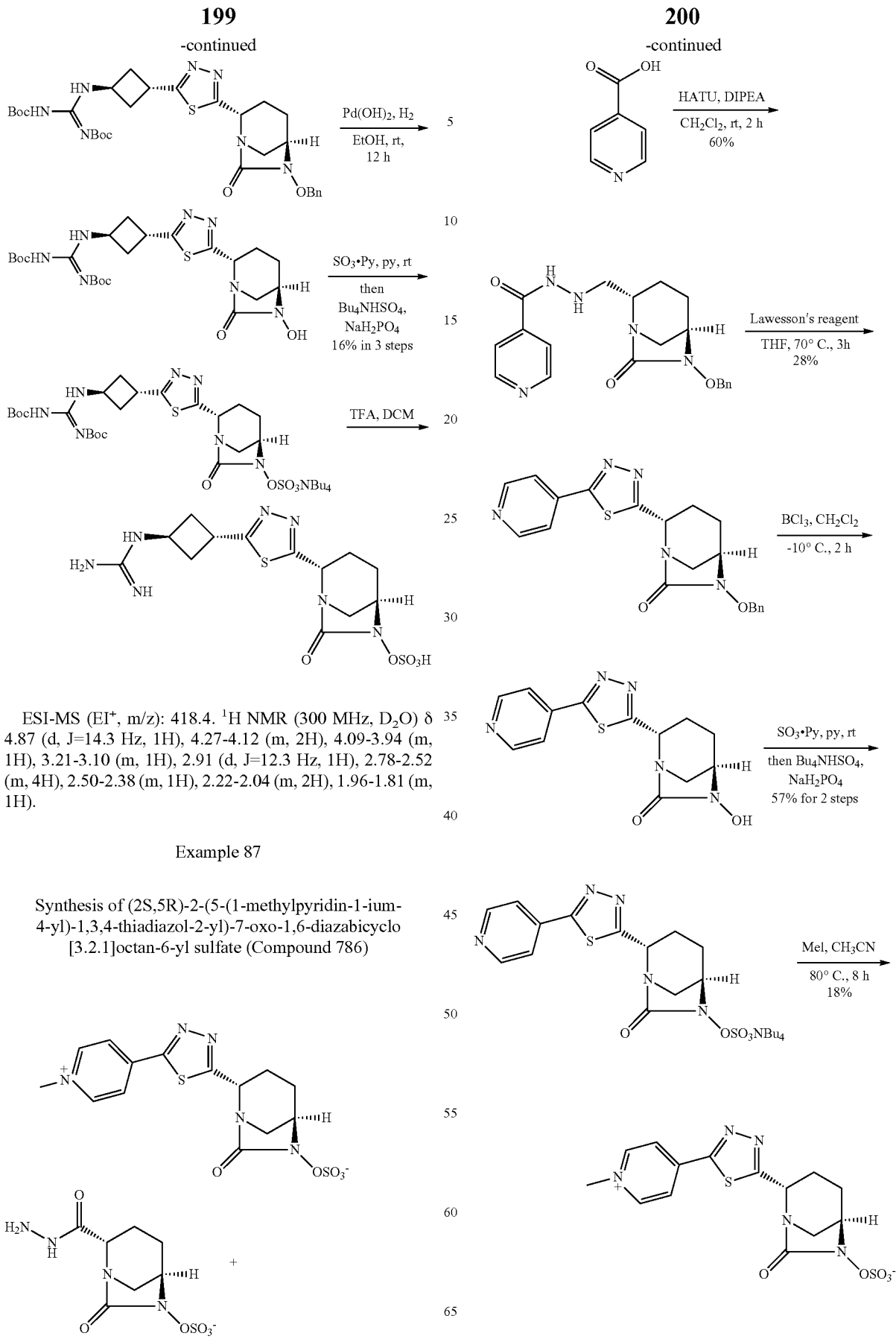
ESI-MS (EI+, m/z): 418.4. ¹H NMR (300 MHz, D₂O) δ 4.87 (d, J=14.3 Hz, 1H), 4.27-4.12 (m, 2H), 4.09-3.94 (m, 1H), 3.21-3.10 (m, 1H), 2.91 (d, J=12.3 Hz, 1H), 2.78-2.52 (m, 4H), 2.50-2.38 (m, 1H), 2.22-2.04 (m, 2H), 1.96-1.81 (m, 1H).
Example 87
Synthesis of (2S,5R)-2-(5-(1-methylpyridin-1-ium-4-yl)-1,3,4-thiadiazol-2-yl)-7-oxo-1,6-diazabicyclo[3.2.1]octan-6-yl sulfate (Compound 786)
ESI-MS (EI⁻, m/z): 396.0.

The compounds described in Examples 88-98 were prepared following similar chemistry and procedures of Examples 1-87.

Example 88

Synthesis of (2S,5R)-2-(5-(1,1-dimethylpiperidin-1-ium-4-yl)-1,3,4-thiadiazol-2-yl)-7-oxo-1,6-diazabicyclo[3.2.1]octan-6-yl sulfate (Compound 796)

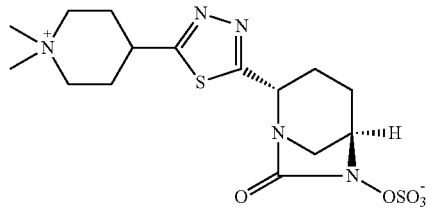

ESI-MS (EI⁻, m/z): 416.1.

Example 89

Synthesis of (2S,5R)-2-(5-(3-(azetidin-3-ylamino)propyl)-1,3,4-oxadiazol-2-yl)-7-oxo-1,6-diazabicyclo[3.2.1]octan-6-yl hydrogen sulfate (Compound 793)

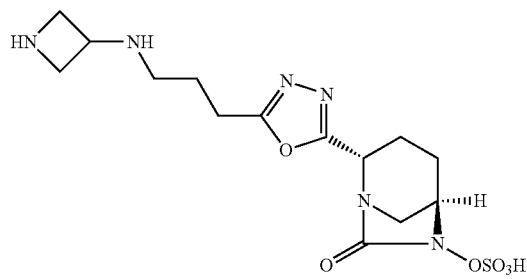

ESI-MS (EI⁺, m/z): 403.3.

Example 90

Synthesis of (2S,5R)-7-oxo-2-(5-(3-(piperazin-1-yl)propyl)-1,3,4-oxadiazol-2-yl)-1,6-diazabicyclo[3.2.1]octan-6-yl hydrogen sulfate (Compound 792)

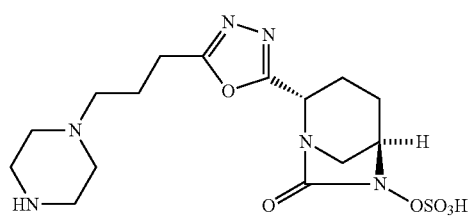

ESI-MS (EI⁺, m/z): 417.2. ¹H NMR (300 MHz, D₂O) δ 4.73 (d, J=7.6 Hz, 1H), 4.16 (br s, 1H), 3.51-3.35 (m, 4H), 3.28 (brs, 4H), 3.22-3.12 (m, 1H), 3.12-2.84 (m, 5H), 2.34-2.03 (m, 5H), 2.02-1.82 (m, 1H).

Example 91

Synthesis of (2S,5R)-2-(5-(6-aminospiro[3.3]heptan-2-yl)-1,3,4-oxadiazol-2-yl)-7-oxo-1,6-diazabicyclo[3.2.1]octan-6-yl hydrogen sulfate (Compound 787)

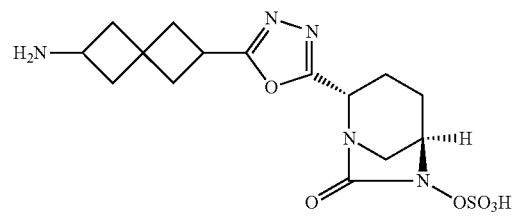

ESI-MS (EI⁺, m/z): 400.0.

Example 92

Synthesis of (2S,5R)-2-(5-(7-azaspiro[3.5]nonan-2-yl)-1,3,4-oxadiazol-2-yl)-7-oxo-1,6-diazabicyclo[3.2.1]octan-6-yl hydrogen sulfate (Compound 788)

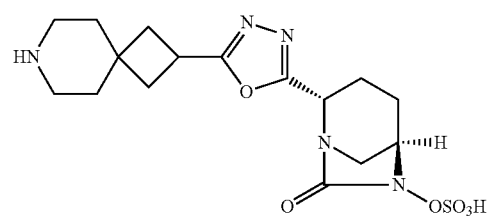

ESI-MS (EI⁺, m/z): 414.0.

Example 93

Synthesis of (2S,5R)-2-(5-(((3-aminocyclobutyl)amino)methyl)-1,3,4-oxadiazol-2-yl)-7-oxo-1,6-diazabicyclo[3.2.1]octan-6-yl hydrogen sulfate (Compound 755)

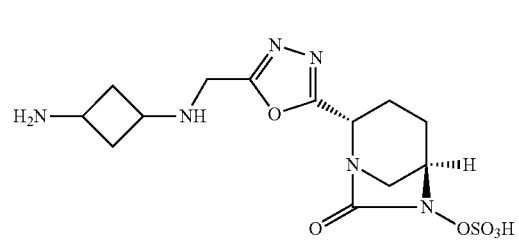

ESI-MS (EI⁺, m/z): 389.4

Example 94

Synthesis of (2S,5R)-2-(5-(((1s,3R)-3-aminocyclobutoxy)methyl)-1,3,4-oxadiazol-2-yl)-7-oxo-1,6-diazabicyclo[3.2.1]octan-6-yl hydrogen sulfate (Compound 789)

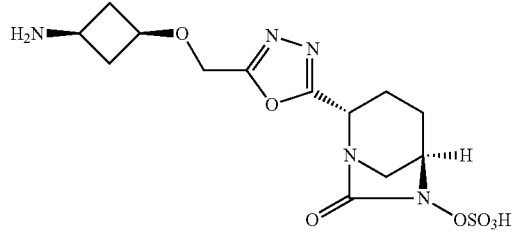

ESI-MS (EI⁺, m/z): 390.1.

Example 95

Synthesis of (2S,5R)-7-oxo-2-(5-((S)-pyrrolidin-3-ylmethyl)-1,3,4-oxadiazol-2-yl)-1,6-diazabicyclo[3.2.1]octan-6-yl hydrogen sulfate (Compound 790)

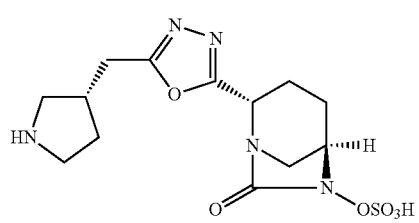

ESI-MS (EI⁺, m/z): 374.2.

Example 96

Synthesis of (2S,5R)-7-oxo-2-(5-((R)-pyrrolidin-3-ylmethyl)-1,3,4-oxadiazol-2-yl)-1,6-diazabicyclo[3.2.1]octan-6-yl hydrogen sulfate (Compound 791)

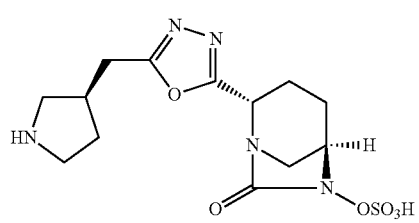

ESI-MS (EI⁺, m/z): 374.3.

Example 97

Synthesis of (2S,5R)-7-oxo-2-(5-(piperazin-1-yl)-1,3,4-thiadiazol-2-yl)-1,6-diazabicyclo[3.2.1]octan-6-yl hydrogen sulfate (Compound 797)

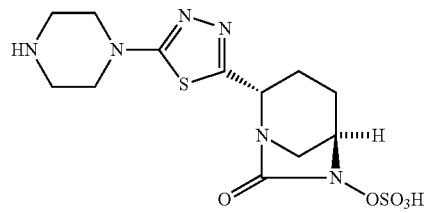

ESI-MS (EI⁺, m/z): 391.1.

Example 98

Synthesis of (2S,5R)-7-oxo-2-(5-(pyridin-4-yl)-1,3,4-thiadiazol-2-yl)-1,6-diazabicyclo[3.2.1]octan-6-yl hydrogen sulfate (Compound 798)

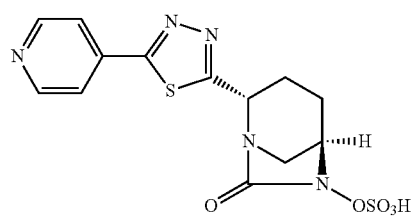

ESI-MS (EI⁻, m/z): 382.0.

Example 99

Construction of Isogenic β-Lactamase Strains

A set of β-lactamase expressing isogenic *E. coli* strains was constructed by cloning a β-lactamase gene into a customized derivative of pBR322 (GenBank Accession Number J01749) and transforming the engineered plasmids into *E. coli*. The NdeI restriction site within the plasmid backbone of pBR322 was removed to generate pBR322 ΔNdeI. The pBR322 ΔNdeI vector itself, minus the blaTEM-1 gene, was amplified using two primers: (1) pBR-Pbla 5'-cg catatgactcttcctttttcaatattattg-3, SEQ ID 1, a primer with an engineered NdeI restriction site at the 3' end of the blaTEM-1 promoter and (2) pBR-vec-1 5'-gc ggatccctgtcagaccaagtttactc-3', SEQ ID 2, a primer with an engineered BamHI restriction site at the 3' end of the blaTEM-1 open reading frame. The chloramphenicol resistance gene, cat, was generated by PCR amplification from pKD3 (GenBank Accession Number AY048742) using primers with an engineered NdeI restriction site at the 5' end (Pbla-cat 5'-gccatatgatggagaaaaaaatcactgg-3', SEQ ID 3) and an engineered BamHI restriction site at the 3' end (Vec-1-cat 5'-cgggatccctagagaataggaacttcgg-3', SEQ ID 4) of the resistance gene. The two PCR products, pBR322 ΔNdeI and cat were ligated together generating pBR-CBST (pBR322 ΔNdeI ΔTEM-1::cat Seq. ID 5) which retains both the pBR322 tetracycline resistance cassette, tetA, and the plasmid origin of replication but the blaTEM-1 gene was replaced by the cat gene.

Using this engineering strategy a number of plasmids producing β-lactamase genes from different classes (see below) were generated using synthetic genes with an engineered NdeI restriction site at the 5' end and BamHI restriction site at the 3' end of each gene (GenScript). Both the synthetic β-lactamase genes and cat gene were ligated into the NdeI/BamHI sites of the pBR322 ΔNdeI PCR product and transformed into electrocompetent E. coli ElectroMax DH10B (Invitrogen/Life Technologies). E. coli DH10B harboring the recombinant plasmids were selected on LB agar (supplemented with 25 μg/mL tetracycline) and single isolated colonies were then inoculated into 5 mL LB media (supplemented with 25 μg/mL tetracycline), and incubated at 37° C. with aeration (250 rpm) for 18 hrs. The cultures were frozen back at −80° C. in 20% glycerol. The DNA sequence of the cloned β-lactamase genes was confirmed. The β-lactamase gene expression in the recombinant E. coli strains was driven by the blaTEM-1 promoter in the pBR-CBST plasmid and was characterized by MIC profiling of the E. coli recombinant strains against comparator β-lactam/BLI combinations in broth microdilution assay.

| β-Lactamase Expressing Strain | Name & SEQ. ID of plasmids producing β-Lactamase | β-Lactamase Class | Species Origin of β-Lactamase Gene | GenBank Accession Number of β-Lactamase Gene Sequence |
|---|---|---|---|---|
| KPC-2 | pBR-CBST-KPC-2 SEQID 6 | A | K. pneumoniae | EU784136 |
| CTX-M-15 | pBR-CBST-CTX-M-15 SEQ ID 7 | A | K. pneumoniae | JF775516 |
| SHV-12 | pBR-CBST-SHV-12 SEQ ID 8 | A | K. pneumoniae | AY008838 |
| P99 AmpC | pBR-CBST-P99 AMPC SEQ ID 9 | C | E. cloacea | X07274 |
| OXA-15 | pBR-CBST-OXA-15 SEQ ID 10 | D | P. aeruginosa | PAU63835 |
| KPC-4 | pBR-CBST-KPC-4 SEQ ID 11 | A | K. pneumoniae | EU447304 |
| DHA-1 | pBR-CBST-DHA-1 SEQ ID 12 | C | K. pneumoniae | AY585202 |
| ADC-33 | pBR-CBST-ADC-33 SEQ ID 13 | C | A. baumannii | EU687478 |

Nucleotide Sequences of pBR-CBST Plasmids (Containing β-Lactamase or cat Genes) Used in the E. coli Isogenic Strains (relevant restriction sites are underlined; β-lactamase sequences in all caps, tetA sequence is in italics)
pBR-CBST-cat SEQ ID 5

```
ttcttgaagacgaaagggcctcgtgatacgcctatttttataggttaatgtcatgataataatggtttcttagacgtcaggtggcacttt
tcggggaaatgtgcgcggaacccctatttgtttatttttctaaatacattcaaatatgtatccgctcatgagacaataaccctgataaat
gcttcaataatattgaaaaaggaagagtcatATGGAGAAAAAATCACTGGATATACCACCGTT
GATATATCCCAATGGCATCGTAAAGAACATTTTGAGGCATTTCAGTCAGTTGC
TCAATGTACCTATAACCAGACCGTTCAGCTGGATATTACGGCCTTTTTAAGA
CCGTAAAGAAAAATAAGCACAAGTTTTATCCGGCCTTTATTCACATTCTTGCC
CGCCTGATGAATGCTCATCGGAATTTCGTATGGCAATGAAAGACGGTGAGC
TGGTGATATGGGATAGTGTTCACCCTTGTTACACCGTTTTCCATGAGCAAACT
GAAACGTTTTCATCGCTCTGGAGTGAATACCACGACGATTTCCGGCAGTTTCT
ACACATATATTCGCAAGATGTGGCGTGTTACGGTGAAAACCTGGCCTATTTCC
CTAAAGGGTTTATTGAGAATATGTTTTTCGTCTCAGCCAATCCCTGGGTGAGT
TTCACCAGTTTTGATTTAAACGTGGCCAATATGGACAACTTCTTCGCCCCCGT
TTTCACTATGGGCAAATATTATACGCAAGGCGACAAGGTGCTGATGCCGCTG
GCGATTCAGGTTCATCATGCCGTCTGTGATGGCTTCCATGTCGGCAGAATGCT
TAATGAATTACAACAGTACTGCGATGAGTGGCAGGGCGGGGCGTAAGTGGCA
GGGCGGGGCGTAAGGCGCGCCATTTAAATGAAGTTCCTATTCCGAAGTTCCT
ATTCTCTAGggatccctgtcagaccaagtttactcatatatactttagattgatttaaaacttcatttttaatttaaaaggatcta
ggtgaagatcctttttgataatctcatgaccaaaatcccttaacgtgagttttcgttccactgagcgtcagaccccgtagaaaagatc
aaaggatcttcttgagatcctttttttctgcgcgtaatctgctgcttgcaaacaaaaaaaccaccgctaccagcggtggtttgtttgcc
ggatcaagagctaccaactctttttccgaaggtaactggcttcagcagagcgcagataccaaatactgtccttctagtgtagccgt
agttaggccaccacttcaagaactctgtagcaccgcctacatacctcgctctgctaatcctgttaccagtggctgctgccagtggc
gataagtcgtgtcttaccgggttggactcaagacgatagttaccggataaggcgcagcggtcgggctgaacggggggttcgtg
cacacagcccagcttggagcgaacgacctacaccgaactgagatacctacagcgtgagctatgagaaagcgccacgcttccc
gaagggagaaaggcggacaggtatccggtaagcggcagggtcggaacaggagagcgcacgagggagcttccaggggga
aacgcctggtatctttatagtcctgtcgggtttcgccacctctgacttgagcgtcgatttttgtgatgctcgtcaggggggcggagc
ctatggaaaaacgccagcaacgcggcctttttacggttcctggccttttgctggccttttgctcacatgttctttcctgcgttatcccct
gattctgtggataaccgtattaccgcctttgagtgagctgataccgctcgccgcagccgaacgaccgagcgcagcgagtcagtg
agcgaggaagcggaagagcgcctgatgcggtattttctccttacgcatctgtgcggtatttcacaccgcatttggtgcactctcagt
```

```
acaatctgctctgatgccgcatagttaagccagtatacactccgctatcgctacgtgactgggtcatggctgcgccccgacaccc
gccaacacccgctgacgcgccctgacgggcttgtctgctcccggcatccgcttacagacaagctgtgaccgtctccgggagct
gcatgtgtcagaggttttcaccgtcatcaccgaaacgcgcgaggcagctgcggtaaagctcatcagcgtggtcgtgaagcgatt
cacagatgtctgcctgttcatccgcgtccagctcgttgagtttctccagaagcgttaatgtctggcttctgataaagcgggccatgtt
aagggcggttttttcctgtttggtcactgatgcctccgtgtaaggggggatttctgttcatggggggtaataccgatgaaacgaga
gaggatgctcacgatacgggttactgatgatgaacatgcccggttactggaacgttgtgagggtaaacaactggcggtatggat
gcggcgggaccagagaaaaatcactcagggtcaatgccagccgcttcgttaatacagatgtaggtgttccacagggtagccagc
agcatcctgcgatgcagatccggaacataatggtgcagggcgctgacttccgcgtttccagactttacgaaacacggaaaccga
agaccattcatgttgttgctcaggtcgcagacgttttgcagcagcagtcgcttcacgttcgctcgcgtatcggtgattcattctgcta
accagtaaggcaaccccgccagcctagccgggtcctcaacgacaggagcacgatcatgcgcacccgtggccaggacccaac
gctgcccgagatgcgccgcgtgcggctgctggagatggcggacgcgatggatatgttctgccaagggttggtttgcgcattcac
agttctccgcaagaattgattggctccaattcttggagtggtgaatccgttagcgaggtgccgccggcttccattcaggtcgaggt
ggcccggctccatgcaccgcgacgcaacgcggggaggcagacaaggtatagggcggcgcctacaatccatgccaaccc
gttccatgtgctcgccgaggcggcataaatcgccgtgacgatcagcggtccagtgatcgaagttaggctggtaagagccgc
gagcgatccttgaagctgtccctgatggtcgtcatctacctgcctggacagcatggcctgcaacgcgggcatcccgatgccg
ccggaagcgagaagaatcataatgggggaaggccatccagcctcgcgtcgcgaacgccagcaagacgtagcccagcgc
gtcggccgccatgccggcgataatggcctgcttctcgccgaaacgtttggtggcgggaccagtgacgaaggcttgagcgag
ggcgtgcaagattccgaataccgcaagcgacaggccgatcgctcgcgctccagccgaaagcggtcctcgccgaaaatg
acccagagcgctgccggcacctgtcctacgagttgcatgataaagaagacagtcataagtgcggcgacgatagtcatgcc
ccgcgcccaccggaaggagctgactgggttgaaggctctcaagggcatcggtcgacgctctcccttatgcgactcctgcatt
aggaagcagccagtagtaggttgaggccgttgagcaccgccgccgcaaggaatggtgcatgcaaggagatggcgccc
aacagtcccccggccatgggggctgccaccatacccacgccgaaacaagcgctaaggccgaagtggcgagcccga
tcttccccatcggtgatgtcggcgatataggccagcaaccgcacctgtggcgccggtgatgccggccacgatgcgtccg
gcgtagaggattcacaggacgggtgtggtcgccatgatcgcgtagtcgatagtggctccaagtagcgaagcgagcaggac
tgggcggcggccaaagcggtcggacagtgctccgagaacgggtgcgcatagaaattgcatcaacgcatatagcgctagc
agcacgccatagtgactggcgatgctgtcggaatggacgatatcccgcaagaggcccggcagtaccggcataaccaagc
ctatgcctacagcatccagggtgacggtgccgaggatgacgatgagcgcattgttagatttcatacacggtgcctgactgcgt
tagcaatttaactgtgataaactaccgcattaaagcttatcgatgataagctgtcaaacatgagaa pBR-CBST-KPC-2 SEQ ID 6 ttcttgaagacgaaagggcctcgtgatacgcctatttttataggttaatgtcatgataataatggtttcttagacgtcaggtggcacttt
tcggggaaatgtgcgcggaaccccctatttgtttatttttctaaatacattcaaatatgtatccgctcatgagacaataaccctgataaat
gcttcaataatattgaaaaaggaagagtcatATGTCACTGTTATCGCCGTCTAGTTCTGCTGTCTTG
TCTCTCATGGCCGCTGGCTGGTTTTCTGCCACCGCGCTGACCAACCTCGTCG
CGGAACCATTCGCTAAACTCGAACAGGACTTTGGCGGCTCCATCGGTGTGTA
CGCGATGGATACCGGCTCAGGCGCAACTGTAAGTTACCGCGCTGAGGAGCGC
TTCCCACTGTGCAGCTCATTCAAGGGCTTTCTTGCTGCCGCTGTGCTGGCTCG
CAGCCAGCAGCAGGCCGGCTTGCTGGACACACCCATCCGTTACGGCAAAAAT
GCGCTGGTTCCGTGGTCACCCATCTCGGAAAAATATCTGACAACAGGCATGA
CGGTGGCGGAGCTGTCCGCGGCCGCCGTGCAATACAGTGATAACGCCGCCGC
CAATTTGTTGCTGAAGGAGTTGGGCGGCCCGGCCGGGCTGACGGCCTTCATG
CGCTCTATCGGCGATACCACGTTCCGTCTGGACCGCTGGGAGCTGGAGCTGA
ACTCCGCCATCCCAGGCGATGCGCGCGATACCTCATCGCCGCGCGCCGTGAC
GGAAAGCTTACAAAAACTGACACTGGGCTCTGCACTGGCTGCGCCGCAGCGG
CAGCAGTTTGTTGATTGGCTAAAGGGAAACACGACCGGCAACCACCGCATCC
GCGCGGCGGTGCCGGCAGACTGGGCAGTCGGAGACAAAACCGGAACCTGCG
GAGTGTATGGCACGGCAAATGACTATGCCGTCGTCTGGCCCACTGGGCGCGC
ACCTATTGTGTTGGCCGTCTACACCCGGGCGCCTAACAAGGATGACAAGCAC
AGCGAGGCCGTCATCGCCGCTGCGGCTAGACTCGCGCTCGAGGGATTGGGCG
TCAACGGGCAGTAAaggatccctgtcagacaagtttactcatatatacttttagattgatttaaaacttcattttttaatttaa
aaggatctaggtgaagatcctttttgataatctcatgaccaaaatcccttaacgtgagttttcgttccactgagcgtcagacccccgta
gaaaagatcaaaggatcttcttgagatcctttttttctgcgcgtaatctgctgcttgcaaacaaaaaaaccaccgctaccagcggtg
gtttgtttgccggatcaagagctaccaactctttttccgaaggtaactggcttcagcagagcgcagataccaaatactgtccttctag
tgtagccgtagttaggccaccacttcaagaactctgtagcaccgcctacatacctcgctctgctaatcctgttaccagtggctgctg
ccagtggcgataagtcgtgtcttaccgggttggactcaagacgatagttaccggataaggcgcagcggtcgggctgaacgggg
ggttcgtgcacacagcccagcttggagcgaacgacctacaccgaactgagatacctacagcgtgagctatgagaaagcgcca
cgcttcccgaagggagaaaggcggacaggtatccggtaagcggcagggtcggaacaggagagcgcacgagggagcttcca
gggggaaacgcctggtatctttatagtcctgtcgggtttcgccacctctgacttgagcgtcgatttttgtgatgctcgtcaggggggg
cggagcctatggaaaaacgccagcaacgcggcctttttacggttcctggccttttgctggccttttgctcacatgttctttcctgcgtt
atcccctgattctgtggataaccgtattaccgcctttgagtgagctgataccgctcgccgcagccgaacgaccgagcgcagcga
gtcagtgagcgaggaagcggaagagcgcctgatgcggtattttctccttacgcatctgtgcggtatttcacaccgcatttggtgca
ctctcagtacaatctgctctgatgccgcatagttaagccagtatacactccgctatcgctacgtgactgggtcatggctgcgcccc
gacacccgccaacacccgctgacgcgccctgacgggcttgtctgctcccggcatccgcttacagacaagctgtgaccgtctccc
gggagctgcatgtgtcagaggttttcaccgtcatcaccgaaacgcgcgaggcagctgcggtaaagctcatcagcgtggtcgtg
aagcgattcacagatgtctgcctgttcatccgcgtccagctcgttgagtttctccagaagcgttaatgtctggcttctgataaagcgg
gccatgttaagggcggttttttcctgtttggtcactgatgcctccgtgtaaggggggatttctgttcatggggtaatgataccgatga
aacgagagaggatgctcacgatacgggttactgatgatgaacatgcccggttactggaacgttgtgagggtaaacaactggcg
gtatggatgcggcgggaccagagaaaaatcactcagggtcaatgccagccgcttcgttaatacagatgtaggtgttccacaggt
agccagcagcatcctgcgatgcagatccggaacataatggtgcagggcgctgacttccgcgtttccagactttacgaaacacgg
aaaccgaagaccattcatgttgttgctcaggtcgcagacgttttgcagcagcagtcgcttcacgttcgctcgcgtatcggtgattca
ttctgctaaccagtaaggcaacccgccagcctagccgggtcctcaacgacaggagcacgatcatgcgcacccgtggccagg
acccaacgctgcccgagatgcgccgcgtgcggctgctggagatggcggacgcgatggatatgttctgccaagggttggtttgc
gcattcacagttctccgcaagaattgattggctccaattcttggagtggtgaatccgttagcgaggtgccgccggcttccattcag
gtcgaggtggcccggctccatgcaccgcgacgcaacgcggggaggcagacaaggtatagggcggcgcctacaatccat
gccaacccgttccatgtgctcgccgaggcggcataaatcgccgtgacgatcagcggtccagtgatcgaagttaggctggta
agagccgcgagcgatccttgaagctgtccctgatggtcgtcatctacctgcctggacagcatggcctgcaacgcgggcatcc
cgatgccgccggaagcgagaagaatcataatgggggaaggccatccagcctcgcgtcgcgaacgccagcaagacgtagc
ccagcgcgtcggccgccatgccggcgataatggcctgcttctcgccgaaacgtttggtggcgggaccagtgacgaaggctt
```

-continued

```
gagcgagggcgtgcaagattccgaataccgcaagcgacaggccgatcatcgtcgcgctccagcgaaagcggtcctcgcc
gaaaatgacccagagcgctgccggcacctgtcctacgagttgcatgataaagaagacagtcataagtgcggcgacgata
gtcatgccccgcgccaccggaaggagctgactgggttgaaggctctcaagggcatcggtcgacgctctcccttatgcgact
cctgcattaggaagcagccagtagtaggttgaggccgttgagcaccgccgccgcaaggaatggtgcatgcaaggagat
ggcgccaacagtcccccggccacggggcctgccaccatacccacgccgaaacaagcgctcatgagcccgaagtggcg
agcccgatcttccccatcggtgatgtcggcgatataggcgccagcaaccgcacctgtggcgccggtgatgccggccacgat
gcgtccggcgtagaggattcacaggacgggtgtggtcgccatgatcgcgtagtcgatagtggctccaagtagcgaagcga
gcaggactgggcggcggccaaagcggtcggacagtgctccgagaacgggtgcgcatagaaattgcatcaacgcatatag
cgctagcagcacgccatagtgactggcgatgctgtcggaatggacgatatcccgcaagaggcccggcagtaccggcata
accaagcctatgcctacagcatccagggtgacggtgccgaggatgacgatgagcgcattgttagatttcatacacggtgcct
gactgcgttagcaatttaactgtgataaactaccgcattaaagcttatcgatgataagagtcaaacatgagaa
``` pBR-CBST-CTX-M-15 SEQ ID 7

```
ttcttgaagacgaaagggcctcgtgatacgcctatttttataggttaatgtcatgataataatggtttcttagacgtcaggtggcacttt
tcggggaaatgtgcgcggaaccccctatttgtttatttttctaaatacattcaaatatgtatccgctcatgagacaataaccctgataaat
gcttcaataatattgaaaaaggaagagtcatATGGAATCTGTTAAATCAGCGAGTTGAGATCAA
AAAATCTGACCTTGTTAACTATAATCCGATTGCGGAAAAGCACGTCAATGGG
ACGATGTCACTGGCTGAGCTTAGCGCGGCCGCGCTACAGTACAGCGATAACG
TGGCGATGAATAAGCTGATTGCTCACGTTGGCGGCCCGGCTAGCGTCACCGC
GTTCGCCCGACAGCTGGGAGACGAAACGTTCCGTCTCGACCGTACCGAGCCG
ACGTTAAACACCGCCATTCCGGGCGATCCGCGTGATACCACTTCACCTCGGG
CAATGGCGCAAACTCTGCGGAATCTGACGCTGGGTAAAGCATTGGGCGACAG
CCAACGGGCGCAGCTGGTGACATGGATGAAAGGCAATACCACCGGTGCAGC
GAGCATTCAGGCTGGACTGCCTGCTTCCTGGGTTGTGGGGATAAAACCGGC
AGCGGTGGCTATGGCACCACCAACGATATCGCGGTGATCTGGCCAAAAGATC
GTGCGCCGCTGATTCTGGTCACTTACTTCACCCAGCCTCAACCTAAGGCAGAA
AGCCGTCGCGATGTATTAGCGTCGGCGGCTAAAATCGTCACCGACGGTTTGT
AAggatccctgtcagaccaagtttactcatatatactttagattgatttaaaacttcatttttaatttaaaaggatctaggtgaagatcc
tttttgataatctcatgaccaaaatcccttaacgtgagttttcgttccactgagcgtcagaccccgtagaaaagatcaaaggatcttct
tgagatcctttttttctgcgcgtaatctgctgcttgcaaacaaaaaaaccaccgctaccagcggtggtttgtttgccggatcaagag
ctaccaactctttttccgaaggtaactggcttcagcagagcgcagataccaaatactgtccttctagtgtagccgtagttaggccac
cacttcaagaactctgtagcaccgcctacatacctcgctctgctaatcctgttaccagtggctgctgccagtggcgataagtcgtgt
cttaccgggttggactcaagacgatagttaccggataaggcgcagcggtcgggctgaacggggggttcgtgcacacagccca
gcttggagcgaacgacctacaccgaactgagataccatacaccaacgacaccaccaccaccacatcatcctacatgagcccaagccga
ggcggacaggtatccggtaagcggcagggtcggaacaggagagcgcacgagggagcttccaggggaaacgcctggtatc
tttatagtcctgtcgggtttcgccacctctgacttgagcgtcgatttttgtgatgctcgtcaggggggcggagcctatgaaaaacg
ccagcaacgcggcctttttacggttcctggccttttgctggccttttgctcacatgttctttcctgcgttatcccctgattctgtggataa
ccgtattaccgcctttgagtgagctgataccgctcgccgcagccgaacgaccgagcgcagcgagtcagtgagcgaggaagcg
gaagagcgcctgatgcggtattttctccttacgcatctgtgcggtatttcacaccgcatttggtgcactctcagtacaatctgctctga
tgccgcatagttaagccagtatacactccgctatcgctacgtgactgggtcatggctgcgccccgacacccgccaacacccgct
gacgcgccctgacgggcttgtctgctcccggcatccgcttacagacaagctgtgaccgtctccgggagctgcatgtgtcagagg
ttttcaccgtcatcaccgaaacgcgcgaggcagctgcggtaaagctcatcagccgcttggtcgttcacagatgtctgcct
gttcatccgcgtccagctcgttgagtttctccagaagcgttaatgtctggcttctgataaagcgggccatgttaagggcggttttttc
ctgtttggtcactgatgcctccgtgtaaggggggattctgttcatggggtaatgataccgatgaaacgagagaggatgctcacga
tacgggttactgatgatgaacatgcccggttactggaacgttgtgagggtaaacaactggcggtatggatgcggcgggaccaga
gaaaaatcactcaggtcaatgccagcgcttcgttaatacagatgtaggtgttccacaggatgctgcagcagcatctgcgatgca
gatccggaacataatggtgcagggcgctgacttccgcgttccagactttacgaaacacggaaaccgaagaccattcatgttgtt
gctcaggtcgcagacgttttgcagcagcagtcgcttcacgttcgctcgcgtatcggtgattcattctgctaaccagtaaggcaacc
ccgccagcctagccgggtcctcaacgacaggagcacgatcatgcgcacccgtggccaggacccaacgctgcccgagatgcg
ccgcgtgcggctgctggagatggcggacgcgatggatatgttctgccaagggttggtttgcgcattcacagttctccgcaagaat
tgattggctccaattcttggagtggtgaatccgttagcgaggtgccgccggcttccattcaggtcgaggtggcccggctccatgc
accgcgacgcaacgcggggaggcagacaaggtatagggcggcgcctacaatccatgccaacccgttccatgtgctcgcc
gaggcggcataaatcgccgtgacgatcagcggtccagtgatcgaagttaggctggtaagagccgcgagcgatccttgaag
ctgtccctgatggtcgtcatctacctgcctggacagcatggcctgcaacgcgggcatcccgatgccgccggaagcgagaag
aatcataatggggaaggccatccagcctcgcgtcgcgaaccgccagcaagacgtagcccagccgcgtcggccgccatgccg
gcgataatggcctgcttctcgccgaaacgtttggtggcgggaccagtgacgaaggcttgagcgagggcgtgcaagattccg
aataccgcaagcgacaggccgatcatcgtcgcgctccagcgaaagcggtcctcgccgaaaatgacccagagcgctgccg
gcacctgtcctacgagttgcatgataaagaagacagtcataagtgcggcgacgatagtcgcccgcgccaccggaag
gagctgactgggttgaaggctctcaagggcatcggtcgacgctctcccttatgcgactcctgcattaggaagcagccagta
gtaggttgaggccgttgagcaccgccgccgcaaggaatggtgcatgcaaggagatggcgcccaacagtcccccggccac
ggggcctgccaccatacccacgccgaaacaagcgctcatgagcccgaagtggcgagcccgatcttccccatcggtgatgt
cggcgatataggcgccagcaaccgcacctgtggcgccggtgatgccggccacgatgcgtccggcgtagaggattcacag
gacgggtgtggtcgccatgatcgcgtagtcgatagtggctccaagtagcgaagcgagcaggactgggcggcggccaaag
cggtcggacagtgctccgagaacgggtgcgcatagaaattgcatcaacgcatatagcgctagcagcacgccatagtgact
ggcgatgctgtcggaatggacgatatcccgcaagaggcccggcagtaccggcataaccaagcctatgcctacagcatcca
gggtgacggtgccgaggatgacgatgagcgcattgttagatttcatacacggtgcctgactgcgttagcaatttaactgtgataa
actaccgcattaaagcttatcgatgataagctgtcaaacatgagaa
``` pBR-CBST-SHV-12 SEQ ID 8

```
ttcttgaagacgaaagggcctcgtgatacgcctatttttataggttaatgtcatgataataatggtttcttagacgtcaggtggcacttt
tcggggaaatgtgcgcggaaccccctatttgtttatttttctaaatacattcaaatatgtatccgctcatgagacaataaccctgataaat
gcttcaataatattgaaaaaggaagagtcatATGCGTTATATTCGCCTGTGTATTATCTCCCTGTT
AGCCACCCTGCCGCTGGCGGTACACGCCAGCCCGCAGCCGCTTGAGCAAATT
AAACAAAGCGAAAGCCAGCTGTCGGGCCGCGTAGGCATGATAGAAATGGAT
CTGGCCAGCGGCCGCACGCTGACCGCCTGGCGCGCCGATGAACGCTTTCCCA
TGATGAGCACCTTTAAAGTAGTGCTCTGCGGCGCAGTGCTGGCGCGGGTGGA
TGCCGGTGACGAACAGCTGGAGCGAAAGATCCACTATCGCCAGCAGGATCTG
```

```
GTGGACTACTCGCCGGTCAGCGAAAAACACCTTGCCGACGGCATGACGGTCG
GCGAACTCTGCGCCGCCGCCATTACCATGAGCGATAACAGCGCCGCCAATCT
GCTGCTGGCCACCGTCGGCGGCCCCGCAGGATTGACTGCCTTTTTGCGCCAG
ATCGGCGACAACGTCACCCGCCTTGACCGCTGGGAAACGGAACTGAATGAGG
CGCTTCCCGGCGACGCCCGCGACACCACTACCCCGGCCAGCATGGCCGGCGAC
CCTGCGCAAGCTGCTGACCAGCCAGCGTCTGAGCGCCCGTTCGCAACGGCAG
CTGCTGCAGTGGATGGTGGACGATCGGGTCGCCGGACCGTTGATCCGCTCCG
TGCTGCCGGCGGGCTGGTTTATCGCCGATAAGACCGGAGCTAGCAAGCGGGG
TGCGCGCGGGATTGTCGCCCTGCTTGGCCCGAATAACAAAGCAGAGCGCATT
GTGGTGATTTATCTGCGGGATACCCCGGCGAGCATGGCCGAGCGAAATCAGC
AAATCGCCGGGATCGGCGCGGCGCTGATCGAGCACTGGCAACGCTAAggatccct
gtcagaccaagtttactcatatatactttagattgatttaaaacttcattttaatttaaaaggatctaggtgaagatcctttttgataatct
catgaccaaaatcccttaacgtgagttttcgttccactgagcgtcagaccccgtagaaaagatcaaaggatcttcttgagatccttttt
tttctgcgcgtaatctgctgcttgcaaacaaaaaaaccaccgctaccagcggtggtttgtttgccggatcaagagctaccaactctt
tttccgaaggtaactggcttcagcagagcgcagataccaaatactgtccttctagtgtagccgtagttaggccaccacttcaagaa
ctctgtagcaccgcctacatacctcgctctgctaatcctgttaccagtggctgctgccagtggcgataagtcgtgtcttaccgggtt
ggactcaagacgatagttaccggataaggcgcagcggtcgggctgaacggggggttcgtgcacacagcccagcttggagcg
aacgacctacaccgaactgagatacctacagcgtgagctatgagaaagcgccacgcttcccgaagggagaaaggcggacag
gtatccggtaagcggcagggtcggaacaggagagcgcacgagggagcttccaggggaaacgcctggtatctttatagtcct
gtcgggtttcgccacctctgacttgagcgtcgatttttgtgatgctcgtcaggggggcggagcctatggaaaaacgccagcaacg
cggcctttttacggttcctggccttttgctggccttttgctcacatgttctttcctgcgttatcccctgattctgtggataaccgtattacc
gcctttgagtgagctgataccgctcgccgcagccgaacgaccgagcgcagcgagtcagtgagcgaggaagcggaagagcg
cctgatgcggtattttctccttacgcatctgtgcggtatttcacaccgcatttggtgcactctcagtacaatctgctctgatgccgcata
gttaagccagtatacactccgctatcgctacgtgactgggtcatggctgcgccccgacacccgccaacacccgctgacgcgcc
ctgacgggcttgtctgctcccggcatccgcttacagacaagctgtgaccgtctccggagctgcatgtgtcagaggttttcaccgt
catcaccgaaacgcgcgaggcagctgcggtaaagctcatcagcgtggtcgtgaagcgattcacagatgtctgcctgttcatccg
cgtccagctcgttgagtttctccagaagcgttaatgtctggcttctgataaagcgggccatgttaagggtgcttttttcctgtttggtc
actgatgcctccgtgtaaggggatttctgttcatgggggtaatgataccgatgaaacgagagaggatgctcacgatacgggtta
ctgatgatgaacatgcccggttactggaacgttgtgagggtaaacaactggcggtatggatgcggcgggaccagagaaaaatc
actcagggtcaatgccagcgcttcgttaatacagatgtaggtgttccacaggtagccagcagcatcctgcgatgcagatccgg
aacataatggtgcagggcgctgacttccgcgtttccagactttacgaaacacggaaaccgaagaccattcatgttgttgctcaggt
cgcagacgttttgcagcagcagtcgcttcacgttcgctcgcgtatcggtgattcattctgctaaccagtaaggcaaccccgccag
cctagccgggtcctcaacgacaggagcacgatcatgcgcacccgtggccaggacccaacgctgcccgagatgcgccgcgtg
cggctgctggagatggcggacgcgatggatatgttctgccaagggttggtttgcgcattcacagttctccgcaagaattgattggc
tccaattcttggagtggtgaatccgttagcgaggtgccgccggcttccattcaggtcgaggtggcccggctccatgcaccgcga
cgcaacgcggggaggcagacaaggtataggcggcgcctacaatccatgccaacccgttccatgtgctcgccgaggcgg
cataaatcgccgtgacgatcagcggtccagtgatcgaagttaggctggtaagagccgcgagcgatccttgaagctgtccct
gatggtcgtcatctacctgcctggacagcatggcctgcaacgcgggcatcccgatgccgccggaagcgagaagaatcata
atggggaaggccatccagcctcgcgtcgcgaacgccagcaagacgtagcccagcgcgtcggccgccatgccggcgata
atggcctgcttctcgccgaaacgtttggtggcgggaccagtgacgaaggcttgagcgagggcgtgcaagattccgaatacc
gcaagcgacaggccgatcatcgtcgcgctccagcgaaagcggtcctcgccgaaaatgacccagagcgctgccggcacct
gtcctacgagttgcatgataaagaagacagtcataagtgcggcgacgatagtcatgccccgcgcccaccggaaggagctg
actgggttgaaggctctcaagggcatcggtcgacgctctccctttatgcgactcctgcattaggaagcgtcattaggtagtaggtt
gaggccgttgagcaccgccgccgcaaggaatggtgcatgcaaggagatggcgcccaacagtcccccggccacggggcc
tgccaccatacccacgccgaaacaagcgctcatgagcccgaagtggcgagcccgatcttccccatcggtgatgtcggcgat
ataggcgccagcaaccgcacctgtggcgccggtgatgccggccacgatgcgtccggcgtagaggattcacaggacgggt
gtggtcgccatgatcgcgtagtcgatagtggctccaagtaggcgaagcgagcaggactggcgacgcggcccaaagcggtcgg
acagtgctccgagaacgggtgcgcatagaaattgcatcaacgcatatagcgctagcagcacgccatagtgactggcgatg
ctgtcggaatgacgatatcccgcaagaggcccggcagtaccggcataaccaagcctatgcctacagcatccagggtgac
ggtgccgaggatgacgatgagcgcattgttagatttcatacacggtgcctgactgcgttagcaatttaactgtgataaactaccg
cattaaagcttatcgatgataagctgtcaaacatgagaa
``` pBR-CBST-P99 SEQ ID 9

```
ttcttgaagacgaaagggcctcgtgatacgcctatttttataggttaatgtcatgataataatggtttcttagacgtcaggtggcactt
tcggggaaatgtgcgcggaacccctatttgtttatttttctaaatacattcaaatatgtatccgctcatgagacaataaccctgataaat
gcttcaataatattgaaaaaggaagagtcatATGATGAGAAATCCCTTTGCTGCGCCCTGCTGC
TCGGCATCTCTTGCTCTGCTCTCGCCACGCCAGTGTCAGAAAAACAGCTGGCG
GAGGTGGTCGCGAATACGATTACCCCGCTGATGAAAGCCCAGTCTGTTCCAG
GCATGGCGGTGGCCGTTATTTATCAGGGAAAACCGCACTATTACACATTTGG
CAAGGCCGATATCGCGGCGAATAAACCCGTTACGCCTCAGACCCTGTTCGAG
CTGGGTTCTATAAGTAAAACCTTCACCGGCGTTTTAGGTGGGGATGCCATTGC
TCGCGGTGAAATTTCGCTGGACGATGCGGTGACCAGATACTGGCCACACCTG
ACGGGCAAGCAGTGGCAGGGTATTCGTATGCTGGATCTCGCCACCTACACCG
CTGGCCGCCTGCCGCTACAGGTACCGGATGAGGTCACGGATAACGCCTCCCT
GCTGCGCTTTTATCAAAACTGGCAGCCGCAGTGGAAGCCTGGCACAACGCGT
CTTTTACGCCAACGCCAGCATCGGTCTTTTTGGTGCGCTGGCCGTCAAACCTTC
TGGCATGCCCTATGAGCAGGCCATGACGACGCGGGTCCTTAAGCCGCTCAAG
CTGGACCATACCTGGATTAACGTGCCGAAAGCGGAAGAGGCGCATTACGCCT
GGGGCTATCGTGACGGTAAAGCGGTGCGCGTTTCGCGGGTATGCTGGATGC
ACAAGCCTATGGCGTGAAACCAACGTGCAGGATATGGCGAACTGGGTCATG
GCAAACATGGCGCCGGAGAACGTTGCTGATGCCTCACTTAAGCAGGGCATCG
CGCTGGCGCAGTCGCGCTACTGGCGTATCGGGTCAATGTATCAGGGTCTGGG
CTGGAGATGCTCAACTGGCCCGTGGAGGCCAACACGGTGGTCGAGGGCAG
CGACAGTAAGGTAGCACTGGCGCCGTTGCCCGTGGCAGAAGTGAATCCACCG
GCTCCCCCGGTCAAAGCGTCCTGGGTCCATAAAACGGGCTCTACTGGCGGGT
TTGGCAGCTACGTGGCCTTTATTCCTGAAAAGCAGATCGGTATTGTGATGCTC
GCGAATACAAGCTATCCGAACCCGGCACGCGTTGAGGCGGCATACCATATCC
TCGAGGCGCTACAGTAAggatccctgtcagaccaagtttactcatatatactttagattgatttaaaacttcattttttaa
```

```
tttaaaaggatctaggtgaagatcctttttgataatctcatgaccaaaatcccttaacgtgagttttcgttccactgagcgtcagaccc
cgtagaaaagatcaaaggatcttcttgagatccttttttctgcgcgtaatctgctgcttgcaaacaaaaaaaccaccgctaccagc
ggtggtttgtttgccggatcaagagctaccaactcttttccgaaggtaactggcttcagcagagcgcagataccaaatactgtcct
tctagtgtagccgtagttaggccaccacttcaagaactctgtagcaccgcctacatacctcgctctgctaatcctgttaccagtggc
tgctgccagtggcgataagtcgtgtcttaccgggttggactcaagacgatagttaccggataaggcgcagcggtcgggctgaac
gggggttcgtgcacacagcccagcttggagcgaacgacctacaccgaactgagatacctacagcgtgagctatgagaaagc
gccacgcttcccgaagggagaaaggcggacaggtatccggtaagcggcagggtcggaacaggagagcgcacgagggagc
ttccaggggaaacgcctggtatctttatagtcctgtcgggtttcgccacctctgacttgagcgtcgattttgtgatgctcgtcagg
ggggcggagcctatggaaaaacgccagcaacgcggccttttacggttcctggccttttgctggccttttgctcacatgttctttcct
gcgttatccctgattctgtggataaccgtattaccgcctttgagtgagctgataccgctcgccgcagccgaacgaccgagcgca
gcgagtcagtgagcgaggaagcggaagagcgcctgatgcggtattttctccttacgcatctgtgcggtatttcacaccgcatttg
gtgcactctcagtacaatctgctctgatgccgcatagttaagccagtatacactccgctatcgctacgtgactgggtcatggctgcg
ccccgacacccgccaacacccgctgacgcgccctgacgggcttgtctgctcccggcatccgcttacagacaagctgtgaccgt
ctccgggagctgcatgtgtcagaggttttcaccgtcatcaccgaaacgcgcgaggcagctgcggtaaagctcatcagcgtggtc
gtgaagcgattcacagatgtctgcctgttcatccgcgtccagctcgttgagtttctccagaagcgttaatgtctggcttctgataaag
cgggccatgttaagggcggttttttcctgtttggtcactgatgcctccgtgtaaggggattttctgttcatgggggtaatgataccga
tgaaacgagagaggatgctcacgatacgggttactgatgatgaacatgcccggttactggaacgttgtgagggtaaacaactgg
cggtatggatgcggcgggacagagaaaaatcactcagggtcaatgccagcgcttcgttaatacagatgtaggtgttccacagg
gtagccagcagcatcctgcgatgcagatccggaacataatggtgcagggcgctgacttccgcgtttccagactttacgaaacac
ggaaaccgaagaccattcatgttgttgctcaggtcgcagacgttttgcagcagcagtcgcttcacgttcgctcgcgtatcggtgatt
cattctgctaaccagtaaggcaaccccgccagcctagccgggtcctcaacgacaggagcacgatcatgcgcacccgtggcca
ggaccaacgctgcccgagatgcgccgcgtgcggctgctggaagcatatgttcgtgccaagggtTggttt
gcgcattcacagttctccgcaagaattgattggctccaattcttggagtggtgaatccgttagcgaggtgccgccggcttccattca
ggtcgaggtggcccggctccatgcaccgcgacgcaacgcggggaggcagacaaggtatagggcggcgcctacaatcca
tgccaacccgttccatgtgctcgccgaggcggcataaatcgccgtgacgatcagcggtccagtgatcgaagttaggctggta
agagccgcgagcgatccttgaagctgtccctgatggtcgtcatctacctgcctgacagcatggcctgcaacgcgggcatcc
cgatgccgccgaagcgagaagaatcataatggggaaggccatccagctccgctcgcgaacgccagcaagacgtagc
ccagcgcgtcggccgccatgccggcgataatggcctgcttctcgccgaaacgtttggtggcgggaccagtgacgaaggctt
gagcgagggcgtgcaagattccgaataccgcaagcgacaggccgatcatcgtcgcgctccagcgaaagcggtcctcgcc
gaaaatgacccagagcgctgccggcacctgtcctacgagttgcatgataaagaagacagtcataagtgcggcgacgata
gtcatgccccgcgcccaccggaaggagctgactgggttgaaggctctcaagggcatcggtcgacgctctcccttatgcgact
cctgcattaggaagcagcccagtagtaggttgaggccgttgagcaccgccgccgcaaggaatggtgcatgcaaggagat
ggcgcccaacagtcccccggccacggggcctgccaccatacccacgccgaaacaagcgctcatgagcccgaagtggcg
agcccgatcttccccatcggtgatgtcggcgatataggcgccagaaccgcacctgtggcgccggtgatgccggccacgat
gcgtccggcgtagaggattcacaggacgggtgtggtcgccatgatcgcgtagtcgatagtggctccaagtagcgaagcga
gcaggactgggcggcggccaaagcggtcggacagtgctccgagaacgggtgcgcatagaaattgcatcaacgcatatag
cgctagcagcacgccatagtgactggcgatgctgtcggaatggacgatatcccgcaagaggcccgcagtaccggcata
accaagcctatgcctacagcatccagggtgacggtgccgaggatgacgatgagcgcattgttagatttcatacacggtgcct
gactgcgttagcaatttaactgtgataaactaccgcattaaagcttatcgatgataagctgtcaaacatgagaa
``` pBR-CBST-OXA-15 SEQ ID 10

```
ttcttgaagacgaaagggcctcgtgatacgcctatttttataggttaatgtcatgataataatggtttcttagacgtcaggtggcacttt
tcggggaaatgtgcgcggaaccccctatttgtttatttttctaaatacattcaaatatgtatccgctcatgagacaataaccctgataaat
gcttcaataatattgaaaaaggaagagtcatATGGCAATCCGAATCTTCGCGATACTTTTCTCCA
TTTTTTCTCTTGCCACTTTCGCGCATGCGCAAGAAGGCACGCTAGAACGTTCT
GACTGGAGGAAGTTTTTCAGCGAATTTCAAGCCAAAGGCACGATAGTTGTGG
CAGACGAACGCCAAGCGGATCGTGCCATGTTGGTTTTTGATCCTGTGCGATCG
AAGAAACGCTACTCGCCTGCATCGACATTCAAGATACCTCATACACTTTTTGC
ACTTGATGCAGGCGCTGTTCGTGATGAGTTCCAGATTTTTCGATGGGACGGCG
TTAACAGGGGCTTTGCAGGCCACAATCAAGACCAAGATTTTGCGATCAGCAAT
GCGGAATTCTACTGTTTGGGTGTATGAGCTATTTGCAAAGGAAATTGGTGATG
ACAAAGCTCGGCGCTATTTGAAGAAAATCGACTATGGCAACGCCGGTCCTTC
GACAAGTAATGGCGATTACTGGATAGAAGGCAGCCTTGCAATCTCGGCGCAG
GAGCAAATTGCATTTCTCAGGAAGCTCTATCGTAACGAGCTGCCCTTTCGGGT
AGAACATCAGCGCTTGGTCAAGGATCTCATGATTGTGGAAGCCGGTCGCAAC
TGGATACTGCGTGCAAAGACGGGCTGGGAAGGCCGTATGGGTTGGTGGGTAG
GATGGGTTGAGTGGCCGACTGGCTCCGTATTCTTCGCACTGAATATTGATACG
CCAAACAGAATGGATGATCTTTTCAAGAGGGAGGCAATCGTGCGGGCAATCC
TTCGCTCTATTGAAGCGTTACCGCCCAACCCGGCAGTCAACTCGGACGCTGC
GCGATAAggatccctgtcagaccaagtttactcatatatactttagattgatttaaaacttcatttttaatttaaaaggatctaggt
gaagatcctttttgataatctcatgaccaaaatcccttaacgtgagttttcgttccactgagcgtcagacccgtagaaaagatcaaa
ggatcttcttgagatccttttttctgcgcgtaatctgctgcttgcaaacaaaaaaaccaccgctaccagcggtggtttgtttgccgga
tcaagagctaccaactcttttccgaaggtaactggcttcagcagagcgcagataccaaatactgtccttctagtgtagccgtagtt
aggccaccacttcaagaactctgtagcaccgcctacatacctcgctctgctaatcctgttaccagtggctgctgccagtggcgata
agtcgtgtcttaccgggttggactcaagacgatagttaccggataaggcgcagcggtcgggctgaacggggggttcgtgcaca
cagcccagcttggagcgaacgacctacaccgaactgagatacctacagcgtgagctatgagaaagcgccacgcttcccgaag
ggagaaaggcggacaggtatccggtaagcggcagggtcggaacaggagagcgcacgagggagcttccaggggaaacg
cctggtatctttatagtcctgtcgggtttcgccacctctgacttgagcgtcgattttgtgatgctcgtcaggggggcggagcctatg
gaaaaacgccagcaacgcggcctttttacggttcctggccttttgctggccttttgctcacatgttctttcctgcgttatccctgattc
tgtggataaccgtattaccgcctttgagtgagctgataccgctcgccgcagccgaacgaccgagcgcagcgagtcagtgagcg
aggaagcggaagagcgcctgatgcggtattttctccttacgcatctgtgcggtatttcacaccgcatttggtgcactctcagtacaa
tctgctctgatgccgcatagttaagccagtatacactccgctatcgctacgtgactgggtcatggctgcgccccgacacccgcca
acacccgctgacgcgccctgacgggcttgtctgctcccggcatccgcttacagacaagctgtgaccgtctccgggagctgcatg
tgtcagaggttttcaccgtcatcaccgaaacgcgcgaggcagctgcggtaaagctcatcagcgtggtcgtgaagcgattcacag
atgtctgcctgttcatccgcgtccagctcgttgagtttctccagaagcgttaatgtctggcttctgataaagcgggccatgttaaggg
cggttttttcctgtttggtcactgatgcctccgtgtaaggggattttctgttcatgggggtaatgataccgatgaaacgagagaggat
gctcacgatacgggttactgatgatgaacatgcccggttactggaacgttgtgagggtaaacaactggcggtatggatgcggcg
ggaccagagaaaaatcactcagggtcaatgccagcgcttcgttaatacagatgtaggtgttccacagggtagccagcagcatcc
```

```
tgcgatgcagatccggaacataatggtgcagggcgctgacttccgcgtttccagactttacgaaacacggaaaccgaagaccat
tcatgttgttgctcaggtcgcagacgttttgcagcagcagtcgcttcacgttcgctcgcgtatcggtgattcattctgctaaccagta
aggcaacccgccagcctagccgggtcctcaacgacaggagcacgatcatgcgcacccgtggccaggacccaacgctgcc
cgagatgcgccgcgtgcggctgctggagatggcggacgcgatggatatgttctgccaagggttggtttgcgcattcacagttctc
cgcaagaattgattggctccaattcttggagtggtgaatccgttagcgaggtaatccgcagcgccggcttccattcaggtcgaggtggcccg
gctccatgcaccgcgacgcaacgcggggaggcagacaaggtatagggcggcgcctacaatccatgccaacccgttccat
gtgctcgccgaggcggcataaatcgccgtgacgatcagcggtccagtgatcgaagttaggctggtaagagccgcgagcga
tccttgaagctgtccctgatggtcgtcatctacctgcctggacagcatggcctgcaacgcgggcatcccgatgccgccggaa
gcgagaagaatcataatgggaaggccatccagcctcgcgtcgcgaacgccagcaagacgtagcccagcgcgtcggcc
gccatgccggcgataatggcctgcttctcgccgaaacgtttggtggcgggaccagtgacgaaggcttgagcgagggcgtgc
aagattccgaataccgcaagcgacaggccgatcatcgtcgcgctccagcgaaagcggtcctcgccgaaaatgacccaga
gcgctgccggcacctgtcctacgagttgcatgataaagaagacagtcataagtgcggcgacgatagtcatgccccgcgccc
accggaaggagctgactgggttgaaggctctcaagggcatcggtcgacgctctcccttatgcgactcctgcattaggaagca
gcccagtagtaggttgaggccgttgagcaccgccgccgcaaggaatggtgcatgcaaggagatggcgcccaacagtccc
ccggccacggggcctgccaccatacccacgccgaaacaagcgctcatgagcccgaagtggcgagcccgatcttcccccat
cggtgatgtcggcgatataggcgccagcaaccgcacctgtggcgccggtgatgccggccacgatgcgtccggcgtagagg
attcacaggacgggtgtggtcgccatgatcgcgtagtcgatagtggctccaagtagcgaagcgagcaggactgggcggcg
gccaaagcggtcgacagtgctccgagaacgggtgcgcatagaaattgcatcaacgcatatagcgctagcagcacgcca
tagtgactggcgatgctgtcggaatggacgatatcccgcaagaggcccggcagtaccggcataaccaagcctatgcctac
agcatccagggtgacggtgccgaggatgacgatgagcgcattgttagatttcatacacggtgcctgactgcgttagcaattta
actgtgataaactaccgcattaaagcttatcgatgataagctgtcaaacatgagaa
``` pBR-CBST-KPC-4 SEQ ID 11

```
ttcttgaagacgaaaggggcctcgtgatacgcctattttataggttaatgtcatgataataatggtttcttagacgtcaggtggcacttt
tcggggaaatgtgcgcggaaccccctatttgttttattttttctaaatacattcaaatatgtatccgctcatgagacaataaccctgataaat
gcttcaataatattgaaaaaggaagagtcatATGTCACTGTATCGCCGTCTAGTTCTGCTGTCTTG
TCTCTCATGGCCGCTGGCTGGCTTTTCTGCCACCGCGCTGACCAACCTCGTCG
CGGAACCATTCGCTAAACTCGAACAGGACTTTGGCGGCTCCATCGGTGTGTA
CGCGATGGATACCGGCTCAGGCGCAACTGTAAGTTACCGCGCTGAGGAGCGC
TTCCCACTGTGCAGCTCATTCAAGGGCTTTCTTGCTGCCGCTGTGCTGGCTCG
CAGCCAGCAGCAGGCCGGCTTGCTGGACACACCCATCCGTTACGGCAAAAAT
GCGCTGGTTCGGTGGTCACCCATCTCGGAAAAATATCTGACAACAGGCATGA
CGGTGGCGGAGCTGTCCGCGGCCGCCGTGCAATACAGTGATAACGCCGCCGC
CAATTTGTTGCTGAAGGAGTTGGGCGGCCCGGCCGGGCTGACGGCCTTCATG
CGCTCTATCGGCGATACCACGTTCCGTCTGGACCGCTGGGAGCTGGAGCTGA
ACTCCGCCATCCCAGGCGATGCGCGCGATACCTCATCGCCGCGCGCCGTGAC
GGAAAGCTTACAAAAACTGACACTGGGCTCTGCACTGGCTGCGCCGCAGCGG
CAGCAGTTTGTTGATTGGCTAAAGGGAAACACGACCGGCAACCACCGCATCC
GCGCGGCGGTGCCGGCAGACTGGGCAGTCGGAGACAAAACCGGAACCTGCG
GAGGGTATGGCACGGCAAATGACTATGCCGTCGTCTGGCCCACTGGGCGCGC
ACCTATTGTGTTGGCGTCTACACCCGGGCGCCTAACAAGGATGACAAGCAC
AGCGAGGCCGTCATCGCCGCTGCGGCTAGACTCGCGCTCGAGGGATTGGGCG
TCAACGGGCAGTAAggatccctgtcagaccaagtttactcatatatactttagattgatttaaaacttcattttttaatttaa
aaggatctaggtgaagatcctttttgataatctcatgaccaaaatcccttaacgtgagttttcgttccactgagcgtcagacccgta
gaaaagatcaaaggatcttcttgagatcctttttttctgcgcgtaatctgctgcttgcaaacaaaaaaaccaccgctaccagcggtg
gtttgtttgccggatcaagagctaccaactctttttccgaaggtaactggcttcagcagagcgcagataccaaatactgtccttctag
tgtagccgtagttaggccaccacttcaagaactctgtagcaccgcctacatacctcgctctgctaatcctgttaccagtggctgctg
ccagtggcgataagtcgtgtcttaccgggttggactcaagacgatagttaccggataaggcgcagcggtcgggctgaacgggg
ggttcgtgcacacagcccagcttggagcgaacgacctacaccgaactgagatacctacagcgtgagctatgagaaagcgcca
cgcttcccgaagggagaaaggcggacaggtatccggtaagcggcagggtcggaacaggagagcgcacgagggagcttcca
gggggaaacgcctggtatctttatagtcctgtcgggtttcgccacctctgacttgagcgtcgatttttgtgatgctcgtcaggggg
cggagcctatggaaaaacgccagcaacgcggcctttttacggttcctggccttttgctggccttttgctcacatgttctttcctgcgtt
atccctgattctgtggataaccgtattaccgcctttgagtgagctgataccgctcgccgcagccgaacgaccgagcgcagcga
gtcagtgagcgaggaagcggaagagcgcctgatgcggtattttctccttacgcatctgtgcggtatttcacaccgcatttggtgca
ctctcagtacaatctgctctgatgccgcatagttaagccagtatacactccgctatcgctacgtgactgggtcatggctgcgcccc
gacacccgccaacacccgctgacgcgccctgacgggcttgtctgctcccggcatccgcttacagacaagctgtgaccgtctcc
gggagctgcatgtgtcagaggttttcaccgtcatcaccgaaacgcgcgaggcagctgcggtaaagctcatcagcgtggtcgtg
aagcgattcacagatgtctgcctgttcatccgcgtccagctcgttgagtttctccagaagcgttaatgtctggcttctgataaagcgg
gccatgttaagggcggttttttcctgtttggtcactgatgcctccgtgtaagggggattttctgttcatgggggtaatgataccgatga
aacgagagaggatgctcacgatacgggttactgatgatgaacatgcccggttactggaacgttgtgagggtaaacaactggcg
gtatggatgcggcgggaccagagaaaaatcactcagggtcaatgccagcgcttcgttaatacagatgtaggtgttccacagggt
agccagcagcatcctgcgatgcagatccggaacataatggtgcagggcgctgacttccgcgtttccagactttacgaaacacgg
aaaccgaagaccattcatgttgttgctcaggtcgcagacgttttgcagcagcagtcgcttcacgttcgctcgcgtatcggtgattca
ttctgctaaccagtaaggcaacccgccagcctagccgggtcctcaacgacaggagcacgatcatgcgcacccgtggccagg
acccaacgctgcccgagatgcgccgcgtgcggctgctggagatggcggacgcgatggatatgttctgccaagggttggtttgc
gcattcacagttctccgcaagaattgattggctccaattcttggagtggtgaatccgttagcgaggtgccgccggcttccattcag
gtcgaggtggcccggctccatgcaccgcgacgcaacgcggggaggcagacaaggtatagggcggcgcctacaatccat
gccaacccgttccatgtgctcgccgaggcggcataaatcgccgtgacgatcagcggtccagtgatcgaagttaggctggta
agagccgcgagcgatccttgaagctgtccctgatggtcgtcatctacctgcctggacagcatggcctgcaacgcgggcatcc
cgatgccgccggaagcgagaagaatcataatgggaaggccatccagcctcgcgtcgcgaacgccagcaagacgtagc
ccagcgcgtcggccgccatgccggcgataatggcctgcttctcgccgaaacgtttggtggcgggaccagtgacgaaggctt
gagcgagggcgtgcaagattccgaataccgcaagcgacaggccgatcatcgtcgcgctccagcgaaagcggtcctcgcc
gaaaatgacccagagcgctgccggcacctgtcctacgagttgcatgataaagaagacagtcataagtgcggcgacgata
gtcatgccccgcgcccaccggaaggagctgactgggttgaaggctctcaagggcatcggtcgacgctctcccttatgcgact
cctgcattaggaagcagcccagtagtaggttgaggccgttgagcaccgccgccgcaaggaatggtgcatgcaaggagat
ggcgcccaacagtcccccggccacggggcctgccaccatacccacgccgaaacaagcgctcatgagcccgaagtggcg
agcccgatcttcccccatcggtgatgtcggcgatataggcgccagcaaccgcacctgtggcgccggtgatgccggccacgat
gcgtccggcgtagaggattcacaggacgggtgtggtcgccatgatcgcgtagtcgatagtggctccaagtagcgaagcga
``` pBR-CBST-DHA-1 SEQ ID 12

```
ttcttgaagacgaaagggcctcgtgatacgcctattttataggttaatgtcatgataataatggtttcttagacgtcaggtggcacttt
tcggggaaatgtgcgcggaaccccctatttgtttattttttctaaatacattcaaatatgtatccgctcatgagacaataaccctgataaat
gcttcaataatattgaaaaaggaagagtcatATGAAAAAATCGTTATCTGCAACACTGATTTCCG
CTCTGCTGGCGTTTTCCGCCCCGGGGTTTTCTGCCGCTGATAATGTCGCGGCG
GTGGTGGACAGCACCATTAAACCGCTGATGGCACAGCAGGATATTCCCGGGA
TGGCGGTTGCCGTCTCCGTAAAGGGTAAGCCCTATTATTTCAATTATGGTTTT
GCCGATATTCAGGCAAAACAGCCGGTCACTGAAAATACACTATTTGAGCTCG
GATCTGTAAGTAAAACTTTCACAGGTGTGCTGGGTGCGGTTTCTGTGGCGAA
AAAAGAGATGGCGCTGAATGATCCGGCGGCAAAATACCAGCCGGAGCTGGC
TCTGCCGCAGTGGAAGGGGATCACATTGCTGGATCTGGCTACCTATACCGCA
GGCGGACTGCCGTTACAGGTGCCGGATGCGGTAAAAAGCCGTGCGGATCTGC
TGAATTTCTATCAGCAGTGGCAGCCGTCCCGGAAACCGGGCGATATGCGTCT
GTATGCAAACAGCAGTATCGGCCTGTTTGGTGCTCTGACCGCAAACGCGGCG
GGGATGCCGTATGAGCAGTTGCTGACTGCACGCATCCTGGCACCGCTGGGGT
TATCTCACACCTTTATTACTGTGCCGGAAAGTGCGCAAAGCCAGTATGCGTAC
GGTTATAAAACAAAAAACCGGTCCGCGTGTCGCCGGGACAGCTTGATGCGG
AATCTTACGGCGTGAAATCCGCCTCAAAAGATATGCTGCGCTGGGCGGAAAT
GAATATGGAGCCGTCACGGGCCGGTAATGCGGATCTGGAAATGGCAATGTAT
CTCGCCCAGACCCGCTACTATAAAACCGCGCGATTAACCAGGGGCTGGGCT
GGGAAATGTATGACTGGCCGCAGCAGAAAGATATGATCATTAACGGTGTGAC
CAACGAGGTCGCATTGCAGCCGCATCCGGTAACAGACAACCAGGTTCAGCCG
TATAACCGTGCTTCCTGGGTGCATAAAACGGGCGCAACAACTGGTTTCGGCG
CCTATGTCGCCTTTATTCCGGAAAAACAGGTGGCGATTGTGATTCTGGCGAAT
AAAAACTACCCGAATACCGAAAGAGTCAAAGCTGCACAGGCTATTTTGAGTG
CACTGGAATAAggatccctgtcagaccaagtttactcatatatactttagattgatttaaaacttcatttttaatttaaaagga
tctaggtgaagatccttttttgataatctcatgaccaaaatcccttaacgtgagttttcgttccactgagcgtcagacccccgtagaaaa
gatcaaaggatcttcttgagatcctttttttctgcgcgtaatctgctgcttgcaaacaaaaaaaccaccgctaccagcggtggtttgtt
tgccggatcaagagctaccaactctttttccgaaggtaactggcttcagcagagcgcagataccaaatactgtccttctagtgtag
ccgtagttaggccaccacttcaagaactctgtagcaccgcctacatacctcgctctgctaatcctgttaccagtggctgctgccagt
ggcgataagtcgtgtcttaccgggttggactcaagacgatagttaccggataaggcgcagcggtcgggctgaacggggggttc
gtgcacacagcccagcttggagcgaacgacctacaccgaactgagatacctacagcgtgagctatgagaaagcgccacgctt
cccgaagggagaaaggcggacaggtatccggtaagcggcagggtcggaacaggagagcgcacgagggagcttccaggg
ggaaacgcctggtatctttatagtcctgtcgggtttcgccacctctgacttgagcgtcgatttttgtgatgctcgtcaggggggcgg
agcctatggaaaaacgccagcaacgcggcctttttacggttcctggccttttgctggccttttgctcacatgttcttttcctgcgttatc
ccctgattctgtggataaccgtattaccgcctttgagtgagctgataccgctcgccgcagccgaacgaccgagcgcagcgagtc
agtgagcgaggaagcggaagagcgcctgatgcggtattttctccttacgcatctgtgcggtatttcacaccgcatttggtgcactc
tcagtacaatctgctctgatgccgcatagttaagccagtatacactccgctatcgctacgtgactgggtcatggctgcgccccgac
acccgccaacacccgctgacgcgccctgacgggcttgtctgctcccggcatccgcttacagacaagctgtgaccgtctccggg
agctgcatgtgtcagaggttttcaccgtcatcaccgaaacgcgcgaggcagctgcggtaaagctcatcagcgtggtcgtgaagc
gattcacagatgtctgcctgttcatccgcgtccagctcgttgagtttctccagaagcgttaatgtctggcttctgataaagcgggcca
tgttaagggcggttttttcctgtttggtcactgatgcctccgtgtaagggggatttctgttcatgggggtaatgataccgatgaaacg
agagaggatgctcacgatacgggttactgatgatgaacatgcccggttactggaacgttgtgagggtaaacaactggcggtatg
gatgcggcgggaccagagaaaaatcactcagggtcaatgccagcgcttcgttaatacagatgtaggtgttccacagggtagcc
agcagcatcctgcgatgcagatccggaacataatggtgcagggcgctgacttccgcgtttccagactttacgaaacacggaaac
cgaagaccattcatgttgttgctcaggtcgcagacgttttgcagcagcagtcgcttcacgttcgctcgcgtatcggtgattcattctg
ctaaccagtaaggcaacccccgccagcctagcgggtcctcaacgacaggagcacgatcatgcgcacccgtggccaggaccc
aacgctgcccgagatgcgccgcgtgcggctgctggagatggcggacgcgatggatatgttctgccaagggttggtttgcgcatt
cacagttctccgcaagaattgattggctccaattcttggagtggtgaatccgttagcgaggtgccgccggcttccattcaggtcga
ggtggcccggctccatgcaccgcgacgcaacgcggggaggcagacaaggtataggcggcgcctacaatccatgccaa
cccgttccatgtgctcgccgaggcggcataaatcgccgtgacgatcagcggtccagtgatcgaagttaggctggtaagagc
cgcgagcgatccttgaagctgtccctgatggtcgtcatctacctgcctggacagcatggcctgcaacgcgggcatcccgatg
ccgccggaagcgagaagaatcataatggggaaggccatccgcgtcgcatcaaggcaccagcaagattagccag
cgcgtcggccgccatgccggcgataatggcctgcttctcgccgaaacgtttggtggcgggaccagtgacgaaggcttgagc
gagggcgtgcaagattccgaataccgcaagcgacaggccgatcatcgtcgcgctccagcgaaagcggtcctcgccgaaa
atgacccagagcgctgccggcacctgtcctacgagttgcatgataaagaagacagtcataagtgcggcgacgatagtcat
gccccgcgcccaccggaaggagctgactgggttgaaggctctcaagggcatcggtcgacgctctcccttatgcgactcctg
cattaggaagcagccagtagtaggttgaggccgttgagcaccgccaaggaatggtcatgcaaggagatggcg
cccaacagtccccggccacggggcctgccaccatacccacgccgaaacaagcgctcatgagcccgaagtggcgagcc
cgatcttccccatcggtgatgtcggcgatataggcgccagcaaccgcacctgtggcgccggtgatgccggccacgatgcgt
ccggcgtagaggattcacaggacgggtgtggtcgccatgatcgcgtagtcgatagtggctccaagtagcgaagcgagcag
gactgggcggcggccaaagcggtcggacagtgctccgagaacgggtgcgcatagaaattgcatcaacgcatatagcgct
agcagcacgccatagtgactggcgatgctgtcggaatggacgatatcccgcaagaggcccggcagtaccggcataacca
agcctatgcctacagcatccagggtgacggtgccgaggatgacgatgagcgcattgttagatttcatacacggtgcctgactg
cgttagcaatttaactgtgataaactaccgcattaaagcttatcgatgataagctgtcaaacatgagaa
``` pBR-CBST-ADC-33 SEQ ID 13

```
ttcttgaagacgaaagggcctcgtgatacgcctattttataggttaatgtcatgataataatggtttcttagacgtcaggtggcacttt
tcggggaaatgtgcgcggaaccccctatttgtttattttttctaaatacattcaaatatgtatccgctcatgagacaataaccctgataaat
gcttcaataatattgaaaaaggaagagtcatATGCGATTTAAAAAAATTTCTTGTCTACTTTTATC
CCCGCTTTTTATTTTTAGTACCTCAATTTATGCGGGCAATACACCAAAAGACC
AAGAAATTAAAAAACTGGTAGATCAAAACTTTTAAACCGTTATTAGAAAAAATA
```

-continued

```
TGATGTGCCAGGTATGGCTGTGGGTGTTATTCAAAATAATAAAAAGTATGAA
ATGTATTATGGTCTTCAATCTGTTCAAGATAAAAAAGCCGTAAATAGCAGTA
CCATTTTTGAGCTAGGTTCTGTCAGTAAATTATTTACCGCGACAGCAGGTGGA
TATGCAAAAAATAAAGGAAAAATCTCTTTTGACGATACGCCTGGTAAATATT
GGAAAGAACTAAAAAACACACCGATTGACCAAGTTAACTTACTTCAACTCGC
GACGTATACAAGTGGTAACCTTGCCTTGCAGTTTCCAGATGAAGTAAAAACA
GACCAACAAGTTTTAACTTTTTTCAAAGACTGGAAACCTAAAAACTCAATCG
GTGAATACAGACAATATTCAAATCCAAGTATTGGCCTATTTGGAAAGGTTGT
GGCTTTGTCTATGAATAAACCTTTCGACCAAGTCTTAGAAAAAACAATTTTTC
CGGCCCTTGGCTTAAAACATAGCTATGTAAATGTACCTAAGACCCAGATGCA
AAACTATGCATTTGGTTATAACCAAGAAAATCAGCCGATTCGAGTTAACCGC
GGCCCACTCGATGCCGCCCTGCGTATGGCGTCAAATCGACACTACCCGACA
TGTTGAGTTTTATTCATGCCAACCTTAACCCACAGAAATATCCGGCTGATATT
CAACGGGCAATTAATGAAACACATCAAGGGCGCTATCAAGTAAATACCATGT
ATCAGGCACTCGGTTGGGAAGAGTTTTCTTATCCGGCAACGTTACAAACTTTA
TTAGACAGTAATTCAGAACAGATTGTGATGAAACCTAATAAAGTGACTGCTA
TTTCAAAGGAACCTTCAGTTAAGATGTACCATAAAACTGGCTCAACCAACGG
TTTCGGAACGTATGTAGTGTTTATTCCTAAAGAAAATATTGGCTTAGTCATGT
TAACCAATAAACGTATTCCAAATGAAGAGCGCATTAAGGCAGCTTATGCTGT
GCTGAATGCAATAAAGAAATAAggatccctgtcagaccaagtttactcatatatactttagattgatttaaaac
ttcattttttaatttaaaaggatctaggtgaagatccttttttgataatctcatgaccaaaatcccttaacgtgagttttcgttccactgagc
gtcagaccccgtagaaaagatcaaaggatcttcttgagatccttttttttctgcgcgtaatctgctgcttgcaaacaaaaaaaccacc
gctaccagcggtggtttgtttgccggatcaagagctaccaactcttttttccgaaggtaactggcttcagcagagcgcagataccaa
atactgtccttctagtgtagccgtagttaggccaccacttcaagaactctgtagcaccgcctacatacctcgctctgctaatcctgtt
accagtggctgctgccagtggcgataagtcgtgtcttaccgggttggactcaagacgatagttaccggataaggcgcagcggtc
gggctgaacggggggttcgtgcacacagcccagcttggagcgaacgacctacaccgaactgagataccctacagcgtgagcta
tgagaaagcgccacgcttcccgaagggagaaaggcggacaggtatccggtaagcggcagggtcggaacaggagagcgca
cgagggagcttccagggggaaacgcctggtatctttatagtcctgtcgggtttcgccacctctgacttgagcgtcgattttttgtgat
gctcgtcagggggcggagcctatggaaaaacgccagcaacgcggccttttttacggttcctggcttttgctggcctttttgctcac
atgttctttcctgcgttatcccctgattctgtggataaccgtattaccgcctttgagtgagctgataccgctcgccgcagccgaacga
ccgagcgcagcgagtcagtgagcgaggaagcggaagagcgcctgatgcggtattttctccttacgcatctgtgcggtatttcac
accgcatttggtgcactctcagtacaatctgctctgatgccgcatagttaagccagtatacactccgctatcgctacgtgactgggt
catggctgcgccccgacaccccgccaacacccgctgacgcgccctgacgggcttgtctgctcccggcatccgcttacagacaa
gctgtgaccgtctccgggagctgcatgtgtcagaggttttcaccgtcatcaccgaaacgcgcgaggcagctgcggtaaagctca
tcagcgtggtcgtgaagcgattcacagatgtctgcctgttcatccgcgtccagctcgttgagtttctccagaagcgttaatgtctgg
cttctgataaagcgggccatgttaaggggcggttttttcctgtttggtcactgatgcctccgtgtaaggggggatttctgttcatgggggt
aatgataccgatgaaacgagagaggatgctcacgatacgggttactgatgatgaacatgcccggttactggaacgttgtgaggg
taaacaactggcggtatggatgcggcgggaccagagaaaaatcactcagggtcaatgccagcgcttcgttaatacagatgtag
gtgttccacagggtagccagcagcatcctgcgatgcagatccggaacataatggtgcagggcgctgacttccgcgtttccagac
tttacgaaacacggaaaccgaagaccattcatgttgttgctcaggtcgcagacgttttgcagcagcagtcgcttcacgttcgctcg
cgtatcggtgattcattctgctaaccagtaaggcaaccccgccagcctagccgggtcctcaacgacaggagcacgatcatgcgc
acccgtggccaggacccaacgctgcccgagatgcgccgcgtgcggctgctggagatggcggacgcgatggatatgttctgcc
aagggttggtttgcgcattcacagttctccgcaagaattgattggctccaattcttggagtggtgaatccgttagcgaggtgccgcc
ggcttccattcaggtcgaggtggcccggctccatgcaccgcgacgcaacgcggggaggcagacaaggtatagggcggcg
cctacaatccatgccaacccgttccatgtgctcgccgaggcggcataaatcgccgtgacgatcagcggtccagtgagcgaa
gttaggctggtaagagccgtgagcgatccttgaagctgtccctgatggtcgtcatctacctgcctggacagcatggcctgcaa
cgcgggcatcccgatgccgccggaagcgagaagaatcataatggggagtccagcctcgcgtcgcgaacgccag
caagacgtagcccagcgcgtcggccgccatgccggcgataatggcctgcttctcgccgaaacgtttggtggcgggaccagt
gacgaaggcttgagcgagggcgtgcaagattccgaataccgcaagcgacaggccgatcatcgtcgcgctccagcgaaa
gcggtcctcgccgaaaatgaccccagagcgctgccggcacctgtcctacgagttgcatgataaagaagacagtcataagtg
cggcgacgatagtcatgcccccgcccaccggaaggagctgactgggttgaaggctctcaagggcatcggtcgacgctct
cccttatgcgactcctgcattaggaagcagcccagtagtaggttgaggccgttgagcaccgccgccgcaaggaatggtgca
tgcaaggagatggcgccaacagtcccccggccacgggcctgccaccatacccacgccgaaacaagcgctcatgagc
ccgaagtggcgagcccgatcttcccatcggtgatgtcggcgatataggcgccagcaaccgcacctgtggcgccggtgatg
ccggccacgatgcgtccggcgtagaggattcacaggacgggtgtggtcgccatgatcgcgtagtggctccaagt
agcgaagcgagcaggactgggcggcggccaaagcggtcggacagtgctccgagaacgggtgcgcatagaaattgcatc
aacgcatatagcgctagcagcatgccatagtgactggcgatgctgtcggaatggacgatatcccgcaagaggcccggca
gtaccggcataaccaagcctatgcctacagcatccagggtgacggtgccgaggatgacgatgagcgcattgttagatttcat
acacggtgcctgactgcgttagcaatttaactgtgataaactaccgcattaaagcttatcgatgataagctgtcaaacatgagaa
```

Example 100

Standard BLI Potentiation MIC Assay

The ability of compounds to potentiate the activity of β-lactams was demonstrated by determining the minimum inhibitory concentrations (MIC) of β-lactam and BLI compound combinations against various β-lactamase producing bacterial strains using the broth microdilution method. The experimental protocol was performed according to Clinical and Laboratory Standards Institute (CLSI) guidelines with modifications as described below (CLSI guidelines can be derived from the CLSI document M07-A9 published in January 2012: "Methods for Dilution Antimicrobial Susceptibility Tests for Bacteria That Grow Aerobically; Approved Standard-Ninth Edition").

To prepare for MIC testing, frozen glycerol stocks of clinical isolates (*Klebsiella pneumoniae, Eschericia coli, Enterobacter* spp, *Citrobacter* spp, or *Pseudomonas aeruginosa*) were used to streak for isolated colonies on rich, non-selective, tryptic soy agar containing 5% sheep's blood (TSAB). Frozen glycerol stocks of laboratory engineered, isogenic *E. coli* strains, which contain cloned β-lactamase expressing plasmids were used to streak for isolated colonies on rich, selective LB agar supplemented with 25 µg/mL tetracycline to maintain the plasmid. All strains were incubated at 37° C. for 18-24 hrs.

On the day of testing, primary cultures were started by scraping off 5-10 colonies from the TSAB plates containing clinical strains or the tetracycline supplemented LB plates containing engineered strains. The clinical strain material was suspended in ~5 mL of cation adjusted Mueller Hinton Broth (CAMHB) in 14 mL culture tubes. The engineered strain material was suspended in CAMHB (supplemented with 25 µg/mL tetracycline) in 14 mL culture tubes. All strains were incubated at 37° C. with aeration (200 rpm) for ~2 hrs until the optical density at 600 nm (OD600) was ≥0.1.

The two compound components of the assay were each diluted in CAMHB and added to the 96-well broth microdilution assay plates. 50 µL of the β-lactam was added to each well of the assay plate in 2-fold dilutions with final concentrations ranging from 128 to 0.13 µg/mL. 25 µL of the BLI compound was added to all wells in the broth microdilution plates at a final concentration of 4 µg/mL. Inoculum cultures were prepared by standardizing the primary cultures to OD600=0.1 and then adding 20 µL of the adjusted primary culture per 1 mL CAMHB for clinical strains or CAMHB (supplemented with tetracycline at 100 µg/mL) for engineered strains, so that the final inoculum density was ~$10^5$ colony forming units per milliliter. Diluted inoculum cultures were used to inoculate 25 µL per well in 96-well broth microdilution assay plates. The final volume of each well was 100 µL and contained a β-lactam at different concentrations, a BLIcompound at 4 µg/mL concentration, the bacterial culture at an OD600 of approximately 0.001 and when necessary tetracycline at 25 µg/mL.

Plates were incubated for 18-20 hours at 37° C. with aeration (200 rpm). Following incubation, growth was confirmed visually placing plates over a viewing apparatus (stand with a mirror underneath) and then OD600 was measured using a SpectraMax 340PC384 plate reader (Molecular Devices, Sunnyvale, Calif.). Growth was defined as turbidity that could be detected with the naked eye or achieving minimum OD600 of 0.1. MIC values were defined as the lowest concentration producing no visible turbidity.

MIC values of representative compounds are shown in Table II.

Example 101

Synergy MIC (sMIC) Assay

The synergy MIC (sMIC) assay determines the concentration of the BLI required to potentiate the activity of a fixed concentration of a β-lactam antibiotic against β-lactamase producing bacterial strains. The experimental protocol was performed according to Clinical and Laboratory Standards Institute (CLSI) guidelines with modifications as described below (CLSI guidelines can be derived from the CLSI document M07-A9 published in January 2012: "Methods for Dilution Antimicrobial Susceptibility Tests for Bacteria That Grow Aerobically; Approved Standard-Ninth Edition"). The assay is set-up by serially diluting the BLI across 11 of the 12 wells in each row of a 96-well broth microdilution assay plate, adding the β-lactam at a fixed concentration to all wells in the assay plate, inoculating the assay plate with bacterial strains, and determining the lowest concentration of BLI required to inhibit overnight bacterial growth. Bacterial growth in the $12^{th}$ well of the assay plate, which contains the β-lactam at a fixed concentration but does not contain any BLI, demonstrates that the bacterial strains are resistant to the β-lactam antibiotic (e.g ceftolozane) at the fixed concentration of 4 µg/mL.

To prepare for MIC testing, frozen glycerol stocks of clinical isolates (*Klebsiella pneumoniae, Eschericia coli, Enterobacter* spp, *Citrobacter* spp, or *Pseudomonas aeruginosa*) were used to streak for isolated colonies on rich, non-selective, tryptic soy agar containing 5% sheep's blood (TSAB). Frozen glycerol stocks of laboratory engineered, isogenic *E. coli* strains, which contain cloned β-lactamase expressing plasmids were used to streak for isolated colonies on rich, selective LB agar supplemented with 25 µg/mL tetracycline to maintain the plasmid. All strains were incubated at 37° C. for 18-24 hrs.

On the day of testing, primary cultures were started by scraping off 5-10 colonies from the TSAB plates containing clinical strains or the tetracycline supplemented LB plates containing engineered strains. The clinical strain material was suspended in ~5 mL of cation adjusted Mueller Hinton Broth (CAMHB) in 14 mL culture tubes. The engineered strain material was suspended in CAMHB (supplemented with tetracycline at 25 µg/mL) in 14 mL culture tubes. All strains were incubated at 37° C. with aeration (200 rpm) for ~2 hrs until the OD600 was ≥0.1.

The two compound components of the assay were each prepared in CAMHB and added to the 96-well broth microdilution assay plates. 50 µL of the BLI was added to each well of the assay plate in 2-fold dilutions with final concentrations ranging from 128 to 0.13 µg/mL. 25 µL of the β-lactam was added to all wells in the broth microdilution plates at a final concentration of 4 µg/mL. Inoculum cultures were prepared by standardizing the primary cultures to OD600=0.1 and then adding 20 µL of the adjusted primary culture per 1 mL CAMHB for clinical strains or CAMHB (supplemented with tetracycline at 100 µg/mL) for isogenic strains, so that the final inoculum density was ~$10^5$ colony forming units per milliliter. Diluted inoculum cultures were used to inoculate 25 µL per well in 96-well broth microdilution assay plates. The final volume of each well was 100 µL and contained a BLI at different concentrations, a β-lactam at 4 µg/mL concentration, the bacterial culture at an OD600 of approximately 0.001 and when necessary tetracycline at 25 ug/mL. Interpreting the sMIC Data:

Plates were incubated for 18-20 hours at 37° C. with aeration (200 rpm). Following incubation, growth was confirmed visually placing plates over a viewing apparatus (stand with a mirror underneath) and then OD600 was measured using a SpectraMax 340PC384 plate reader (Molecular Devices, Sunnyvale, Calif.). Growth was defined as turbidity that could be detected with the naked eye or achieving minimum OD600 of 0.1. sMIC values were defined as the lowest concentration producing no visible turbidity.

The sMIC values represent the amount of BLI required to potentiate the activity of 4 µg/ml of CXA-101 (Ceftolozane) or ceftazidime to inhibit the growth of the β-lactamase producing bacteria.

sMIC values of representative compounds are shown in Table III.

Example 102

Inhibition Kinetics

Inhibition or inactivation of KPC-2 by test inhibitors was assessed using 100 µM nitrocefin (NCF) as a reporter substrate. Assays were performed in 1×PBS pH 7.4, 0.1 mg/ml BSA, in 96-well half area plates, 50 µl reaction volume. NCF was dissolved in DMSO and diluted in assay buffer. Test inhibitors were dissolved in water or DMSO and serially diluted in the assay with final concentrations between 2000-0.195 µM.

The enzyme activity in the presence of varying concentrations of test inhibitor was determined by monitoring the hydrolysis of NCF spectrophotometrically at 486 nm, for 5 minutes, 25° C., using a SpectraMax Plus384 microplate reader with SoftMax Pro software (Molecular Devices). Data analysis was performed using GraphPad Prism (GraphPad Software, Inc.).

Progress curves were fit to a first-order rate decay equation (Eq. 1) to determine $k_{observed}$ ($k_{obs}$).

$k_{obs}$ vs. inhibitor concentration [I] curves were then fit to Eq.2 to determine the inhibitor dissociation constant (K) and the first order rate constant of enzyme inactivation at infinite inhibitor concentration ($k_{inact}$). Table IV shows kinetics results from representative test compounds. A larger $k_{inact}/K$ ratio indicates a more effective enzyme inactivator.

$$Y_t = V_0 * (1 - e^{(-k_{obs}*t)})/k_{obs} \qquad \text{Eq. 1}$$

Where Y is the absorbance at time t, $V_0$ is the uninhibited enzyme velocity, $k_{obs}$ is the observed rate constant of the enzyme inactivation.

$$k_{obs} = k_{inact} * [I]/([I] + K(1 + S/K_m)) \qquad \text{Eq. 2}$$

Where S is the NCF concentration, $K_m$ is the KPC-2 $K_m$ for NCF.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

---

We claim:
1. A compound of the formula:

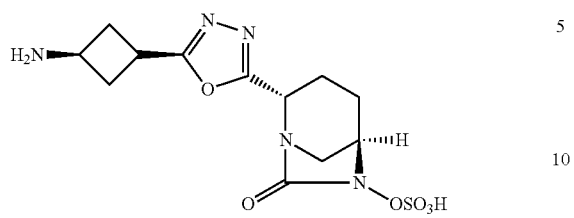

or a pharmaceutically acceptable salt thereof.

2. A pharmaceutical composition comprising a compound of claim 1 and at least 1 β-lactam antibiotic.

3. The pharmaceutical composition of claim 2 wherein the β-lactam antibiotic is a cephalosporin.

4. The pharmaceutical composition of claim 2 wherein the β-lactam antibiotic is a carbapenem.

5. The pharmaceutical composition of claim 2 wherein the β-lactam antibiotic is a monobactam.

* * * * *